(12) United States Patent
Li et al.

(10) Patent No.: US 11,739,156 B2
(45) Date of Patent: Aug. 29, 2023

(54) METHODS AND COMPOSITIONS FOR OVERCOMING IMMUNOSUPPRESSION

(71) Applicants: The Broad Institute, Inc., Cambridge, MA (US); Massachusetts Institute of Technology, Cambridge, MA (US)

(72) Inventors: Amy Li, Cambridge, MA (US); Rebecca H. Herbst, Cambridge, MA (US); Aviv Regev, Cambridge, MA (US); Tyler Jacks, Cambridge, MA (US); David Canner, Cambridge, MA (US)

(73) Assignee: The Broad Institute, Inc. Massachusetts Institute of Technology, Cambridge, MA (US)

( * ) Notice: Subject to any disclaimer, the term of this patent is extended or adjusted under 35 U.S.C. 154(b) by 271 days.

(21) Appl. No.: 16/735,187

(22) Filed: Jan. 6, 2020

(65) Prior Publication Data

US 2020/0216551 A1 Jul. 9, 2020

Related U.S. Application Data

(60) Provisional application No. 62/788,952, filed on Jan. 6, 2019.

(51) Int. Cl.
| | | |
|---|---|---|
| C07K 16/28 | (2006.01) | |
| C07K 16/24 | (2006.01) | |
| C07K 16/30 | (2006.01) | |
| A61P 35/00 | (2006.01) | |
| C12N 9/22 | (2006.01) | |
| A61K 39/00 | (2006.01) | |
| A61K 45/06 | (2006.01) | |

(52) U.S. Cl.
CPC .......... *C07K 16/2866* (2013.01); *A61P 35/00* (2018.01); *C07K 16/244* (2013.01); *C07K 16/30* (2013.01); *C12N 9/22* (2013.01); *A61K 45/06* (2013.01); *A61K 2039/505* (2013.01); *C07K 2317/732* (2013.01)

(58) Field of Classification Search
CPC ..... C07K 16/2866; C07K 16/244; C12N 9/22
See application file for complete search history.

(56) References Cited

U.S. PATENT DOCUMENTS

| | | | |
|---|---|---|---|
| 4,737,323 | A | 4/1988 | Martin et al. |
| 4,837,028 | A | 6/1989 | Allen |
| 5,500,362 | A | 3/1996 | Robinson et al. |
| 5,580,737 | A | 12/1996 | Polisky et al. |
| 5,641,870 | A | 6/1997 | Rinderknecht et al. |
| 5,660,985 | A | 8/1997 | Pieken et al. |
| 5,686,281 | A | 11/1997 | Roberts |
| 5,811,097 | A | 9/1998 | Allison et al. |
| 5,821,337 | A | 10/1998 | Carter et al. |
| 5,843,728 | A | 12/1998 | Seed et al. |
| 5,851,828 | A | 12/1998 | Seed et al. |
| 5,858,358 | A | 1/1999 | June et al. |
| 5,869,326 | A | 2/1999 | Hofmann |
| 5,883,223 | A | 3/1999 | Gray |
| 5,906,936 | A | 5/1999 | Eshhar et al. |
| 5,912,170 | A | 6/1999 | Seed et al. |
| 5,912,172 | A | 6/1999 | Eshhar et al. |
| 6,004,811 | A | 12/1999 | Seed et al. |
| 6,040,177 | A | 3/2000 | Riddell et al. |
| 6,284,240 | B1 | 9/2001 | Seed et al. |
| 6,352,694 | B1 | 3/2002 | June et al. |
| 6,392,013 | B1 | 5/2002 | Seed et al. |
| 6,410,014 | B1 | 6/2002 | Seed et al. |
| 6,479,626 | B1 | 11/2002 | Kim et al. |
| 6,489,458 | B2 | 12/2002 | Hackett et al. |
| 6,534,055 | B1 | 3/2003 | June et al. |
| 6,534,261 | B1 | 3/2003 | Cox et al. |
| 6,607,882 | B1 | 8/2003 | Cox et al. |

(Continued)

FOREIGN PATENT DOCUMENTS

| | | |
|---|---|---|
| EP | 0 404 097 A2 | 12/1990 |
| EP | 2 764 103 A2 | 8/2014 |

(Continued)

OTHER PUBLICATIONS

Molofsky et al., Interleukin-33 in Tissue Homeostasis, Injury and Inflammation, Immunity, 42, 1005-1019, 2015. (Year: 2015).*
Arpaia, et al., "A Distinct Function of Regulatory T Cells in Tissue Protection", Cell, vol. 162, No. 5, Aug. 27, 2015, 29 pages.
Beyersdorf, et al., "Characterization of Mouse CD4 T Cell Subsets Defined by Expression of KLRG1", European Journal of Immunology, vol. 37, 2007, 3445-3454.
Burzyn, et al., "A Special Population of Regulatory T Cells Potentiates Muscle Repair", Cell, vol. 155, No. 6, Dec. 5, 2013, 24 pages.
Campbell, et al., "Control of Regulatory T Cell Migration, Function, and Homeostasis", Journal of Immunology, vol. 195, No. 6, Sep. 15, 2015, 16 pages.

(Continued)

*Primary Examiner* — Elly-Gerald Stoica
(74) *Attorney, Agent, or Firm* — F. Brent Nix, Esq.; Johnson, Marcou, Isaacs & Nix, LLC; Michael B. Scher, Esq.

(57) ABSTRACT

The present invention discloses novel methods, compositions, and uses thereof for removing or overcoming immunosuppression. More specifically, the methods and compositions disclosed herein target effector $T_{reg}$ cells by modulating ST2 and/or IL-33 signaling using pharmaceutical inhibitors and/or genetic ablation, whereby the levels and/or activities of effector $T_{reg}$ cells in a tumor microenvironment are inhibited, and the infiltration of effector $CD8^+$ cytotoxic T cells into tumor microenvironment increases. As a result, tumor growth is inhibited and tumor volume is reduced. The present invention also provides methods for identifying and isolating effector $T_{reg}$ cells in a population of heterogeneous cells.

8 Claims, 22 Drawing Sheets

Specification includes a Sequence Listing.

(56) References Cited

U.S. PATENT DOCUMENTS

| | | |
|---|---|---|
| 6,746,838 B1 | 6/2004 | Choo et al. |
| 6,753,162 B1 | 6/2004 | Seed et al. |
| 6,794,136 B1 | 9/2004 | Eisenberg et al. |
| 6,797,514 B2 | 9/2004 | Berenson et al. |
| 6,824,978 B1 | 11/2004 | Cox et al. |
| 6,866,997 B1 | 3/2005 | Choo et al. |
| 6,867,041 B2 | 3/2005 | Berenson et al. |
| 6,887,466 B2 | 5/2005 | June et al. |
| 6,903,185 B2 | 6/2005 | Kim et al. |
| 6,905,680 B2 | 6/2005 | June et al. |
| 6,905,681 B1 | 6/2005 | June et al. |
| 6,905,874 B2 | 6/2005 | Berenson et al. |
| 6,933,113 B2 | 8/2005 | Case et al. |
| 6,979,539 B2 | 12/2005 | Cox et al. |
| 7,013,219 B2 | 3/2006 | Case et al. |
| 7,030,215 B2 | 4/2006 | Liu et al. |
| 7,144,575 B2 | 12/2006 | June et al. |
| 7,148,203 B2 | 12/2006 | Hackett et al. |
| 7,160,682 B2 | 1/2007 | Hackett et al. |
| 7,175,843 B2 | 2/2007 | June et al. |
| 7,220,719 B2 | 5/2007 | Case et al. |
| 7,232,566 B2 | 6/2007 | June et al. |
| 7,241,573 B2 | 7/2007 | Choo et al. |
| 7,241,574 B2 | 7/2007 | Choo et al. |
| 7,446,190 B2 | 11/2008 | Sadelain et al. |
| 7,560,530 B1 * | 7/2009 | Chackerian ............ A61P 33/12 435/7.2 |
| 7,572,631 B2 | 8/2009 | Berenson et al. |
| 7,585,849 B2 | 9/2009 | Liu et al. |
| 7,595,376 B2 | 9/2009 | Kim et al. |
| 7,741,465 B1 | 6/2010 | Eshhar et al. |
| 7,985,739 B2 | 7/2011 | Kay et al. |
| 8,021,867 B2 | 9/2011 | Smith et al. |
| 8,034,334 B2 | 10/2011 | Dudley et al. |
| 8,088,379 B2 | 1/2012 | Robbins et al. |
| 8,119,361 B2 | 2/2012 | Smith et al. |
| 8,119,381 B2 | 2/2012 | Smith et al. |
| 8,124,369 B2 | 2/2012 | Smith et al. |
| 8,129,134 B2 | 3/2012 | Smith et al. |
| 8,133,697 B2 | 3/2012 | Smith et al. |
| 8,163,514 B2 | 4/2012 | Smith et al. |
| 8,211,422 B2 | 7/2012 | Eshhar et al. |
| 8,227,432 B2 | 7/2012 | Hackett et al. |
| 8,399,645 B2 | 3/2013 | Campana et al. |
| 8,440,431 B2 | 5/2013 | Voytas et al. |
| 8,440,432 B2 | 5/2013 | Voytas et al. |
| 8,450,471 B2 | 5/2013 | Voytas et al. |
| 8,637,307 B2 | 1/2014 | June et al. |
| 8,697,359 B1 | 4/2014 | Zhang |
| 8,697,854 B2 | 4/2014 | Schendel et al. |
| 8,735,553 B1 | 5/2014 | Li et al. |
| 8,771,945 B1 | 7/2014 | Zhang |
| 8,795,965 B2 | 8/2014 | Zhang |
| 8,865,406 B2 | 10/2014 | Zhang et al. |
| 8,871,445 B2 | 10/2014 | Cong et al. |
| 8,889,356 B2 | 11/2014 | Zhang |
| 8,889,418 B2 | 11/2014 | Zhang et al. |
| 8,895,308 B1 | 11/2014 | Zhang et al. |
| 8,906,616 B2 | 12/2014 | Zhang et al. |
| 8,906,620 B2 | 12/2014 | June et al. |
| 8,911,993 B2 | 12/2014 | June et al. |
| 8,916,381 B1 | 12/2014 | June et al. |
| 8,932,814 B2 | 1/2015 | Cong et al. |
| 8,945,839 B2 | 2/2015 | Zhang |
| 8,975,071 B1 | 3/2015 | June et al. |
| 8,993,233 B2 | 3/2015 | Zhang et al. |
| 8,999,641 B2 | 4/2015 | Zhang et al. |
| 9,062,111 B2 | 6/2015 | Nichol et al. |
| 9,101,584 B2 | 8/2015 | June et al. |
| 9,102,760 B2 | 8/2015 | June et al. |
| 9,102,761 B2 | 8/2015 | June et al. |
| 9,132,281 B2 | 9/2015 | Zeng et al. |
| 9,181,527 B2 | 11/2015 | Sentman |
| 9,233,125 B2 | 1/2016 | Davila et al. |
| 9,320,811 B2 | 4/2016 | Jure-Kunkel |
| 9,327,014 B2 | 5/2016 | Gurney et al. |
| 9,790,490 B2 | 10/2017 | Zhang et al. |
| 2004/0171156 A1 | 9/2004 | Hartley et al. |
| 2004/0224402 A1 | 11/2004 | Bonyhadi et al. |
| 2010/0104509 A1 | 4/2010 | King et al. |
| 2011/0265198 A1 | 10/2011 | Gregory et al. |
| 2012/0017290 A1 | 1/2012 | Cui et al. |
| 2012/0244133 A1 | 9/2012 | Rosenberg et al. |
| 2013/0071414 A1 | 3/2013 | Dotti et al. |
| 2013/0236946 A1 | 9/2013 | Gouble |
| 2014/0004107 A1 * | 1/2014 | Smith .................... A61P 17/02 435/69.6 |
| 2014/0170753 A1 | 6/2014 | Zhang |
| 2014/0179006 A1 | 6/2014 | Zhang |
| 2014/0179770 A1 | 6/2014 | Zhang et al. |
| 2014/0186843 A1 | 7/2014 | Zhang et al. |
| 2014/0186919 A1 | 7/2014 | Zhang et al. |
| 2014/0186958 A1 | 7/2014 | Zhang et al. |
| 2014/0189896 A1 | 7/2014 | Zhang et al. |
| 2014/0227787 A1 | 8/2014 | Zhang |
| 2014/0234972 A1 | 8/2014 | Zhang |
| 2014/0242664 A1 | 8/2014 | Zhang et al. |
| 2014/0242699 A1 | 8/2014 | Zhang |
| 2014/0242700 A1 | 8/2014 | Zhang et al. |
| 2014/0248702 A1 | 9/2014 | Zhang et al. |
| 2014/0256046 A1 | 9/2014 | Zhang et al. |
| 2014/0273231 A1 | 9/2014 | Zhang et al. |
| 2014/0273232 A1 | 9/2014 | Zhang et al. |
| 2014/0273234 A1 | 9/2014 | Zhang et al. |
| 2014/0273238 A1 | 9/2014 | Zhang et al. |
| 2014/0310830 A1 | 10/2014 | Zhang et al. |
| 2015/0150947 A1 * | 6/2015 | Unemori ................ A61P 17/06 514/12.7 |
| 2015/0184139 A1 | 7/2015 | Zhang et al. |
| 2015/0368342 A1 | 12/2015 | Wu et al. |
| 2015/0368360 A1 | 12/2015 | Liang et al. |
| 2016/0046724 A1 | 2/2016 | Brogdon et al. |
| 2016/0129109 A1 | 5/2016 | Davila et al. |
| 2016/0166613 A1 | 6/2016 | Spencer et al. |
| 2016/0175359 A1 | 6/2016 | Spencer et al. |
| 2017/0037134 A1 * | 2/2017 | Behrens ................ C07K 14/54 |
| 2017/0047193 A1 | 2/2017 | Jiang et al. |
| 2017/0107300 A1 * | 4/2017 | Kuchroo .......... A61K 39/39566 |
| 2017/0211142 A1 | 7/2017 | Smargon et al. |
| 2017/0283504 A1 | 10/2017 | Wiltzius et al. |
| 2017/0283831 A1 | 10/2017 | Zhang et al. |
| 2017/0306335 A1 | 10/2017 | Zhang et al. |
| 2017/0349894 A1 | 12/2017 | Dahlman et al. |
| 2018/0057810 A1 | 3/2018 | Zhang et al. |
| 2018/0085444 A1 | 3/2018 | Morgan et al. |
| 2018/0163265 A1 | 6/2018 | Zhang et al. |
| 2018/0312824 A1 | 11/2018 | Zhang et al. |
| 2019/0153476 A1 | 5/2019 | Zhang |
| 2019/0359971 A1 | 11/2019 | Zhang et al. |

FOREIGN PATENT DOCUMENTS

| | | |
|---|---|---|
| EP | 2 771 468 A1 | 9/2014 |
| EP | 2 784 162 A1 | 10/2014 |
| EP | 3 009 511 A2 | 4/2016 |
| EP | 3 470 089 A1 | 4/2019 |
| WO | 92/15322 A1 | 9/1992 |
| WO | 93/11161 A1 | 6/1993 |
| WO | 96/40281 A2 | 12/1996 |
| WO | 97/49450 A1 | 12/1997 |
| WO | 98/52609 A1 | 11/1998 |
| WO | 03/020763 A2 | 3/2003 |
| WO | 03/057171 A2 | 7/2003 |
| WO | 2004/033685 A1 | 4/2004 |
| WO | 2004/044004 A2 | 5/2004 |
| WO | 2004/074322 A1 | 9/2004 |
| WO | 2005/113595 A2 | 12/2005 |
| WO | 2005/114215 A2 | 12/2005 |
| WO | 2006/000830 A2 | 1/2006 |
| WO | 2006/125962 A2 | 11/2006 |
| WO | 2008/038002 A2 | 4/2008 |
| WO | 2008/039818 A2 | 4/2008 |
| WO | 2009/012418 A2 | 1/2009 |
| WO | 2011/146862 A1 | 11/2011 |

(56) References Cited

FOREIGN PATENT DOCUMENTS

| | | |
|---|---|---|
| WO | 2012/058460 A2 | 5/2012 |
| WO | 2012/079000 A1 | 6/2012 |
| WO | 2013/039889 A1 | 3/2013 |
| WO | 2013/040371 A2 | 3/2013 |
| WO | 2013/044225 A1 | 3/2013 |
| WO | 2013/154760 A1 | 10/2013 |
| WO | 2013/166321 A1 | 11/2013 |
| WO | 2013/176915 A1 | 11/2013 |
| WO | 2014/011987 A1 | 1/2014 |
| WO | 2014/018423 A2 | 1/2014 |
| WO | 2014/018863 A1 | 1/2014 |
| WO | 2014/059173 A2 | 4/2014 |
| WO | 2014/083173 A1 | 6/2014 |
| WO | 2014/093595 A1 | 6/2014 |
| WO | 2014/093622 A2 | 6/2014 |
| WO | 2014/093635 A1 | 6/2014 |
| WO | 2014/093655 A2 | 6/2014 |
| WO | 2014/093661 A2 | 6/2014 |
| WO | 2014/093694 A1 | 6/2014 |
| WO | 2014/093701 A1 | 6/2014 |
| WO | 2014/093709 A1 | 6/2014 |
| WO | 2014/093712 A1 | 6/2014 |
| WO | 2014/093718 A1 | 6/2014 |
| WO | 2014/133567 A1 | 9/2014 |
| WO | 2014/133568 A1 | 9/2014 |
| WO | 2014/134165 A1 | 9/2014 |
| WO | 2014/172606 A1 | 10/2014 |
| WO | 2014/184744 A1 | 11/2014 |
| WO | 2014/191128 A1 | 12/2014 |
| WO | 2014/204723 A1 | 12/2014 |
| WO | 2014/204724 A1 | 12/2014 |
| WO | 2014/204725 A1 | 12/2014 |
| WO | 2014/204726 A1 | 12/2014 |
| WO | 2014/204727 A1 | 12/2014 |
| WO | 2014/204728 A1 | 12/2014 |
| WO | 2014/204729 A1 | 12/2014 |
| WO | 2015/057834 A1 | 4/2015 |
| WO | 2015/057852 A1 | 4/2015 |
| WO | 2015/058052 A1 | 4/2015 |
| WO | 2015/070083 A1 | 5/2015 |
| WO | 2015/089351 A1 | 6/2015 |
| WO | 2015/089354 A1 | 6/2015 |
| WO | 2015/089364 A1 | 6/2015 |
| WO | 2015/089419 A2 | 6/2015 |
| WO | 2015/089427 A1 | 6/2015 |
| WO | 2015/089462 A1 | 6/2015 |
| WO | 2015/089465 A1 | 6/2015 |
| WO | 2015/089473 A1 | 6/2015 |
| WO | 2015/089486 A2 | 6/2015 |
| WO | 2015/120096 A2 | 8/2015 |
| WO | 2015/142675 A2 | 9/2015 |
| WO | 2015/158671 A1 | 10/2015 |
| WO | 2015/187528 A1 | 10/2015 |
| WO | 2016/000304 A1 | 1/2016 |
| WO | 2016/011210 A2 | 1/2016 |
| WO | 2016/014789 A2 | 1/2016 |
| WO | 2016/028682 A1 | 2/2016 |
| WO | 2016/049024 A2 | 3/2016 |
| WO | 2016/049258 A2 | 3/2016 |
| WO | 2016/070061 A1 | 5/2016 |
| WO | 2016/094867 A1 | 6/2016 |
| WO | 2016/094872 A1 | 6/2016 |
| WO | 2016/094874 A1 | 6/2016 |
| WO | 2016/106244 A1 | 6/2016 |
| WO | 2016/161516 A1 | 10/2016 |
| WO | 2016/191756 A1 | 12/2016 |
| WO | 2016/196388 A1 | 12/2016 |
| WO | 2017/004916 A1 | 1/2017 |
| WO | 2017/011804 A1 | 1/2017 |
| WO | 2017/070395 A1 | 4/2017 |
| WO | 2017/070605 A1 | 4/2017 |
| WO | 2017/189308 A1 | 11/2017 |
| WO | 2017/211900 A1 | 12/2017 |
| WO | 2018/028647 A1 | 2/2018 |
| WO | 2018/035250 A1 | 2/2018 |
| WO | WO2018112033 | * 6/2018 ........... A61K 39/395 |
| WO | 2019/005866 A1 | 1/2019 |

OTHER PUBLICATIONS

Cheng, et al., "IL-2 Receptor Signaling Is Essential for the Development of Klrg1+ Terminally Differentiated T Regulatory Cells", The Journal of Immunology, vol. 189, No. 4, Aug. 15, 2012, 1780-1791.

De Simone, et al., "Transcriptional Landscape of Human Tissue Lymphocytes Unveils Uniqueness of Tumor-Infiltrating T Regulatory Cells", Immunity, vol. 45, No. 5, Nov. 15, 2016, 13 pages.

Delacher, et al., "Genome-Wide DNA Methylation Landscape Defines Specialization of Regulatory T Cells in Tissues", Nature Immunology, vol. 18, No. 10, Oct. 2017, 43 pages.

Guo, et al., "Global Characterization of T Cells In Non-Small-Cell Lung Cancer by Single-Cell Sequencing", Nature Medicine, vol. 24, No. 7, Jul. 2018, 17 pages.

Huehn, et al., "Developmental Stage, Phenotype, and Migration Distinguish Naive- and Effector/Memory-like CD4+ Regulatory T Cells", The Journal of Experimental Medicine, vol. 199, No. 3, Feb. 2, 2004, 303-313.

Joshi, et al., "Regulatory T Cells in Tumor-Associated Tertiary Lymphoid Structures Suppress Anti-Tumor T Cell Responses", Immunity, vol. 43, No. 3, Sep. 15, 2015, 579-590.

Kim, et al., "Generation of RORγt+ Antigen-Specific T Regulatory 17 Cells from Foxp3+ Precursors in Autoimmunity", Cell Reports, vol. 21, No. 1, Oct. 3, 2017, 25 pages.

Koch, et al., "The Transcription Factor T-Bet Controls Regulatory T Cell Homeostasis and Function During Type 1 Inflammation", Nature Immunology, vol. 10, No. 6, Jun. 2009, 22 pages.—Abstract.

Lehmann, et al., "Expression of the Integrin αEβ7 Identifies Unique Subsets of CD25+ as well as CD25− Regulatory T Cells", Proceedings of the National Academy of Sciences of the United States of America, vol. 99, No. 20, Oct. 1, 2002, 13031-13036.

Levine, et al., "Stability and Function of Regulatory T Cells Expressing the Transcription Factor T-Bet", Nature, vol. 546, No. 7658, Jun. 15, 2017, 30 pages.

Li, et al., "T Cell Receptor Signalling in the Control of Regulatory T Cell Differentiation and Function", Nature Reviews Immunology, vol. 16, No. 4, Apr. 2016, 34 pages.

Magnuson, et al., "Identification and Validation of a Tumor-Infiltrating Treg Transcriptional Signature Conserved Across Species and Tumor Types", Proceedings of the National Academy of Sciences of the United States of America, vol. 115, No. 45, Nov. 6, 2018, 10 pages.

Miragaia, et al., "Single Cell Transcriptomics of Regulatory T Cells Reveals Trajectories of Tissue Adaptation", bioRxiv, Nov. 22, 2017, 39 pages.

Plitas, et al., "Regulatory T Cells Exhibit Distinct Features in Human Breast Cancer", Immunity, vol. 45, No. 5, Nov. 15, 2016, 25 pages.

Sather, et al., "Altering the Distribution of Foxp3(+) Regulatory T Cells Results in Tissue-Specific Inflammatory Disease", Journal of Experimental Medicine, vol. 204, No. 6, Jun. 11, 2007, 1335-1347.

Tanaka, et al., "Regulatory T cells in Cancer Immunotherapy", Cell Research, vol. 27, No. 1, Jan. 2017, 109-118.

Man Der Veeken, et al., "Memory of Inflammation in Regulatory T Cells", Cell, vol. 166, No. 4, Aug. 11, 2016, 22 pages.

Yamazaki, et al., "CCR6 Regulates the Migration of Inflammatory and Regulatory T Cells", Journal of Immunology, vol. 181, No. 12, Dec. 15, 2008, 22 pages.

Zhang, et al., "Comparative Transcriptomics Identifies Genes Differentially Expressed In The Intestine Of A New Fast-growing Strain of Common Carp with Higher Unsaturated Fatty Acid Content in Muscle", PLoS One, vol. 13, No. 11, Nov. 5, 2018, 22 pages.

Zheng, et al., "Landscape of Infiltrating T Cells in Liver Cancer Revealed by Single-Cell Sequencing", Cell, vol. 169, Issue 7, Jun. 15, 2017, 32 pages.

* cited by examiner

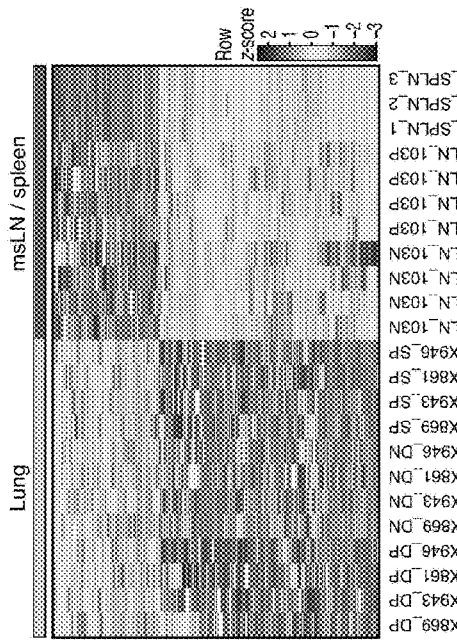
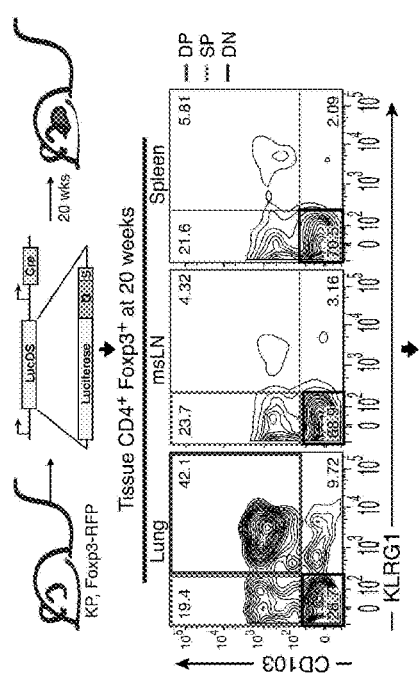
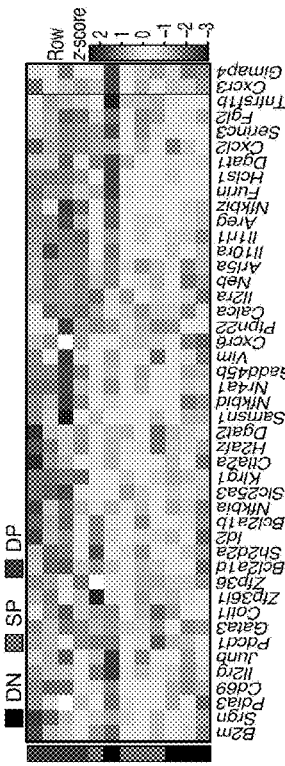
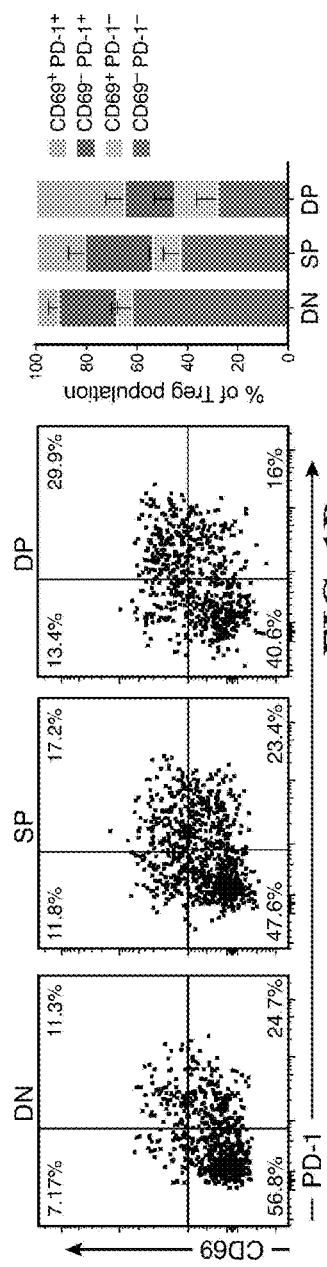

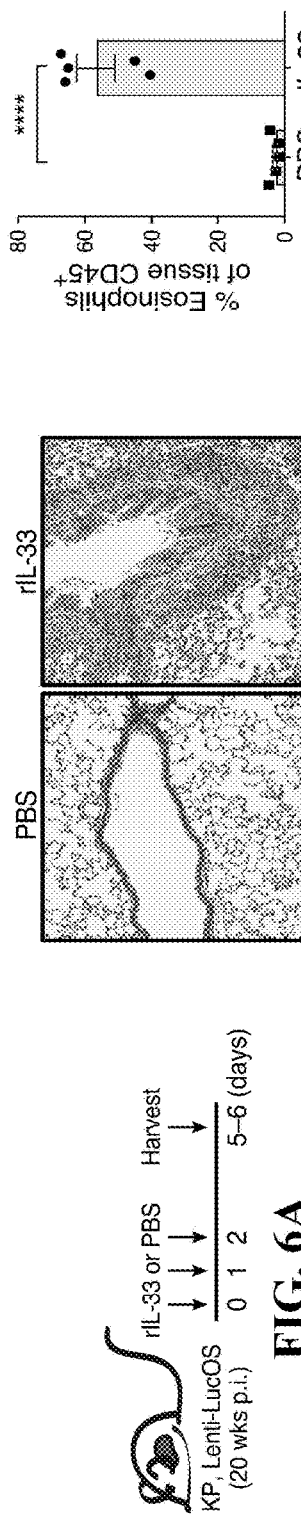
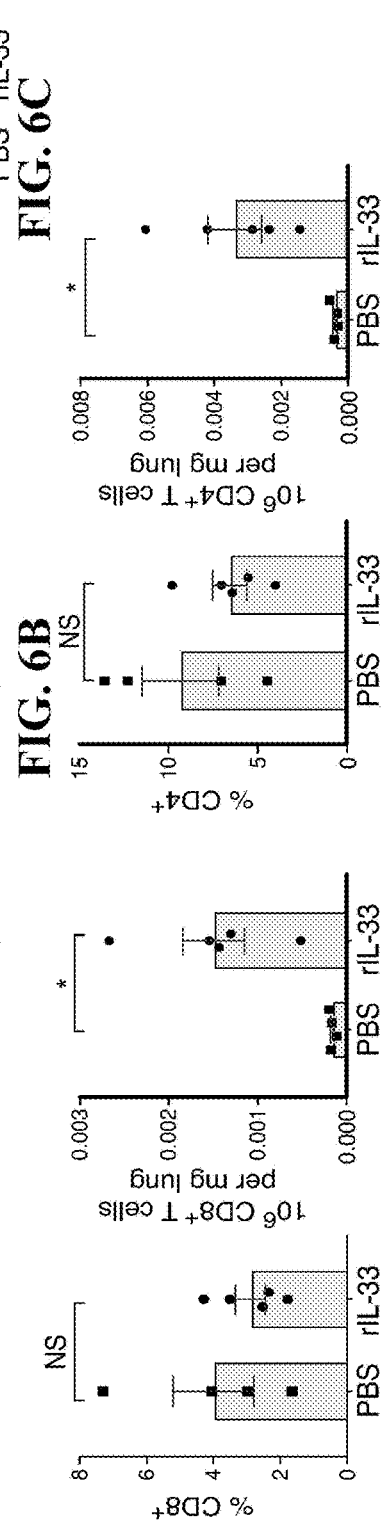
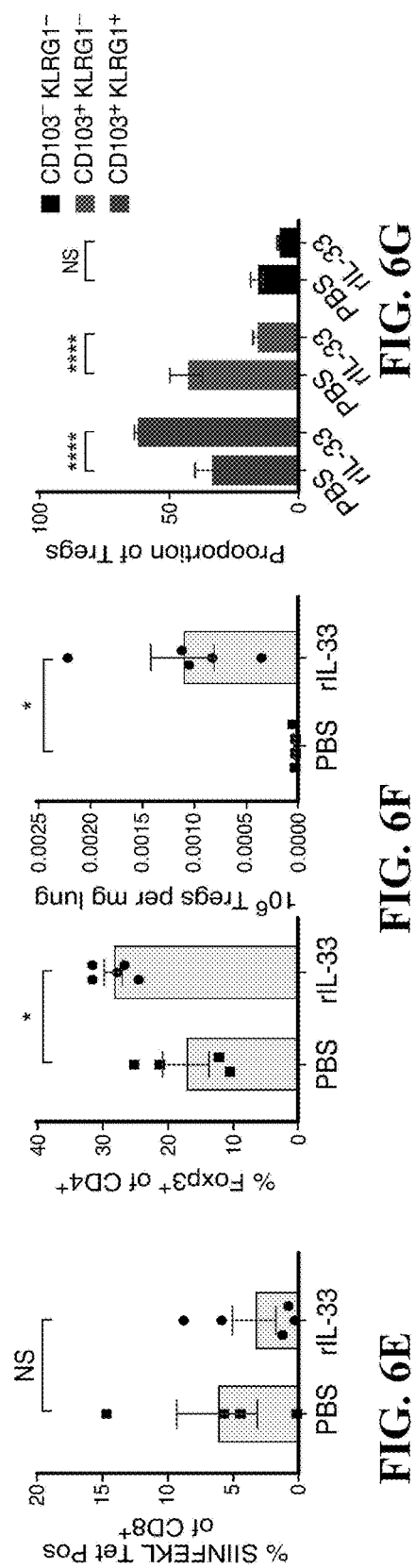

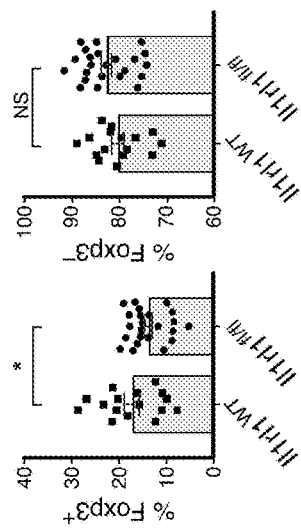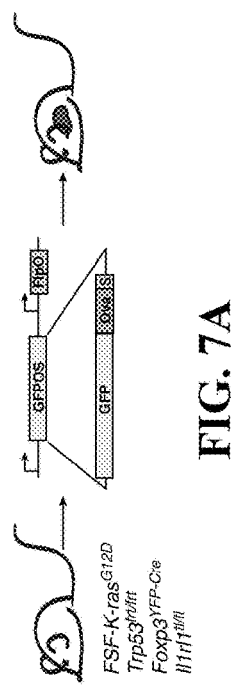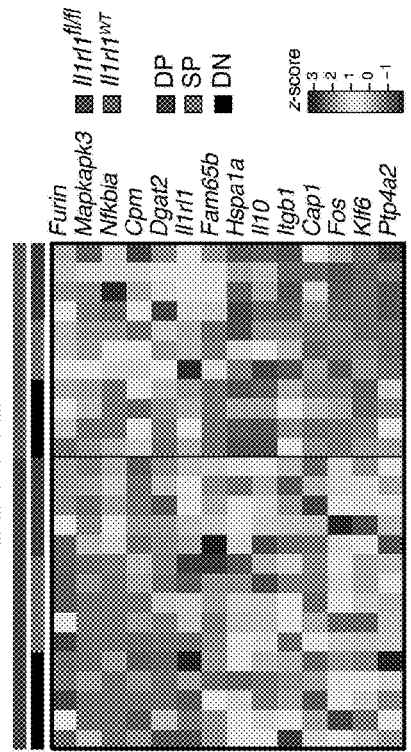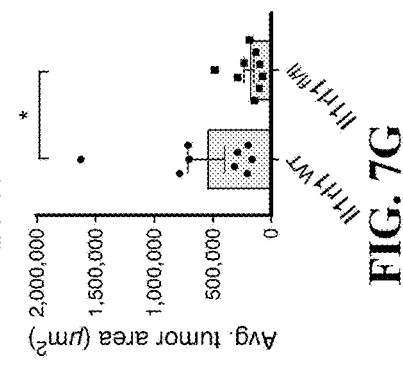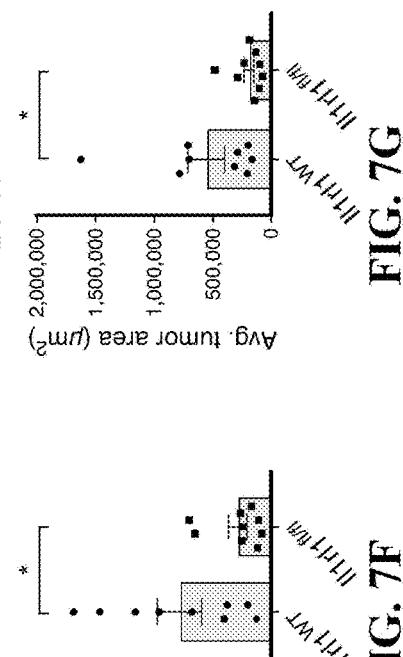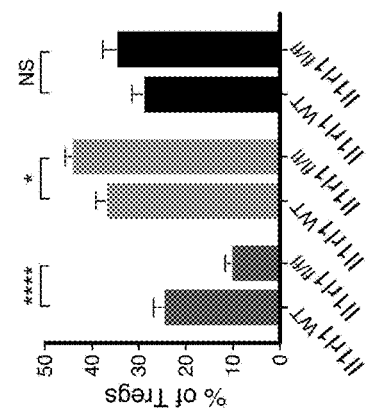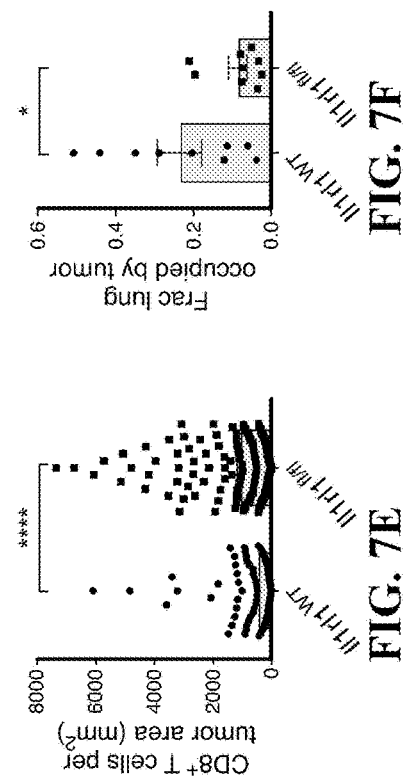
FIG. 7A
FIG. 7B
FIG. 7C
FIG. 7D
FIG. 7E
FIG. 7F
FIG. 7G

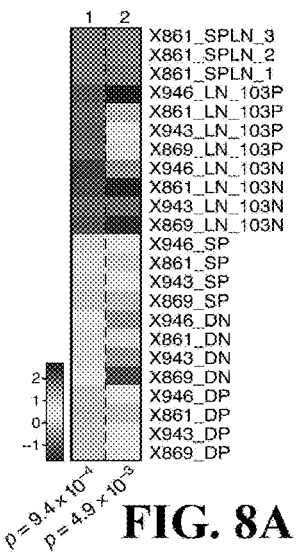
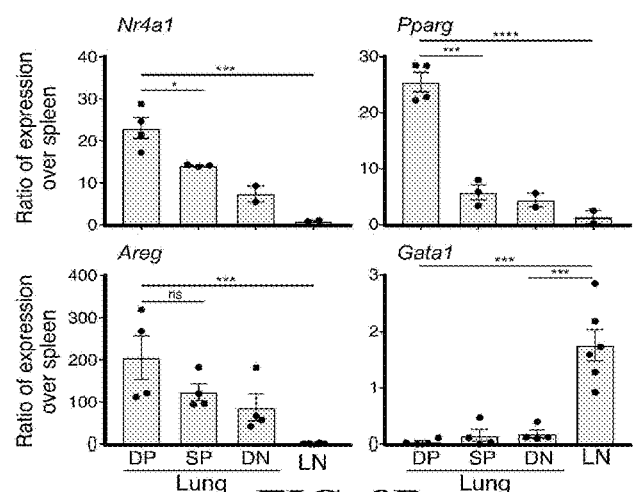
FIG. 8A  FIG. 8B
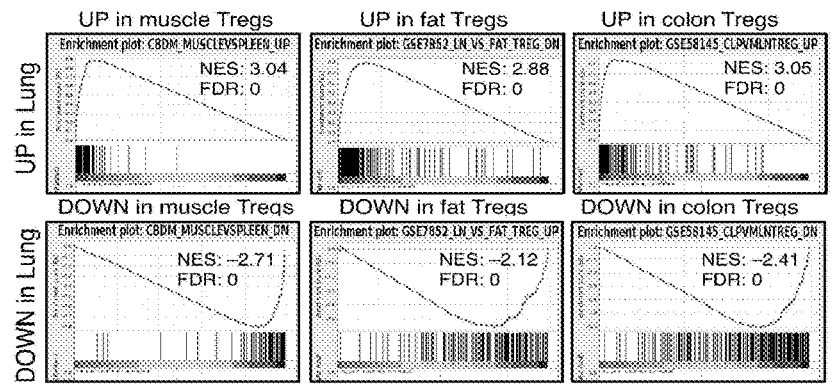
FIG. 8C
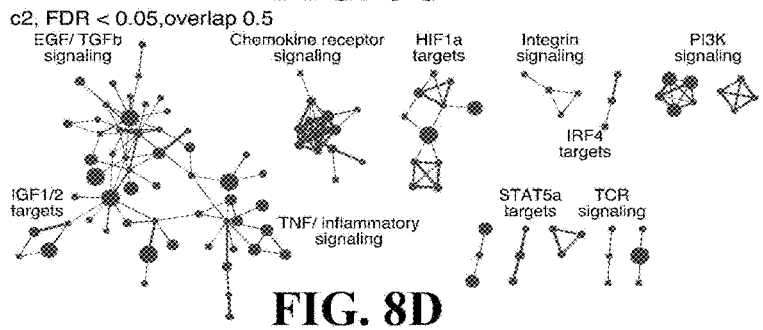
FIG. 8D
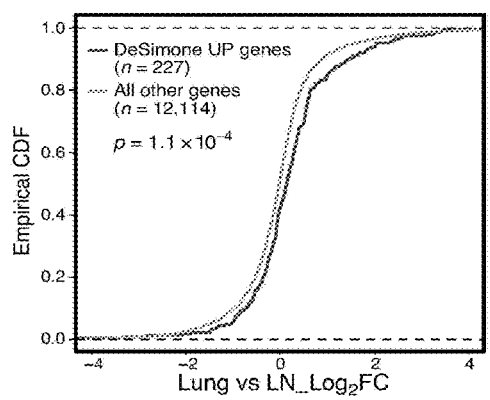
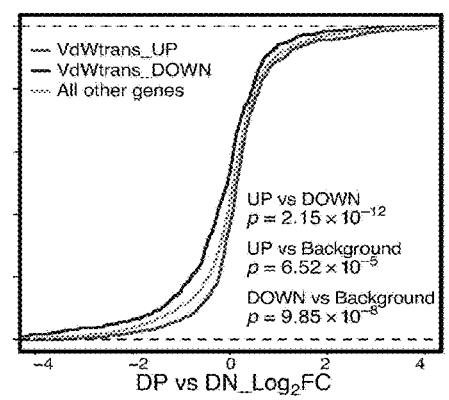
FIG. 8E  FIG. 8F

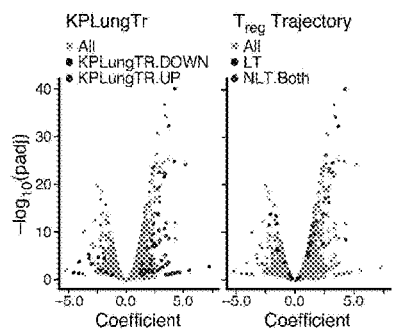
FIG. 9A
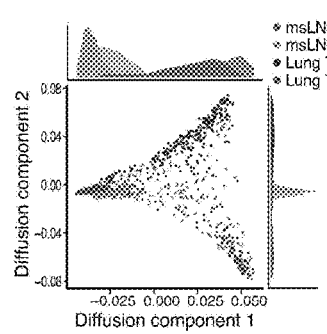
FIG. 9B
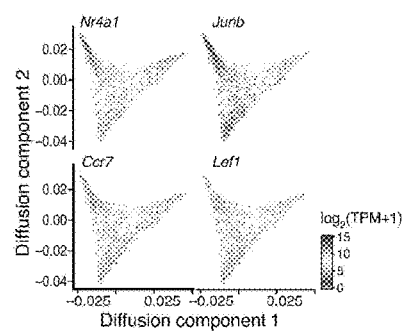
FIG. 9C
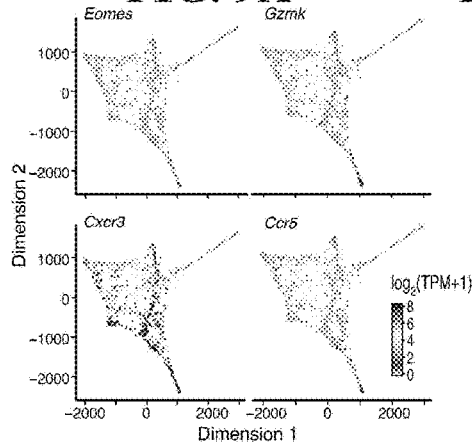
FIG. 9D
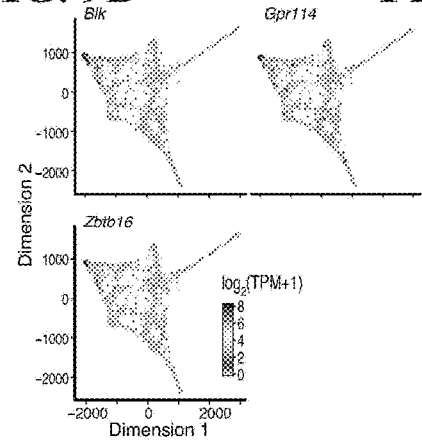
FIG. 9E
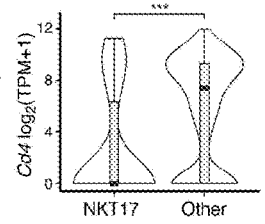
FIG. 9F
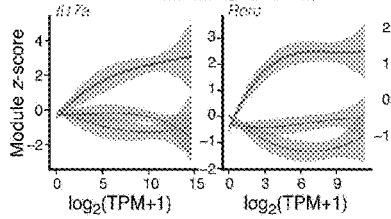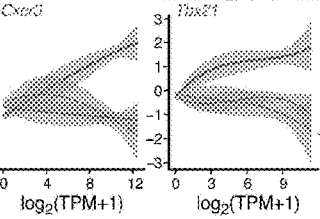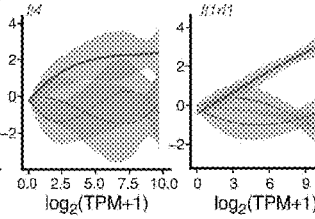
FIG. 9G
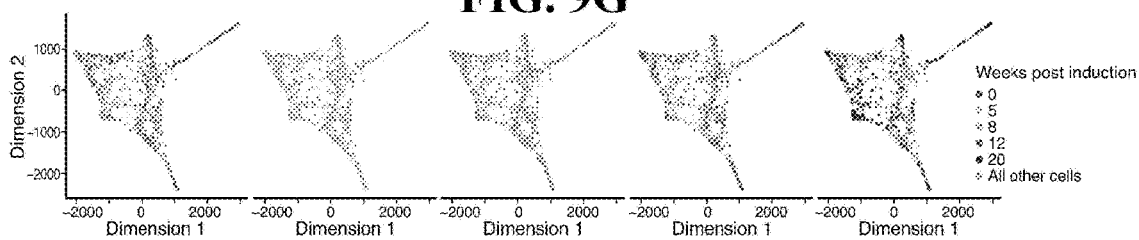
FIG. 9H
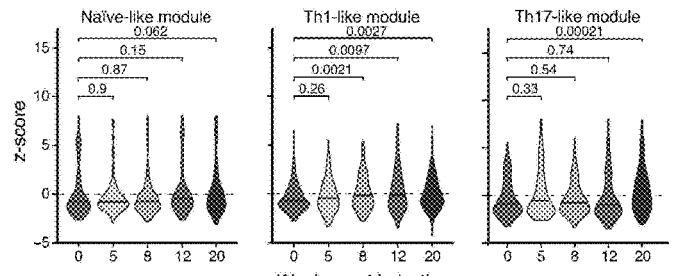
FIG. 9I

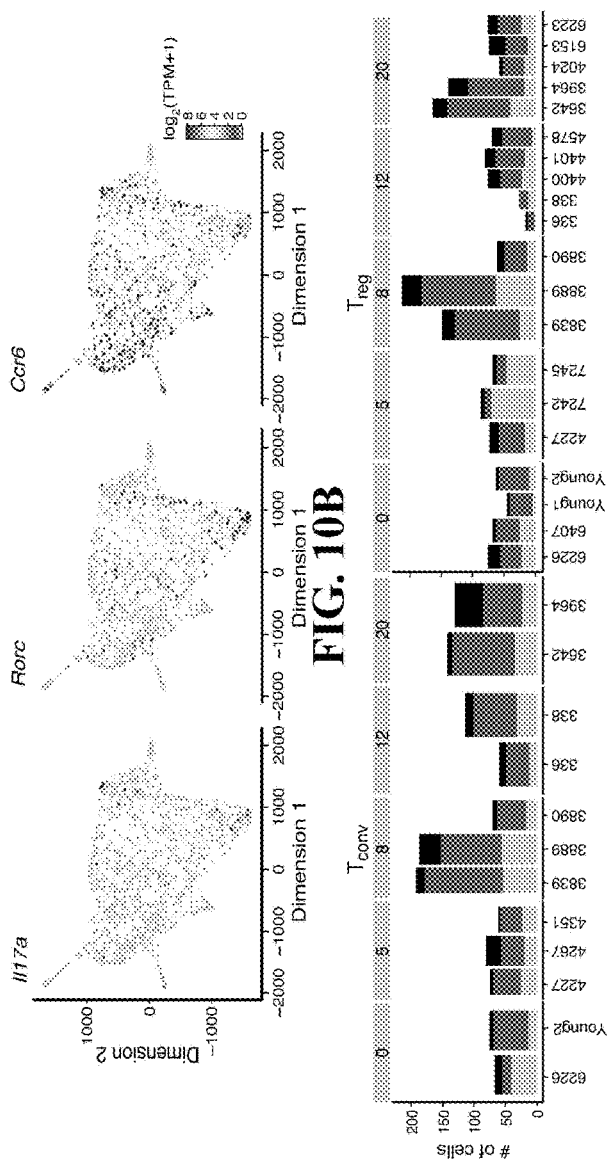
FIG. 10A
FIG. 10B
FIG. 10C
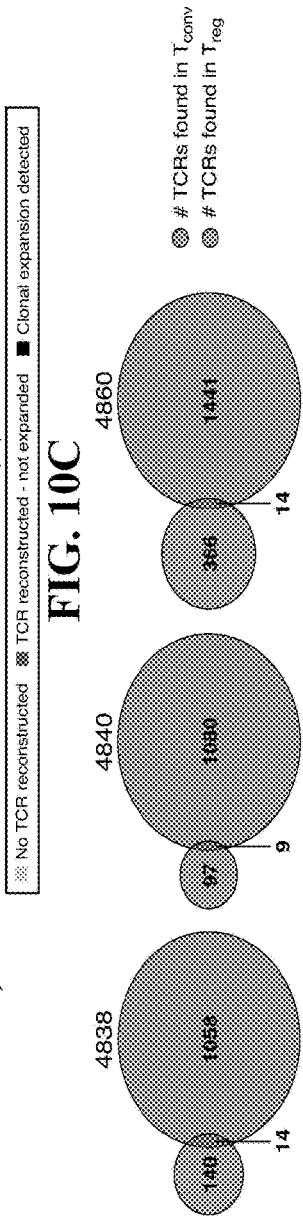
FIG. 10D
FIG. 10E

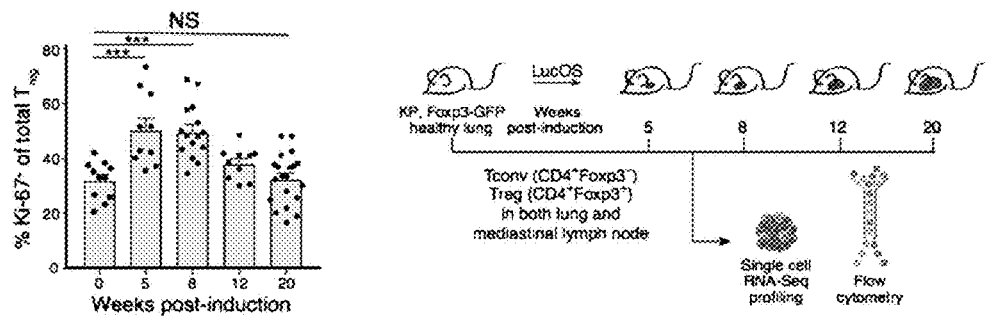
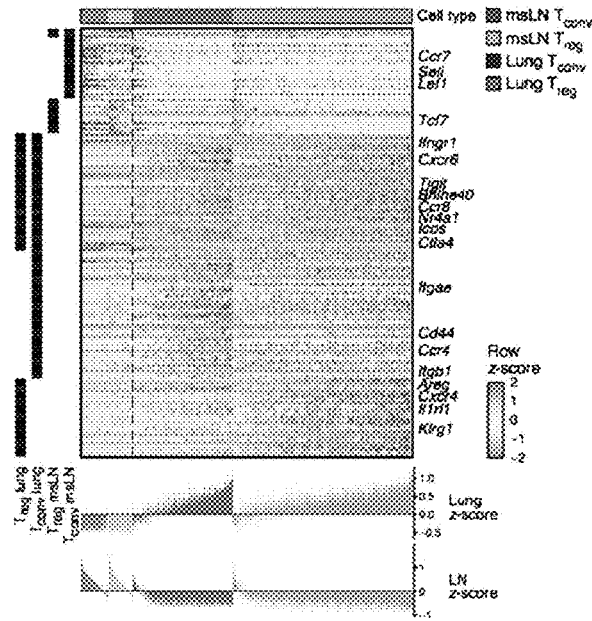
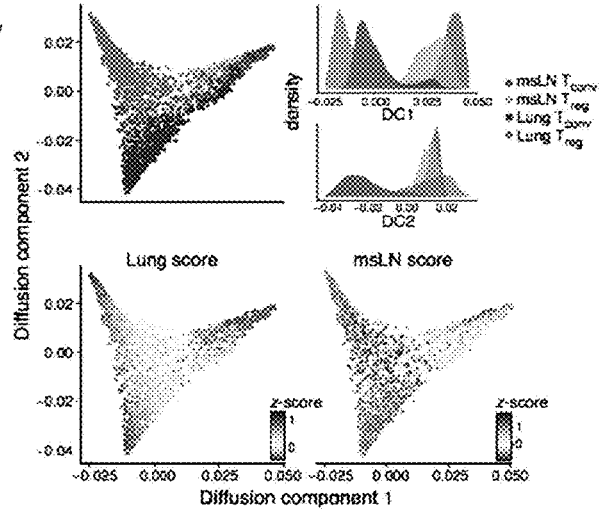
FIG. 15A
FIG. 15B
FIG. 15C
FIG. 15D
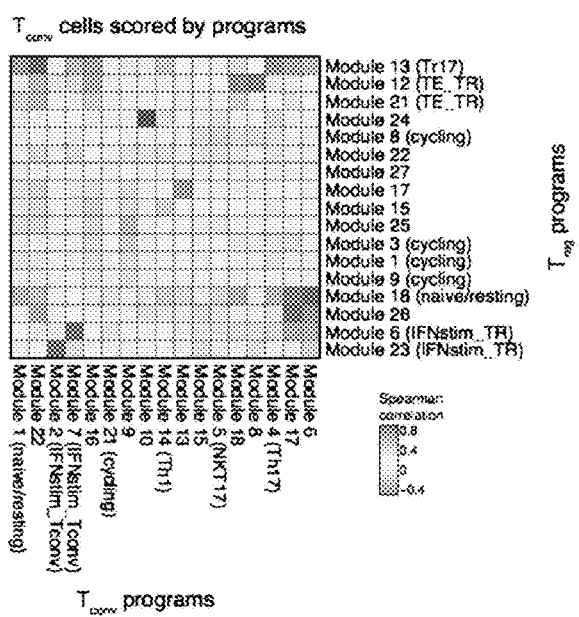
FIG. 15E

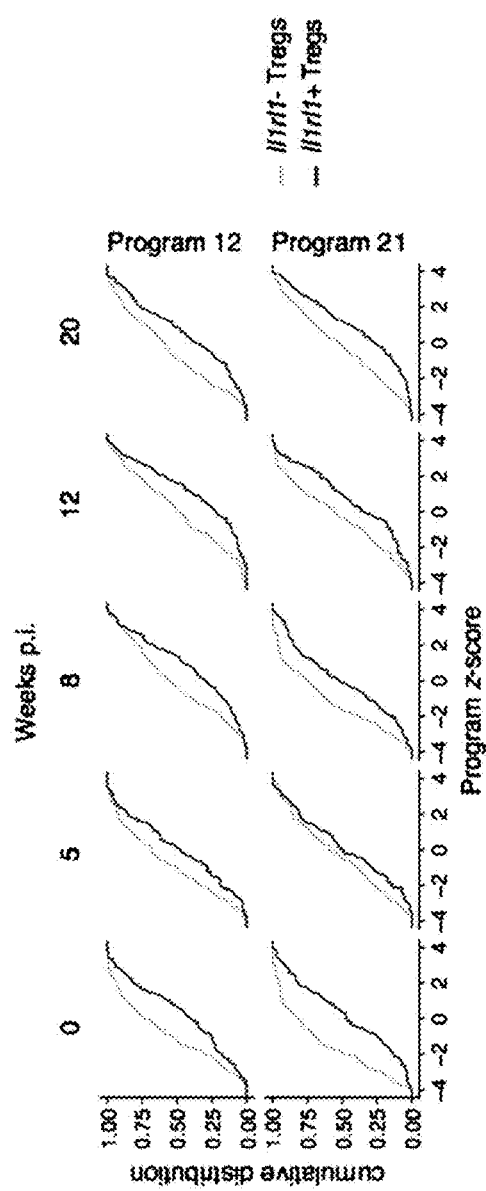
FIG. 17A
FIG. 17B
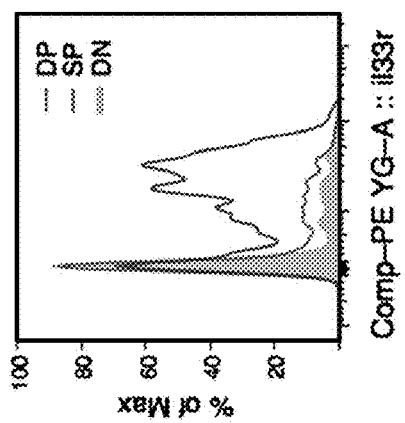
FIG. 17C
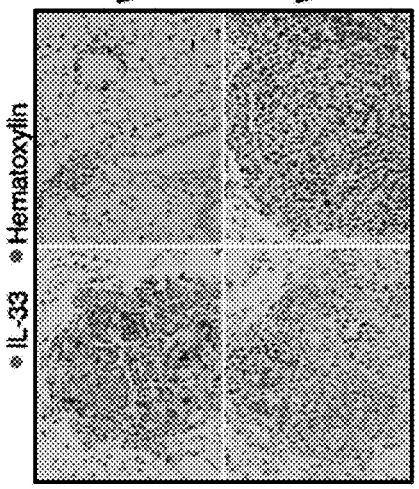
FIG. 17D
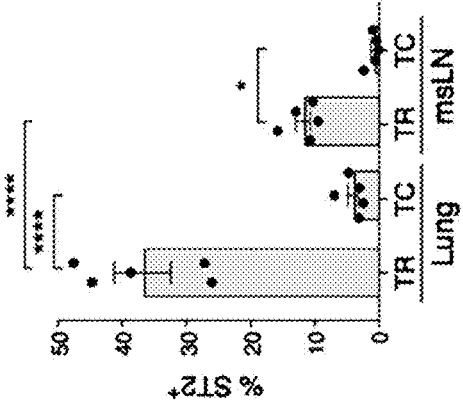
FIG. 17E

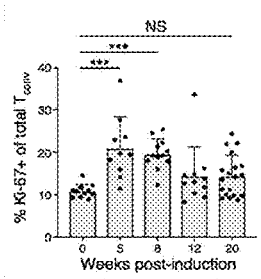
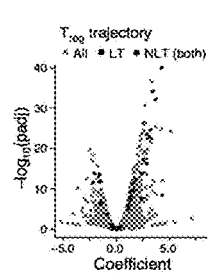
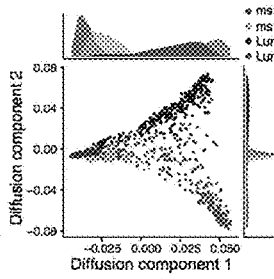
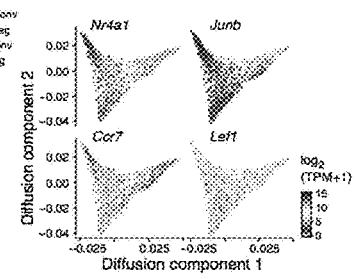
FIG. 19A  FIG. 19B  FIG. 19C  FIG. 19D
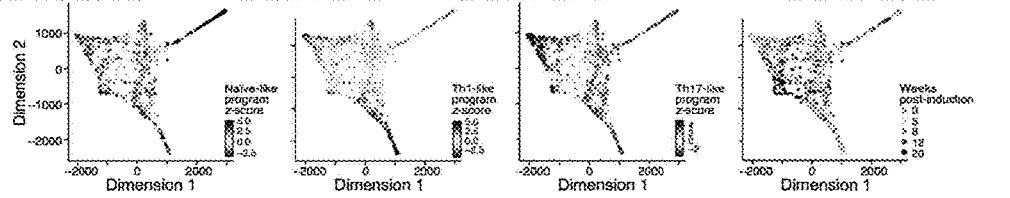
FIG. 19E
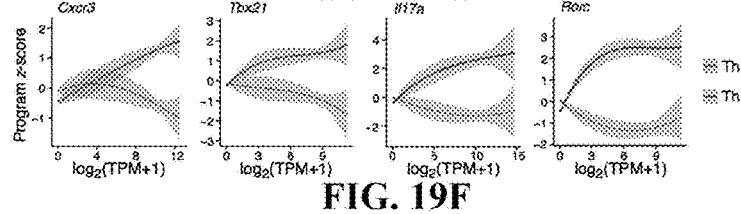
FIG. 19F
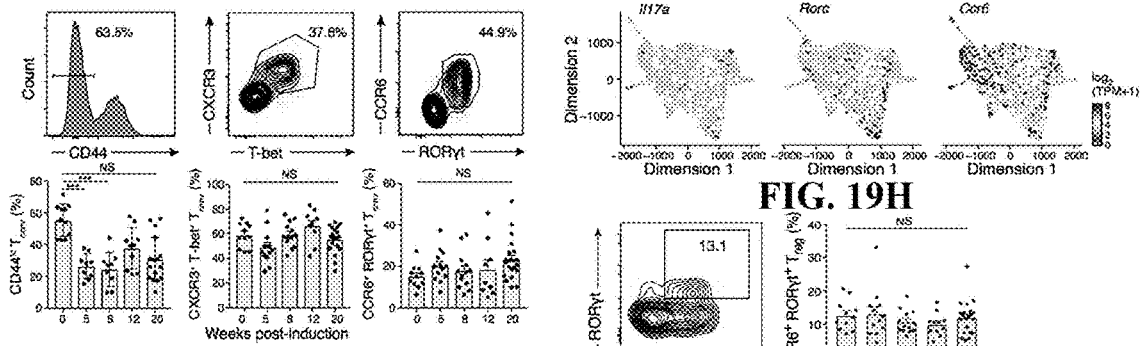
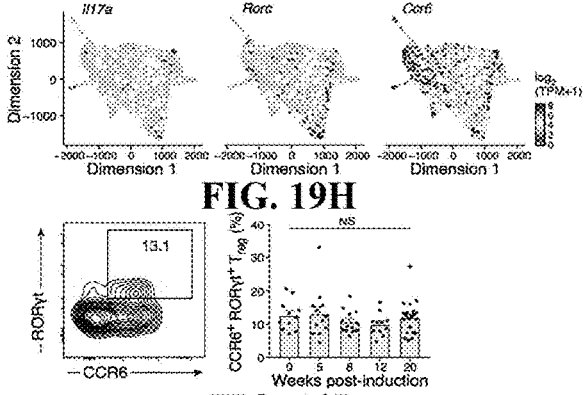
FIG. 19G
FIG. 19H
FIG. 19I
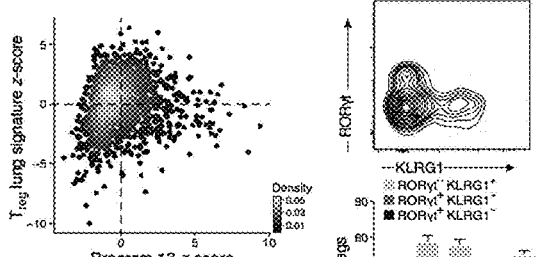
FIG. 19J
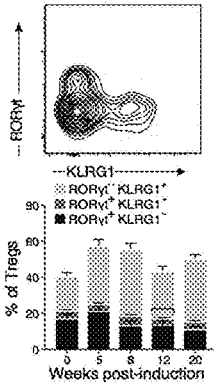
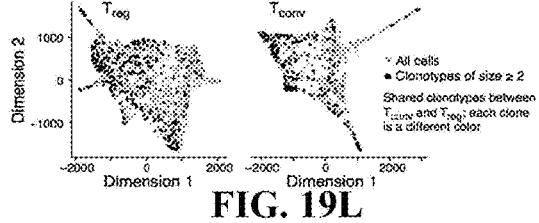
FIG. 19K
FIG. 19L
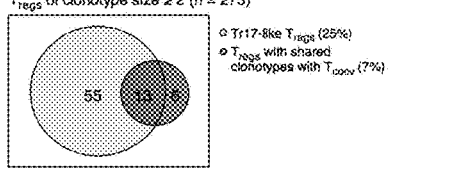
FIG. 19M

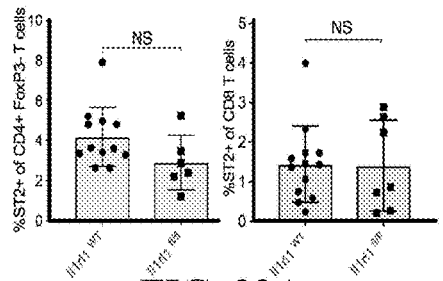
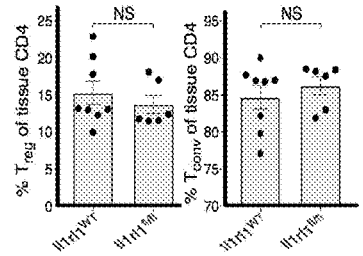
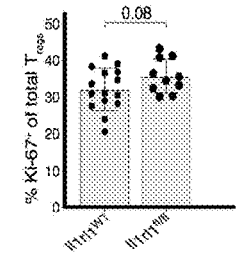
FIG. 22A  FIG. 22B  FIG. 22C
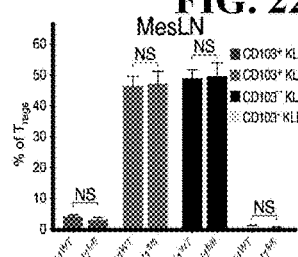
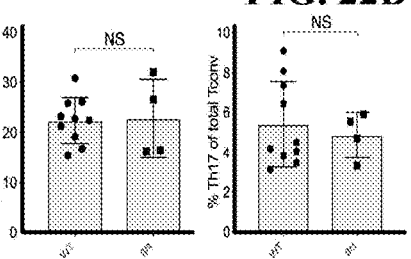
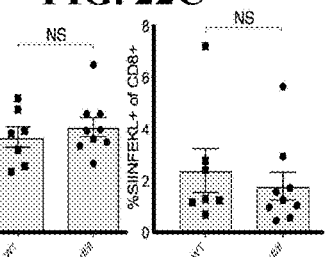
FIG. 22D  FIG. 22E  FIG. 22F  FIG. 22G
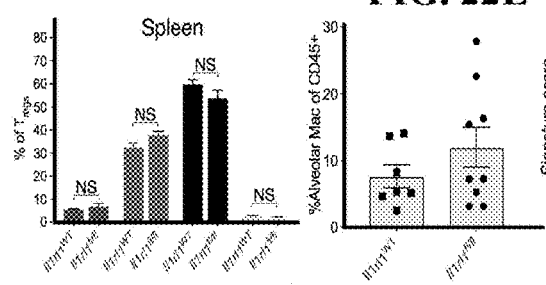
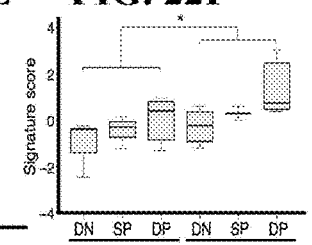
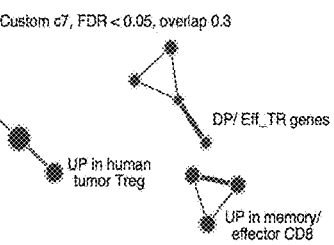
FIG. 22H  FIG. 22I  FIG. 22J
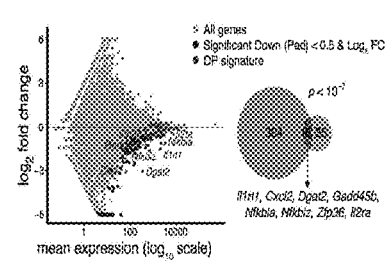
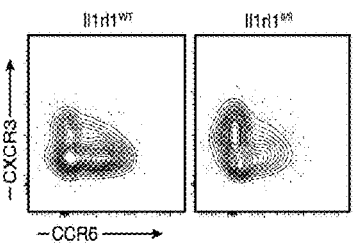
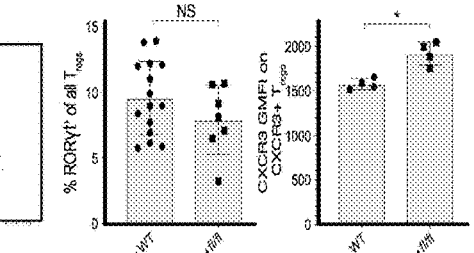
FIG. 22K  FIG. 22L  FIG. 22M  FIG. 22N
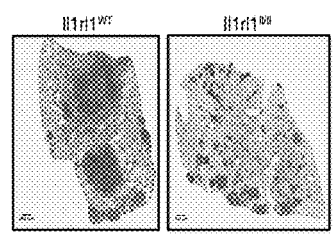
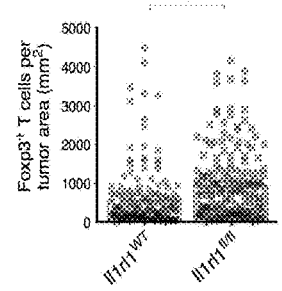
FIG. 22O  FIG. 22P

SEQUENCE LISTING

<160> NUMBER OF SEQ ID NOS: 4

<210> SEQ ID NO 1
<211> LENGTH: 288
<212> TYPE: PRT
<213> ORGANISM: Artificial Sequence
<220> FEATURE:
<223> OTHER INFORMATION: Synthetic

<400> SEQUENCE: 1

```
Met Asp Pro Ile Arg Ser Arg Thr Pro Ser Pro Ala Arg Glu Leu Leu
1               5                   10                  15

Ser Gly Pro Gln Pro Asp Gly Val Gln Pro Thr Ala Asp Arg Gly Val
            20                  25                  30

Ser Pro Pro Ala Gly Gly Pro Leu Asp Gly Leu Pro Ala Arg Arg Thr
        35                  40                  45

Met Ser Arg Thr Arg Leu Pro Ser Pro Ala Pro Ser Pro Ala Phe
    50                  55                  60

Ser Ala Asp Ser Phe Ser Asp Leu Leu Arg Gln Phe Asp Pro Ser Leu
65                  70                  75                  80

Phe Asn Thr Ser Leu Phe Asp Ser Leu Pro Pro Phe Gly Ala His His
                85                  90                  95

Thr Glu Ala Ala Thr Gly Glu Trp Asp Glu Val Gln Ser Gly Leu Arg
            100                 105                 110

Ala Ala Asp Ala Pro Pro Pro Thr Met Arg Val Ala Val Thr Ala Ala
        115                 120                 125

Arg Pro Pro Arg Ala Lys Pro Ala Pro Arg Arg Arg Ala Ala Gln Pro
    130                 135                 140

Ser Asp Ala Ser Pro Ala Ala Gln Val Asp Leu Arg Thr Leu Gly Tyr
145                 150                 155                 160

Ser Gln Gln Gln Gln Glu Lys Ile Lys Pro Lys Val Arg Ser Thr Val
                165                 170                 175

Ala Gln His His Glu Ala Leu Val Gly His Gly Phe Thr His Ala His
            180                 185                 190

Ile Val Ala Leu Ser Gln His Pro Ala Ala Leu Gly Thr Val Ala Val
        195                 200                 205

Lys Tyr Gln Asp Met Ile Ala Ala Leu Pro Glu Ala Thr His Glu Ala
    210                 215                 220

Ile Val Gly Val Gly Lys Gln Trp Ser Gly Ala Arg Ala Leu Glu Ala
225                 230                 235                 240

Leu Leu Thr Val Ala Gly Glu Leu Arg Gly Pro Pro Leu Gln Leu Asp
                245                 250                 255

Thr Gly Gln Leu Leu Lys Ile Ala Lys Arg Gly Gly Val Thr Ala Val
            260                 265                 270

Glu Ala Val His Ala Trp Arg Asn Ala Leu Thr Gly Ala Pro Leu Asn
        275                 280                 285
```

<210> SEQ ID NO 2
<211> LENGTH: 183
<212> TYPE: PRT
<213> ORGANISM: Artificial Sequence
<220> FEATURE:
<223> OTHER INFORMATION: Synthetic

<400> SEQUENCE: 2

```
Arg Pro Ala Leu Glu Ser Ile Val Ala Gln Leu Ser Arg Pro Asp Pro
1               5                   10                  15

Ala Leu Ala Ala Leu Thr Asn Asp His Leu Val Ala Leu Ala Cys Leu
            20                  25                  30

Gly Gly Arg Pro Ala Leu Asp Ala Val Lys Lys Gly Leu Pro His Ala
        35                  40                  45

Pro Ala Leu Ile Lys Arg Thr Asn Arg Arg Ile Pro Glu Arg Thr Ser
    50                  55                  60

His Arg Val Ala Asp His Ala Gln Val Val Arg Val Leu Gly Phe Phe
65                  70                  75                  80

Gln Cys His Ser His Pro Ala Gln Ala Phe Asp Asp Ala Met Thr Gln
                85                  90                  95

Phe Gly Met Ser Arg His Gly Leu Leu Gln Leu Phe Arg Arg Val Gly
            100                 105                 110

Val Thr Glu Leu Glu Ala Arg Ser Gly Thr Leu Pro Pro Ala Ser Gln
        115                 120                 125

Arg Trp Asp Arg Ile Leu Gln Ala Ser Gly Met Lys Arg Ala Lys Pro
    130                 135                 140

Ser Pro Thr Ser Thr Gln Thr Pro Asp Gln Ala Ser Leu His Ala Phe
145                 150                 155                 160

Ala Asp Ser Leu Glu Arg Asp Leu Asp Ala Pro Ser Pro Met His Glu
                165                 170                 175

Gly Asp Gln Thr Arg Ala Ser
            180

<210> SEQ ID NO 3
<211> LENGTH: 9
<212> TYPE: PRT
<213> ORGANISM: Hommo sapiens

<400> SEQUENCE: 3

Ile Glu Val Met Tyr Pro Pro Pro Tyr
1               5

<210> SEQ ID NO 4
<211> LENGTH: 107
<212> TYPE: PRT
<213> ORGANISM: Homo sapiens

<400> SEQUENCE: 4

Ile Glu Val Met Tyr Pro Pro Pro Tyr Leu Asp Asn Glu Lys Ser Asn
1               5                   10                  15

Gly Thr Ile Ile His Val Lys Gly Lys His Leu Cys Pro Ser Pro Leu
            20                  25                  30

Phe Pro Gly Pro Ser Lys Pro Phe Trp Val Leu Val Val Val Gly Gly
        35                  40                  45

Val Leu Ala Cys Tyr Ser Leu Leu Val Thr Val Ala Phe Ile Ile Phe
    50                  55                  60

Trp Val Arg Ser Lys Arg Ser Arg Leu Leu His Ser Asp Tyr Met Asn
65                  70                  75                  80

Met Thr Pro Arg Arg Pro Gly Pro Thr Arg Lys His Tyr Gln Pro Tyr
                85                  90                  95

Ala Pro Pro Arg Asp Phe Ala Ala Tyr Arg Ser
            100                 105
```

METHODS AND COMPOSITIONS FOR OVERCOMING IMMUNOSUPPRESSION

CROSS-REFERENCE TO RELATED APPLICATIONS

This application claims the benefit of U.S. Provisional Application No. 62/788,952, filed Jan. 6, 2019. The entire contents of the above-identified application are hereby fully incorporated herein by reference.

STATEMENT REGARDING FEDERALLY SPONSORED RESEARCH

This invention was made with government support under Grant Nos. GM007753 and CA014051 awarded by the National Institutes of Health. The government has certain rights in the invention.

REFERENCE TO AN ELECTRONIC SEQUENCE LISTING

The contents of the electronic sequence listing (BROD_4000US_ST25.txt"; Size is 6,000 bytes and it was created on Dec. 30, 2019) is herein incorporated by reference in its entirety.

TECHNICAL FIELD

The present invention is generally directed to methods and compositions for inhibiting effector $T_{reg}$ cells and overcoming immunosuppression.

BACKGROUND

The recent clinical success of immune checkpoint inhibitors in the treatment of non-small cell lung cancer (NSCLC) highlights how targeting mechanisms of immunosuppression in the tumor microenvironment may be an effective therapeutic strategy (Makkouk and Weiner, 2015; Soria et al., 2015). However, only a subset of patients respond to immune therapies, suggesting that an improved understanding of other immunosuppressive mechanisms is needed for effective treatment.

One major mechanism of immunosuppression is posed by CD4$^+$ regulatory T cells ($T_{reg}$), which are thought to play a dominant role in impairing anti-tumor immune responses (Tanaka and Sakaguchi, 2017). $T_{reg}$ cells are critical for maintaining peripheral immune tolerance and preventing autoimmunity (Josefowicz et al., 2012). $T_{reg}$ cells can inhibit adaptive immune responses through production of inhibitory cytokines, direct killing of cells, reduction in antigen presentation, and competition with other T cells for antigen or other factors (Caridade et al., 2013; Savage et al., 2013). $T_{reg}$ cells are associated with poor prognosis in several cancers, including lung adenocarcinoma (Shang et al., 2015; Suzuki et al., 2013). In mouse models, $T_{reg}$ depletion can enhance anti-tumor immunity (Bos et al., 2013; Joshi et al., 2015; Marabelle et al., 2013), and antibodies directed against CTLA-4 act in part by depleting $T_{regs}$ in the tumor microenvironment (Simpson et al., 2013).

One of the most challenges in cancer immunotherapy is that the number and activity of anti-tumor cytotoxic CD8$^+$ T cells (CTLs) decline over time. The development of immune tolerance towards the tumor is partially due to the expansion of tumor-infiltrating $T_{regs}$, because $T_{regs}$ actively suppress anti-tumor immune responses. Since $T_{reg}$-depleted animals succumb to systemic autoimmunity, a strategy targeting features of tumor-specific $T_{regs}$ is required to minimize self-directed cytotoxicity.

Citation or identification of any document in this application is not an admission that such a document is available as prior art to the present invention.

SUMMARY

In certain embodiments, methods and compositions are provided for removing or overcoming immunosuppression. In some embodiments, methods are disclosed for shifting T cell balance in a population of cells comprising $T_{reg}$ cells, so the levels and/or activities of $T_{reg}$ cells are decreased or diminished. The methods comprise contacting the population of cells with one or more agents that are capable of reducing, inhibiting, or ablating ST2 and/or IL-33 signaling. In some preferred embodiments, the agents can reduce, inhibit, or ablate ST2 and/or IL-33 signaling in $T_{reg}$ cells. These agents can be pharmacological inhibitors of ST2 and/or IL-33 signaling pathway, or genetic ablation of ST2. For pharmacological inhibitors, the agents can be small molecules, antibodies, antibody fragments, proteins, polypeptides, aptamers, nucleic acids, biologics, or any combination thereof. In certain embodiments, the agents can be antibodies or antibody fragments thereof that specifically bind to ST2 and/or IL-33 proteins. The binding of antibody to ST2 and/or IL-33 can lead to blocking of ST2/IL-33 signaling pathway. In some embodiments, the binding of antibody to ST2 can result in an antibody-dependent cell-mediated cytotoxicity (ADCC) that will destroy the $T_{reg}$ cells bound by the anti-ST2 antibody or antibody fragments thereof.

In some embodiments, the methods disclosed herein use genetic ablation to reduce or remove the expression of ST2 in $T_{reg}$ cells. For genetic ablation, it can be performed using CRISPR-Cas system, RNAi system, zinc finger nucleases, TALEN system, meganucleases, or any combination thereof. For CRISPR-Cas system, it can use Cas9, Cas12, Cas13, or any other Cas enzymes. The CRISPR-Cas system can also comprise a Cas nickase (nCas) fused or linked to a nucleotide deaminase, or a catalytically inactive Cas (dCas) fused or linked to a nucleotide deaminase. The nucleotide deaminase can be cytidine deaminase or adenosine deaminase.

In certain embodiments, methods are provided to treat a disease or a condition such as a tumor or a cancer. The methods disclosed herein including administering the agents disclosed above to reduce or remove ST2 and/or IL-33 signaling. The agents can also include soluble ST2 molecules that bind to extracellular IL-33 so that to block IL-33 binding to $T_{reg}$ cells. In some embodiments, the agents include antibodies or antibody fragments thereof that bind specifically to IL-33, so to block IL-33 binding to $T_{reg}$ cells.

In certain embodiments, additional therapeutic agents or immunotherapies can be used in combination with the methods disclosed herein for treating tumor or cancer or other diseases. For example, the methods include the use of anti-PD1, anti-PD-L1, anti-CTLA4, anti-TIM3, anti-TIGIT, and/or anti-LAG3 antibodies or antibody fragments thereof or any molecules that can bind to PD1, PD-L1, CTLA4, TIM3, TIGIT, and/or LAG3.

In certain embodiments, methods and compositions are provided for treating tumor or cancer in a subject in need thereof. The methods disclosed herein comprise administering to the subject one or more agents that can reduce or removing ST2 and IL-33 signaling and reducing or removing tumor-infiltrating effector $T_{reg}$ cells. As a result, the tumor infiltration of cytotoxic CD8⁺ T effector cells will increase in the tumor or cancer, and tumor volume and/or tumor growth will be inhibited. In some embodiments, the tumor or cancer that can be treated using the methods disclosed herein include tumors or cancers of the colon, rectum, lung, breast, brain, liver, spleen, pancreas, kidney, skin, ovary, uterus, prostate, testis, stomach, hematopoietic system, blood, lymph tissue, bone, bone marrow, cartilage, smooth muscle, skeletal muscle, adipose, or any combination thereof.

In certain embodiments, the methods disclosed herein include using antibodies or antibodies fragments thereof to block ST2 and/or IL-33 signaling, as well as to induce ADCC against Treg cells in the tumor or cancer.

In certain embodiments, methods disclosed herein target $T_{reg}$ cells that are CD103⁺ and KLRG1⁺. In certain embodiments, a signature for the $T_{reg}$ cells includes the expression of Ppargl, Nr4a1, Areg, and Gata1 genes.

In certain embodiments, methods disclosed herein for reducing or diminishing the levels of effector $T_{reg}$ cells can decrease the levels of CD85K, CD69, CXCR6, and/or PD-1 proteins in $T_{reg}$ cells. Further, the methods disclosed herein include using therapeutic agents targeting CD85K, CD69, CXCR6, and/or PD-1 so as to inhibit or reduce the activities or levels of effector Treg cells.

In certain embodiments, a method is disclosed to specifically ablate the expression of ST2 in Treg cells by genetic ablation of IL1RL1 gene, whereby the levels of CD8⁺ effector T cells in tumor are increased.

In certain embodiments, methods and compositions are provided herein for preventing the generation and accumulation of effector $T_{reg}$ cells. The methods include using agents to inhibit the expression of one or more genes or gene products comprising B2M, SRGN, PDIA3, CD69, IL2RG, JUNB, PDCD1, GATA3, COTL1, ZFP36L1, ZFP36, BCL2A1D, SH2D2A, ID2, BCL2A1B, NFKBIA, SLC25A3, KLRG1, CTA2A, H2AFZ, DGAT2, SAMSN, NFKBID, NR4A1, GADD45B, VIM, CXCR6, PTON22, CALCA, IL2RA, NEB, ARL5A, IL10RA, IL1RL1, AREG, NFKBIA, FURIN, HCLS1, DGAT1, CXCL2, SERINC3, FGL2, and TNFRSF1B in $T_{reg}$ cells. In certain embodiments, methods and compositions are provided herein for preventing the generation and accumulation of effector $T_{reg}$ cells by using agent to increase or enhance the expression of one or more genes or gene products in the interferon-responsive effector-like Treg program (IFNstim_TR) comprising ITPR2, IRGM1, NLRC5, GVIN1, GM4070, IRF9, GBP7, XAF1, CD274, TAPBP, ISG20, TAP1, OGFR, IRGM2, PLA2G16, IFI27L2A, GM12250, IIGP1, STAT1, IGTP, TGTP1, ITF1, PSMB9, TGTP2, GBP5, SERPINA3G, and ZBP1. In certain embodiments, the agents disclosed herein include small molecules, proteins, antibodies, antibody fragments, aptamers, biologics, genetic modifying agents, and any combination thereof.

In certain embodiments, methods and compositions are provided herein for treating a disease or a condition such a tumor or a cancer. The methods include using agents to inhibiting or reducing the expression and/or function and/or activity of genes or gene products comprising CD83, NFKBIA, NFKBIZ, REL, NR4A1, CCR8, GATA3, TNFRSF18, TNFRSF4, TNFRSF9, and IL1RL1 in $T_{reg}$ cells. In some embodiments, the tumor or cancer that can be treated using the methods disclosed herein include tumors or cancers in the colon, rectum, lung, breast, brain, liver, spleen, pancreas, kidney, skin, ovary, uterus, prostate, testis, stomach, hematopoietic system, blood, lymph tissue, bone, bone marrow, cartilage, smooth muscle, skeletal muscle, adipose, or any combination thereof.

In certain embodiments, a method is provided for identifying and isolating effector $T_{reg}$ cells in a population of cells. The population of cells can be in vivo, ex vivo, or in vitro, and can be in healthy tissues or diseased tissues including in tumors or cancers. The method includes labeling cells with molecules capable of binding to genes or gene products comprising B2M, SRGN, PDIA3, CD69, IL2RG, JUNB, PDCD1, GATA3, COTL1, ZFP36L1, ZFP36, BCL2A1D, SH2D2A, ID2, BCL2A1B, NFKBIA, SLC25A3, KLRG1, CTA2A, H2AFZ, DGAT2, SAMSN1, NFKBID, NR4A1, GADD45B, VIM, CXCR6, PTON22, CALCA, IL2RA, NEB, ARL5A, IL10RA, IL1RL1, AREG, NFKBIA, FURIN, HCLS1, DGAT1, CXCL2, SERINC3, FGL2, and TNFRSF1B. The biding molecules can be labeled with one or more dyes, for example a fluorescent dye or a chemiluminescent dye. For example, the binding molecule can be an antibody or antibody fragment that binds to proteins encoded by these genes, and the antibody or antibody fragment can be labeled with fluorescent dye, so that effector $T_{reg}$ cell can be identified and isolated. The labeled cells can be identified and/or isolated using FACS, MACS, or other techniques.

BRIEF DESCRIPTION OF THE DRAWINGS

An understanding of the features and advantages of the present invention will be obtained by reference to the following detailed description that sets forth illustrative embodiments, in which the principles of the invention may be utilized, and the accompanying drawings of which:

FIG. 1A-1D—Effector lung $T_{reg}$ cells from tumor-bearing KP mice bear similarities to activated tissue Tregs while demonstrating considerable heterogeneity. 1A. Experiment overview. Top: KP, Foxp3 RFP mice were sacrificed at 20 weeks p.i. Bottom: RNAseq was performed on CD103– KLRG1– (DN, black), CD103+ KLRG1– (SP, blue), and CD103+KLRG1+ (DP, red) Treg cells isolated from tumor-bearing lungs, SP and DN Treg cells from the draining mediastinal lymph node (msLN), and DN Treg from one spleen as control. 1B. Gene expression differences (KPLungTR signature genes, |z-score|>3, |fold change|>2) between lung (left, gray) vs. msLN/spleen (right, black) Tregs (columns). 1C. 45 gene signature (43 up-regulated, 2 down-regulated) distinguishing DP lung Tregs (red) from other populations (black and blue). 1D. Heterogeneity of CD69 and PD-1 expression among Treg subsets. Representative flow cytometry plots (left) and average cell proportions (right, 3 experiments, each with n=5-6 mice) of CD69 and PD-1 expression among DN, SP, and DP $T_{reg}$ cells. Populations shown are i.v.$^{neg}$ CD8– CD4⁺ Foxp3⁺. Error bars: SEM.

Figure 2A:
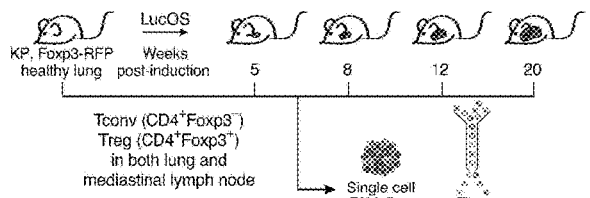
FIG. 2A-2F—Single-cell RNAseq reveals a distinctive lung CD4+ T cell signature and $T_{conv}$ diversity that is stable throughout KP tumor development. 2A. Overview of longitudinal experiment. KP, Foxp3 GFP mice were harvested at the indicated weeks after tumor induction with Lenti-LucOS. 1,254 $T_{conv}$ (i.v.$^{neg}$,Thy1.2+CD4+Foxp3–) and 1,679 $T_{reg}$ cells (i.v.$^{neg}$,Thy1.2+CD4+Foxp3+) cells from lung and msLN were single-cell sorted and profiled by plate-based scRNAseq. 2B. Shared and lung tissue-specific gene expression program includes genes shared by $T_{conv}$ and Tregs, and genes unique to each. Genes (rows, row-normalized) differentially-expressed (Methods) between cells (columns) from lung (purple, teal) vs. msLN (pink, light blue)

for both $T_{reg}$ and $T_{conv}$. Left black bars indicate whether a gene is significantly differentially expressed for Treg and/or $T_{conv}$. Bottom: Each cell's score (y-axis) for its expression of the corresponding lung and LN signatures, which are different for Treg and $T_{conv}$. Color indicates whether a cell was sorted as a Treg or $T_{conv}$, and tissue of origin. 2C. Lung and msLN cells span a phenotypic continuum, with lung cells showing particular diversity. Diffusion component embedding of all cells (dots), colored by sorted identity and tissue of origin (top left), or by z-score of the lung (bottom left) or msLN (bottom right) signatures as in B. Top right: distribution of diffusion component (DC) scores for cells from each of the four sorted populations, showing greater range of scores for lung cells. 2D-2F. Lung $T_{conv}$ subsets expressed programs associated with naive/central memory T, Th17, Th1, Th9, and NKT17 cells. D. Two-dimensional force-directed layout embedding of the first four diffusion components of all lung resident $T_{conv}$ cells (Methods), with cells colored by expression z-score for the indicated gene module, or by timepoint after tumor induction (bottom right). 2E-2F. Left: Representative flow cytometry plots demonstrating naive/central memory (E, top), Th1 (E, middle), Th17 (E, bottom), and Th1/Th17 (F, T-bet+RORγt+) CD4+ T cell populations. Right: Corresponding barplots showing the percentage (y-axis) of the indicated $T_{conv}$ (i.v.$^{neg}$ CD8$^-$ CD4$^+$ Foxp3$^-$) subset throughout tumor development (x-axis) across 2-3 experiments (dot: one mouse). Error bars: SEM. ***p<0.001, Tukey's multiple comparisons test. NS: non-significant.

FIG. 3A-3E—A Th17-like $T_{reg}$ population is present throughout tumor development and may have shared clonal origin with $T_{conv}$ cells. 3A-3B. Cells expressing a Tr17-like program are present throughout tumor development. 3A. Two-dimensional force-directed layout embedding of the first six diffusion components of all lung-derived Tregs where each cell (dot) is colored by the normalized average gene expression (z-score) of the genes in module 13, which represents Rorc$^+$ $T_{reg}$ cells (left) or by timepoint after induction (right). 3B. Left: Representative flow cytometry plot demonstrating RORγt$^+$ CCR6$^+$ $T_{reg}$ cells (i.v.$^{neg}$ CD8$^-$ CD4$^+$Foxp3$^+$). Right: Percentage of $T_{reg}$ cells that are RORγt$^+$ CCR6$^+$ (y-axis) across tumor development (x-axis) across 2-3 experiments. Error bars: SEM. NS: non-significant, Tukey's multiple comparisons test. 3C-3D. Tr17-like and Treg programs are inversely correlated. 3C. Two-dimensional force-directed layout embedding of all lung-derived Tregs as in A, with each cell (dot) colored by normalized average gene expression (z-score) of the genes upregulated in lung vs. msLN T regs (as in FIG. 2B). 3D. Left: Representative flow cytometry plot of Treg (i.v.$^{neg}$ CD8$^-$ CD4$^+$ Foxp3$^+$) expression of RORγt and KLRG1 (left). Right: Percentage of Tregs that are RORγt+KLRG1+, RORγt+KLRG1-, and RORγt-KLRG1+ across tumor development (x-axis) across 2-3 experiments (dot=one mouse). Error bars: SEM. 3E. Shared clonotypes between Treg and $T_{conv}$ are predominantly in Tr-17 like and Th17-like cells. Two-dimensional force-directed layout embedding of lung-resident $T_{reg}$ cells (left, as in A) and $T_{conv}$ (right, as in FIG. 2D) with each cell colored by clonal analysis. Grey: not clonal at our resolution or no TCR was reconstructed. Black: cells that share a TCR with at least one other cell. Color: Shared clones between $T_{reg}$ and $T_{conv}$, with numeric identifiers.

FIG. 4A-4E—An effector Treg phenotype becomes dominant during tumor development. 4A. Changes in prominence of cycling, interferon-stimulated, and $T_{reg}$ effector programs with tumor development. Linear regression analysis of module expression z-scores as a function of time since tumor initiation, where non-tumor bearing lung is the reference for the timepoint covariate. Dot plot shows for each module (row) and timepoint (column) the coefficients of the timepoint covariate of the regression (color), and the percentage of cells with a z-score >1.5 (dot size). Brown/blue: increased/decreased expression over time compared to non-tumor bearing lung. 4B. $T_{reg}$ proliferation peaks early in tumor development. The percentage of Ki-67+Tregs (y-axis) throughout KP tumor development (x-axis) from 2-3 experiments (dot=one mouse). Error bars: SEM. *p<0.001, Tukey's multiple comparisons test. NS: non-significant. 4C-4E. An interferon and an effector program peak early and late in tumor development, respectively. 4C-4D. Two-dimensional force-directed layout embedding of all lung-infiltrating Tregs (as in FIG. 3A) colored by normalized signature z-score for the IFNstim_TR modules (C, Modules 6 and 23) and the Eff_TR modules (C, Modules 12 and 21), or timepoint after tumor induction (D). 4E. Percentage of $T_{reg}$ cells expressing the indicated protein (y-axis) throughout KP tumor development (x-axis) from 2-3 experiments (dot: one mouse). Error bars: SEM. p<0.01, *p<0.001, **p<0.0001, Tukey's multiple comparisons test.

FIG. 5A-5D—ST2 is upregulated in terminally-differentiated $T_{reg}$ cells in lung tumor-bearing mice. 5A. ST2 is most highly expressed in DP lung Tregs. Representative distributions of ST2 expression on CD103−KLRG1− (DN, grey), CD103+KLRG1− (SP, blue), and CD103+KLRG1+ (DP, red) Tregs isolated from tumor-bearing lungs. 5B. New MS FIG. 3E Lung Tregs are enriched for ST2+ cells in late-stage tumors. Percent ST2+ (y-axis) among lung and msLN Tregs (i.v.$^{neg}$ CD4+Foxp3+) and $T_{conv}$ cells (i.v.$^{neg}$ CD4+Foxp3−) (x-axis) from tumor-bearing LucOS mice at week 20 p.i. as measured by flow cytometry. ****p<0.0001, *p<0.05, Tukey's multiple comparisons test. 5C. $T_{reg}$ cells from tumor-bearing mice express both the membrane-bound and soluble isoforms of ST2. Relative expression (y-axis, 2-ΔΔCt, qRT-PCR, with splenic Treg expression as control) of NM_001025602.3 (left, Il1rl1 transcript variant 1 encoding membrane-bound ST2) and NM_010743.3 (right, Il1rl1 transcript variant 2 encoding soluble ST2) in DP, SP, and DN lung Tregs and SP and DN msLN Tregs (x-axis) (dot: one mouse). Error bars: SEM. ***p<0.001, *p<0.05, Tukey's multiple comparisons test. 5D. New MS FIG. 3D IL-33 is highly expressed in lung adenocarcinoma. Immunohistochemical staining of tumor-bearing lungs from KP mice at weeks 13 and 22 p.i. with Lenti-LucOS. Two representative images are shown per timepoint.

FIG. 6A-6G—rIL-33 is sufficient to promote an increase in effector $T_{reg}$ cells in tumor-bearing lungs. 6A. Experimental overview. Recombinant IL-33 (rIL-33) or PBS control were administered to late-stage, tumor-bearing KP mice. All rIL-33 experiments are representative of 2-3 separate experiments, each with n=4-5 mice per group. 6B-6D. rIL-33 induced inflammatory infiltration and epithelial thickening. B. Representative hematoxylin and eosin (H&E)-stained histological images of control (left) and rIL-33-treated (right) lungs at 10× magnification. 6C. Proportion of eosinophils (y-axis, i.v.$^{neg}$ CD45.2$^+$ CD11$^{-/low}$, SiglecF$^+$) of i.v.$^{neg}$ CD45+ lung cells from control and rIL-33-treated mice. Data is representative of 2 independent experiments. Error bars: SEM. ****p<0.0001, two-tailed Student's t test. 6D. Proportions (y-axis, left) and absolute numbers (y-axis, right) of lung CD8+ and CD4+ T cells of i.v.$^{neg}$ cells in control and rIL-33-treated mice (x-axis). Error bars: SEM. *p=0.01, two-tailed Student's t test. 6E. No change in proportion of SIINFEKL tetramer-positive CD8+ T cells. Percentage of SIINFEKL/Kb tetramer-positive cells out of lung i.v.$^{neg}$ CD8+ T cells (y-axis) in control and rIL-33-treated mice (x-axis). Error bars: SEM. NS: non-significant, Tukey's multiple comparisons test. 6F. Increase in Treg proportions in rTL-33-treated mice. Proportion (y-axis, left) and absolute number (y-axis, right) of $T_{reg}$ cells out of i.v.$^{neg}$ CD4+ lung T cells in control and rIL-33-treated mice (x-axis). Error bars: SEM. *p=0.02, two-tailed Student's t test. 6G. Reduced changes in Treg proportions in rIL-33-treated, ST2-deficient mice. Percent of cells (y-axis) that are CD103−KLRG1− (DN, black), CD103+KLRG1− (SP, blue), or CD103+KLRG1+ (DP, red) out of Treg cells from tumor-bearing lungs of control and rTL-33-treated mice. Error bars: SEM. ****p<0.0001, Sidak's multiple comparisons test. NS: non-significant.

FIG. 7A-7G—$T_{reg}$-specific ST2 ablation impairs expansion of effector $T_{reg}$ cells and enhances CD8+ T cell infiltration of tumors. 7A. Experiment overview. KPfrt, Foxp3 YFP-Cre ("Il1rl1 WT") and KPfrt, Foxp3 YFP-Cre, Il1rl1 fl/fl ("Il1rl1 fl/fl") mice were infected with Lenti-FlpO-GFP-OS. B-C. Changes in $T_{reg}$ cells and their subsets in Il1rl1 fl/fl mice with advanced lung tumors. 7B. Percent of Foxp3+(y-axis, left) and of Foxp3− (y-axis, right) of i.v.$^{neg}$ CD4+ lung cells in KPfrt, Foxp3 YFP-Cre vs. KPfrt, Foxp3 YFP-Cre, Il1rl1 fl/fl mice at 24-25 weeks p.i across 3 experiments, each with n=3-5 mice per group. Error bars: SEM. *p<0.05, two-tailed Student's t test. NS: non-significant. 7C. Percent of CD103−KLRG1− (DN, black), CD103+KLRG1− (SP, blue), and CD103+KLRG1+ (DP, red) out of Tregs isolated from the tumor-bearing lungs of KPfrt, Foxp3 YFP-Cre vs. KPfrt, Foxp3 YFP-Cre, Il1rl1 fl/fl mice across 3 experiments, each with n=3-5 mice per group. Error bars: SEM. ****p<0.0001, *p<0.05, Sidak's multiple comparisons test. NS: non-significant. 7D. Expression signature distinguishing Il1rl1 WT from ST2-deficient Tregs from tumor-bearing mice. Row-normalized expression (z-score) of select signature genes (rows, Methods) across CD103−KLRG1− (DN, black), CD103+KLRG1− (SP, blue), and CD103+KLRG1+ (DP, red) $T_{reg}$ cells (columns, lower color bar) from KPfrt, Foxp3 YFP-Cre (gray) vs. KPfrt, Foxp3 YFP-Cre, Il1rl1 fl/fl (purple) mice. 7E. Increased CD8+ T cell infiltration in mice with Treg-specific ST2 deficiency. Number of CD8+ cells per tumor area (y-axis) in pooled tumors from KPfrt, Foxp3 YFP-Cre and KPfrt, Foxp3 YFP-Cre, Il1rl1 fl/fl mice across two experiments, with n=4-5 mice per group. CD8 was measured by immunohistochemical (IHC) staining of histological cross-sections of tumor-bearing lungs. Error bars: SEM. ****p<0.0001, Mann-Whitney test. 7F-7G. Reduced tumor burden in mice with Treg-specific ST2 deficiency. Percent of total lung occupied by tumor (F, y-axis) and average tumor size (G, y-axis, μm 2) in KPfrt, Foxp3 YFP-Cre vs. KPfrt, Foxp3 YFP-Cre, Il1rl1 fl/fl mice in histological cross-sections of tumor-bearing lungs across two experiments, with n=4-5 mice per group. Error bars: SEM. *p=0.0315 (F), 0.0106 (G), Mann-Whitney test.

FIG. 8A-8F—Characteristics of effector lung Tregs from tumor-bearing KP mice. 8A. Significant expression signatures identified by ICA. Mixing weight z-scores (color bar) per sample (row) for two gene expression signatures (columns). Signature 1 distinguishes lung populations (DP, DN, SP) from spleen and LN ones. Signature 2 distinguishes CD103+Tregs from CD103− populations. P-values for these distinctions: Kruskal-Wallis test. 8B. Validation of expression differences. qRT-PCR of expression of Pparg, Nr4a1, Gata1, and Areg1 (y-axis, 2 ΔΔCt values, with splenic Treg expression as control) in DP, SP, and DN lung $T_{reg}$ cells and in SP and DN msLN Treg cells. Error bars: SEM. *p<0.05, *p<0.001, **p<0.0001, Tukey's multiple comparisons test. NS: non-significant. 8C-8D. GSEA of enriched functional categories in the KPLungTR signature. 8C. Test details for gene sets induced (top) or repressed (bottom) in the KPLung_TR signature. 8D. Network representation of GSEA gene sets (nodes) from the curated collection (c2) enriched in the KPLung_TR signature (p<0.05, FDR<0.05; in all significant gene sets, the upregulated genes were enriched). Node size: gene set size. Edge thickness: overlap between gene sets (minimum: 50% overlap). Related pathways were manually annotated. 8E. Signature enrichment for orthologs of genes included in human CRC and NSCLC-associated Tregs. Empirical cumulative distribution functions (ECDFs) of Lung vs LN log 2 (fold-change) of expression for genes upregulated in CRC and NSCLC $T_{reg}$ cells (DeSimone_UP, red) (De Simone et al., 2016) and all other expressed genes (gray). p=1.137×10$^{-4}$, two-sided Kolmogorov-Smirnov test. 8F. DP cells have features similar to activated $T_{reg}$ cells. ECDFs of DP vs. DN $T_{reg}$ cells log 2 (fold-change) of expression of genes transiently upregulated (VdWtrans_UP, red), downregulated (VdWtrans_DN, blue) in activated $T_{reg}$ cells (van der Veeken et al., 2016), or all other genes (gray). P-values: two-sided Kolmogorov-Smirnov test.

FIG. 9A-9I—scRNAseq reveals lung CD4+ $T_{conv}$ diversity in KP tumors. 9A. Differentially expressed genes between lung and msLN Tregs. Shown for each gene (dot) is its differential expression between lung and msLN Tregs (x-axis) and associated significance on the y-axis, log 10 (p-value) (logistic regression, Methods). Red/blue genes are upregulated/downregulated from the KPLungTR signature (left) or upregulated in both skin and colon compared to lymph node (Miragaia et al., 2017) (right), highlighting overlapping genes. 9B. Lung cells are more variable. Map of the first two diffusion components of $T_{reg}$ and $T_{conv}$ cells from the lung and msLN, where lung samples were downsampled to equal numbers as in msLN. Histograms: distribution of the cell scores in each diffusion component. 9C. Naive and central memory gene expression in CD4+ T cells. Diffusion component embedding for all CD4+ T cells (as in FIG. 2C) colored by log 2(TPM+1) expression (color bar) of Ccr7 and Lef1 (naive and central memory markers), and Junb and Nr4a1 (T cell activation markers). 9D-9E. Cytotoxic, Th1, and NKT17 cell-associated gene expression in $T_{conv}$ lung cells. Two dimensional (2D) force directed layout embedding of $T_{conv}$ lung cells (as in FIG. 2D) colored by log 2(TPM+1) expression (color bar) of Eomes, Gzmk, Cxcr3 or Ccr5 (D, cytotoxic and Th1 cells) or Blk, Gpr114 and Zbtb16 (E, NKT17 cells). 9F. Cd4 is significantly downregulated in NKT17-like cells. Distribution of log 2 (TPM+1) Cd4 gene expression (y-axis) of NKT17 cells and all other $T_{conv}$ of the lung. p<0.001, Kolmogorov-Smirnov test. 9G. Th1, Th17, and Th9 modules. Smoothed loess distribution of log 2 (TPM+1) expression (x-axis) of key genes (label top, color code) for the Th1 (green), Th17 (orange), and Th9 (red) modules in cells and the associated activity z-score (y-axis) of each module in these cells. Bold curve: score for module in which each gene is a member. 9H. Temporal changes. Two-dimensional force-directed layout embedding of $T_{conv}$ lung cells (as in FIG. 2D) colored by timepoint after tumor induction. 9I. $T_{conv}$ subsets remain largely stable over tumor development. Distributions of module activity z-scores (y-axis) for each module (label, top). P-values: Kolmogorov-Smirnov test (vs. non tumor-bearing lung).

FIG. 10A-10E—Th17-like Treg population in tumor development. 10A. $T_{reg}$ modules are associated with previously-described gene expression programs. Spearman correlation coefficient (color bar) between module (columns)

z-scores across cells and z-scores for published signatures (rows) of various $T_{reg}$ states. 10B. Expression of key Th17 cell-associated genes. Two dimensional force directed layout embedding of $T_{reg}$ lung cells (as in FIG. 3C) colored by normalized expression (z-score) of Il17a, Rorc or Ccr6. 10C. T cell clones inferred by TCR reconstruction. Number of $T_{conv}$ (left) and $T_{reg}$ (right) cells (y-axis) in each mouse (x-axis) for which we did not identify a TCR (light gray), identified a TCR but not a shared clone (medium gray), or identified a clone (dark gray). 10D. Validation of shared clonotypes between $T_{reg}$ and $T_{conv}$ cells. Bulk TCR sequencing results of three replicates, showing the number of identified clonotypes in each subset and overall, and the overlap. We estimated that about 5% of Treg clonotypes are shared with $T_{conv}$. 10E. $T_{reg}$ cells that have a shared clonotype with $T_{conv}$ are enriched for Tr17-like cell. Numbers of Tr17-like cells (green), of Tregs with shared clonotype with $T_{conv}$ (purple), and the overlap. p<10-5, hypergeometric test.

FIG. 11A-11G—Effector Treg cells become predominant later in tumor development. 11A. Different modules pick up on similar signals and are correlated in expression across cells. Spearman correlation coefficient (color bar) between module z-scores across cells (rows and columns). Module correlations with themselves (diagonals) of 1 were set to "NA" and are shown in grey. 11B. IFN response genes peak early in tumor development. Effect size of differential expression compared to non tumor-bearing lung (color bar, mixed effect logistic regression analysis, Methods) for genes (rows) from the IFN response modules 6 and 23 at each timepoint (columns). 11C. Association of T-bet with the IFNstim_TR module 23. Shown is the relation (red curve, loess fit) across cells (dots) between the log 2(TPM+1) expression (y-axis) of Tbx21 and the z-score of Module 23 (x-axis) in the cell. 11D. $T_{reg}$ module similarity to previously-described expression programs. Spearman correlation coefficient (color bar) between module (columns) z-scores across cells and z-scores for published signatures (rows, as in FIG. S3A) of $T_{reg}$ cellular states. 11E. Modules 12 and 21 are enriched for genes of the DP UP signature. Number of genes in the union of modules 12 and 21 (blue), the induced genes in the DP signatures (brown), and their overlap. p<10-25, hypergeometric test. 11F. Example genes whose expression varies significantly over tumor development. Distribution of log 2(TPM+1) expression of selected genes across time (x-axis). P-value: Kolmogorov-Smirnov test. 11G. DP cells are associated with higher expression of Eff_TR and lower expression of IFNstim_TR genes. ECDF plots of DP vs DN $T_{reg}$ log 2(fold-change) in gene expression of IFNstim_TR genes (Modules 6 and 23, red, left) or Eff_TR genes (Modules 12 and 21, red, right), and all other genes (gray). P-values: two-sided Kolmogorov-Smirnov tests.

Figure 12:
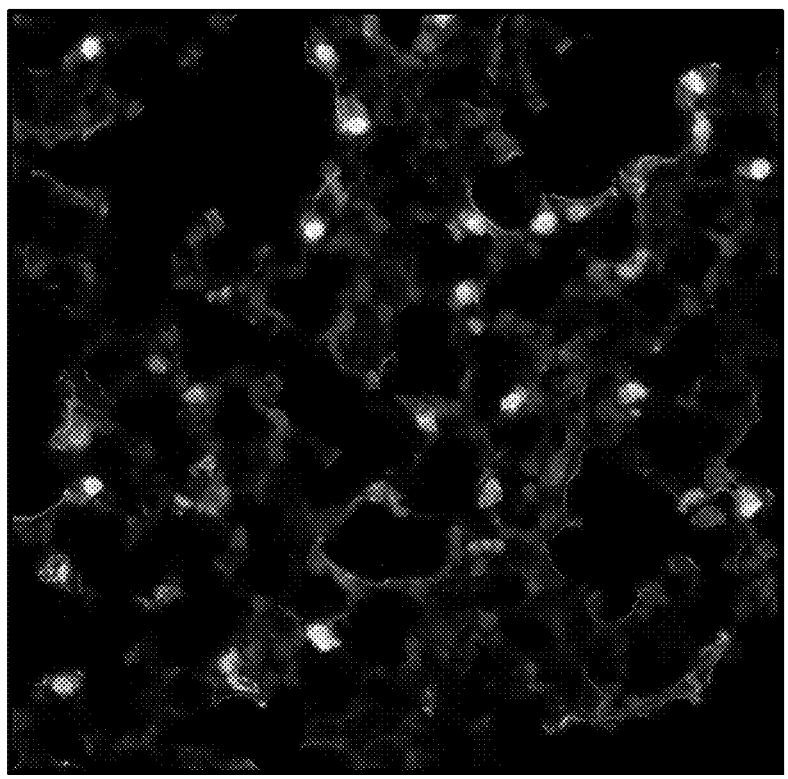

FIG. 12—IL-33 is expressed by type II epithelial cells in normal lung. Representative immunofluorescent staining of healthy, non-tumor bearing lung.

Figure 13:
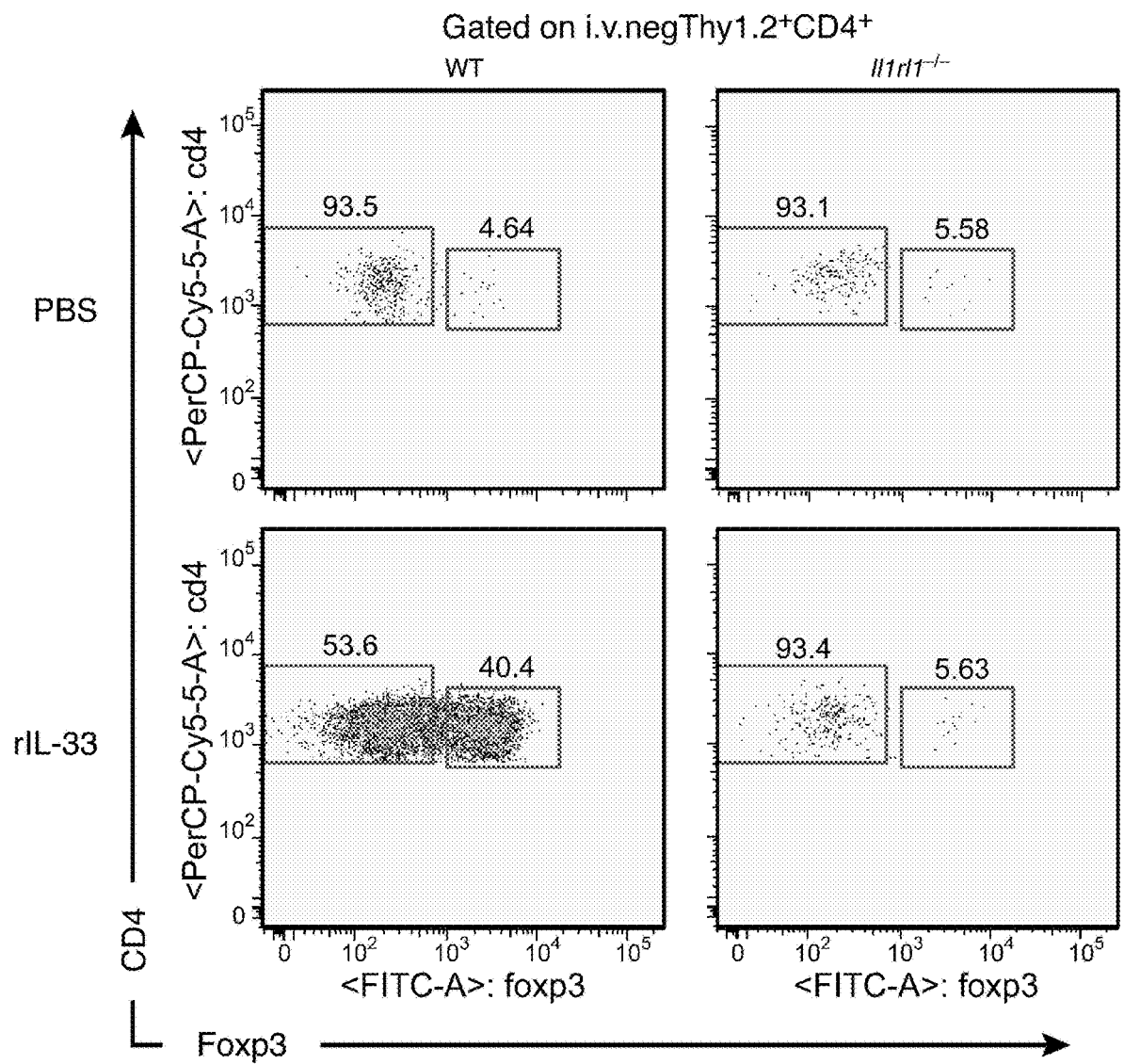

FIG. 13—rIL-33 treatment of ST2-deficient mice failed to elicit a change in the proportion of Tregs. Representative flow cytometry plots of the percentage of $T_{conv}$ (Foxp3-) and $T_{reg}$ (Foxp3+) of i.v.$^{neg}$ Thy1.2+CD4+ cells in wild-type and ST2-deficient non-tumor bearing mice after challenge with rIL-33 or PBS as control. Data are representative of 2-3 mice per group.

FIG. 14A-14D—Impact of Treg-specific ST2 ablation on effector Tregs. 14A. No change in the fraction of $T_{conv}$ or Tregs early in tumor development in mice with Treg-specific ST2 deficiency. Percent Foxp3+ (left) and % Foxp3- (right) of i.v.$^{neg}$ CD4+ lung cells in KPfrt, Foxp3 YFP-Cre ("Il1rl1 WT") vs. KPfrt, Foxp3 YFP-Cre, Il1rl1 fl/fl ("Il1rl1 fl/fl") mice at 10 weeks p.i. 14B-14D. An expression signature lower in ST2-deficient Tregs compared to ST2-wild-type Tregs is highest among wild-type DP Tregs. 14B. Standardized signature score (y-axis) of the expression signature distinguishing Il1rl1 WT and Il1rl1 fl/fl Tregs for each lung Treg subpopulation in tumor-bearing mice (x-axis). Box: 25th to 75th percentiles, whiskers: minimum to maximum. Bar: median. No data point is beyond the limit of lines. *p=0.02, two-sided Mann-Whitney test. 14C. Gene sets enriched in the expression signature distinguishing ST2-deficient Tregs. GSEA gene sets (nodes) from the custom immune signature database (custom c7, Methods) enriched in the signature distinguishing ST2-deficient Tregs (p<0.05, FDR<0.05; in all significant gene sets. Red: enrichment of upregulated genes. Node size: gene set size. Edge thickness: overlap between gene sets (minimum: 30% overlap). Related pathways were manually annotated. 14D. Left: differential, log 2(fold change) expression (y-axis) and mean expression (x-axis) for each gene (dot) in CD103+KLRG1+ (DP) Tregs from KPfrt, Foxp3 YFP-Cre, Il1rl1 fl/fl vs. KPfrt, Foxp3 YFP-Cre mice. Purple: genes in the DP signature. Blue: Top significantly downregulated genes. Right: Venn diagram shows the overlap between the top differentially downregulated genes in Il1rl1 fl/fl vs. Il1rl1 WT $T_{reg}$ cells (blue) and the DP signature (purple). P<10$^{-7}$, hypergeometric test.

FIG. 15A-15E Single-cell RNAseq reveals distinctive lung CD4+ T cell signatures and overlapping $T_{conv}$ and $T_{reg}$ diversity. 15A. $T_{reg}$ proliferation peaks early in tumor development. The percentage of Ki-67+ $T_{regs}$ (y-axis) throughout KP tumor development (x-axis) from 2-3 experiments (dot=one mouse). Error bars: SEM. *p<0.001, Tukey's multiple comparisons test. NS: non-significant. 15B. Overview of experiment. KP, Foxp3$^{GFP}$ mice were harvested at the indicated weeks after tumor induction with Lenti-LucOS. 1,254 $T_{conv}$ (i.v.$^{neg}$,Thy1.2+CD4+Foxp3-) and 1,679 $T_{regs}$ (i.v.$^{neg}$,Thy1.2+CD4+Foxp3+) cells from lung and msLN were single-cell sorted and profiled by plate-based scRNAseq. 15C. Shared and lung tissue-specific gene expression program includes genes shared by $T_{conv}$ and $T_{regs}$, and genes unique to each. Genes (rows, row-normalized) differentially-expressed (STAR Methods) between cells (columns) from lung (purple, teal) vs. msLN (pink, light blue) for both $T_{reg}$ and Tconv. Left black bars indicate whether a gene is significantly differentially expressed for $T_{reg}$ and/or Tconv. Bottom: Each cell's score (y-axis) for its expression of the corresponding lung and LN signatures, which are different for $T_{reg}$ and $T_{conv}$. Color indicates whether a cell was sorted as a $T_{reg}$ or $T_{conv}$, and tissue of origin. 15D. Lung and msLN cells span a phenotypic continuum, with lung cells showing particular diversity. Diffusion component embedding of all cells (dots), colored by sorted identity and tissue of origin (top left), or by z-score of the lung (bottom left) or msLN (bottom right) signatures as in 15B. Top right: distribution of diffusion component (DC) scores for cells from each of the four sorted populations, showing greater range of scores for lung cells. 15E.** Lung $T_{reg}$ and $T_{conv}$ have overlapping, highly-correlated programs. Spearman correlation coefficient (color bar) between $T_{conv}$ program z-scores (columns) and $T_{reg}$ program z-scores across $T_{conv}$ lung cells (rows).

FIG. 16A-16D Klrg1+Areg+ $T_{reg}$ phenotype becomes dominant during tumor development. 16A. Changes in prominence of cycling, interferon-stimulated, and $T_{reg}$ effector-like programs with tumor development. Linear regression analysis of program expression z-scores as a function of time since tumor initiation, where non-tumor bearing lung is the reference for the timepoint covariate. Dot plot shows for each program (row) and timepoint (column) the coefficients of the timepoint covariate of the regression (color), and the percentage of cells with a z-score >1.5 (dot size). Brown/blue: increased/decreased expression over time compared to non-tumor bearing lung. 16B-16C. An interferon and a Klrg1$^+$Areg$^+$ effector-like program peak early and late in tumor development, respectively. Two-dimensional force-directed layout embedding of all lung-infiltrating T$_{regs}$ colored by normalized program z-score for the KA_TR program (B. top, Programs 12 and 21), IFNstim_TR programs (B. bottom, Programs 6 and 23), and the timepoint after tumor induction C. 16D. Percentage of T$_{regs}$ expressing the indicated protein (y-axis) throughout KP tumor development (x-axis) from 2-3 experiments (dot: one mouse). Error bars: SEM. p<0.01, *p<0.001, ****p<0.0001, Tukey's multiple comparisons test.

FIG. 17A-17E. ST2 marks a diverse population of KA/DP T$_{regs}$ in lung tumor-bearing mice. 17A. ST2 is most highly expressed in DP lung T$_{reg}$ s. Representative distributions of ST2 expression on CD103$^-$KLRG1$^-$ (DN, grey), CD103$^+$KLRG1$^-$ (SP, blue), and CD103+KLRG1+(DP, red) T$_{regs}$ isolated from tumor-bearing lungs. 17B. KA_TR genes are upregulated in Il1rl1-positive T$_{regs}$ throughout tumor development. ECDFs of the scores of Program 12 (top) and 21 (bottom) of Il1rl1-positive (blue) vs. Il1rl1-negative T$_{regs}$ (gray) across timepoints after tumor induction. 17C. Il1rl1-positive T$_{regs}$ in human colon cancer have higher expression of KA_TR genes. Overlap of genes upregulated in Il1rl1-positive T$_{regs}$ in human colon cancer (blue) (Zhang et al., 2018) and Program 12 (green, top) and 21 (orange, bottom) genes. P-values: hypergeometric test. 17D. IL-33 is highly expressed in lung adenocarcinoma. Immunohistochemical staining of tumor-bearing lungs from KP mice at weeks 13 and 22 p.i. with Lenti-LucOS. Two representative images are shown per timepoint. 17E. Lung T$_{regs}$ are enriched for ST2$^+$ cells in late-stage tumors. Percent ST2$^+$ (y-axis) among lung and msLN T$_{regs}$ (i.v.$^{neg}$CD4$^+$Foxp3$^+$) and T$_{conv}$ cells (i.v.$^{neg}$CD4$^+$Foxp3$^-$) (x-axis) from tumor-bearing LucOS mice at week 20 p.i. as measured by flow cytometry. ****p<0.0001, *p<0.05, Tukey's multiple comparisons test.

FIG. 18A-18G T$_{reg}$-specific ST2 ablation alters T$_{reg}$ diversity and enhances CD8$^+$ T cell infiltration of tumors. 18A. Experiment overview. KPfrt, Foxp3$^{YFP-Cre}$ ("Il1rl1$^{WT}$") and KPfrt, Foxp3$^{YFP-Cre}$, Il1rl1$^{fl/fl}$ ("Il1rl1Il1rl1$^{fl/fl}$") mice were infected with Lenti-FlpO-GFP-OS. All data shown are from 2-3 experiments, with n=3-5 mice per group. 18B-18C. Changes in T$_{reg}$ subsets in Il1rl1$^{fl/fl}$ mice with advanced lung tumors. b. Percent Foxp3$^+$ (left) and Foxp3$^-$ (right) of i.v.$^{neg}$CD4$^+$ lung cells in KPfrt, Foxp3$^{YFP-Cre}$ vs. KPfrt, Foxp3$^{YFP-Cre}$, Il1rl1$^{fl/fl}$ mice at 24-25 weeks p.i. Error bars: SEM. *p<0.05, two-tailed Student's t test. NS: non-significant. c. Percent of CD103$^-$KLRG1$^+$ (gray), CD103$^-$KLRG1$^-$ (DN, black), CD103$^+$KLRG1$^-$ (SP, blue), and CD103$^+$KLRG1$^+$ (DP, red) out of T$_{regs}$ isolated from the tumor-bearing lungs of KPfrt, Foxp3$^{YFP-Cre}$ vs. KPfrt, Foxp3$^{YFP-Cre}$, Il1rl1$^{fl/fl}$ mice. Error bars: SEM. ****p<0.0001, *p<0.05, Sidak's multiple comparisons test. NS: non-significant. 18D. Expression signature distinguishing Il1rl1$^{WT}$ from ST2-deficient T$_{regs}$ from tumor-bearing mice. Row-normalized expression (z-score) of select signature genes (rows, STAR Methods) across CD103$^-$KLRG1$^-$ (DN, black), CD103$^+$KLRG1$^-$ (SP, blue), and CD103$^+$KLRG1$^+$ (DP, red) T$_{regs}$ (columns, lower color bar) from KPfrt, Foxp3$^{YFP-Cre}$ (gray) vs. KPfrt, Foxp3$^{YFP-Cre}$, Il1rl1$^{fl/fl}$ (purple) mice. 18E. Phenotypic changes in T$_{regs}$ from KPfrt, Foxp3$^{YFP-Cre}$, Il1rl1$^{fl/fl}$ mice. Percent of CXCR3+CCR6− (left) and CXCR3−CCR6$^+$ (right) of i.v.$^{neg}$CD4$^+$Foxp3$^+$ T$_{regs}$ in KPfrt, Foxp3$^{YFP-Cre}$ vs. KPfrt, Foxp3$^{YFP-Cre}$, Il1rl1$^{fl/fl}$ mice at 24-25 weeks p.i. p<0.01, two-tailed Student's t test. 18F. Increased CD8$^+$ T cell infiltration in mice with T$_{reg}$-specific ST2 deficiency. CD8$^+$ cells per tumor area (left) and CD8:T$_{reg}$ ratio (right) in pooled tumors from KPfrt, Foxp3$^{YFP-Cre}$ and KPfrt, Foxp3$^{YFP-Cre}$, Il1rl1$^{fl/fl}$ mice. Immunohistochemical (IHC) staining for CD8 and Foxp3 on tumor-bearing lungs. Error bars: SEM. p<0.01, ****p<0.0001, Mann-Whitney test. 18G. Reduced tumor burden in mice with T$_{reg}$-specific ST2 deficiency. Percent of total lung occupied by tumor (bottom left, y-axis) and average tumor size (bottom right, y-axis, μm$^2$) in KPfrt, Foxp3$^{YFP-Cre}$ vs. KPfrt, Foxp3$^{YFP-Cre}$ Il1rl1$^{fl/fl}$ mice. Error bars: SEM. *p=0.0315 (bottom left), 0.0106 (bottom right), Mann-Whitney test.

FIG. 19A-19M scRNAseq reveals overlapping diversity of lung CD4$^+$ T$_{conv}$ and T$_{regs}$ in KP tumors. 19A. T$_{conv}$ proliferation peaks early in tumor development. The percentage of Ki-67$^+$ T$_{conv}$ (y-axis) throughout KP tumor development (x-axis) from 2-3 experiments (dot=one mouse). Error bars: SEM. *p<0.001, Sidak's multiple comparisons test. NS: non-significant. 19B. Differentially-expressed genes between lung and msLN T$_{regs}$. Shown for each gene (dot) is its differential expression between lung and msLN T$_{regs}$ (x-axis) and associated significance on the y-axis, log$_{10}$(p-value) (logistic regression, STAR Methods). Red/blue genes are upregulated in both skin and colon compared to lymph node (Miragaia et al., 2019), highlighting overlapping genes. 19C. Lung cells are more variable. Map of the first two diffusion components of T$_{reg}$ and T$_{conv}$ cells from the lung and msLN, where lung samples were downsampled to equal numbers as in msLN. Histograms: distribution of the cell scores in each diffusion component. 19D. Naive and central memory gene expression in CD4$^+$ T cells. Diffusion component embedding for all CD4$^+$ T cells (as in FIG. 15D) colored by log 2(TPM+1) expression (color bar) of Ccr7 and Lef1 (naive and central memory markers), and Junb and Nr4a1 (T cell activation markers). 19E. Lung T$_{conv}$ subsets expressed programs associated with naive/central memory T, Th17, and Th1 cells. Two-dimensional force-directed layout embedding of the first four diffusion components of all lung resident T$_{conv}$ cells (STAR Methods), with cells colored by expression z-score for the indicated gene program, or by timepoint after tumor induction (bottom right). 19F. Th1 and Th17 programs. Smoothed loess distribution of log$_2$(TPM+1) expression (x-axis) of key genes (label top, color code) for the Th1 (green) and Th17 (orange) programs in cells and the associated activity z-score (y-axis) of each program in these cells. Bold curve: score for program in which each gene is a member. 19G. T$_{conv}$ subsets remain largely stable over tumor development. Top: Representative flow cytometry plots demonstrating naïve/central memory (left), Th1 (middle), and Th17 (right) CD4$^+$ T cell populations. Naive/central memory T$_{conv}$ are shown as a percentage of i.v.$^{neg}$CD8$^-$CD4$^+$Foxp3$^-$ cells, while Th1 and Th17 populations are shown as percentages of i.v.$^{neg}$CD8$^-$CD4$^+$Foxp3$^-$CD44$^{hi}$ T cells. Bottom: Corresponding barplots showing the percentage (y-axis) of the indicated T$_{conv}$ subset throughout tumor development (x-axis) across 2-3 experiments (dot: one mouse). Error bars: SEM. *p<0.001, Tukey's multiple comparisons test. NS: non-significant. 19H. Cells expressing a Tr17-like program are present throughout tumor development. Two-dimensional force-directed layout embedding of the first six diffusion components of all lung-derived T$_{regs}$ where each cell (dot) is colored by the gene expression ($\log_2$(TPM+1)) of Il17a (left), Rorc (middle), and Ccr6 (right). 19I. CCR6 marks RORγT$^+$ T$_{regs}$ in tumor-bearing lungs. Left: Representative flow cytometry plot demonstrating RORγt$^+$CCR6$^+$ T$_{regs}$ (i.v.$^{neg}$CD8$^-$CD4$^+$Foxp3$^+$). Right: Percentage of T$_{regs}$ that are RORγt$^+$CCR6$^+$ (y-axis) across tumor development (x-axis) across 2-3 experiments. Error bars: SEM. NS: non-significant, Tukey's multiple comparisons test. 19J. Tr17-like and lung T$_{reg}$ programs are inversely correlated. Two dimensional density plot of all lung T$_{reg}$ cells z-scored by Program 13 (Th17-like, x axis) versus T$_{reg}$ lung signature (FIG. 15C, y-axis). 19K. RORγt and KLRG1 mark distinct populations of T$_{regs}$. Top: Representative flow cytometry plot of T$_{reg}$ (i.v.$^{neg}$CD8$^-$CD4$^+$Foxp3$^+$) expression of RORγt and KLRG1. Bottom: Percentage of T$_{regs}$ that are RORγt$^+$KLRG1$^+$, RORγt$^+$KLRG1$^-$, and RORγt$^-$KLRG1$^+$ across tumor development (x-axis) across 2-3 experiments (dot=one mouse). Error bars: SEM. 19L. Shared clonotypes between T$_{reg}$ and T$_{conv}$ are predominantly Tr-17 like and Th17-like cells. Two-dimensional force-directed layout embedding of lung-resident T$_{regs}$ (left) and T$_{conv}$ (right) with each cell colored by clonal analysis. Grey: not clonal at our resolution or no TCR was reconstructed. Black: cells that share a TCR with at least one other cell. Color: Shared clones between T$_{reg}$ and T$_{conv}$, with numeric identifiers. 19M. T$_{regs}$ that have a shared clonotype with T$_{conv}$ are enriched for Tr17-like cells. Numbers of Tr17-like cells (green), of T$_{regs}$ with shared clonotype with T$_{conv}$ (purple), and the overlap. Percentages indicate the percentage of T$_{regs}$ that have a shared TCR with at least one other T$_{reg}$ that have a Tr17-like phenotype or have a shared TCR with a T$_{conv}$ clonotype. Overlap of the two populations is significant with a p-value <$10^{-5}$, hypergeometric test.

FIG. 20A-20K Klrg1$^+$Areg$^+$ effector-like T$_{reg}$ cells become predominant later in tumor development. 20A. Different programs pick up on similar signals and are correlated in expression across cells. Spearman correlation coefficient (color bar) between program z-scores across cells (rows and columns). Program correlations with themselves (diagonals) of 1 were set to "NA" and are shown in grey. 20B. Klrg1 and Areg expression mark Program 12 and 21 T$_{regs}$. Top: Two dimensional force directed layout embedding of T$_{reg}$ lung cells colored by normalized expression (z-score) of Klrg1 or Areg. Bottom: Smoothed loess distribution of $\log_2$(TPM+1) expression (x-axis) of Klrg1 and Areg for the activity z-score (y-axis) of Program 12 (red) and Program 21 (teal) in cells. Bold curve: score for program in which each gene is a member. 20C. IFN response genes peak early in tumor development. Effect size of differential expression compared to non tumor-bearing lung (color bar, mixed effect logistic regression analysis, STAR Methods) for genes (rows) from the IFN response programs 6 and 23 at each timepoint (columns). 20D. Association of T-bet with the IFNstim_TR program 23. Shown is the relation (red curve, loess fit) across cells (dots) between the $\log_2$(TPM+1) expression (y-axis) of Tbx21 and the z-score of Program 23 (x-axis) in the cell. 20E. T$_{reg}$ program similarity to previously-described expression programs. Spearman correlation coefficient (color bar) between program (columns) z-scores across cells and z-scores for published signatures (rows) of T$_{reg}$ cellular states. 20F. Resting T$_{reg}$ and IFNstim_TR programs are preferentially expressed in msLN T$_{regs}$. ECDFs of the program scores of msLN (gray) vs. lung-infiltrating (blue) T$_{regs}$. 20G. Ccr6 but not Cxcr3 is preferentially expressed by T$_{regs}$ that express the KA_TR program. Two-dimensional force-directed layout embedding of all lung-derived T$_{regs}$ (as in FIG. 16B) where each cell (dot) is colored by the gene expression ($\log_2$(TPM+1)) of Ccr6 (top) and Cxcr3 (bottom). 20H. 45 gene signature (43 up-regulated, 2 down-regulated) distinguishing CD103+KLRG1+ (DP) lung T$_{regs}$ (red) from other populations (black and blue) (STAR Methods). 20I. Programs 12 and 21 are enriched for genes of the DP UP signature. Number of genes in the union of programs 12 and 21 (blue), the induced genes in the DP signatures (brown), and their overlap. p<$10^{-25}$, hypergeometric test. 20J. Example genes whose expression varies significantly over tumor development. Distribution of $\log_2$(TPM+1) expression of selected genes across time (x-axis). P-value: Kolmogorov-Smirnov test. 20K. DP cells are associated with higher expression of KA_TR and lower expression of IFNstim_TR genes. ECDF plots of DP vs DN T$_{reg}$ $\log_2$(fold-change) in gene expression of IFNstim_TR genes (Programs 6 and 23, red, left) or KA_TR genes (Programs 12 and 21, red, right), and all other genes (gray). P-values: two-sided Kolmogorov-Smirnov tests.

FIG. 21A-21H Characteristics of Il1rl1- and IL-33-expressing cells in tumor-bearing lung. 21A. Il1rl1 marks a distinct and diverse population of T$_{regs}$ at all timepoints. Two dimensional force directed layout embedding of T$_{reg}$ lung cells colored by expression of Il1rl1 across timepoint after tumor induction. 21B. Il1rl1-positive and Il1rl1-negative T$_{regs}$ show similar transcriptional diversity. Sum of the squared distance to the centroid over the z-scores of the major programs (shown in c) for Il1rl1-positive (green) and Il1rl1-negative (gray) T$_{regs}$ at each timepoint after tumor induction. P-values: Kolmogorov-Smirnov test. 21C. Change in differential expression of gene programs by Il1rl1-positive T$_{regs}$ vs. Il1rl1-negative T$_{regs}$. Dot plot shows for each program (row) and timepoint (column) the difference between the percentage of Il1rl1-positive T$_{regs}$ with a z-score >1.5 and the percentage of Il1rl1-negative T$_{regs}$ with a z-score >1.5 (dot size) and signed log 10 adjusted p-value (color) (ks-test). 21D. ST2-positive and ST2-negative T$_{regs}$ have similar fractions of dividing cells. Bar plot showing percent of Ki-67$^+$ of ST2-positive (red) or ST2-negative (black) T$_{regs}$ at all time points. NS: non-significant, Tukey's multiple comparisons test. 21E. KA_TR and DP genes are upregulated in Il1rl1-positive vs. Il1rl1-negative T$_{regs}$. Differential, log 2(fold change) expression (x-axis) by logistic regression and $\log_{10}$(p-value) (y-axis) for each gene (dot) in Il1rl1-positive vs. Il1rl1-negative T$_{regs}$. 25 top significantly differentially-expressed genes are labeled (up-regulated: red, down-regulated: blue). 21F. Representative immunofluorescent staining of healthy, non-tumor bearing lung. 21G. AT2 cells are a major source of Il33 expression in tumor bearing lungs. Top: Il33 $\log_2$(TPM+1) expression by cell type identified using droplet-based single-cell RNA-seq (STAR Methods) shown as violin plot with the total number of cells profiled indicated in parentheses. Bottom: Proportion of total Il33 UMI expression by indicated cell type using droplet-based single-cell RNA-seq with percentages indicated in parentheses. 21H. Few CD8$^+$ T cells express ST2 throughout KP tumor development. Percentage of CD8$^+$ T cells that express ST2 throughout KP tumor development (x-axis) from 2-3 experiments (dot: one mouse). NS: non-significant, Tukey's multiple comparisons test.

FIG. 22A-22P Impact of T$_{reg}$-specific ST2 ablation on T$_{reg}$ diversity and tumor growth. 22A. No change in ST2 expression among CD8+ T cells and T$_{conv}$ in mice with T$_{reg}$-specific ST2 deficiency. Percent ST2+ of i.v. $^{neg}$CD4$^+$Foxp3$^-$ lung cells (left) and CD8$^+$ T cells (right). NS: non-significant, two-tailed Student's t test. 22B. No change in the fraction of T$_{conv}$ or T$_{regs}$ early in tumor development in mice with T$_{reg}$-specific ST2 deficiency. Percent Foxp3$^+$ (left) and % Foxp3⁻ (right) of i.v. $^{neg}$CD4⁺ lung cells in KPfrt, Foxp3$^{YFP-Cre}$ ("Il1rl1$^{WT}$") vs. KPfrt, Foxp3$^{YFP-Cre}$, Il1rl1$^{fl/fl}$ ("Il1rl1$^{fl/fl}$") mice at 10 weeks p.i. NS: non-significant, two-tailed Student's t test. 22C. Proliferation is comparable between DP T$_{regs}$ from KPfrt, Foxp3$^{YFP-Cre}$, Il1rl1$^{fl/fl}$ and KPfrt, Foxp3$^{YFP-Cre}$ mice. The percentage of Ki-67⁺ T$_{regs}$ (y-axis) from CD103⁺KLRG1⁺ T$_{regs}$ from KPfrt, Foxp3$^{YFP-Cre}$, Il1rl1$^{fl/fl}$ vs. KPfrt, Foxp3$^{YFP-Cre}$ mice across 2-3 experiments (dot=one mouse). Error bars: SEM. Two-tailed Student's t test. NS: non-significant. 22D. Expression of CD103 and KLRG1 is comparable in msLN and splenic T$_{regs}$ from KPfrt, Foxp3$^{YFP-Cre}$, Il1rl$^{fl/fl}$ and KPfrt, Foxp3$^{YFP-Cre}$ mice. Percent of CD103⁻KLRG1⁺ (gray), CD103⁻KLRG1⁻ (DN, black), CD103⁺KLRG1⁻ (SP, blue), CD103⁺KLRG1⁺ (DP, red) out of T$_{regs}$ isolated from msLNs (top) and spleens (bottom) of KPfrt, Foxp3$^{YFP-Cre}$ vs. KPfrt, Foxp3$^{YFP-Cre}$, Il1rl1$^{fl/fl}$ mice. Error bars: SEM. NS: non-significant, Sidak's multiple comparisons test. 22E-22H. Proportions of T$_{conv}$, CD8+ T cells, and alveolar macrophages are similar between tumor-bearing KPfrt, Foxp3$^{YFP-Cre}$, Il1rl1$^{fl/fl}$ and KPfrt, Foxp3$^{YFP-Cre}$ mice. Percent Th1 (e, CXCR3⁺T-bet⁺) and Th17 (f, CCR6⁺RORγT⁺) of i.v. $^{neg}$CD4⁺Foxp3⁻CD44$^{hi}$ cells, percent CD8+ of i.v. $^{neg}$Thy1.2⁺ cells (g, left) and % SIINFEKL tetramer-positive of i.v. $^{neg}$Thy1.2⁺CD8⁺ T cells (g, right), and percent alveolar macrophages (% CD11c$^{hi}$SiglecF⁺) of total i.v.negCD45+ cells (h) in KPfrt, Foxp3$^{YFP-Cre}$ ("Il1rl1$^{WT}$") vs. KPfrt, Foxp3$^{YFP-Cre}$, Il1rl1$^{fl/fl}$ ("Il1rl1$^{fl/fl}$") mice at 24-25 weeks p.i (as in FIG. 18B). NS: non-significant, two-tailed Student's t test. 22I-22J. An expression signature lower in ST2-deficient T$_{regs}$ compared to ST2-wild-type T$_{regs}$ is highest among wild-type DP T$_{regs}$. i. Standardized signature score (y-axis) of the expression signature distinguishing Il1rl1$^{WT}$ and Il1rl1$^{fl/fl}$ T$_{regs}$ for each lung T$_{reg}$ subpopulation in tumor-bearing mice (x-axis). Box: 25th to 75th percentiles, whiskers: minimum to maximum. Bar: median. No data point is beyond the limit of lines. *p=0.02, two-sided Mann-Whitney test. j. Gene sets enriched in the expression signature distinguishing ST2-deficient T$_{regs}$. GSEA gene sets (nodes) from the custom immune signature database (custom c7, STAR Methods) enriched in the signature distinguishing ST2-deficient T$_{regs}$ (p<0.05, FDR<0.05; in all significant gene sets. Red: enrichment of upregulated genes. Node size: gene set size. Edge thickness: overlap between gene sets (minimum: 30% overlap). Related pathways were manually annotated. 22K. Left: differential, log 2(fold change) expression (y-axis) and mean expression (x-axis) for each gene (dot) in CD103⁺KLRG1⁺ (DP) T$_{regs}$ from KPfrt, Foxp3$^{YFP-Cre}$, Il1rl1$^{fl/fl}$ vs. KPfrt, Foxp3$^{YFP-Cre}$ mice. Purple: genes in the DP signature. Blue: Top significantly downregulated genes. Right: Venn diagram shows the overlap between the top differentially downregulated genes in Il1rl1$^{fl/fl}$ vs. Il1rl1$^{WT}$ T$_{regs}$ (blue) and the DP signature (purple). P<10⁻⁷, hypergeometric test. 22L. CXCR3⁺CCR6⁻ and CXCR3⁻CCR6⁺ Tregs represent distinct T$_{reg}$ populations that have different proportions in KPfrt, Foxp3$^{YFP-Cre}$, Il1rl1$^{fl/fl}$ mice. Representative plots showing T$_{reg}$ (i.v.$^{neg}$CD8⁻CD4⁺Foxp3⁺) expression of CXCR3 (y-axis) and CCR6 (x-axis) in KPfrt, Foxp3$^{YFP-Cre}$, Il1rl1$^{fl/fl}$ mice and controls. 22M. Comparable expression of RORγT on T$_{regs}$ from KPfrt, Foxp3$^{YFP-Cre}$, Il1rl1$^{fl/fl}$ mice and controls. Percentage of T$_{regs}$ that are RORγT⁺ from KPfrt, Foxp3$^{YFP-Cre}$, Il1rl1$^{fl/fl}$ vs. KPfrt, Foxp3$^{YFP-Cre}$ mice at 24-25 weeks p.i across 3 experiments, each with n=3-5 mice per group. NS: non-significant, two-tailed Student's t test. 22N. Increased expression of CXCR3 on T$_{regs}$ from KPfrt, Foxp3$^{YFP-Cre}$, Il1rl1$^{fl/fl}$ mice. Geometric mean fluorescence intensity (GMFI) of CXCR3 on CXCR3⁺ T$_{regs}$ from KPfrt, Foxp3$^{YFP-Cre}$, Il1rl1$^{fl/fl}$ vs. KPfrt, Foxp3$^{YFP-Cre}$ mice at week 10 p.i. across 2 experiments (dot=one mouse). Error bars: SEM. *p<0.05, two-tailed Student's t test. 22O. Reduced tumor burden in mice with T$_{reg}$-specific ST2 deficiency. Representative cross-sections from KPfrt, Foxp3$^{YFP-Cre}$ vs. KPfrt, Foxp3$^{YFP-Cre}$ Il1rl1$^{fl/fl}$ mice (scale bar: 500 um). 22P. Increased Foxp3⁺ T cell infiltration in mice with T$_{reg}$-specific ST2 deficiency. Number of Foxp3⁺ cells per tumor area in pooled tumors from KPfrt, Foxp3$^{YFP-Cre}$ and KPfrt, Foxp3$^{YFP-Cre}$, Il1rl1$^{fl/fl}$ mice across two experiments, with n=4-5 mice per group. Foxp3 was measured by immunohistochemical (IHC) staining of histological cross-sections of tumor-bearing lungs. Error bars: SEM. ****p<0.0001, Mann-Whitney test.

The figures herein are for illustrative purposes only and are not necessarily drawn to scale.

DETAILED DESCRIPTION OF THE EXAMPLE EMBODIMENTS

General Definitions

Unless defined otherwise, technical and scientific terms used herein have the same meaning as commonly understood by one of ordinary skill in the art to which this disclosure pertains. Definitions of common terms and techniques in molecular biology may be found in Molecular Cloning: A Laboratory Manual, 2$^{nd}$ edition (1989) (Sambrook, Fritsch, and Maniatis); Molecular Cloning: A Laboratory Manual, 4$^{th}$ edition (2012) (Green and Sambrook); Current Protocols in Molecular Biology (1987) (F. M. Ausubel et al. eds.); the series Methods in Enzymology (Academic Press, Inc.): PCR 2: A Practical Approach (1995) (M. J. MacPherson, B. D. Hames, and G. R. Taylor eds.): Antibodies, A Laboratory Manual (1988) (Harlow and Lane, eds.): Antibodies A Laboratory Manual, 2$^{nd}$ edition 2013 (E. A. Greenfield ed.); Animal Cell Culture (1987) (R. I. Freshney, ed.); Benjamin Lewin, Genes IX, published by Jones and Bartlett, 2008 (ISBN 0763752223); Kendrew et al. (eds.), The Encyclopedia of Molecular Biology, published by Blackwell Science Ltd., 1994 (ISBN 0632021829); Robert A. Meyers (ed.), Molecular Biology and Biotechnology: a Comprehensive Desk Reference, published by VCH Publishers, Inc., 1995 (ISBN 9780471185710); Singleton et al., Dictionary of Microbiology and Molecular Biology 2nd ed., J. Wiley & Sons (New York, N.Y. 1994), March, Advanced Organic Chemistry Reactions, Mechanisms and Structure 4th ed., John Wiley & Sons (New York, N.Y. 1992); and Marten H. Hofker and Jan van Deursen, Transgenic Mouse Methods and Protocols, 2$^{nd}$ edition (2011).

As used herein, the singular forms "a", "an", and "the" include both singular and plural referents unless the context clearly dictates otherwise.

The term "optional" or "optionally" means that the subsequent described event, circumstance or substituent may or may not occur, and that the description includes instances where the event or circumstance occurs and instances where it does not.

The recitation of numerical ranges by endpoints includes all numbers and fractions subsumed within the respective ranges, as well as the recited endpoints.

The terms "about" or "approximately" as used herein when referring to a measurable value such as a parameter, an amount, a temporal duration, and the like, are meant to encompass variations of and from the specified value, such as variations of +/−10% or less, +/−5% or less, +/−1% or less, and +/−0.1% or less of and from the specified value, insofar such variations are appropriate to perform in the disclosed invention. It is to be understood that the value to which the modifier "about" or "approximately" refers is itself also specifically, and preferably, disclosed.

As used herein, the terms "$T_{reg}$" and "Treg" both mean regulatory T cell or cells, and these terms are interchangeable. The terms "$T_{reg}$ cells" and "Treg cells" both mean regulatory T cells, and these terms are interchangeable.

As used herein, a "biological sample" may contain whole cells and/or live cells and/or cell debris. The biological sample may contain (or be derived from) a "bodily fluid". The present invention encompasses embodiments wherein the bodily fluid is selected from amniotic fluid, aqueous humour, vitreous humour, bile, blood serum, breast milk, cerebrospinal fluid, cerumen (earwax), chyle, chyme, endolymph, perilymph, exudates, feces, female ejaculate, gastric acid, gastric juice, lymph, mucus (including nasal drainage and phlegm), pericardial fluid, peritoneal fluid, pleural fluid, pus, rheum, saliva, sebum (skin oil), semen, sputum, synovial fluid, sweat, tears, urine, vaginal secretion, vomit and mixtures of one or more thereof. Biological samples include cell cultures, bodily fluids, cell cultures from bodily fluids. Bodily fluids may be obtained from a mammal organism, for example by puncture, or other collecting or sampling procedures.

The terms "subject," "individual," and "patient" are used interchangeably herein to refer to a vertebrate, preferably a mammal, more preferably a human. Mammals include, but are not limited to, murine animals, simians, humans, farm animals, sport animals, and pets. Tissues, cells and their progeny of a biological entity obtained in vivo or cultured in vitro are also encompassed.

Various embodiments are described hereinafter. It should be noted that the specific embodiments are not intended as an exhaustive description or as a limitation to the broader aspects discussed herein. One aspect described in conjunction with a particular embodiment is not necessarily limited to that embodiment and can be practiced with any other embodiment(s). Reference throughout this specification to "one embodiment", "an embodiment," "an example embodiment," means that a particular feature, structure or characteristic described in connection with the embodiment is included in at least one embodiment of the present invention. Thus, appearances of the phrases "in one embodiment," "in an embodiment," or "an example embodiment" in various places throughout this specification are not necessarily all referring to the same embodiment, but may. Furthermore, the particular features, structures or characteristics may be combined in any suitable manner, as would be apparent to a person skilled in the art from this disclosure, in one or more embodiments. Furthermore, while some embodiments described herein include some but not other features included in other embodiments, combinations of features of different embodiments are meant to be within the scope of the invention. For example, in the appended claims, any of the claimed embodiments can be used in any combination.

Reference is made to Li et al., (2019), IL-33 Signaling Alters Regulatory T Cell Diversity in Support of Tumor Development. Cell Reports 29, 2998-3008. All publications, published patent documents, and patent applications cited herein are hereby incorporated by reference to the same extent as though each individual publication, published patent document, or patent application was specifically and individually indicated as being incorporated by reference.

Overview

The present invention discloses methods and compositions for overcoming or removing immunosuppression. In some embodiments, the methods and compositions are directed to inhibit and reduce the activity and levels of effector $T_{reg}$ cells. Inhibition of effector $T_{reg}$ cells can relieve immunosuppression and increase the infiltration of effector CD8$^+$ T cytotoxic cells into a tumor or cancer tissue microenvironment for killing tumor or cancerous cells. In some preferred embodiments, methods are provided for using pharmacological inhibitors and/or genetic ablation to remove ST2 and/or IL-33 signaling, so that effector $T_{reg}$ cells are inhibited.

In some embodiments, methods are provided for identifying and isolating effector $T_{reg}$ cells from a population of heterogeneous cells. Specific biomarkers for effector $T_{reg}$ cells are disclosed, and can be used to target these cells for immunotherapy.

In some embodiments, methods and compositions are provided for treating a disease or a condition such as a tumor or a cancer. The methods and compositions are directed to inhibit the levels and/or activities of ST2 and/or IL-33 signaling in effector $T_{reg}$ cells in a tumor microenvironment, whereby the levels and activities of CD8$^+$ cells increase in the tumor microenvironment.

Method of Modulating T Cell Balance

Embodiments disclosed here provide methods for shifting T cell balance in a population of cells, promoting tumor infiltration of CD8 T cells, reducing tumor growth, or reducing tumor size, comprising administering one or more agents that reduce and/or inhibit ST2 and/or IL33 signaling and/or reduce infiltration of tumor-infiltration Treg cells.

Modulating Agents

As used herein, "modulating" or "to modulate" generally means either reducing or inhibiting the expression or activity of, or alternatively increasing the expression or activity of a target (e.g., IL33 signalling). In particular, "modulating" or "to modulate" can mean either reducing or inhibiting the activity of, or alternatively increasing a (relevant or intended) biological activity of, a target or antigen as measured using a suitable in vitro, cellular or in vivo assay (which will usually depend on the target involved), by at least 5%, at least 10%, at least 25%, at least 50%, at least 60%, at least 70%, at least 80%, at least 90%, or more, compared to activity of the target in the same assay under the same conditions but without the presence of an agent. An "increase" or "decrease" refers to a statistically significant increase or decrease respectively. For the avoidance of doubt, an increase or decrease will be at least 10% relative to a reference, such as at least 10%, at least 20%, at least 30%, at least 40%, at least 50%, at least 60%, at least 70%, at least 80%, at least 90%, at least 95%, at least 97%, at least 98%, or more, up to and including at least 100% or more, in the case of an increase, for example, at least 2-fold, at least 3-fold, at least 4-fold, at least 5-fold, at least 6-fold, at least 7-fold, at least 8-fold, at least 9-fold, at least 10-fold, at least 50-fold, at least 100-fold, or more. "Modulating" can also involve effecting a change (which can either be an increase or a decrease) in affinity, avidity, specificity and/or selectivity of a target or antigen, such as IL-33 binding. "Modulating" can also mean effecting a change with respect to one or more biological or physiological mechanisms, effects, responses, functions, pathways or activities in which the target or antigen (or in which its substrate(s), ligand(s) or pathway(s) are involved, such as its signaling pathway or metabolic pathway and their associated biological or physiological effects) is involved. Again, as will be clear to the skilled person, such an action as an agonist or an antagonist can be determined in any suitable manner and/or using any suitable assay known or described herein (e.g., in vitro or cellular assay), depending on the target or antigen involved.

Modulating can, for example, also involve allosteric modulation of the target and/or reducing or inhibiting the binding of the target to one of its substrates or ligands and/or competing with a natural ligand, substrate for binding to the target. Modulating can also involve activating the target or the mechanism or pathway in which it is involved. Modulating can for example also involve effecting a change in respect of the folding or confirmation of the target, or in respect of the ability of the target to fold, to change its conformation (for example, upon binding of a ligand), to associate with other (sub)units, or to disassociate. Modulating can for example also involve effecting a change in the ability of the target to signal, phosphorylate, dephosphorylate, and the like.

Checkpoint Inhibitor Therapy

Immunotherapy can include immune checkpoint inhibitor, chimeric antigen receptors (CARs), and adoptive T-cell therapy. Antibodies that block the activity of checkpoint receptors, including CTLA-4, PD-1, TIM-3, LAG-3, and TIGIT, either alone or in combination, have been associated with improved effector $CD8^+$ T cell responses in multiple pre-clinical cancer models (Johnston et al., 2014. The immunoreceptor TIGIT regulates antitumor and antiviral $CD8^+$ T cell effector function. Cancer cell 26, 923-937; Ngiow et al., 2011. Anti-TIM3 antibody promotes T cell IFN-gamma-mediated antitumor immunity and suppresses established tumors. Cancer research 71, 3540-3551; Sakuishi et al., 2010. Targeting TIM-3 and PD-1 pathways to reverse T cell exhaustion and restore anti-tumor immunity. The Journal of experimental medicine 207, 2187-2194; and Woo et al., 2012. Immune inhibitory molecules LAG-3 and PD-1 synergistically regulate T-cell function to promote tumoral immune escape. Cancer research 72, 917-927). Similarly, blockade of CTLA-4 and PD-1 in patients (Brahmer et al., 2012. Safety and activity of anti-PD-L1 antibody in patients with advanced cancer. The New England journal of medicine 366, 2455-2465; Hodi et al., 2010. Improved survival with ipilimumab in patients with metastatic melanoma. The New England journal of medicine 363, 711-723; Schadendorf et al., 2015. Pooled Analysis of Long-Term Survival Data From Phase II and Phase III Trials of Ipilimumab in Unresectable or Metastatic Melanoma. Journal of clinical oncology. official journal of the American Society of Clinical Oncology 33, 1889-1894; Topalian et al., 2012. Safety, activity, and immune correlates of anti-PD-1 antibody in cancer. The New England journal of medicine 366, 2443-2454; and Wolchok et al., 2017. Overall Survival with Combined Nivolumab and Ipilimumab in Advanced Melanoma. The New England journal of medicine 377, 1345-1356) has shown increased frequencies of proliferating T cells, often with specificity for tumor antigens, as well as increased $CD8^+$ T cell effector function (Ayers et al., 2017. IFN-gamma-related mRNA profile predicts clinical response to PD-1 blockade. The Journal of clinical investigation 127, 2930-2940; Das et al., 2015. Combination therapy with anti-CTLA-4 and anti-PD-1 leads to distinct immunologic changes in vivo. Journal of immunology 194, 950-959; Gubin et al., 2014. Checkpoint blockade cancer immunotherapy targets tumour-specific mutant antigens. Nature 515, 577-581; Huang et al., 2017. T-cell invigoration to tumour burden ratio associated with anti-PD-1 response. Nature 545, 60-65; Kamphorst et al., 2017. Proliferation of PD-1+ CD8 T cells in peripheral blood after PD-1-targeted therapy in lung cancer patients. Proceedings of the National Academy of Sciences of the United States of America 114, 4993-4998; Kvistborg et al., 2014. Anti-CTLA-4 therapy broadens the melanoma-reactive $CD8^+$ T cell response. Science translational medicine 6, 254rai28; van Rooij et al., 2013. Tumor exome analysis reveals neoantigen-specific T-cell reactivity in an ipilimumab-responsive melanoma. Journal of clinical oncology. official journal of the American Society of Clinical Oncology 31, e439-442; and Yuan et al., 2008. CTLA-4 blockade enhances polyfunctional NY-ESO-1 specific T cell responses in metastatic melanoma patients with clinical benefit. Proceedings of the National Academy of Sciences of the United States of America 105, 20410-20415). Accordingly, the success of checkpoint receptor blockade has been attributed to the binding of blocking antibodies to checkpoint receptors expressed on dysfunctional $CD8^+$ T cells and restoring effector function in these cells. The check point blockade therapy may be an inhibitor of any check point protein described herein. The checkpoint blockade therapy may comprise anti-TIM3, anti-CTLA4, anti-PD-L1, anti-PD1, anti-TIGIT, anti-LAG3, or combinations thereof. Anti-PD1 antibodies are disclosed in U.S. Pat. No. 8,735,553. Antibodies to LAG-3 are disclosed in U.S. Pat. No. 9,132,281. Anti-CTLA4 antibodies are disclosed in U.S. Pat. Nos. 9,327,014; 9,320,811; and 9,062,111. Specific check point inhibitors include, but are not limited to anti-CTLA4 antibodies (e.g., Ipilimumab and tremelimumab), anti-PD-1 antibodies (e.g., Nivolumab, Pembrolizumab), and anti-PD-L1 antibodies (e.g., Atezolizumab).

In certain embodiments, immunotherapy leads to immune-related adverse events (irAEs) (see, e.g., Byun et al., (2017) Cancer immunotherapy-immune checkpoint blockade and associated endocrinopathies. Nat Rev Endocrinol. 2017 April; 13(4): 195-207; Abdel-Wahab et al., (2016) Adverse Events Associated with Immune Checkpoint Blockade in Patients with Cancer: A Systematic Review of Case Reports. PLoS ONE 11 (7): e0160221. doi:10.1371/journal.pone.0160221; and Gelao et al., Immune Checkpoint Blockade in Cancer Treatment: A Double-Edged Sword Cross-Targeting the Host as an "Innocent Bystander", Toxins 2014, 6, 914-933; doi:10.3390/toxins6030914). Thus, patients receiving immunotherapy are at risk for adverse autoimmune responses.

In certain embodiments, irAEs are related to Th17 pathogenicity. In one study, patients treated with ipilimumab had fluctuations in serum IL-17 levels, such that serum IL-17 levels in patients with colitis versus no irAEs demonstrated significantly higher serum IL-17 levels in the patients with colitis (Callahan et al., (2011) Evaluation of serum IL-17 levels during ipilimumab therapy: Correlation with colitis. Journal of Clinical Oncology 29, no. 15_suppl 2505-2505).

In certain embodiments, the modulating agents can be used to shift T cell balance away from Th17 autoimmune responses in patients treated with checkpoint blockade therapy.

Small Molecules

In certain embodiments, the one or more agents is a small molecule. The term "small molecule" refers to compounds, preferably organic compounds, with a size comparable to those organic molecules generally used in pharmaceuticals. The term excludes biological macromolecules (e.g., proteins, peptides, nucleic acids, etc.). Preferred small organic molecules range in size up to about 5000 Da, e.g., up to about 4000 Da, preferably up to 3000 Da, more preferably up to 2000 Da, even more preferably up to about 1000 Da, e.g., up to about 900, 800, 700, 600 or up to about 500 Da. In certain embodiments, the small molecule may act as an antagonist or agonist (e.g., blocking an enzyme active site or activating a receptor by binding to a ligand binding site).

One type of small molecule applicable to the present invention is a degrader molecule. Proteolysis Targeting Chimera (PROTAC) technology is a rapidly emerging alternative therapeutic strategy with the potential to address many of the challenges currently faced in modern drug development programs. PROTAC technology employs small molecules that recruit target proteins for ubiquitination and removal by the proteasome (see, e.g., Zhou et al., Discovery of a Small-Molecule Degrader of Bromodomain and Extra-Terminal (BET) Proteins with Picomolar Cellular Potencies and Capable of Achieving Tumor Regression. J. Med. Chem. 2018, 61, 462-481; Bondeson and Crews, Targeted Protein Degradation by Small Molecules, Annu Rev Pharmacol Toxicol. 2017 Jan. 6; 57: 107-123; and Lai et al., Modular PROTAC Design for the Degradation of Oncogenic BCR-ABL Angew Chem Int Ed Engl. 2016 Jan. 11; 55(2): 807-810).

Genetic Modifying Agents

In certain embodiments, the one or more modulating agents may be a genetic modifying agent. The genetic modifying agent may comprise a CRISPR system, a zinc finger nuclease system, a TALEN, a meganuclease or RNAi system.

In general, a CRISPR-Cas or CRISPR system as used in herein and in documents, such as WO 2014/093622 (PCT/US2013/074667), refers collectively to transcripts and other elements involved in the expression of or directing the activity of CRISPR-associated ("Cas") genes, including sequences encoding a Cas gene, a tracr (trans-activating CRISPR) sequence (e.g. tracrRNA or an active partial tracrRNA), a tracr-mate sequence (encompassing a "direct repeat" and a tracrRNA-processed partial direct repeat in the context of an endogenous CRISPR system), a guide sequence (also referred to as a "spacer" in the context of an endogenous CRISPR system), or "RNA(s)" as that term is herein used (e.g., RNA(s) to guide Cas, such as Cas9, e.g. CRISPR RNA and transactivating (tracr) RNA or a single guide RNA (sgRNA) (chimeric RNA)) or other sequences and transcripts from a CRISPR locus. In general, a CRISPR system is characterized by elements that promote the formation of a CRISPR complex at the site of a target sequence (also referred to as a protospacer in the context of an endogenous CRISPR system). See, e.g, Shmakov et al. (2015) "Discovery and Functional Characterization of Diverse Class 2 CRISPR-Cas Systems", Molecular Cell, DOI: dx.doi.org/10.1016/j.molcel.2015.10.008.

In certain embodiments, a protospacer adjacent motif (PAM) or PAM-like motif directs binding of the effector protein complex as disclosed herein to the target locus of interest. In some embodiments, the PAM may be a 5' PAM (i.e., located upstream of the 5' end of the protospacer). In other embodiments, the PAM may be a 3' PAM (i.e., located downstream of the 5' end of the protospacer). The term "PAM" may be used interchangeably with the term "PFS" or "protospacer flanking site" or "protospacer flanking sequence".

In a preferred embodiment, the CRISPR effector protein may recognize a 3' PAM. In certain embodiments, the CRISPR effector protein may recognize a 3' PAM which is 5'H, wherein H is A, C or U.

In the context of formation of a CRISPR complex, "target sequence" refers to a sequence to which a guide sequence is designed to have complementarity, where hybridization between a target sequence and a guide sequence promotes the formation of a CRISPR complex. A target sequence may comprise RNA polynucleotides. The term "target RNA" refers to an RNA polynucleotide being or comprising the target sequence. In other words, the target RNA may be an RNA polynucleotide or a part of a RNA polynucleotide to which a part of the gRNA, i.e. the guide sequence, is designed to have complementarity and to which the effector function mediated by the complex comprising CRISPR effector protein and a gRNA is to be directed. In some embodiments, a target sequence is located in the nucleus or cytoplasm of a cell.

In certain example embodiments, the CRISPR effector protein may be delivered using a nucleic acid molecule encoding the CRISPR effector protein. The nucleic acid molecule encoding a CRISPR effector protein, may advantageously be a codon optimized CRISPR effector protein. An example of a codon optimized sequence, is in this instance a sequence optimized for expression in eukaryote, e.g., humans (i.e. being optimized for expression in humans), or for another eukaryote, animal or mammal as herein discussed; see, e.g., SaCas9 human codon optimized sequence in WO 2014/093622 (PCT/US2013/074667). Whilst this is preferred, it will be appreciated that other examples are possible and codon optimization for a host species other than human, or for codon optimization for specific organs is known. In some embodiments, an enzyme coding sequence encoding a CRISPR effector protein is a codon optimized for expression in particular cells, such as eukaryotic cells. The eukaryotic cells may be those of or derived from a particular organism, such as a plant or a mammal, including but not limited to human, or non-human eukaryote or animal or mammal as herein discussed, e.g., mouse, rat, rabbit, dog, livestock, or non-human mammal or primate. In some embodiments, processes for modifying the germ line genetic identity of human beings and/or processes for modifying the genetic identity of animals which are likely to cause them suffering without any substantial medical benefit to man or animal, and also animals resulting from such processes, may be excluded. In general, codon optimization refers to a process of modifying a nucleic acid sequence for enhanced expression in the host cells of interest by replacing at least one codon (e.g. about or more than about 1, 2, 3, 4, 5, 10, 15, 20, 25, 50, or more codons) of the native sequence with codons that are more frequently or most frequently used in the genes of that host cell while maintaining the native amino acid sequence. Various species exhibit particular bias for certain codons of a particular amino acid. Codon bias (differences in codon usage between organisms) often correlates with the efficiency of translation of messenger RNA (mRNA), which is in turn believed to be dependent on, among other things, the properties of the codons being translated and the availability of particular transfer RNA (tRNA) molecules. The predominance of selected tRNAs in a cell is generally a reflection of the codons used most frequently in peptide synthesis. Accordingly, genes can be tailored for optimal gene expression in a given organism based on codon optimization. Codon usage tables are readily available, for example, at the "Codon Usage Database" available at kazusa.or.jp/codon/and these tables can be adapted in a number of ways. See Nakamura, Y., et al. "Codon usage tabulated from the international DNA sequence databases: status for the year 2000" Nucl. Acids Res. 28:292 (2000). Computer algorithms for codon optimizing a particular sequence for expression in a particular host cell are also available, such as Gene Forge (Aptagen; Jacobus, Pa.), are also available. In some embodiments, one or more codons (e.g. 1, 2, 3, 4, 5, 10, 15, 20, 25, 50, or more, or all codons) in a sequence encoding a Cas correspond to the most frequently used codon for a particular amino acid.

In certain embodiments, the methods as described herein may comprise providing a Cas transgenic cell in which one or more nucleic acids encoding one or more guide RNAs are provided or introduced operably connected in the cell with a regulatory element comprising a promoter of one or more gene of interest. As used herein, the term "Cas transgenic cell" refers to a cell, such as a eukaryotic cell, in which a Cas gene has been genomically integrated. The nature, type, or origin of the cell are not particularly limiting according to the present invention. Also the way the Cas transgene is introduced in the cell may vary and can be any method as is known in the art. In certain embodiments, the Cas transgenic cell is obtained by introducing the Cas transgene in an isolated cell. In certain other embodiments, the Cas transgenic cell is obtained by isolating cells from a Cas transgenic organism. By means of example, and without limitation, the Cas transgenic cell as referred to herein may be derived from a Cas transgenic eukaryote, such as a Cas knock-in eukaryote. Reference is made to WO 2014/093622 (PCT/US13/74667), incorporated herein by reference. Methods of US Patent Publication Nos. 20120017290 and 20110265198 assigned to Sangamo BioSciences, Inc. directed to targeting the Rosa locus may be modified to utilize the CRISPR Cas system of the present invention. Methods of US Patent Publication No. 20130236946 assigned to Cellectis directed to targeting the Rosa locus may also be modified to utilize the CRISPR Cas system of the present invention. By means of further example reference is made to Platt et. al. (Cell; 159(2):440-455 (2014)), describing a Cas9 knock-in mouse, which is incorporated herein by reference. The Cas transgene can further comprise a Lox-Stop-polyA-Lox(LSL) cassette thereby rendering Cas expression inducible by Cre recombinase. Alternatively, the Cas transgenic cell may be obtained by introducing the Cas transgene in an isolated cell. Delivery systems for transgenes are well known in the art. By means of example, the Cas transgene may be delivered in for instance eukaryotic cell by means of vector (e.g., AAV, adenovirus, lentivirus) and/or particle and/or nanoparticle delivery, as also described herein elsewhere.

It will be understood by the skilled person that the cell, such as the Cas transgenic cell, as referred to herein may comprise further genomic alterations besides having an integrated Cas gene or the mutations arising from the sequence specific action of Cas when complexed with RNA capable of guiding Cas to a target locus.

In certain aspects the invention involves vectors, e.g. for delivering or introducing in a cell Cas and/or RNA capable of guiding Cas to a target locus (i.e. guide RNA), but also for propagating these components (e.g. in prokaryotic cells). A used herein, a "vector" is a tool that allows or facilitates the transfer of an entity from one environment to another. It is a replicon, such as a plasmid, phage, or cosmid, into which another DNA segment may be inserted so as to bring about the replication of the inserted segment. Generally, a vector is capable of replication when associated with the proper control elements. In general, the term "vector" refers to a nucleic acid molecule capable of transporting another nucleic acid to which it has been linked. Vectors include, but are not limited to, nucleic acid molecules that are single-stranded, double-stranded, or partially double-stranded; nucleic acid molecules that comprise one or more free ends, no free ends (e.g. circular); nucleic acid molecules that comprise DNA, RNA, or both; and other varieties of polynucleotides known in the art. One type of vector is a "plasmid," which refers to a circular double stranded DNA loop into which additional DNA segments can be inserted, such as by standard molecular cloning techniques. Another type of vector is a viral vector, wherein virally-derived DNA or RNA sequences are present in the vector for packaging into a virus (e.g. retroviruses, replication defective retroviruses, adenoviruses, replication defective adenoviruses, and adeno-associated viruses (AAVs)). Viral vectors also include polynucleotides carried by a virus for transfection into a host cell. Certain vectors are capable of autonomous replication in a host cell into which they are introduced (e.g. bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively-linked. Such vectors are referred to herein as "expression vectors." Common expression vectors of utility in recombinant DNA techniques are often in the form of plasmids.

Recombinant expression vectors can comprise a nucleic acid of the invention in a form suitable for expression of the nucleic acid in a host cell, which means that the recombinant expression vectors include one or more regulatory elements, which may be selected on the basis of the host cells to be used for expression, that is operatively-linked to the nucleic acid sequence to be expressed. Within a recombinant expression vector, "operably linked" is intended to mean that the nucleotide sequence of interest is linked to the regulatory element(s) in a manner that allows for expression of the nucleotide sequence (e.g. in an in vitro transcription/translation system or in a host cell when the vector is introduced into the host cell). With regards to recombination and cloning methods, mention is made of U.S. patent application Ser. No. 10/815,730, published Sep. 2, 2004 as US 2004-0171156 A1, the contents of which are herein incorporated by reference in their entirety. Thus, the embodiments disclosed herein may also comprise transgenic cells comprising the CRISPR effector system. In certain example embodiments, the transgenic cell may function as an individual discrete volume. In other words samples comprising a masking construct may be delivered to a cell, for example in a suitable delivery vesicle and if the target is present in the delivery vesicle the CRISPR effector is activated and a detectable signal generated.

The vector(s) can include the regulatory element(s), e.g., promoter(s). The vector(s) can comprise Cas encoding sequences, and/or a single, but possibly also can comprise at least 3 or 8 or 16 or 32 or 48 or 50 guide RNA(s) (e.g., sgRNAs) encoding sequences, such as 1-2, 1-3, 1-4 1-5, 3-6, 3-7, 3-8, 3-9, 3-10, 3-8, 3-16, 3-30, 3-32, 3-48, 3-50 RNA(s) (e.g., sgRNAs). In a single vector there can be a promoter for each RNA (e.g., sgRNA), advantageously when there are up to about 16 RNA(s); and, when a single vector provides for more than 16 RNA(s), one or more promoter(s) can drive expression of more than one of the RNA(s), e.g., when there are 32 RNA(s), each promoter can drive expression of two RNA(s), and when there are 48 RNA(s), each promoter can drive expression of three RNA(s). By simple arithmetic and well established cloning protocols and the teachings in this disclosure one skilled in the art can readily practice the invention as to the RNA(s) for a suitable exemplary vector such as AAV, and a suitable promoter such as the U6 promoter. For example, the packaging limit of AAV is ~4.7 kb. The length of a single U6-gRNA (plus restriction sites for cloning) is 361 bp. Therefore, the skilled person can readily fit about 12-16, e.g., 13 U6-gRNA cassettes in a single vector. This can be assembled by any suitable means, such as a golden gate strategy used for TALE assembly (genome-engineering.org/taleffectors/). The skilled person can also use a tandem guide strategy to increase the number of U6-gRNAs by approximately 1.5 times, e.g., to increase from 12-16, e.g., 13 to approximately 18-24, e.g., about 19 U6-gRNAs. Therefore, one skilled in the art can readily reach approximately 18-24, e.g., about 19 promoter-RNAs, e.g., U6-gRNAs in a single vector, e.g., an AAV vector. A further means for increasing the number of promoters and RNAs in a vector is to use a single promoter (e.g., U6) to express an array of RNAs separated by cleavable sequences. And an even further means for increasing the number of promoter-RNAs in a vector, is to express an array of promoter-RNAs separated by cleavable sequences in the intron of a coding sequence or gene; and, in this instance it is advantageous to use a polymerase II promoter, which can have increased expression and enable the transcription of long RNA in a tissue specific manner. (see, e.g., nar.oxford-journals.org/content/34/7/e53.short and nature.com/mt/journal/v16/n9/abs/mt2008144a .html). In an advantageous embodiment, AAV may package U6 tandem gRNA targeting up to about 50 genes. Accordingly, from the knowledge in the art and the teachings in this disclosure the skilled person can readily make and use vector(s), e.g., a single vector, expressing multiple RNAs or guides under the control or operatively or functionally linked to one or more promoters-especially as to the numbers of RNAs or guides discussed herein, without any undue experimentation.

The guide RNA(s) encoding sequences and/or Cas encoding sequences, can be functionally or operatively linked to regulatory element(s) and hence the regulatory element(s) drive expression. The promoter(s) can be constitutive promoter(s) and/or conditional promoter(s) and/or inducible promoter(s) and/or tissue specific promoter(s). The promoter can be selected from the group consisting of RNA polymerases, pol I, pol II, pol III, T7, U6, H1, retroviral Rous sarcoma virus (RSV) LTR promoter, the cytomegalovirus (CMV) promoter, the SV40 promoter, the dihydrofolate reductase promoter, the β-actin promoter, the phosphoglycerol kinase (PGK) promoter, and the EF1α promoter. An advantageous promoter is U6 promoter.

Additional effectors for use according to the invention can be identified by their proximity to cas1 genes, for example, though not limited to, within the region 20 kb from the start of the cas1 gene and 20 kb from the end of the cas1 gene. In certain embodiments, the effector protein comprises at least one HEPN domain and at least 500 amino acids, and wherein the C2c2 effector protein is naturally present in a prokaryotic genome within 20 kb upstream or downstream of a Cas gene or a CRISPR array. Non-limiting examples of Cas proteins include Cas1, Cas1B, Cas2, Cas3, Cas4, Cas5, Cas6, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, homologues thereof, or modified versions thereof. In certain example embodiments, the C2c2 effector protein is naturally present in a prokaryotic genome within 20 kb upstream or downstream of a Cas 1 gene. The terms "orthologue" (also referred to as "ortholog" herein) and "homologue" (also referred to as "homolog" herein) are well known in the art. By means of further guidance, a "homologue" of a protein as used herein is a protein of the same species which performs the same or a similar function as the protein it is a homologue of. Homologous proteins may but need not be structurally related, or are only partially structurally related. An "orthologue" of a protein as used herein is a protein of a different species which performs the same or a similar function as the protein it is an orthologue of. Orthologous proteins may but need not be structurally related, or are only partially structurally related.

Guide Molecules

The methods described herein may be used to screen inhibition of CRISPR systems employing different types of guide molecules. As used herein, the term "guide sequence" and "guide molecule" in the context of a CRISPR-Cas system, comprises any polynucleotide sequence having sufficient complementarity with a target nucleic acid sequence to hybridize with the target nucleic acid sequence and direct sequence-specific binding of a nucleic acid-targeting complex to the target nucleic acid sequence. The guide sequences made using the methods disclosed herein may be a full-length guide sequence, a truncated guide sequence, a full-length sgRNA sequence, a truncated sgRNA sequence, or an E+F sgRNA sequence. In some embodiments, the degree of complementarity of the guide sequence to a given target sequence, when optimally aligned using a suitable alignment algorithm, is about or more than about 50%, 60%, 75%, 80%, 85%, 90%, 95%, 97.5%, 99%, or more. In certain example embodiments, the guide molecule comprises a guide sequence that may be designed to have at least one mismatch with the target sequence, such that a RNA duplex formed between the guide sequence and the target sequence. Accordingly, the degree of complementarity is preferably less than 99%. For instance, where the guide sequence consists of 24 nucleotides, the degree of complementarity is more particularly about 96% or less. In particular embodiments, the guide sequence is designed to have a stretch of two or more adjacent mismatching nucleotides, such that the degree of complementarity over the entire guide sequence is further reduced. For instance, where the guide sequence consists of 24 nucleotides, the degree of complementarity is more particularly about 96% or less, more particularly, about 92% or less, more particularly about 88% or less, more particularly about 84% or less, more particularly about 80% or less, more particularly about 76% or less, more particularly about 72% or less, depending on whether the stretch of two or more mismatching nucleotides encompasses 2, 3, 4, 5, 6 or 7 nucleotides, etc. In some embodiments, aside from the stretch of one or more mismatching nucleotides, the degree of complementarity, when optimally aligned using a suitable alignment algorithm, is about or more than about 50%, 60%, 75%, 80%, 85%, 90%, 95%, 97.5%, 99%, or more. Optimal alignment may be determined with the use of any suitable algorithm for aligning sequences, non-limiting example of which include the Smith-Waterman algorithm, the Needleman-Wunsch algorithm, algorithms based on the Burrows-Wheeler Transform (e.g., the Burrows Wheeler Aligner), ClustalW, Clustal X, BLAT, Novoalign (Novocraft Technologies; available at www.novocraft.com), ELAND (Illumina, San Diego, Calif.), SOAP (available at soap.genomics.org.cn), and Maq (available at maq.sourceforge.net). The ability of a guide sequence (within a nucleic acid-targeting guide RNA) to direct sequence-specific binding of a nucleic acid-targeting complex to a target nucleic acid sequence may be assessed by any suitable assay. For example, the components of a nucleic acid-targeting CRISPR system sufficient to form a nucleic acid-targeting complex, including the guide sequence to be tested, may be provided to a host cell having the corresponding target nucleic acid sequence, such as by transfection with vectors encoding the components of the nucleic acid-targeting complex, followed by an assessment of preferential targeting (e.g., cleavage) within the target nucleic acid sequence, such as by Surveyor assay as described herein. Similarly, cleavage of a target nucleic acid sequence (or a sequence in the vicinity thereof) may be evaluated in a test tube by providing the target nucleic acid sequence, components of a nucleic acid-targeting complex, including the guide sequence to be tested and a control guide sequence different from the test guide sequence, and comparing binding or rate of cleavage at or in the vicinity of the target sequence between the test and control guide sequence reactions. Other assays are possible, and will occur to those skilled in the art. A guide sequence, and hence a nucleic acid-targeting guide RNA may be selected to target any target nucleic acid sequence.

In certain embodiments, the guide sequence or spacer length of the guide molecules is from 15 to 50 nt. In certain embodiments, the spacer length of the guide RNA is at least 15 nucleotides. In certain embodiments, the spacer length is from 15 to 17 nt, e.g., 15, 16, or 17 nt, from 17 to 20 nt, e.g., 17, 18, 19, or 20 nt, from 20 to 24 nt, e.g., 20, 21, 22, 23, or 24 nt, from 23 to 25 nt, e.g., 23, 24, or 25 nt, from 24 to 27 nt, e.g., 24, 25, 26, or 27 nt, from 27-30 nt, e.g., 27, 28, 29, or 30 nt, from 30-35 nt, e.g., 30, 31, 32, 33, 34, or 35 nt, or 35 nt or longer. In certain example embodiment, the guide sequence is 15, 16, 17, 18, 19, 20, 21, 22, 23, 24, 25, 26, 27, 28, 29, 30, 31, 32, 33, 34, 35, 36, 37, 38, 39 40, 41, 42, 43, 44, 45, 46, 47 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 nt.

In some embodiments, the guide sequence is an RNA sequence of between 10 to 50 nt in length, but more particularly of about 20-30 nt advantageously about 20 nt, 23-25 nt or 24 nt. The guide sequence is selected so as to ensure that it hybridizes to the target sequence. This is described more in detail below. Selection can encompass further steps which increase efficacy and specificity.

In some embodiments, the guide sequence has a canonical length (e.g., about 15-30 nt) is used to hybridize with the target RNA or DNA. In some embodiments, a guide molecule is longer than the canonical length (e.g., >30 nt) is used to hybridize with the target RNA or DNA, such that a region of the guide sequence hybridizes with a region of the RNA or DNA strand outside of the Cas-guide target complex. This can be of interest where additional modifications, such deamination of nucleotides is of interest. In alternative embodiments, it is of interest to maintain the limitation of the canonical guide sequence length.

In some embodiments, the sequence of the guide molecule (direct repeat and/or spacer) is selected to reduce the degree secondary structure within the guide molecule. In some embodiments, about or less than about 75%, 50%, 40%, 30%, 25%, 20%, 15%, 10%, 5%, 1%, or fewer of the nucleotides of the nucleic acid-targeting guide RNA participate in self-complementary base pairing when optimally folded. Optimal folding may be determined by any suitable polynucleotide folding algorithm. Some programs are based on calculating the minimal Gibbs free energy. An example of one such algorithm is mFold, as described by Zuker and Stiegler (Nucleic Acids Res. 9 (1981), 133-148). Another example folding algorithm is the online webserver RNAfold, developed at Institute for Theoretical Chemistry at the University of Vienna, using the centroid structure prediction algorithm (see e.g., A. R. Gruber et al., 2008, Cell 106(1): 23-24; and PA Carr and GM Church, 2009, Nature Biotechnology 27(12): 1151-62).

In some embodiments, it is of interest to reduce the susceptibility of the guide molecule to RNA cleavage, such as to cleavage by Cas13. Accordingly, in particular embodiments, the guide molecule is adjusted to avoid cleavage by Cas13 or other RNA-cleaving enzymes.

In certain embodiments, the guide molecule comprises non-naturally occurring nucleic acids and/or non-naturally occurring nucleotides and/or nucleotide analogs, and/or chemically modifications. Preferably, these non-naturally occurring nucleic acids and non-naturally occurring nucleotides are located outside the guide sequence. Non-naturally occurring nucleic acids can include, for example, mixtures of naturally and non-naturally occurring nucleotides. Non-naturally occurring nucleotides and/or nucleotide analogs may be modified at the ribose, phosphate, and/or base moiety. In an embodiment of the invention, a guide nucleic acid comprises ribonucleotides and non-ribonucleotides. In one such embodiment, a guide comprises one or more ribonucleotides and one or more deoxyribonucleotides. In an embodiment of the invention, the guide comprises one or more non-naturally occurring nucleotide or nucleotide analog such as a nucleotide with phosphorothioate linkage, a locked nucleic acid (LNA) nucleotides comprising a methylene bridge between the 2' and 4' carbons of the ribose ring, or bridged nucleic acids (BNA). Other examples of modified nucleotides include 2'-O-methyl analogs, 2'-deoxy analogs, or 2'-fluoro analogs. Further examples of modified bases include, but are not limited to, 2-aminopurine, 5-bromo-uridine, pseudouridine, inosine, 7-methylguanosine. Examples of guide RNA chemical modifications include, without limitation, incorporation of 2'-O-methyl (M), 2'-O-methyl 3'phosphorothioate (MS), S-constrained ethyl (cEt), or 2'-O-methyl 3'thioPACE (MSP) at one or more terminal nucleotides. Such chemically modified guides can comprise increased stability and increased activity as compared to unmodified guides, though on-target vs. off-target specificity is not predictable. (See, Hendel, 2015, Nat Biotechnol. 33(9):985-9, doi: 10.1038/nbt.3290, published online 29 Jun. 2015 Ragdarm et al., 0215, *PNAS*, E7110-E7111; Allerson et al., *J. Med. Chem.* 2005, 48:901-904; Bramsen et al., *Front. Genet.*, 2012, 3:154; Deng et al., *PNAS*, 2015, 112:11870-11875; Sharma et al., *MedChemComm.*, 2014, 5:1454-1471; Hendel et al., *Nat. Biotechnol.* (2015) 33(9): 985-989; Li et al., *Nature Biomedical Engineering*, 2017, 1, 0066 DOI:10.1038/s41551-017-0066). In some embodiments, the 5' and/or 3' end of a guide RNA is modified by a variety of functional moieties including fluorescent dyes, polyethylene glycol, cholesterol, proteins, or detection tags. (See Kelly et al., 2016, *J. Biotech.* 233:74-83). In certain embodiments, a guide comprises ribonucleotides in a region that binds to a target RNA and one or more deoxyribonucleotides and/or nucleotide analogs in a region that binds to Cas13. In an embodiment of the invention, deoxyribonucleotides and/or nucleotide analogs are incorporated in engineered guide structures, such as, without limitation, stem-loop regions, and the seed region. For Cas13 guide, in certain embodiments, the modification is not in the 5'-handle of the stem-loop regions. Chemical modification in the 5'-handle of the stem-loop region of a guide may abolish its function (see Li, et al., *Nature Biomedical Engineering*, 2017, 1:0066). In certain embodiments, at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, or 75 nucleotides of a guide is chemically modified. In some embodiments, 3-5 nucleotides at either the 3' or the 5' end of a guide is chemically modified. In some embodiments, only minor modifications are introduced in the seed region, such as 2'-F modifications. In some embodiments, 2'-F modification is introduced at the 3' end of a guide. In certain embodiments, three to five nucleotides at the 5' and/or the 3' end of the guide are chemically modified with 2'-O-methyl (M), 2'-O-methyl 3' phosphorothioate (MS), S-constrained ethyl (cEt), or 2'-O-methyl 3' thioPACE (MSP). Such modification can enhance genome editing efficiency (see Hendel et al., *Nat. Biotechnol.* (2015) 33(9): 985-989). In certain embodiments, all of the phosphodiester bonds of a guide are substituted with phosphorothioates (PS) for enhancing levels of gene disruption. In certain embodiments, more than five nucleotides at the 5' and/or the 3' end of the guide are chemically modified with 2'-O-Me, 2'-F or S-constrained ethyl (cEt). Such chemically modified guide can mediate enhanced levels of gene disruption (see Ragdarm et al., 0215, PNAS, E7110-E7111). In an embodiment of the invention, a guide is modified to comprise a chemical moiety at its 3' and/or 5' end. Such moieties include, but are not limited to amine, azide, alkyne, thio, dibenzocyclooctyne (DBCO), or Rhodamine. In certain embodiment, the chemical moiety is conjugated to the guide by a linker, such as an alkyl chain. In certain embodiments, the chemical moiety of the modified guide can be used to attach the guide to another molecule, such as DNA, RNA, protein, or nanoparticles. Such chemically modified guide can be used to identify or enrich cells generically edited by a CRISPR system (see Lee et al., *eLife*, 2017, 6:e25312, DOI:10.7554).

In some embodiments, the modification to the guide is a chemical modification, an insertion, a deletion or a split. In some embodiments, the chemical modification includes, but is not limited to, incorporation of 2'-O-methyl (M) analogs, 2'-deoxy analogs, 2-thiouridine analogs, N6-methyladenosine analogs, 2'-fluoro analogs, 2-aminopurine, 5-bromo-uridine, pseudouridine (Ψ), N1-methylpseudouridine (me1Ψ), 5-methoxyuridine(5moU), inosine, 7-methylguanosine, 2'-O-methyl 3'phosphorothioate (MS), S-constrained ethyl (cEt), phosphorothioate (PS), or 2'-O-methyl 3'thioPACE (MSP). In some embodiments, the guide comprises one or more of phosphorothioate modifications. In certain embodiments, at least 1, 2, 3, 4, 5, 6, 7, 8, 9, 10, 11, 12, 13, 14, 15, 16, 17, 18, 19, 20, or 25 nucleotides of the guide are chemically modified. In certain embodiments, one or more nucleotides in the seed region are chemically modified. In certain embodiments, one or more nucleotides in the 3'-terminus are chemically modified. In certain embodiments, none of the nucleotides in the 5'-handle is chemically modified. In some embodiments, the chemical modification in the seed region is a minor modification, such as incorporation of a 2'-fluoro analog. In a specific embodiment, one nucleotide of the seed region is replaced with a 2'-fluoro analog. In some embodiments, 5 to 10 nucleotides in the 3'-terminus are chemically modified. Such chemical modifications at the 3'-terminus of the Cas13 CrRNA may improve Cas13 activity. In a specific embodiment, 1, 2, 3, 4, 5, 6, 7, 8, 9 or 10 nucleotides in the 3'-terminus are replaced with 2'-fluoro analogues. In a specific embodiment, 1, 2, 3, 4, 5, 6, 7, 8, 9 or 10 nucleotides in the 3'-terminus are replaced with 2'-O-methyl (M) analogs.

In some embodiments, the loop of the 5'-handle of the guide is modified. In some embodiments, the loop of the 5'-handle of the guide is modified to have a deletion, an insertion, a split, or chemical modifications. In certain embodiments, the modified loop comprises 3, 4, or 5 nucleotides. In certain embodiments, the loop comprises the sequence of UCUU, UUUU, UAUU, or UGUU.

In some embodiments, the guide molecule forms a stem-loop with a separate non-covalently linked sequence, which can be DNA or RNA. In particular embodiments, the sequences forming the guide are first synthesized using the standard phosphoramidite synthetic protocol (Herdewijn, P., ed., Methods in Molecular Biology Col 288, Oligonucleotide Synthesis: Methods and Applications, Humana Press, New Jersey (2012)). In some embodiments, these sequences can be functionalized to contain an appropriate functional group for ligation using the standard protocol known in the art (Hermanson, G. T., Bioconjugate Techniques, Academic Press (2013)). Examples of functional groups include, but are not limited to, hydroxyl, amine, carboxylic acid, carboxylic acid halide, carboxylic acid active ester, aldehyde, carbonyl, chlorocarbonyl, imidazolylcarbonyl, hydrozide, semicarbazide, thio semicarbazide, thiol, maleimide, haloalkyl, sulfonyl, ally, propargyl, diene, alkyne, and azide. Once this sequence is functionalized, a covalent chemical bond or linkage can be formed between this sequence and the direct repeat sequence. Examples of chemical bonds include, but are not limited to, those based on carbamates, ethers, esters, amides, imines, amidines, aminotrizines, hydrozone, disulfides, thioethers, thioesters, phosphorothioates, phosphorodithioates, sulfonamides, sulfonates, sulfones, sulfoxides, ureas, thioureas, hydrazide, oxime, triazole, photolabile linkages, C—C bond forming groups such as Diels-Alder cyclo-addition pairs or ring-closing metathesis pairs, and Michael reaction pairs.

In some embodiments, these stem-loop forming sequences can be chemically synthesized. In some embodiments, the chemical synthesis uses automated, solid-phase oligonucleotide synthesis machines with 2'-acetoxyethyl orthoester (2'-ACE) (Scaringe et al., J. Am. Chem. Soc. (1998) 120: 11820-11821; Scaringe, Methods Enzymol. (2000) 317: 3-18) or 2'-thionocarbamate (2'-TC) chemistry (Dellinger et al., J. Am. Chem. Soc. (2011) 133: 11540-11546; Hendel et al., Nat. Biotechnol. (2015) 33:985-989).

In certain embodiments, the guide molecule comprises (1) a guide sequence capable of hybridizing to a target locus and (2) a tracr mate or direct repeat sequence whereby the direct repeat sequence is located upstream (i.e., 5') from the guide sequence. In a particular embodiment the seed sequence (i.e. the sequence essential critical for recognition and/or hybridization to the sequence at the target locus) of th guide sequence is approximately within the first 10 nucleotides of the guide sequence.

In a particular embodiment the guide molecule comprises a guide sequence linked to a direct repeat sequence, wherein the direct repeat sequence comprises one or more stem loops or optimized secondary structures. In particular embodiments, the direct repeat has a minimum length of 16 nts and a single stem loop. In further embodiments the direct repeat has a length longer than 16 nts, preferably more than 17 nts, and has more than one stem loops or optimized secondary structures. In particular embodiments the guide molecule comprises or consists of the guide sequence linked to all or part of the natural direct repeat sequence. A typical Type V or Type VI CRISPR-cas guide molecule comprises (in 3' to 5' direction or in 5' to 3' direction): a guide sequence a first complimentary stretch (the "repeat"), a loop (which is typically 4 or 5 nucleotides long), a second complimentary stretch (the "anti-repeat" being complimentary to the repeat), and a poly A (often poly U in RNA) tail (terminator). In certain embodiments, the direct repeat sequence retains its natural architecture and forms a single stem loop. In particular embodiments, certain aspects of the guide architecture can be modified, for example by addition, subtraction, or substitution of features, whereas certain other aspects of guide architecture are maintained. Preferred locations for engineered guide molecule modifications, including but not limited to insertions, deletions, and substitutions include guide termini and regions of the guide molecule that are exposed when complexed with the CRISPR-Cas protein and/or target, for example the stemloop of the direct repeat sequence.

In particular embodiments, the stem comprises at least about 4 bp comprising complementary X and Y sequences, although stems of more, e.g., 5, 6, 7, 8, 9, 10, 11 or 12 or fewer, e.g., 3, 2, base pairs are also contemplated. Thus, for example X2-10 and Y2-10 (wherein X and Y represent any complementary set of nucleotides) may be contemplated. In one aspect, the stem made of the X and Y nucleotides, together with the loop will form a complete hairpin in the overall secondary structure; and, this may be advantageous and the amount of base pairs can be any amount that forms a complete hairpin. In one aspect, any complementary X:Y basepairing sequence (e.g., as to length) is tolerated, so long as the secondary structure of the entire guide molecule is preserved. In one aspect, the loop that connects the stem made of X:Y basepairs can be any sequence of the same length (e.g., 4 or 5 nucleotides) or longer that does not interrupt the overall secondary structure of the guide molecule. In one aspect, the stemloop can further comprise, e.g., an MS2 aptamer. In one aspect, the stem comprises about 5-7 bp comprising complementary X and Y sequences, although stems of more or fewer basepairs are also contemplated. In one aspect, non-Watson Crick basepairing is contemplated, where such pairing otherwise generally preserves the architecture of the stemloop at that position.

In particular embodiments the natural hairpin or stemloop structure of the guide molecule is extended or replaced by an extended stemloop. It has been demonstrated that extension of the stem can enhance the assembly of the guide molecule with the CRISPR-Cas protein (Chen et al. Cell. (2013); 155(7): 1479-1491). In particular embodiments the stem of the stemloop is extended by at least 1, 2, 3, 4, 5 or more complementary basepairs (i.e. corresponding to the addition of 2, 4, 6, 8, 10 or more nucleotides in the guide molecule). In particular embodiments these are located at the end of the stem, adjacent to the loop of the stemloop.

In particular embodiments, the susceptibility of the guide molecule to RNAses or to decreased expression can be reduced by slight modifications of the sequence of the guide molecule which do not affect its function. For instance, in particular embodiments, premature termination of transcription, such as premature transcription of U6 Pol-III, can be removed by modifying a putative Pol-III terminator (4 consecutive U's) in the guide molecules sequence. Where such sequence modification is required in the stemloop of the guide molecule, it is preferably ensured by a basepair flip.

In a particular embodiment, the direct repeat may be modified to comprise one or more protein-binding RNA aptamers. In a particular embodiment, one or more aptamers may be included such as part of optimized secondary structure. Such aptamers may be capable of binding a bacteriophage coat protein as detailed further herein.

In some embodiments, the guide molecule forms a duplex with a target RNA comprising at least one target cytosine residue to be edited. Upon hybridization of the guide RNA molecule to the target RNA, the cytidine deaminase binds to the single strand RNA in the duplex made accessible by the mismatch in the guide sequence and catalyzes deamination of one or more target cytosine residues comprised within the stretch of mismatching nucleotides.

A guide sequence, and hence a nucleic acid-targeting guide RNA may be selected to target any target nucleic acid sequence. The target sequence may be mRNA.

In certain embodiments, the target sequence should be associated with a PAM (protospacer adjacent motif) or PFS (protospacer flanking sequence or site); that is, a short sequence recognized by the CRISPR complex. Depending on the nature of the CRISPR-Cas protein, the target sequence should be selected such that its complementary sequence in the DNA duplex (also referred to herein as the non-target sequence) is upstream or downstream of the PAM. In the embodiments of the present invention where the CRISPR-Cas protein is a Cas13 protein, the complementary sequence of the target sequence is downstream or 3' of the PAM or upstream or 5' of the PAM. The precise sequence and length requirements for the PAM differ depending on the Cas13 protein used, but PAMs are typically 2-5 base pair sequences adjacent the protospacer (that is, the target sequence). Examples of the natural PAM sequences for different Cas13 orthologues are provided herein below and the skilled person will be able to identify further PAM sequences for use with a given Cas13 protein.

Further, engineering of the PAM Interacting (PI) domain may allow programing of PAM specificity, improve target site recognition fidelity, and increase the versatility of the CRISPR-Cas protein, for example as described for Cas9 in Kleinstiver B P et al. Engineered CRISPR-Cas9 nucleases with altered PAM specificities. Nature. 2015 Jul. 23; 523 (7561):481-5. doi: 10.1038/nature14592. As further detailed herein, the skilled person will understand that Cas13 proteins may be modified analogously.

In particular embodiment, the guide is an escorted guide. By "escorted" is meant that the CRISPR-Cas system or complex or guide is delivered to a selected time or place within a cell, so that activity of the CRISPR-Cas system or complex or guide is spatially or temporally controlled. For example, the activity and destination of the 3 CRISPR-Cas system or complex or guide may be controlled by an escort RNA aptamer sequence that has binding affinity for an aptamer ligand, such as a cell surface protein or other localized cellular component. Alternatively, the escort aptamer may for example be responsive to an aptamer effector on or in the cell, such as a transient effector, such as an external energy source that is applied to the cell at a particular time.

The escorted CRISPR-Cas systems or complexes have a guide molecule with a functional structure designed to improve guide molecule structure, architecture, stability, genetic expression, or any combination thereof. Such a structure can include an aptamer.

Aptamers are biomolecules that can be designed or selected to bind tightly to other ligands, for example using a technique called systematic evolution of ligands by exponential enrichment (SELEX; Tuerk C, Gold L: "Systematic evolution of ligands by exponential enrichment: RNA ligands to bacteriophage T4 DNA polymerase." Science 1990, 249:505-510). Nucleic acid aptamers can for example be selected from pools of random-sequence oligonucleotides, with high binding affinities and specificities for a wide range of biomedically relevant targets, suggesting a wide range of therapeutic utilities for aptamers (Keefe, Anthony D., Supriya Pai, and Andrew Ellington. "Aptamers as therapeutics." Nature Reviews Drug Discovery 9.7 (2010): 537-550). These characteristics also suggest a wide range of uses for aptamers as drug delivery vehicles (Levy-Nissenbaum, Etgar, et al. "Nanotechnology and aptamers: applications in drug delivery." Trends in biotechnology 26.8

(2008): 442-449; and, Hicke B J, Stephens A W. "Escort aptamers: a delivery service for diagnosis and therapy." J Clin Invest 2000, 106:923-928.). Aptamers may also be constructed that function as molecular switches, responding to a que by changing properties, such as RNA aptamers that bind fluorophores to mimic the activity of green fluorescent protein (Paige, Jeremy S., Karen Y. Wu, and Samie R. Jaffrey. "RNA mimics of green fluorescent protein." Science 333.6042 (2011): 642-646). It has also been suggested that aptamers may be used as components of targeted siRNA therapeutic delivery systems, for example targeting cell surface proteins (Zhou, Jiehua, and John J. Rossi. "Aptamer-targeted cell-specific RNA interference." Silence 1.1 (2010): 4).

Accordingly, in particular embodiments, the guide molecule is modified, e.g., by one or more aptamer(s) designed to improve guide molecule delivery, including delivery across the cellular membrane, to intracellular compartments, or into the nucleus. Such a structure can include, either in addition to the one or more aptamer(s) or without such one or more aptamer(s), moiety(ies) so as to render the guide molecule deliverable, inducible or responsive to a selected effector. The invention accordingly comprehends a guide molecule that responds to normal or pathological physiological conditions, including without limitation pH, hypoxia, $O_2$ concentration, temperature, protein concentration, enzymatic concentration, lipid structure, light exposure, mechanical disruption (e.g. ultrasound waves), magnetic fields, electric fields, or electromagnetic radiation.

Light responsiveness of an inducible system may be achieved via the activation and binding of cryptochrome-2 and CIB1. Blue light stimulation induces an activating conformational change in cryptochrome-2, resulting in recruitment of its binding partner CIB1. This binding is fast and reversible, achieving saturation in <15 sec following pulsed stimulation and returning to baseline <15 min after the end of stimulation. These rapid binding kinetics result in a system temporally bound only by the speed of transcription/translation and transcript/protein degradation, rather than uptake and clearance of inducing agents. Crytochrome-2 activation is also highly sensitive, allowing for the use of low light intensity stimulation and mitigating the risks of phototoxicity. Further, in a context such as the intact mammalian brain, variable light intensity may be used to control the size of a stimulated region, allowing for greater precision than vector delivery alone may offer.

The invention contemplates energy sources such as electromagnetic radiation, sound energy or thermal energy to induce the guide. Advantageously, the electromagnetic radiation is a component of visible light. In a preferred embodiment, the light is a blue light with a wavelength of about 450 to about 495 nm. In an especially preferred embodiment, the wavelength is about 488 nm. In another preferred embodiment, the light stimulation is via pulses. The light power may range from about 0-9 mW/cm$^2$. In a preferred embodiment, a stimulation paradigm of as low as 0.25 sec every 15 sec should result in maximal activation.

The chemical or energy sensitive guide may undergo a conformational change upon induction by the binding of a chemical source or by the energy allowing it act as a guide and have the Cas13 CRISPR-Cas system or complex function. The invention can involve applying the chemical source or energy so as to have the guide function and the Cas13 CRISPR-Cas system or complex function; and optionally further determining that the expression of the genomic locus is altered.

There are several different designs of this chemical inducible system: 1. ABI-PYL based system inducible by Abscisic Acid (ABA) (see, e.g., stke.sciencemag.org/cgi/content/abstract/sigtrans; 4/164/rs2), 2. FKBP-FRB based system inducible by rapamycin (or related chemicals based on rapamycin) (see, e.g., www.nature.com/nmeth/journal/v2/n6/full/nmeth763.html), 3. GID1-GAI based system inducible by Gibberellin (GA) (see, e.g., www.nature.com/nchembio/journal/v8/n5/full/nchembio.922.html).

A chemical inducible system can be an estrogen receptor (ER) based system inducible by 4-hydroxytamoxifen (4OHT) (see, e.g., www.pnas.org/content/104/3/1027.abstract). A mutated ligand-binding domain of the estrogen receptor called ERT2 translocates into the nucleus of cells upon binding of 4-hydroxytamoxifen. In further embodiments of the invention any naturally occurring or engineered derivative of any nuclear receptor, thyroid hormone receptor, retinoic acid receptor, estrogen receptor, estrogen-related receptor, glucocorticoid receptor, progesterone receptor, androgen receptor may be used in inducible systems analogous to the ER based inducible system.

Another inducible system is based on the design using Transient receptor potential (TRP) ion channel-based system inducible by energy, heat or radio-wave (see, e.g., www.sciencemag.org/content/336/6081/604). These TRP family proteins respond to different stimuli, including light and heat. When this protein is activated by light or heat, the ion channel will open and allow the entering of ions such as calcium into the plasma membrane. This influx of ions will bind to intracellular ion interacting partners linked to a polypeptide including the guide and the other components of the Cas13 CRISPR-Cas complex or system, and the binding will induce the change of sub-cellular localization of the polypeptide, leading to the entire polypeptide entering the nucleus of cells. Once inside the nucleus, the guide protein and the other components of the Cas13 CRISPR-Cas complex will be active and modulating target gene expression in cells.

While light activation may be an advantageous embodiment, sometimes it may be disadvantageous especially for in vivo applications in which the light may not penetrate the skin or other organs. In this instance, other methods of energy activation are contemplated, in particular, electric field energy and/or ultrasound which have a similar effect.

Electric field energy is preferably administered substantially as described in the art, using one or more electric pulses of from about 1 Volt/cm to about 10 kVolts/cm under in vivo conditions. Instead of or in addition to the pulses, the electric field may be delivered in a continuous manner. The electric pulse may be applied for between 1 μs and 500 milliseconds, preferably between 1 μs and 100 milliseconds. The electric field may be applied continuously or in a pulsed manner for 5 about minutes.

As used herein, 'electric field energy' is the electrical energy to which a cell is exposed. Preferably the electric field has a strength of from about 1 Volt/cm to about 10 kVolts/cm or more under in vivo conditions (see WO97/49450).

As used herein, the term "electric field" includes one or more pulses at variable capacitance and voltage and including exponential and/or square wave and/or modulated wave and/or modulated square wave forms. References to electric fields and electricity should be taken to include reference the presence of an electric potential difference in the environment of a cell. Such an environment may be set up by way of static electricity, alternating current (AC), direct current (DC), etc, as known in the art. The electric field may be uniform, non-uniform or otherwise, and may vary in strength and/or direction in a time dependent manner.

Single or multiple applications of electric field, as well as single or multiple applications of ultrasound are also possible, in any order and in any combination. The ultrasound and/or the electric field may be delivered as single or multiple continuous applications, or as pulses (pulsatile delivery).

Electroporation has been used in both in vitro and in vivo procedures to introduce foreign material into living cells. With in vitro applications, a sample of live cells is first mixed with the agent of interest and placed between electrodes such as parallel plates. Then, the electrodes apply an electrical field to the cell/implant mixture. Examples of systems that perform in vitro electroporation include the Electro Cell Manipulator ECM600 product, and the Electro Square Porator T820, both made by the BTX Division of Genetronics, Inc (see U.S. Pat. No. 5,869,326).

The known electroporation techniques (both in vitro and in vivo) function by applying a brief high voltage pulse to electrodes positioned around the treatment region. The electric field generated between the electrodes causes the cell membranes to temporarily become porous, whereupon molecules of the agent of interest enter the cells. In known electroporation applications, this electric field comprises a single square wave pulse on the order of 1000 V/cm, of about 100.mu.s duration. Such a pulse may be generated, for example, in known applications of the Electro Square Porator T820.

Preferably, the electric field has a strength of from about 1 V/cm to about 10 kV/cm under in vitro conditions. Thus, the electric field may have a strength of 1 V/cm, 2 V/cm, 3 V/cm, 4 V/cm, 5 V/cm, 6 V/cm, 7 V/cm, 8 V/cm, 9 V/cm, 10 V/cm, 20 V/cm, 50 V/cm, 100 V/cm, 200 V/cm, 300 V/cm, 400 V/cm, 500 V/cm, 600 V/cm, 700 V/cm, 800 V/cm, 900 V/cm, 1 kV/cm, 2 kV/cm, 5 kV/cm, 10 kV/cm, 20 kV/cm, 50 kV/cm or more. More preferably from about 0.5 kV/cm to about 4.0 kV/cm under in vitro conditions. Preferably the electric field has a strength of from about 1 V/cm to about 10 kV/cm under in vivo conditions. However, the electric field strengths may be lowered where the number of pulses delivered to the target site are increased. Thus, pulsatile delivery of electric fields at lower field strengths is envisaged.

Preferably the application of the electric field is in the form of multiple pulses such as double pulses of the same strength and capacitance or sequential pulses of varying strength and/or capacitance. As used herein, the term "pulse" includes one or more electric pulses at variable capacitance and voltage and including exponential and/or square wave and/or modulated wave/square wave forms.

Preferably the electric pulse is delivered as a waveform selected from an exponential wave form, a square wave form, a modulated wave form and a modulated square wave form.

A preferred embodiment employs direct current at low voltage. Thus, applicants disclose the use of an electric field which is applied to the cell, tissue or tissue mass at a field strength of between 1V/cm and 20V/cm, for a period of 100 milliseconds or more, preferably 15 minutes or more.

Ultrasound is advantageously administered at a power level of from about 0.05 W/cm2 to about 100 W/cm2. Diagnostic or therapeutic ultrasound may be used, or combinations thereof.

As used herein, the term "ultrasound" refers to a form of energy which consists of mechanical vibrations the frequencies of which are so high they are above the range of human hearing. Lower frequency limit of the ultrasonic spectrum may generally be taken as about 20 kHz. Most diagnostic applications of ultrasound employ frequencies in the range 1 and 15 MHz' (From Ultrasonics in Clinical Diagnosis, P. N. T. Wells, ed., 2nd. Edition, Publ. Churchill Livingstone [Edinburgh, London & NY, 1977]).

Ultrasound has been used in both diagnostic and therapeutic applications. When used as a diagnostic tool ("diagnostic ultrasound"), ultrasound is typically used in an energy density range of up to about 100 mW/cm2 (FDA recommendation), although energy densities of up to 750 mW/cm2 have been used. In physiotherapy, ultrasound is typically used as an energy source in a range up to about 3 to 4 W/cm2 (WHO recommendation). In other therapeutic applications, higher intensities of ultrasound may be employed, for example, HIFU at 100 W/cm up to 1 kW/cm2 (or even higher) for short periods of time. The term "ultrasound" as used in this specification is intended to encompass diagnostic, therapeutic and focused ultrasound.

Focused ultrasound (FUS) allows thermal energy to be delivered without an invasive probe (see Morocz et al 1998 Journal of Magnetic Resonance Imaging Vol. 8, No. 1, pp. 136-142. Another form of focused ultrasound is high intensity focused ultrasound (HIFU) which is reviewed by Moussatov et al in Ultrasonics (1998) Vol. 36, No. 8, pp. 893-900 and Tran Huu Hue et al. in Acustica (1997) Vol. 83, No. 6, pp. 1103-1106.

Preferably, a combination of diagnostic ultrasound and a therapeutic ultrasound is employed. This combination is not intended to be limiting, however, and the skilled reader will appreciate that any variety of combinations of ultrasound may be used. Additionally, the energy density, frequency of ultrasound, and period of exposure may be varied.

Preferably the exposure to an ultrasound energy source is at a power density of from about 0.05 to about 100 Wcm-2. Even more preferably, the exposure to an ultrasound energy source is at a power density of from about 1 to about 15 Wcm-2.

Preferably the exposure to an ultrasound energy source is at a frequency of from about 0.015 to about 10.0 MHz. More preferably the exposure to an ultrasound energy source is at a frequency of from about 0.02 to about 5.0 MHz or about 6.0 MHz. Most preferably, the ultrasound is applied at a frequency of 3 MHz.

Preferably the exposure is for periods of from about 10 milliseconds to about 60 minutes. Preferably the exposure is for periods of from about 1 second to about 5 minutes. More preferably, the ultrasound is applied for about 2 minutes. Depending on the particular target cell to be disrupted, however, the exposure may be for a longer duration, for example, for 15 minutes.

Advantageously, the target tissue is exposed to an ultrasound energy source at an acoustic power density of from about 0.05 Wcm-2 to about 10 Wcm-2 with a frequency ranging from about 0.015 to about 10 MHz (see WO 98/52609). However, alternatives are also possible, for example, exposure to an ultrasound energy source at an acoustic power density of above 100 Wcm-2, but for reduced periods of time, for example, 1000 Wcm-2 for periods in the millisecond range or less.

Preferably the application of the ultrasound is in the form of multiple pulses; thus, both continuous wave and pulsed wave (pulsatile delivery of ultrasound) may be employed in any combination. For example, continuous wave ultrasound may be applied, followed by pulsed wave ultrasound, or vice versa. This may be repeated any number of times, in any order and combination. The pulsed wave ultrasound may be applied against a background of continuous wave ultrasound, and any number of pulses may be used in any number of groups.

Preferably, the ultrasound may comprise pulsed wave ultrasound. In a highly preferred embodiment, the ultrasound is applied at a power density of 0.7 Wcm-2 or 1.25 Wcm-2 as a continuous wave. Higher power densities may be employed if pulsed wave ultrasound is used.

Use of ultrasound is advantageous as, like light, it may be focused accurately on a target. Moreover, ultrasound is advantageous as it may be focused more deeply into tissues unlike light. It is therefore better suited to whole-tissue penetration (such as but not limited to a lobe of the liver) or whole organ (such as but not limited to the entire liver or an entire muscle, such as the heart) therapy. Another important advantage is that ultrasound is a non-invasive stimulus which is used in a wide variety of diagnostic and therapeutic applications. By way of example, ultrasound is well known in medical imaging techniques and, additionally, in orthopedic therapy. Furthermore, instruments suitable for the application of ultrasound to a subject vertebrate are widely available and their use is well known in the art.

In particular embodiments, the guide molecule is modified by a secondary structure to increase the specificity of the CRISPR-Cas system and the secondary structure can protect against exonuclease activity and allow for 5' additions to the guide sequence also referred to herein as a protected guide molecule.

In one aspect, the invention provides for hybridizing a "protector RNA" to a sequence of the guide molecule, wherein the "protector RNA" is an RNA strand complementary to the 3' end of the guide molecule to thereby generate a partially double-stranded guide RNA. In an embodiment of the invention, protecting mismatched bases (i.e. the bases of the guide molecule which do not form part of the guide sequence) with a perfectly complementary protector sequence decreases the likelihood of target RNA binding to the mismatched basepairs at the 3' end. In particular embodiments of the invention, additional sequences comprising an extended length may also be present within the guide molecule such that the guide comprises a protector sequence within the guide molecule. This "protector sequence" ensures that the guide molecule comprises a "protected sequence" in addition to an "exposed sequence" (comprising the part of the guide sequence hybridizing to the target sequence). In particular embodiments, the guide molecule is modified by the presence of the protector guide to comprise a secondary structure such as a hairpin. Advantageously there are three or four to thirty or more, e.g., about 10 or more, contiguous base pairs having complementarity to the protected sequence, the guide sequence or both. It is advantageous that the protected portion does not impede thermodynamics of the CRISPR-Cas system interacting with its target. By providing such an extension including a partially double stranded guide molecule, the guide molecule is considered protected and results in improved specific binding of the CRISPR-Cas complex, while maintaining specific activity.

In particular embodiments, use is made of a truncated guide (tru-guide), i.e. a guide molecule which comprises a guide sequence which is truncated in length with respect to the canonical guide sequence length. As described by Nowak et al. (Nucleic Acids Res (2016) 44 (20): 9555-9564), such guides may allow catalytically active CRISPR-Cas enzyme to bind its target without cleaving the target RNA. In particular embodiments, a truncated guide is used which allows the binding of the target but retains only nickase activity of the CRISPR-Cas enzyme.

CRISPR RNA-Targeting Effector Proteins

In one example embodiment, the CRISPR system effector protein is an RNA-targeting effector protein. In certain embodiments, the CRISPR system effector protein is a Type VI CRISPR system targeting RNA (e.g., Cas13a, Cas13b, Cas13c or Cas13d). Example RNA-targeting effector proteins include Cas13b and C2c2 (now known as Cas13a). It will be understood that the term "C2c2" herein is used interchangeably with "Cas13a". "C2c2" is now referred to as "Cas13a", and the terms are used interchangeably herein unless indicated otherwise. As used herein, the term "Cas13" refers to any Type VI CRISPR system targeting RNA (e.g., Cas13a, Cas13b, Cas13c or Cas13d). When the CRISPR protein is a C2c2 protein, a tracrRNA is not required. C2c2 has been described in Abudayyeh et al. (2016) "C2c2 is a single-component programmable RNA-guided RNA-targeting CRISPR effector"; Science; DOI: 10.1126/science.aaf5573; and Shmakov et al. (2015) "Discovery and Functional Characterization of Diverse Class 2 CRISPR-Cas Systems", Molecular Cell, DOI: dx.doi.org/10.1016/j.molcel.2015.10.008; which are incorporated herein in their entirety by reference. Cas13b has been described in Smargon et al. (2017) "Cas13b Is a Type VI-B CRISPR-Associated RNA-Guided RNases Differentially Regulated by Accessory Proteins Csx27 and Csx28," Molecular Cell. 65, 1-13; dx.doi.org/10.1016/j.molcel.2016.12.023., which is incorporated herein in its entirety by reference.

In some embodiments, one or more elements of a nucleic acid-targeting system is derived from a particular organism comprising an endogenous CRISPR RNA-targeting system. In certain example embodiments, the effector protein CRISPR RNA-targeting system comprises at least one HEPN domain, including but not limited to the HEPN domains described herein, HEPN domains known in the art, and domains recognized to be HEPN domains by comparison to consensus sequence motifs. Several such domains are provided herein. In one non-limiting example, a consensus sequence can be derived from the sequences of C2c2 or Cas13b orthologs provided herein. In certain example embodiments, the effector protein comprises a single HEPN domain. In certain other example embodiments, the effector protein comprises two HEPN domains.

In one example embodiment, the effector protein comprise one or more HEPN domains comprising a RxxxxH motif sequence. The RxxxxH motif sequence can be, without limitation, from a HEPN domain described herein or a HEPN domain known in the art. RxxxxH motif sequences further include motif sequences created by combining portions of two or more HEPN domains. As noted, consensus sequences can be derived from the sequences of the orthologs disclosed in U.S. Provisional Patent Application 62/432,240 entitled "Novel CRISPR Enzymes and Systems," U.S. Provisional Patent Application 62/471,710 entitled "Novel Type VI CRISPR Orthologs and Systems" filed on Mar. 15, 2017, and U.S. Provisional Patent Application entitled "Novel Type VI CRISPR Orthologs and Systems," filed on Apr. 12, 2017.

In certain other example embodiments, the CRISPR system effector protein is a C2c2 nuclease (also referred to as Cas13a). The activity of C2c2 may depend on the presence of two HEPN domains. These have been shown to be RNase domains, i.e. nuclease (in particular an endonuclease) cutting RNA. C2c2 HEPN may also target DNA, or potentially DNA and/or RNA. On the basis that the HEPN domains of C2c2 are at least capable of binding to and, in their wild-type form, cutting RNA, then it is preferred that the C2c2 effector protein has RNase function. Regarding C2c2 CRISPR systems, reference is made to U.S. Provisional 62/351,662 filed on Jun. 17, 2016 and U.S. Provisional 62/376,377 filed on Aug. 17, 2016. Reference is also made to U.S. Provisional 62/351,803 filed on Jun. 17, 2016. Reference is also made to U.S. Provisional entitled "Novel Crispr Enzymes and Systems" filed Dec. 8, 2016 bearing Broad Institute No. 10035.PA4. Reference is further made to East-Seletsky et al. "Two distinct RNase activities of CRISPR-C2c2 enable guide-RNA processing and RNA detection" Nature doi:10/1038/nature19802 and Abudayyeh et al. "C2c2 is a single-component programmable RNA-guided RNA targeting CRISPR effector" bioRxiv doi:10.1101/054742.

In certain embodiments, the C2c2 effector protein is from an organism of a genus selected from the group consisting of: Leptotrichia, Listeria, Corynebacterium, Sutterella, Legionella, Treponema, Filifactor, Eubacterium, Streptococcus, Lactobacillus, Mycoplasma, Bacteroides, Fluviicola, Flavobacterium, Sphaerochaeta, Azospirillum, Gluconacetobacter, Neisseria, Roseburia, Parvibaculum, Staphylococcus, Nitratifractor, Mycoplasma, Campylobacter, and Lachnospira, or the C2c2 effector protein is an organism selected from the group consisting of: Leptotrichia shahii, Leptotrichia. wadei, Listeria seeligeri, Clostridium aminophilum, Carnobacterium gallinarum, Paludibacter propionicigenes, Listeria weihenstephanensis, or the C2c2 effector protein is a L. wadei F0279 or L. wadei F0279 (Lw2) C2C2 effector protein. In another embodiment, the one or more guide RNAs are designed to detect a single nucleotide polymorphism, splice variant of a transcript, or a frameshift mutation in a target RNA or DNA.

In certain example embodiments, the RNA-targeting effector protein is a Type VI-B effector protein, such as Cas13b and Group 29 or Group 30 proteins. In certain example embodiments, the RNA-targeting effector protein comprises one or more HEPN domains. In certain example embodiments, the RNA-targeting effector protein comprises a C-terminal HEPN domain, a N-terminal HEPN domain, or both. Regarding example Type VI-B effector proteins that may be used in the context of this invention, reference is made to U.S. application Ser. No. 15/331,792 entitled "Novel CRISPR Enzymes and Systems" and filed Oct. 21, 2016, International Patent Application No. PCT/US2016/058302 entitled "Novel CRISPR Enzymes and Systems", and filed Oct. 21, 2016, and Smargon et al. "Cas13b is a Type VI-B CRISPR-associated RNA-Guided RNase differentially regulated by accessory proteins Csx27 and Csx28" Molecular Cell, 65, 1-13 (2017); dx.doi.org/10.1016/j.molcel.2016.12.023, and U.S. Provisional Application No. to be assigned, entitled "Novel Cas13b Orthologues CRISPR Enzymes and System" filed Mar. 15, 2017. In particular embodiments, the Cas13b enzyme is derived from Bergeyella zoohelcum.

In certain example embodiments, the RNA-targeting effector protein is a Cas13c effector protein as disclosed in U.S. Provisional Patent Application No. 62/525,165 filed Jun. 26, 2017, and PCT Application No. US 2017/047193 filed Aug. 16, 2017.

In some embodiments, one or more elements of a nucleic acid-targeting system is derived from a particular organism comprising an endogenous CRISPR RNA-targeting system. In certain embodiments, the CRISPR RNA-targeting system is found in Eubacterium and Ruminococcus. In certain embodiments, the effector protein comprises targeted and collateral ssRNA cleavage activity. In certain embodiments, the effector protein comprises dual HEPN domains. In certain embodiments, the effector protein lacks a counterpart to the Helical-1 domain of Cas13a. In certain embodiments, the effector protein is smaller than previously characterized class 2 CRISPR effectors, with a median size of 928 aa. This median size is 190 aa (17%) less than that of Cas13c, more than 200 aa (18%) less than that of Cas13b, and more than 300 aa (26%) less than that of Cas13a. In certain embodiments, the effector protein has no requirement for a flanking sequence (e.g., PFS, PAM).

In certain embodiments, the effector protein locus structures include a WYL domain containing accessory protein (so denoted after three amino acids that were conserved in the originally identified group of these domains; see, e.g., WYL domain IPR026881). In certain embodiments, the WYL domain accessory protein comprises at least one helix-turn-helix (HTH) or ribbon-helix-helix (RHH) DNA-binding domain. In certain embodiments, the WYL domain containing accessory protein increases both the targeted and the collateral ssRNA cleavage activity of the RNA-targeting effector protein. In certain embodiments, the WYL domain containing accessory protein comprises an N-terminal RHH domain, as well as a pattern of primarily hydrophobic conserved residues, including an invariant tyrosine-leucine doublet corresponding to the original WYL motif. In certain embodiments, the WYL domain containing accessory protein is WYLL. WYL1 is a single WYL-domain protein associated primarily with Ruminococcus.

In other example embodiments, the Type VI RNA-targeting Cas enzyme is Cas13d. In certain embodiments, Cas13d is Eubacterium siraeum DSM 15702 (EsCas13d) or Ruminococcus sp. N15.MGS-57 (RspCas13d) (see, e.g., Yan et al., Cas13d Is a Compact RNA-Targeting Type VI CRISPR Effector Positively Modulated by a WYL-Domain-Containing Accessory Protein, Molecular Cell (2018), doi.org/10.1016/j.molcel.2018.02.028). RspCas13d and EsCas13d have no flanking sequence requirements (e.g., PFS, PAM).

Cas13 RNA Editing

In one aspect, the invention provides a method of modifying or editing a target transcript in a eukaryotic cell. In some embodiments, the method comprises allowing a CRISPR-Cas effector module complex to bind to the target polynucleotide to effect RNA base editing, wherein the CRISPR-Cas effector module complex comprises a Cas effector module complexed with a guide sequence hybridized to a target sequence within said target polynucleotide, wherein said guide sequence is linked to a direct repeat sequence. In some embodiments, the Cas effector module comprises a catalytically inactive CRISPR-Cas protein. In some embodiments, the guide sequence is designed to introduce one or more mismatches to the RNA/RNA duplex formed between the target sequence and the guide sequence. In particular embodiments, the mismatch is an A-C mismatch. In some embodiments, the Cas effector may associate with one or more functional domains (e.g. via fusion protein or suitable linkers). In some embodiments, the effector domain comprises one or more cytidine or adenosine deaminases that mediate endogenous editing of via hydrolytic deamination. In particular embodiments, the effector domain comprises the adenosine deaminase acting on RNA (ADAR) family of enzymes. In particular embodiments, the adenosine deaminase protein or catalytic domain thereof capable of deaminating adenosine or cytidine in RNA or is an RNA specific adenosine deaminase and/or is a bacterial, human, cephalopod, or Drosophila adenosine deaminase protein or catalytic domain thereof, preferably TadA, more preferably ADAR, optionally huADAR, optionally (hu)ADAR1 or (hu)ADAR2, preferably huADAR2 or catalytic domain thereof.

The present application relates to modifying a target RNA sequence of interest (see, e.g, Cox et al., Science. 2017 Nov. 24; 358(6366):1019-1027). Using RNA-targeting rather than DNA targeting offers several advantages relevant for therapeutic development. First, there are substantial safety benefits to targeting RNA: there will be fewer off-target events because the available sequence space in the transcriptome is significantly smaller than the genome, and if an off-target event does occur, it will be transient and less likely to induce negative side effects. Second, RNA-targeting therapeutics will be more efficient because they are cell-type independent and not have to enter the nucleus, making them easier to deliver.

A further aspect of the invention relates to the method and composition as envisaged herein for use in prophylactic or therapeutic treatment, preferably wherein said target locus of interest is within a human or animal and to methods of modifying an Adenine or Cytidine in a target RNA sequence of interest, comprising delivering to said target RNA, the composition as described herein. In particular embodiments, the CRISPR system and the adenosine deaminase, or catalytic domain thereof, are delivered as one or more polynucleotide molecules, as a ribonucleoprotein complex, optionally via particles, vesicles, or one or more viral vectors. In particular embodiments, the invention thus comprises compositions for use in therapy. This implies that the methods can be performed in vivo, ex vivo or in vitro. In particular embodiments, when the target is a human or animal target, the method is carried out ex vivo or in vitro.

A further aspect of the invention relates to the method as envisaged herein for use in prophylactic or therapeutic treatment, preferably wherein said target of interest is within a human or animal and to methods of modifying an Adenine or Cytidine in a target RNA sequence of interest, comprising delivering to said target RNA, the composition as described herein. In particular embodiments, the CRISPR system and the adenosine deaminase, or catalytic domain thereof, are delivered as one or more polynucleotide molecules, as a ribonucleoprotein complex, optionally via particles, vesicles, or one or more viral vectors.

In one aspect, the invention provides a method of generating a eukaryotic cell comprising a modified or edited gene. In some embodiments, the method comprises (a) introducing one or more vectors into a eukaryotic cell, wherein the one or more vectors drive expression of one or more of. Cas effector module, and a guide sequence linked to a direct repeat sequence, wherein the Cas effector module associate one or more effector domains that mediate base editing, and (b) allowing a CRISPR-Cas effector module complex to bind to a target polynucleotide to effect base editing of the target polynucleotide within said disease gene, wherein the CRISPR-Cas effector module complex comprises a Cas effector module complexed with the guide sequence that is hybridized to the target sequence within the target polynucleotide, wherein the guide sequence may be designed to introduce one or more mismatches between the RNA/RNA duplex formed between the guide sequence and the target sequence. In particular embodiments, the mismatch is an A-C mismatch. In some embodiments, the Cas effector may associate with one or more functional domains (e.g. via fusion protein or suitable linkers). In some embodiments, the effector domain comprises one or more cytidine or adenosine deaminases that mediate endogenous editing of via hydrolytic deamination. In particular embodiments, the effector domain comprises the adenosine deaminase acting on RNA (ADAR) family of enzymes. In particular embodiments, the adenosine deaminase protein or catalytic domain thereof capable of deaminating adenosine or cytidine in RNA or is an RNA specific adenosine deaminase and/or is a bacterial, human, cephalopod, or *Drosophila* adenosine deaminase protein or catalytic domain thereof, preferably TadA, more preferably ADAR, optionally huADAR, optionally (hu)ADAR1 or (hu)ADAR2, preferably huADAR2 or catalytic domain thereof.

The present invention may also use a Cas12 CRISPR enzyme. Cas12 enzymes include Cas12a (Cpf1), Cas12b (C2c1), and Cas12c (C2c3), described further herein.

A further aspect relates to an isolated cell obtained or obtainable from the methods described herein comprising the composition described herein or progeny of said modified cell, preferably wherein said cell comprises a hypoxanthine or a guanine in replace of said Adenine in said target RNA of interest compared to a corresponding cell not subjected to the method. In particular embodiments, the cell is a eukaryotic cell, preferably a human or non-human animal cell, optionally a therapeutic T cell or an antibody-producing B-cell.

In some embodiments, the modified cell is a therapeutic T cell, such as a T cell suitable for adoptive cell transfer therapies (e.g., CAR-T therapies). The modification may result in one or more desirable traits in the therapeutic T cell, as described further herein.

The invention further relates to a method for cell therapy, comprising administering to a patient in need thereof the modified cell described herein, wherein the presence of the modified cell remedies a disease in the patient.

The present invention may be further illustrated and extended based on aspects of CRISPR-Cas development and use as set forth in the following articles and particularly as relates to delivery of a CRISPR protein complex and uses of an RNA guided endonuclease in cells and organisms:

Multiplex genome engineering using CRISPR-Cas systems. Cong, L., Ran, F. A., Cox, D., Lin, S., Barretto, R., Habib, N., Hsu, P. D., Wu, X., Jiang, W., Marraffini, L. A., & Zhang, F. Science February 15; 339(6121):819-23 (2013);

RNA-guided editing of bacterial genomes using CRISPR-Cas systems. Jiang W., Bikard D., Cox D., Zhang F, Marraffini L A. Nat Biotechnol March; 31(3):233-9 (2013);

One-Step Generation of Mice Carrying Mutations in Multiple Genes by CRISPR-Cas-Mediated Genome Engineering. Wang H., Yang H., Shivalila C S., Dawlaty M M., Cheng A W., Zhang F., Jaenisch R. Cell May 9; 153(4): 910-8 (2013);

Optical control of mammalian endogenous transcription and epigenetic states. Konermann S, Brigham M D, Trevino A E, Hsu P D, Heidenreich M, Cong L, Platt R J, Scott D A, Church G M, Zhang F. Nature. August 22; 500(7463): 472-6. doi: 10.1038/Nature12466. Epub 2013 Aug. 23 (2013);

Double Nicking by RNA-Guided CRISPR Cas9 for Enhanced Genome Editing Specificity. Ran, F A., Hsu, P D., Lin, C Y., Gootenberg, J S., Konermann, S., Trevino, A E., Scott, D A., Inoue, A., Matoba, S., Zhang, Y., & Zhang, F. Cell August 28. pii: S0092-8674(13)01015-5 (2013-A);

DNA targeting specificity of RNA-guided Cas9 nucleases. Hsu, P., Scott, D., Weinstein, J., Ran, F A., Konermann, S., Agarwala, V., Li, Y., Fine, E., Wu, X., Shalem, O., Cradick, T J., Marraffini, L A., Bao, G., & Zhang, F. Nat Biotechnol doi:10.1038/nbt.2647 (2013);

Genome engineering using the CRISPR-Cas9 system. Ran, F A., Hsu, P D., Wright, J., Agarwala, V., Scott, D A., Zhang, F. Nature Protocols November; 8(11):2281-308 (2013-B);

Genome-Scale CRISPR-Cas9 Knockout Screening in Human Cells. Shalem, O., Sanjana, N E., Hartenian, E., Shi, X., Scott, D A., Mikkelson, T., Heckl, D., Ebert, B L., Root, D E., Doench, J G., Zhang, F. Science December 12. (2013);

Crystal structure of cas9 in complex with guide RNA and target DNA. Nishimasu, H., Ran, F A., Hsu, P D., Konermann, S., Shehata, S I., Dohmae, N., Ishitani, R., Zhang, F., Nureki, O. Cell February 27, 156(5):935-49 (2014);

Genome-wide binding of the CRISPR endonuclease Cas9 in mammalian cells. Wu X., Scott D A., Kriz A J., Chiu A C., Hsu P D., Dadon D B., Cheng A W., Trevino A E., Konermann S., Chen S., Jaenisch R., Zhang F., Sharp P A. Nat Biotechnol. April 20. doi: 10.1038/nbt.2889 (2014);

CRISPR-Cas9 Knockin Mice for Genome Editing and Cancer Modeling. Platt R J, Chen S, Zhou Y, Yim M J, Swiech L, Kempton H R, Dahlman J E, Parnas O, Eisenhaure T M, Jovanovic M, Graham D B, Jhunjhunwala S, Heidenreich M, Xavier R J, Langer R, Anderson D G, Hacohen N, Regev A, Feng G, Sharp P A, Zhang F. Cell 159(2): 440-455 DOI: 10.1016/j.cell.2014.09.014(2014);

Development and Applications of CRISPR-Cas9 for Genome Engineering, Hsu P D, Lander E S, Zhang F., Cell. June 5; 157(6):1262-78 (2014).

Genetic screens in human cells using the CRISPR-Cas9 system, Wang T, Wei J J, Sabatini D M, Lander E S., Science. January 3; 343(6166): 80-84. doi:10.1126/science.1246981 (2014);

Rational design of highly active sgRNAs for CRISPR-Cas9-mediated gene inactivation, Doench J G, Hartenian E, Graham D B, Tothova Z, Hegde M, Smith I, Sullender M, Ebert B L, Xavier R J, Root D E., (published online 3 Sep. 2014) Nat Biotechnol. December; 32(12):1262-7 (2014);

In vivo interrogation of gene function in the mammalian brain using CRISPR-Cas9, Swiech L, Heidenreich M, Banerjee A, Habib N, Li Y, Trombetta J, Sur M, Zhang F., (published online 19 Oct. 2014) Nat Biotechnol. January; 33(1):102-6 (2015);

Genome-scale transcriptional activation by an engineered CRISPR-Cas9 complex, Konermann S, Brigham M D, Trevino A E, Joung J, Abudayyeh O O, Barcena C, Hsu P D, Habib N, Gootenberg J S, Nishimasu H, Nureki O, Zhang F., Nature. January 29; 517(7536):583-8 (2015).

A split-Cas9 architecture for inducible genome editing and transcription modulation, Zetsche B, Volz S E, Zhang F., (published online 2 Feb. 2015) Nat Biotechnol. February; 33(2):139-42 (2015);

Genome-wide CRISPR Screen in a Mouse Model of Tumor Growth and Metastasis, Chen S, Sanjana N E, Zheng K, Shalem O, Lee K, Shi X, Scott D A, Song J, Pan J Q, Weissleder R, Lee H, Zhang F, Sharp P A. Cell 160, 1246-1260, Mar. 12, 2015 (multiplex screen in mouse), and In vivo genome editing using Staphylococcus aureus Cas9, Ran F A, Cong L, Yan W X, Scott D A, Gootenberg J S, Kriz A J, Zetsche B, Shalem O, Wu X, Makarova K S, Koonin E V, Sharp P A, Zhang F., (published online 1 Apr. 2015), Nature. April 9; 520(7546):186-91(2015).

Shalem et al., "High-throughput functional genomics using CRISPR-Cas9," Nature Reviews Genetics 16, 299-311 (May 2015).

Xu et al., "Sequence determinants of improved CRISPR sgRNA design," Genome Research 25, 1147-1157 (August 2015).

Parnas et al., "A Genome-wide CRISPR Screen in Primary Immune Cells to Dissect Regulatory Networks," Cell 162, 675-686 (Jul. 30, 2015).

Ramanan et al., "CRISPR-Cas9 cleavage of viral DNA efficiently suppresses hepatitis B virus," Scientific Reports 5:10833. doi: 10.1038/srep10833 (Jun. 2, 2015).

Nishimasu et al., "Crystal Structure of *Staphylococcus aureus* Cas9," Cell 162, 1113-1126 (Aug. 27, 2015).

BCL11A enhancer dissection by Cas9-mediated in situ saturating mutagenesis, Canver et al., Nature 527(7577): 192-7 (Nov. 12, 2015) doi: 10.1038/nature15521. Epub 2015 Sep. 16.

Cpf1 Is a Single RNA-Guided Endonuclease of a Class 2 CRISPR-Cas System, Zetsche et al., Cell 163, 759-71 (Sep. 25, 2015).

Discovery and Functional Characterization of Diverse Class 2 CRISPR-Cas Systems, Shmakov et al., Molecular Cell, 60(3), 385-397 doi: 10.1016/j.molcel.2015.10.008 Epub Oct. 22, 2015.

Rationally engineered Cas9 nucleases with improved specificity, Slaymaker et al., Science 2016 Jan. 1 351(6268): 84-88 doi: 10.1126/science.aad5227. Epub 2015 Dec. 1.

Gao et al, "Engineered Cpf1 Enzymes with Altered PAM Specificities," bioRxiv 091611; doi: http://dx.doi.org/10.1101/091611 (Dec. 4, 2016).

Cox et al., "RNA editing with CRISPR-Cas13," Science. 2017 Nov. 24; 358(6366):1019-1027. doi: 10.1126/science.aaq0180. Epub 2017 Oct. 25.

Gaudelli et al. "Programmable base editing of A-T to G-C in genomic DNA without DNA cleavage" Nature 464(551); 464-471 (2017).

each of which is incorporated herein by reference, may be considered in the practice of the instant invention, and discussed briefly below:

Cong et al. engineered type II CRISPR-Cas systems for use in eukaryotic cells based on both *Streptococcus thermophilus* Cas9 and also *Streptococcus pyogenes* Cas9 and demonstrated that Cas9 nucleases can be directed by short RNAs to induce precise cleavage of DNA in human and mouse cells. Their study further showed that Cas9 as converted into a nicking enzyme can be used to facilitate homology-directed repair in eukaryotic cells with minimal mutagenic activity. Additionally, their study demonstrated that multiple guide sequences can be encoded into a single CRISPR array to enable simultaneous editing of several at endogenous genomic loci sites within the mammalian genome, demonstrating easy programmability and wide applicability of the RNA-guided nuclease technology. This ability to use RNA to program sequence specific DNA cleavage in cells defined a new class of genome engineering tools. These studies further showed that other CRISPR loci are likely to be transplantable into mammalian cells and can also mediate mammalian genome cleavage. Importantly, it can be envisaged that several aspects of the CRISPR-Cas system can be further improved to increase its efficiency and versatility.

Jiang et al. used the clustered, regularly interspaced, short palindromic repeats (CRISPR)-associated Cas9 endonuclease complexed with dual-RNAs to introduce precise mutations in the genomes of *Streptococcus pneumoniae* and *Escherichia coli*. The approach relied on dual-RNA:Cas9-directed cleavage at the targeted genomic site to kill unmutated cells and circumvents the need for selectable markers or counter-selection systems. The study reported reprogramming dual-RNA:Cas9 specificity by changing the sequence of short CRISPR RNA (crRNA) to make single- and multinucleotide changes carried on editing templates. The study showed that simultaneous use of two crRNAs enabled multiplex mutagenesis. Furthermore, when the approach was used in combination with recombineering, in *S. pneumoniae*, nearly 100% of cells that were recovered using the described approach contained the desired mutation, and in *E. coli*, 65% that were recovered contained the mutation.

Wang et al. (2013) used the CRISPR-Cas system for the one-step generation of mice carrying mutations in multiple genes which were traditionally generated in multiple steps by sequential recombination in embryonic stem cells and/or time-consuming intercrossing of mice with a single mutation. The CRISPR-Cas system will greatly accelerate the in vivo study of functionally redundant genes and of epistatic gene interactions.

Konermann et al. (2013) addressed the need in the art for versatile and robust technologies that enable optical and chemical modulation of DNA-binding domains based CRISPR Cas9 enzyme and also Transcriptional Activator Like Effectors.

Ran et al. (2013-A) described an approach that combined a Cas9 nickase mutant with paired guide RNAs to introduce targeted double-strand breaks. This addresses the issue of the Cas9 nuclease from the microbial CRISPR-Cas system being targeted to specific genomic loci by a guide sequence, which can tolerate certain mismatches to the DNA target and thereby promote undesired off-target mutagenesis. Because individual nicks in the genome are repaired with high fidelity, simultaneous nicking via appropriately offset guide RNAs is required for double-stranded breaks and extends the number of specifically recognized bases for target cleavage. The authors demonstrated that using paired nicking can reduce off-target activity by 50- to 1,500-fold in cell lines and to facilitate gene knockout in mouse zygotes without sacrificing on-target cleavage efficiency. This versatile strategy enables a wide variety of genome editing applications that require high specificity.

Hsu et al. (2013) characterized SpCas9 targeting specificity in human cells to inform the selection of target sites and avoid off-target effects. The study evaluated >700 guide RNA variants and SpCas9-induced indel mutation levels at >100 predicted genomic off-target loci in 293T and 293FT cells. The authors that SpCas9 tolerates mismatches between guide RNA and target DNA at different positions in a sequence-dependent manner, sensitive to the number, position and distribution of mismatches. The authors further showed that SpCas9-mediated cleavage is unaffected by DNA methylation and that the dosage of SpCas9 and guide RNA can be titrated to minimize off-target modification. Additionally, to facilitate mammalian genome engineering applications, the authors reported providing a web-based software tool to guide the selection and validation of target sequences as well as off-target analyses.

Ran et al. (2013-B) described a set of tools for Cas9-mediated genome editing via non-homologous end joining (NHEJ) or homology-directed repair (HDR) in mammalian cells, as well as generation of modified cell lines for downstream functional studies. To minimize off-target cleavage, the authors further described a double-nicking strategy using the Cas9 nickase mutant with paired guide RNAs. The protocol provided by the authors experimentally derived guidelines for the selection of target sites, evaluation of cleavage efficiency and analysis of off-target activity. The studies showed that beginning with target design, gene modifications can be achieved within as little as 1-2 weeks, and modified clonal cell lines can be derived within 2-3 weeks.

Shalem et al. described a new way to interrogate gene function on a genome-wide scale. Their studies showed that delivery of a genome-scale CRISPR-Cas9 knockout (GeCKO) library targeted 18,080 genes with 64,751 unique guide sequences enabled both negative and positive selection screening in human cells. First, the authors showed use of the GeCKO library to identify genes essential for cell viability in cancer and pluripotent stem cells. Next, in a melanoma model, the authors screened for genes whose loss is involved in resistance to vemurafenib, a therapeutic that inhibits mutant protein kinase BRAF. Their studies showed that the highest-ranking candidates included previously validated genes NF1 and MED12 as well as novel hits NF2, CUL3, TADA2B, and TADA1. The authors observed a high level of consistency between independent guide RNAs targeting the same gene and a high rate of hit confirmation, and thus demonstrated the promise of genome-scale screening with Cas9.

Nishimasu et al. reported the crystal structure of *Streptococcus pyogenes* Cas9 in complex with sgRNA and its target DNA at 2.5 A° resolution. The structure revealed a bilobed architecture composed of target recognition and nuclease lobes, accommodating the sgRNA:DNA heteroduplex in a positively charged groove at their interface. Whereas the recognition lobe is essential for binding sgRNA and DNA, the nuclease lobe contains the HNH and RuvC nuclease domains, which are properly positioned for cleavage of the complementary and non-complementary strands of the target DNA, respectively. The nuclease lobe also contains a carboxyl-terminal domain responsible for the interaction with the protospacer adjacent motif (PAM). This high-resolution structure and accompanying functional analyses have revealed the molecular mechanism of RNA-guided DNA targeting by Cas9, thus paving the way for the rational design of new, versatile genome-editing technologies.

Wu et al. mapped genome-wide binding sites of a catalytically inactive Cas9 (dCas9) from *Streptococcus pyogenes* loaded with single guide RNAs (sgRNAs) in mouse embryonic stem cells (mESCs). The authors showed that each of the four sgRNAs tested targets dCas9 to between tens and thousands of genomic sites, frequently characterized by a 5-nucleotide seed region in the sgRNA and an NGG protospacer adjacent motif (PAM). Chromatin inaccessibility decreases dCas9 binding to other sites with matching seed sequences; thus 70% of off-target sites are associated with genes. The authors showed that targeted sequencing of 295 dCas9 binding sites in mESCs transfected with catalytically active Cas9 identified only one site mutated above background levels. The authors proposed a two-state model for Cas9 binding and cleavage, in which a seed match triggers binding but extensive pairing with target DNA is required for cleavage.

Platt et al. established a Cre-dependent Cas9 knockin mouse. The authors demonstrated in vivo as well as ex vivo genome editing using adeno-associated virus (AAV)-, lentivirus-, or particle-mediated delivery of guide RNA in neurons, immune cells, and endothelial cells.

Hsu et al. (2014) is a review article that discusses generally CRISPR-Cas9 history from yogurt to genome editing, including genetic screening of cells.

Wang et al. (2014) relates to a pooled, loss-of-function genetic screening approach suitable for both positive and negative selection that uses a genome-scale lentiviral single guide RNA (sgRNA) library.

Doench et al. created a pool of sgRNAs, tiling across all possible target sites of a panel of six endogenous mouse and three endogenous human genes and quantitatively assessed their ability to produce null alleles of their target gene by antibody staining and flow cytometry. The authors showed that optimization of the PAM improved activity and also provided an on-line tool for designing sgRNAs.

Swiech et al. demonstrate that AAV-mediated SpCas9 genome editing can enable reverse genetic studies of gene function in the brain.

Konermann et al. (2015) discusses the ability to attach multiple effector domains, e.g., transcriptional activator, functional and epigenomic regulators at appropriate positions on the guide such as stem or tetraloop with and without linkers.

Zetsche et al. demonstrates that the Cas9 enzyme can be split into two and hence the assembly of Cas9 for activation can be controlled.

Chen et al. relates to multiplex screening by demonstrating that a genome-wide in vivo CRISPR-Cas9 screen in mice reveals genes regulating lung metastasis.

Ran et al. (2015) relates to SaCas9 and its ability to edit genomes and demonstrates that one cannot extrapolate from biochemical assays.

Shalem et al. (2015) described ways in which catalytically inactive Cas9 (dCas9) fusions are used to synthetically repress (CRISPRi) or activate (CRISPRa) expression, showing. advances using Cas9 for genome-scale screens, including arrayed and pooled screens, knockout approaches that inactivate genomic loci and strategies that modulate transcriptional activity.

Xu et al. (2015) assessed the DNA sequence features that contribute to single guide RNA (sgRNA) efficiency in CRISPR-based screens. The authors explored efficiency of CRISPR-Cas9 knockout and nucleotide preference at the cleavage site. The authors also found that the sequence preference for CRISPRi/a is substantially different from that for CRISPR-Cas9 knockout.

Parnas et al. (2015) introduced genome-wide pooled CRISPR-Cas9 libraries into dendritic cells (DCs) to identify genes that control the induction of tumor necrosis factor (Tnf) by bacterial lipopolysaccharide (LPS). Known regulators of Tlr4 signaling and previously unknown candidates were identified and classified into three functional modules with distinct effects on the canonical responses to LPS.

Ramanan et al(2015) demonstrated cleavage of viral episomal DNA (cccDNA) in infected cells. The HBV genome exists in the nuclei of infected hepatocytes as a 3.2 kb double-stranded episomal DNA species called covalently closed circular DNA (cccDNA), which is a key component in the HBV life cycle whose replication is not inhibited by current therapies. The authors showed that sgRNAs specifically targeting highly conserved regions of HBV robustly suppresses viral replication and depleted cccDNA.

Nishimasu et al. (2015) reported the crystal structures of SaCas9 in complex with a single guide RNA (sgRNA) and its double-stranded DNA targets, containing the 5'-TTGAAT-3' PAM and the 5'-TTGGGT-3' PAM. A structural comparison of SaCas9 with SpCas9 highlighted both structural conservation and divergence, explaining their distinct PAM specificities and orthologous sgRNA recognition.

Canver et al. (2015) demonstrated a CRISPR-Cas9-based functional investigation of non-coding genomic elements. The authors developed pooled CRISPR-Cas9 guide RNA libraries to perform in situ saturating mutagenesis of the human and mouse BCL11A enhancers which revealed critical features of the enhancers.

Zetsche et al. (2015) reported characterization of Cpf1, a class 2 CRISPR nuclease from *Francisella novicida* U112 having features distinct from Cas9. Cpf1 is a single RNA-guided endonuclease lacking tracrRNA, utilizes a T-rich protospacer-adjacent motif, and cleaves DNA via a staggered DNA double-stranded break.

Shmakov et al. (2015) reported three distinct Class 2 CRISPR-Cas systems. Two system CRISPR enzymes (C2c1 and C2c3) contain RuvC-like endonuclease domains distantly related to Cpf1. Unlike Cpf1, C2c1 depends on both crRNA and tracrRNA for DNA cleavage. The third enzyme (C2c2) contains two predicted HEPN RNase domains and is tracrRNA independent.

Slaymaker et al (2016) reported the use of structure-guided protein engineering to improve the specificity of *Streptococcus pyogenes* Cas9 (SpCas9). The authors developed "enhanced specificity" SpCas9 (eSpCas9) variants which maintained robust on-target cleavage with reduced off-target effects.

Cox et al., (2017) reported the use of catalytically inactive Cas13 (dCas13) to direct adenosine-to-inosine deaminase activity by ADAR2 (adenosine deaminase acting on RNA type 2) to transcripts in mammalian cells. The system, referred to as RNA Editing for Programmable A to I Replacement (REPAIR), has no strict sequence constraints and can be used to edit full-length transcripts. The authors further engineered the system to create a high-specificity variant and minimized the system to facilitate viral delivery.

The methods and tools provided herein may be designed for use with or Cas13, a type II nuclease that does not make use of tracrRNA. Orthologs of Cas13 have been identified in different bacterial species as described herein. Further type II nucleases with similar properties can be identified using methods described in the art (Shmakov et al. 2015, 60:385-397; Abudayeh et al. 2016, Science, 5; 353(6299)). In particular embodiments, such methods for identifying novel CRISPR effector proteins may comprise the steps of selecting sequences from the database encoding a seed which identifies the presence of a CRISPR Cas locus, identifying loci located within 10 kb of the seed comprising Open Reading Frames (ORFs) in the selected sequences, selecting therefrom loci comprising ORFs of which only a single ORF encodes a novel CRISPR effector having greater than 700 amino acids and no more than 90% homology to a known CRISPR effector. In particular embodiments, the seed is a protein that is common to the CRISPR-Cas system, such as Cas1. In further embodiments, the CRISPR array is used as a seed to identify new effector proteins.

Also, "Dimeric CRISPR RNA-guided FokI nucleases for highly specific genome editing", Shengdar Q. Tsai, Nicolas Wyvekens, Cyd Khayter, Jennifer A. Foden, Vishal Thapar, Deepak Reyon, Mathew J. Goodwin, Martin J. Aryee, J. Keith Joung Nature Biotechnology 32(6): 569-77 (2014), relates to dimeric RNA-guided FokI Nucleases that recognize extended sequences and can edit endogenous genes with high efficiencies in human cells.

Also, Harrington et al. "Programmed DNA destruction by miniature CRISPR-Cas14 enzymes" Science 2018 doi:10/1126/science.aav4293, relates to Cas14.

With respect to general information on CRISPR/Cas Systems, components thereof, and delivery of such components, including methods, materials, delivery vehicles, vectors, particles, and making and using thereof, including as to amounts and formulations, as well as CRISPR-Cas-expressing eukaryotic cells, CRISPR-Cas expressing eukaryotes, such as a mouse, reference is made to: U.S. Pat. Nos. 8,999,641, 8,993,233, 8,697,359, 8,771,945, 8,795,965, 8,865,406, 8,871,445, 8,889,356, 8,889,418, 8,895,308, 8,906,616, 8,932,814, and 8,945,839; US Patent Publications US 2014-0310830 (U.S. application Ser. No. 14/105,031), US 2014-0287938 A1 (U.S. application Ser. No. 14/213,991), US 2014-0273234 A1 (U.S. application Ser. No. 14/293,674), US 2014-0273232 A1 (U.S. application Ser. No. 14/290,575), US 2014-0273231 (U.S. application Ser. No. 14/259,420), US 2014-0256046 A1 (U.S. application Ser. No. 14/226,274), US 2014-0248702 A1 (U.S. application Ser. No. 14/258,458), US 2014-0242700 A1 (U.S. application Ser. No. 14/222,930), US 2014-0242699 A1 (U.S. application Ser. No. 14/183,512), US 2014-0242664 A1 (U.S. application Ser. No. 14/104,990), US 2014-0234972 A1 (U.S. application Ser. No. 14/183,471), US 2014-0227787 A1 (U.S. application Ser. No. 14/256,912), US 2014-0189896 A1 (U.S. application Ser. No. 14/105,035), US 2014-0186958 (U.S. application Ser. No. 14/105,017), US 2014-0186919 A1 (U.S. application Ser. No. 14/104,977), US 2014-0186843 A1 (U.S. application Ser. No. 14/104,900), US 2014-0179770 A1 (U.S. application Ser. No. 14/104,837) and US 2014-0179006 A1 (U.S. application Ser. No. 14/183,486), US 2014-0170753 (U.S. application Ser. No. 14/183,429); US 2015-0184139 (U.S. application Ser. No. 14/324,960); Ser. No. 14/054,414 European Patent Applications EP 2 771 468 (EP13818570.7), EP 2 764 103 (EP13824232.6), and EP 2 784 162 (EP14170383.5); and PCT Patent Publications WO2014/093661 (PCT/US2013/074743), WO2014/093694 (PCT/US2013/074790), WO2014/093595 (PCT/US2013/074611), WO2014/093718 (PCT/US2013/074825), WO2014/093709 (PCT/US2013/074812), WO2014/093622 (PCT/US2013/074667), WO2014/093635 (PCT/US2013/074691), WO2014/093655 (PCT/US2013/074736), WO2014/093712 (PCT/US2013/074819), WO2014/093701 (PCT/US2013/074800), WO2014/018423 (PCT/US2013/051418), WO2014/204723 (PCT/US2014/041790), WO2014/204724 (PCT/US2014/041800), WO2014/204725 (PCT/US2014/041803), WO2014/204726 (PCT/US2014/041804), WO2014/204727 (PCT/US2014/041806), WO2014/204728 (PCT/US2014/041808), WO2014/204729 (PCT/US2014/041809), WO2015/089351 (PCT/US2014/069897), WO2015/089354 (PCT/US2014/069902), WO2015/089364 (PCT/US2014/069925), WO2015/089427 (PCT/US2014/070068), WO2015/089462 (PCT/US2014/070127), WO2015/089419 (PCT/US2014/070057), WO2015/089465 (PCT/US2014/070135), WO2015/089486 (PCT/US2014/070175), WO2015/058052 (PCT/US2014/061077), WO2015/070083 (PCT/US2014/064663), WO2015/089354 (PCT/US2014/069902), WO2015/089351 (PCT/US2014/069897), WO2015/089364 (PCT/US2014/069925), WO2015/089427 (PCT/US2014/070068), WO2015/089473 (PCT/US2014/070152), WO2015/089486 (PCT/US2014/070175), WO2016/049258 (PCT/US2015/051830), WO2016/094867 (PCT/US2015/065385), WO2016/094872 (PCT/US2015/065393), WO2016/094874 (PCT/US2015/065396), WO2016/106244 (PCT/US2015/067177).

Mention is also made of U.S. application 62/180,709, 17 Jun. 2015, PROTECTED GUIDE RNAS (PGRNAS); U.S. application 62/091,455, filed, 12 Dec. 2014, PROTECTED GUIDE RNAS (PGRNAS); U.S. application 62/096,708, 24 December 14, PROTECTED GUIDE RNAS (PGRNAS); U.S. applications 62/091,462, 12 December 14, 62/096,324, 23 December 20 14, 62/180,681, 17 Jun. 2015, and 62/237,496, 5 Oct. 2015, DEAD GUIDES FOR CRISPR TRANSCRIPTION FACTORS; U.S. application 62/091,456, 12 Dec. 2014 and 62/180,692, 17 Jun. 2015, ESCORTED AND FUNCTIONALIZED GUIDES FOR CRISPR-CAS SYSTEMS; U.S. application 62/091,461, 12. December 14, DELIVERY, USE AND THERAPEUTIC APPLICATIONS OF THE CRISPR-CAS SYSTEMS AND COMPOSITIONS FOR GENOME EDITING AS TO HEMATOPOIETIC STEM CELLS (HSCs); U.S. application 62/094,903, 19 December 14, UNBIASED IDENTIFICATION OF DOUBLE-STRAND BREAKS AND GENOMIC REARRANGEMENT BY GENOME-WISE INSERT CAPTURE SEQUENCING; U.S. application 62/096,761, 24 December 14, ENGINEERING OF SYSTEMS, METHODS AND OPTIMIZED ENZYME AND GUIDE SCAFFOLDS FOR SEQUENCE MANIPULATION; U.S. application 62/098,059, 30 December 14, 62/181,641, 18 Jun. 2015, and 62/181,667, 18 Jun. 2015, RNA-TARGETING SYSTEM; U.S. application 62/096,656, 24 December 14 and 62/181,151, 17 Jun. 2015, CRISPR HAVING OR ASSOCIATED WITH DESTABILIZATION DOMAINS; U.S. application 62/096,697, 24 December 14, CRISPR HAVING OR ASSOCIATED WITH AAV; U.S. application 62/098,158, 30 December 14, ENGINEERED CRISPR COMPLEX INSERTIONAL TARGETING SYSTEMS; U.S. application 62/151,052, 22 Apr. 2015, CELLULAR TARGETING FOR EXTRACELLULAR EXOSOMAL REPORTING; U.S. application 62/054,490, 24 Sep. 2014, DELIVERY, USE AND THERAPEUTIC APPLICATIONS OF THE CRISPR-CAS SYSTEMS AND COMPOSITIONS FOR TARGETING DISORDERS AND DISEASES USING PARTICLE DELIVERY COMPONENTS; U.S. application 61/939,154, 12 Feb. 2014, SYSTEMS, METHODS AND COMPOSITIONS FOR SEQUENCE MANIPULATION WITH OPTIMIZED FUNCTIONAL CRISPR-CAS SYSTEMS; U.S. application 62/055,484, 25 Sep. 2014, SYSTEMS, METHODS AND COMPOSITIONS FOR SEQUENCE MANIPULATION WITH OPTIMIZED FUNCTIONAL CRISPR-CAS SYSTEMS; U.S. application 62/087,537, 4 Dec. 2014, SYSTEMS, METHODS AND COMPOSITIONS FOR SEQUENCE MANIPULATION WITH OPTIMIZED FUNCTIONAL CRISPR-CAS SYSTEMS; U.S. application 62/054,651, 24 Sep. 2014, DELIVERY, USE AND THERAPEUTIC APPLICATIONS OF THE CRISPR-CAS SYSTEMS AND COMPOSITIONS FOR MODELING COMPETITION OF MULTIPLE CANCER MUTATIONS IN VIVO; U.S. application 62/067,886, 23 Oct. 2014, DELIVERY, USE AND THERAPEUTIC APPLICATIONS OF THE CRISPR-CAS SYSTEMS AND COMPOSITIONS FOR MODELING COMPETITION OF MULTIPLE CANCER MUTATIONS IN VIVO; U.S. applications 62/054,675, 24 Sep. 2014 and 62/181,002, 17 Jun. 2015, DELIVERY, USE AND THERAPEUTIC APPLICATIONS OF THE CRISPR-CAS SYSTEMS AND COMPOSITIONS IN NEURONAL CELLS/TISSUES; U.S. application 62/054,528, 24 Sep. 2014, DELIVERY, USE AND THERAPEUTIC APPLICATIONS OF THE CRISPR-CAS SYSTEMS AND COMPOSITIONS IN IMMUNE DISEASES OR DISORDERS; U.S. application 62/055,454, 25 September 14, DELIVERY, USE AND THERAPEUTIC APPLICATIONS OF THE CRISPR-CAS SYSTEMS AND COMPOSITIONS FOR TARGETING DISORDERS AND DISEASES USING CELL PENETRATION PEPTIDES (CPP); U.S. application 62/055,460, 25 Sep. 2014, MULTIFUNCTIONAL-CRISPR COMPLEXES AND/OR OPTIMIZED ENZYME LINKED FUNCTIONAL-CRISPR COMPLEXES; U.S. application 62/087,475, 4 Dec. 2014 and 62/181,690, 18 Jun. 2015, FUNCTIONAL SCREENING WITH OPTIMIZED FUNCTIONAL CRISPR-CAS SYSTEMS; U.S. application 62/055,487, 25 Sep. 2014, FUNCTIONAL SCREENING WITH OPTIMIZED FUNCTIONAL CRISPR-CAS SYSTEMS; U.S. application 62/087,546, 4 Dec. 2014 and 62/181,687, 18 Jun. 2015, MULTIFUNCTIONAL CRISPR COMPLEXES AND/OR OPTIMIZED ENZYME LINKED FUNCTIONAL-CRISPR COMPLEXES; and U.S. application 62/098,285, 30 Dec. 2014, CRISPR MEDIATED IN VIVO MODELING AND GENETIC SCREENING OF TUMOR GROWTH AND METASTASIS.

Mention is made of U.S. applications 62/181,659, 18 Jun. 2015 and 62/207,318, 19 Aug. 2015, ENGINEERING AND OPTIMIZATION OF SYSTEMS, METHODS, ENZYME AND GUIDE SCAFFOLDS OF CAS9 ORTHOLOGS AND VARIANTS FOR SEQUENCE MANIPULATION. Mention is made of U.S. applications 62/181,663, 18 Jun. 2015 and 62/245,264, 22 Oct. 2015, NOVEL CRISPR ENZYMES AND SYSTEMS, U.S. applications 62/181,675, 18 Jun. 2015, 62/285,349, 22 Oct. 2015, 62/296,522, 17 Feb. 2016, and 62/320,231, 8 Apr. 2016, NOVEL CRISPR ENZYMES AND SYSTEMS, U.S. application 62/232,067, 24 Sep. 2015, U.S. application Ser. No. 14/975,085, 18 Dec. 2015, European application No. 16150428.7, U.S. application 62/205,733, 16 Aug. 2015, U.S. application 62/201,542, 5 Aug. 2015, U.S. application 62/193,507, 16 Jul. 2015, and U.S. application 62/181,739, 18 Jun. 2015, each entitled NOVEL CRISPR ENZYMES AND SYSTEMS and of U.S. application 62/245,270, 22 Oct. 2015, NOVEL CRISPR ENZYMES AND SYSTEMS. Mention is also made of U.S. application 61/939,256, 12 Feb. 2014, and WO 2015/089473 (PCT/US2014/070152), 12 Dec. 2014, each entitled ENGINEERING OF SYSTEMS, METHODS AND OPTIMIZED GUIDE COMPOSITIONS WITH NEW ARCHITECTURES FOR SEQUENCE MANIPULATION. Mention is also made of PCT/US2015/045504, 15 Aug. 2015, U.S. application 62/180,699, 17 Jun. 2015, and U.S. application 62/038,358, 17 Aug. 2014, each entitled GENOME EDITING USING CAS9 NICKASES.

Each of these patents, patent publications, and applications, and all documents cited therein or during their prosecution ("appln cited documents") and all documents cited or referenced in the appln cited documents, together with any instructions, descriptions, product specifications, and product sheets for any products mentioned therein or in any document therein and incorporated by reference herein, are hereby incorporated herein by reference, and may be employed in the practice of the invention. All documents (e.g., these patents, patent publications and applications and the appln cited documents) are incorporated herein by reference to the same extent as if each individual document was specifically and individually indicated to be incorporated by reference.

In particular embodiments, pre-complexed guide RNA and CRISPR effector protein, (optionally, adenosine deaminase fused to a CRISPR protein or an adaptor) are delivered as a ribonucleoprotein (RNP). RNPs have the advantage that they lead to rapid editing effects even more so than the RNA method because this process avoids the need for transcription. An important advantage is that both RNP delivery is transient, reducing off-target effects and toxicity issues. Efficient genome editing in different cell types has been observed by Kim et al. (2014, Genome Res. 24(6):1012-9), Paix et al. (2015, Genetics 204(1):47-54), Chu et al. (2016, BMC Biotechnol. 16:4), and Wang et al. (2013, Cell. 9; 153(4):910-8).

In particular embodiments, the ribonucleoprotein is delivered by way of a polypeptide-based shuttle agent as described in WO2016161516. WO2016161516 describes efficient transduction of polypeptide cargos using synthetic peptides comprising an endosome leakage domain (ELD) operably linked to a cell penetrating domain (CPD), to a histidine-rich domain and a CPD. Similarly these polypeptides can be used for the delivery of CRISPR-effector based RNPs in eukaryotic cells.

Tale Systems

As disclosed herein editing can be made by way of the transcription activator-like effector nucleases (TALENs) system. Transcription activator-like effectors (TALEs) can be engineered to bind practically any desired DNA sequence. Exemplary methods of genome editing using the TALEN system can be found for example in Cermak T. Doyle E L. Christian M. Wang L. Zhang Y. Schmidt C, et al. Efficient design and assembly of custom TALEN and other TAL effector-based constructs for DNA targeting. Nucleic Acids Res. 2011; 39:e82; Zhang F. Cong L. Lodato S. Kosuri S. Church G M. Arlotta P Efficient construction of sequence-specific TAL effectors for modulating mammalian transcription. Nat Biotechnol. 2011; 29:149-153 and U.S. Pat. Nos. 8,450,471, 8,440,431 and 8,440,432, all of which are specifically incorporated by reference.

In advantageous embodiments of the invention, the methods provided herein use isolated, non-naturally occurring, recombinant or engineered DNA binding proteins that comprise TALE monomers as a part of their organizational structure that enable the targeting of nucleic acid sequences with improved efficiency and expanded specificity.

Naturally occurring TALEs or "wild type TALEs" are nucleic acid binding proteins secreted by numerous species of proteobacteria. TALE polypeptides contain a nucleic acid binding domain composed of tandem repeats of highly conserved monomer polypeptides that are predominantly 33, 34 or 35 amino acids in length and that differ from each other mainly in amino acid positions 12 and 13. In advantageous embodiments the nucleic acid is DNA. As used herein, the term "polypeptide monomers", or "TALE monomers" will be used to refer to the highly conserved repetitive polypeptide sequences within the TALE nucleic acid binding domain and the term "repeat variable di-residues" or "RVD" will be used to refer to the highly variable amino acids at positions 12 and 13 of the polypeptide monomers. As provided throughout the disclosure, the amino acid residues of the RVD are depicted using the IUPAC single letter code for amino acids. A general representation of a TALE monomer which is comprised within the DNA binding domain is X1-11-(X12X13)-X14-33 or 34 or 35, where the subscript indicates the amino acid position and X represents any amino acid. X12X13 indicate the RVDs. In some polypeptide monomers, the variable amino acid at position 13 is missing or absent and in such polypeptide monomers, the RVD consists of a single amino acid. In such cases the RVD may be alternatively represented as X*, where X represents X12 and (*) indicates that X13 is absent. The DNA binding domain comprises several repeats of TALE monomers and this may be represented as (X1-11-(X12X13)-X14-33 or 34 or 35)z, where in an advantageous embodiment, z is at least 5 to 40. In a further advantageous embodiment, z is at least 10 to 26.

The TALE monomers have a nucleotide binding affinity that is determined by the identity of the amino acids in its RVD. For example, polypeptide monomers with an RVD of NI preferentially bind to adenine (A), polypeptide monomers with an RVD of NG preferentially bind to thymine (T), polypeptide monomers with an RVD of HD preferentially bind to cytosine (C) and polypeptide monomers with an RVD of NN preferentially bind to both adenine (A) and guanine (G). In yet another embodiment of the invention, polypeptide monomers with an RVD of IG preferentially bind to T. Thus, the number and order of the polypeptide monomer repeats in the nucleic acid binding domain of a TALE determines its nucleic acid target specificity. In still further embodiments of the invention, polypeptide monomers with an RVD of NS recognize all four base pairs and may bind to A, T, G or C. The structure and function of TALEs is further described in, for example, Moscou et al., Science 326:1501 (2009); Boch et al., Science 326:1509-1512 (2009); and Zhang et al., Nature Biotechnology 29:149-153 (2011), each of which is incorporated by reference in its entirety.

The TALE polypeptides used in methods of the invention are isolated, non-naturally occurring, recombinant or engineered nucleic acid-binding proteins that have nucleic acid or DNA binding regions containing polypeptide monomer repeats that are designed to target specific nucleic acid sequences.

As described herein, polypeptide monomers having an RVD of HN or NH preferentially bind to guanine and thereby allow the generation of TALE polypeptides with high binding specificity for guanine containing target nucleic acid sequences. In a preferred embodiment of the invention, polypeptide monomers having RVDs RN, NN, NK, SN, NH, KN, HN, NQ, HH, RG, KH, RH and SS preferentially bind to guanine. In a much more advantageous embodiment of the invention, polypeptide monomers having RVDs RN, NK, NQ, HH, KH, RH, SS and SN preferentially bind to guanine and thereby allow the generation of TALE polypeptides with high binding specificity for guanine containing target nucleic acid sequences. In an even more advantageous embodiment of the invention, polypeptide monomers having RVDs HH, KH, NH, NK, NQ, RH, RN and SS preferentially bind to guanine and thereby allow the generation of TALE polypeptides with high binding specificity for guanine containing target nucleic acid sequences. In a further advantageous embodiment, the RVDs that have high binding specificity for guanine are RN, NH RH and KH. Furthermore, polypeptide monomers having an RVD of NV preferentially bind to adenine and guanine. In more preferred embodiments of the invention, polypeptide monomers having RVDs of H*, HA, KA, N*, NA, NC, NS, RA, and S* bind to adenine, guanine, cytosine and thymine with comparable affinity.

The predetermined N-terminal to C-terminal order of the one or more polypeptide monomers of the nucleic acid or DNA binding domain determines the corresponding predetermined target nucleic acid sequence to which the TALE polypeptides will bind. As used herein the polypeptide monomers and at least one or more half polypeptide monomers are "specifically ordered to target" the genomic locus or gene of interest. In plant genomes, the natural TALE-binding sites always begin with a thymine (T), which may be specified by a cryptic signal within the non-repetitive N-terminus of the TALE polypeptide; in some cases this region may be referred to as repeat 0. In animal genomes, TALE binding sites do not necessarily have to begin with a thymine (T) and TALE polypeptides may target DNA sequences that begin with T, A, G or C. The tandem repeat of TALE monomers always ends with a half-length repeat or a stretch of sequence that may share identity with only the first 20 amino acids of a repetitive full length TALE monomer and this half repeat may be referred to as a half-monomer (FIG. 8), which is included in the term "TALE monomer". Therefore, it follows that the length of the nucleic acid or DNA being targeted is equal to the number of full polypeptide monomers plus two.

As described in Zhang et al., Nature Biotechnology 29:149-153 (2011), TALE polypeptide binding efficiency may be increased by including amino acid sequences from the "capping regions" that are directly N-terminal or C-terminal of the DNA binding region of naturally occurring TALEs into the engineered TALEs at positions N-terminal or C-terminal of the engineered TALE DNA binding region. Thus, in certain embodiments, the TALE polypeptides described herein further comprise an N-terminal capping region and/or a C-terminal capping region.

An exemplary amino acid sequence of a N-terminal capping region is:

```
                                        (SEQ. I.D. No. 1)
M D P I R S R T P S P A R E L L S G P Q P D G V Q

P T A D R G V S P P A G G P L D G L P A R R T M S

R T R L P S P P A P S P A F S A D S F S D L L R Q

F D P S L F N T S L F D S L P P F G A H H T E A A

T G E W D E V Q S G L R A A D A P P P T M R V A V

T A A R P P R A K P A P R R R A A Q P S D A S P A

A Q V D L R T L G Y S Q Q Q Q E K I K P K V R S T

V A Q H H E A L V G H G F T H A H I V A L S Q H P

A A L G T V A V K Y Q D M I A A L P E A T H E A I

V G V G K Q W S G A R A L E A L L T V A G E L R G

P P L Q L D T G Q L L K I A K R G G V T A V E A V

H A W R N A L T G A P L N
```

An exemplary amino acid sequence of a C-terminal capping region is:

```
                                        (SEQ. I.D. No. 2)
R P A L E S I V A Q L S R P D P A L A A L T N D H

L V A L A C L G G R P A L D A V K K G L P H A P A

L I K R T N R R I P E R T S H R V A D H A Q V V R

V L G F F Q C H S H P A Q A F D D A M T Q F G M S

R H G L L Q L F R R V G V T E L E A R S G T L P P

A S Q R W D R I L Q A S G M K R A K P S P T S T Q

T P D Q A S L H A F A D S L E R D L D A P S P M H

E G D Q T R A S
```

As used herein the predetermined "N-terminus" to "C terminus" orientation of the N-terminal capping region, the DNA binding domain comprising the repeat TALE monomers and the C-terminal capping region provide structural basis for the organization of different domains in the d-TALEs or polypeptides of the invention.

The entire N-terminal and/or C-terminal capping regions are not necessary to enhance the binding activity of the DNA binding region. Therefore, in certain embodiments, fragments of the N-terminal and/or C-terminal capping regions are included in the TALE polypeptides described herein.

In certain embodiments, the TALE polypeptides described herein contain a N-terminal capping region fragment that included at least 10, 20, 30, 40, 50, 54, 60, 70, 80, 87, 90, 94, 100, 102, 110, 117, 120, 130, 140, 147, 150, 160, 170, 180, 190, 200, 210, 220, 230, 240, 250, 260 or 270 amino acids of an N-terminal capping region. In certain embodiments, the N-terminal capping region fragment amino acids are of the C-terminus (the DNA-binding region proximal end) of an N-terminal capping region. As described in Zhang et al., Nature Biotechnology 29:149-153 (2011), N-terminal capping region fragments that include the C-terminal 240 amino acids enhance binding activity equal to the full length capping region, while fragments that include the C-terminal 147 amino acids retain greater than 80% of the efficacy of the full length capping region, and fragments that include the C-terminal 117 amino acids retain greater than 50% of the activity of the full-length capping region.

In some embodiments, the TALE polypeptides described herein contain a C-terminal capping region fragment that included at least 6, 10, 20, 30, 37, 40, 50, 60, 68, 70, 80, 90, 100, 110, 120, 127, 130, 140, 150, 155, 160, 170, 180 amino acids of a C-terminal capping region. In certain embodiments, the C-terminal capping region fragment amino acids are of the N-terminus (the DNA-binding region proximal end) of a C-terminal capping region. As described in Zhang et al., Nature Biotechnology 29:149-153 (2011), C-terminal capping region fragments that include the C-terminal 68 amino acids enhance binding activity equal to the full length capping region, while fragments that include the C-terminal 20 amino acids retain greater than 50% of the efficacy of the full length capping region.

In certain embodiments, the capping regions of the TALE polypeptides described herein do not need to have identical sequences to the capping region sequences provided herein. Thus, in some embodiments, the capping region of the TALE polypeptides described herein have sequences that are at least 50%, 60%, 70%, 80%, 85%, 90%, 91%, 92%, 93%, 94%, 95%, 96%, 97%, 98% or 99% identical or share identity to the capping region amino acid sequences provided herein. Sequence identity is related to sequence homology. Homology comparisons may be conducted by eye, or more usually, with the aid of readily available sequence comparison programs. These commercially available computer programs may calculate percent (%) homology between two or more sequences and may also calculate the sequence identity shared by two or more amino acid or nucleic acid sequences. In some preferred embodiments, the capping region of the TALE polypeptides described herein have sequences that are at least 95% identical or share identity to the capping region amino acid sequences provided herein.

Sequence homologies may be generated by any of a number of computer programs known in the art, which include but are not limited to BLAST or FASTA. Suitable computer program for carrying out alignments like the GCG Wisconsin Bestfit package may also be used. Once the software has produced an optimal alignment, it is possible to calculate % homology, preferably % sequence identity. The software typically does this as part of the sequence comparison and generates a numerical result.

In advantageous embodiments described herein, the TALE polypeptides of the invention include a nucleic acid binding domain linked to the one or more effector domains. The terms "effector domain" or "regulatory and functional domain" refer to a polypeptide sequence that has an activity other than binding to the nucleic acid sequence recognized by the nucleic acid binding domain. By combining a nucleic acid binding domain with one or more effector domains, the polypeptides of the invention may be used to target the one or more functions or activities mediated by the effector domain to a particular target DNA sequence to which the nucleic acid binding domain specifically binds.

In some embodiments of the TALE polypeptides described herein, the activity mediated by the effector domain is a biological activity. For example, in some embodiments the effector domain is a transcriptional inhibitor (i.e., a repressor domain), such as an mSin interaction domain (SID). SID4X domain or a Kruppel-associated box (KRAB) or fragments of the KRAB domain. In some embodiments the effector domain is an enhancer of transcription (i.e. an activation domain), such as the VP16, VP64 or p65 activation domain. In some embodiments, the nucleic acid binding is linked, for example, with an effector domain that includes but is not limited to a transposase, integrase, recombinase, resolvase, invertase, protease, DNA methyltransferase, DNA demethylase, histone acetylase, histone deacetylase, nuclease, transcriptional repressor, transcriptional activator, transcription factor recruiting, protein nuclear-localization signal or cellular uptake signal.

In some embodiments, the effector domain is a protein domain which exhibits activities which include but are not limited to transposase activity, integrase activity, recombinase activity, resolvase activity, invertase activity, protease activity, DNA methyltransferase activity, DNA demethylase activity, histone acetylase activity, histone deacetylase activity, nuclease activity, nuclear-localization signaling activity, transcriptional repressor activity, transcriptional activator activity, transcription factor recruiting activity, or cellular uptake signaling activity. Other preferred embodiments of the invention may include any combination the activities described herein.

Zinc Finger Nucleases

Other preferred tools for genome editing for use in the context of this invention include zinc finger systems. One type of programmable DNA-binding domain is provided by artificial zinc-finger (ZF) technology, which involves arrays of ZF modules to target new DNA-binding sites in the genome. Each finger module in a ZF array targets three DNA bases. A customized array of individual zinc finger domains is assembled into a ZF protein (ZFP).

ZFPs can comprise a functional domain. The first synthetic zinc finger nucleases (ZFNs) were developed by fusing a ZF protein to the catalytic domain of the Type IIS restriction enzyme FokI. (Kim, Y. G. et al., 1994, Chimeric restriction endonuclease, Proc. Natl. Acad. Sci. U.S.A. 91, 883-887; Kim, Y. G. et al., 1996, Hybrid restriction enzymes: zinc finger fusions to Fok I cleavage domain. Proc. Natl. Acad. Sci. U.S.A. 93, 1156-1160). Increased cleavage specificity can be attained with decreased off target activity by use of paired ZFN heterodimers, each targeting different nucleotide sequences separated by a short spacer. (Doyon, Y. et al., 2011, Enhancing zinc-finger-nuclease activity with improved obligate heterodimeric architectures. Nat. Methods 8, 74-79). ZFPs can also be designed as transcription activators and repressors and have been used to target many genes in a wide variety of organisms. Exemplary methods of genome editing using ZFNs can be found for example in U.S. Pat. Nos. 6,534,261, 6,607,882, 6,746,838, 6,794,136, 6,824,978, 6,866,997, 6,933,113, 6,979,539, 7,013,219, 7,030,215, 7,220,719, 7,241,573, 7,241,574, 7,585,849, 7,595,376, 6,903,185, and 6,479,626, all of which are specifically incorporated by reference.

Meganucleases

As disclosed herein editing can be made by way of meganucleases, which are endodeoxyribonucleases characterized by a large recognition site (double-stranded DNA sequences of 12 to 40 base pairs). Exemplary method for using meganucleases can be found in U.S. Pat. Nos. 8,163, 514; 8,133,697; 8,021,867; 8,119,361; 8,119,381; 8,124, 369; and 8,129,134, which are specifically incorporated by reference.

RNAi

In certain embodiments, the genetic modifying agent is RNAi (e.g., shRNA). As used herein, "gene silencing" or "gene silenced" in reference to an activity of an RNAi molecule, for example a siRNA or miRNA refers to a decrease in the mRNA level in a cell for a target gene by at least about 5%, about 10%, about 20%, about 30%, about 40%, about 50%, about 60%, about 70%, about 80%, about 90%, about 95%, about 99%, about 100% of the mRNA level found in the cell without the presence of the miRNA or RNA interference molecule. In one preferred embodiment, the mRNA levels are decreased by at least about 70%, about 80%, about 90%, about 95%, about 99%, about 100%.

As used herein, the term "RNAi" refers to any type of interfering RNA, including but not limited to, siRNAi, shRNAi, endogenous microRNA and artificial microRNA. For instance, it includes sequences previously identified as siRNA, regardless of the mechanism of down-stream processing of the RNA (i.e. although siRNAs are believed to have a specific method of in vivo processing resulting in the cleavage of mRNA, such sequences can be incorporated into the vectors in the context of the flanking sequences described herein). The term "RNAi" can include both gene silencing RNAi molecules, and also RNAi effector molecules which activate the expression of a gene.

As used herein, a "siRNA" refers to a nucleic acid that forms a double stranded RNA, which double stranded RNA has the ability to reduce or inhibit expression of a gene or target gene when the siRNA is present or expressed in the same cell as the target gene. The double stranded RNA siRNA can be formed by the complementary strands. In one embodiment, a siRNA refers to a nucleic acid that can form a double stranded siRNA. The sequence of the siRNA can correspond to the full-length target gene, or a subsequence thereof. Typically, the siRNA is at least about 15-50 nucleotides in length (e.g., each complementary sequence of the double stranded siRNA is about 15-50 nucleotides in length, and the double stranded siRNA is about 15-50 base pairs in length, preferably about 19-30 base nucleotides, preferably about 20-25 nucleotides in length, e.g., 20, 21, 22, 23, 24, 25, 26, 27, 28, 29, or 30 nucleotides in length).

As used herein "shRNA" or "small hairpin RNA" (also called stem loop) is a type of siRNA. In one embodiment, these shRNAs are composed of a short, e.g. about 19 to about 25 nucleotide, antisense strand, followed by a nucleotide loop of about 5 to about 9 nucleotides, and the analogous sense strand. Alternatively, the sense strand can precede the nucleotide loop structure and the antisense strand can follow.

The terms "microRNA" or "miRNA" are used interchangeably herein are endogenous RNAs, some of which are known to regulate the expression of protein-coding genes at the posttranscriptional level. Endogenous microRNAs are small RNAs naturally present in the genome that are capable of modulating the productive utilization of mRNA. The term artificial microRNA includes any type of RNA sequence, other than endogenous microRNA, which is capable of modulating the productive utilization of mRNA. MicroRNA sequences have been described in publications such as Lim, et al., Genes & Development, 17, p. 991-1008 (2003), Lim et al Science 299, 1540 (2003), Lee and Ambros Science, 294, 862 (2001), Lau et al., Science 294, 858-861 (2001), Lagos-Quintana et al, Current Biology, 12, 735-739 (2002), Lagos Quintana et al, Science 294, 853-857 (2001), and Lagos-Quintana et al, RNA, 9, 175-179 (2003), which are incorporated by reference. Multiple microRNAs can also be incorporated into a precursor molecule. Furthermore, miRNA-like stem-loops can be expressed in cells as a vehicle to deliver artificial miRNAs and short interfering RNAs (siRNAs) for the purpose of modulating the expression of endogenous genes through the miRNA and/or RNAi pathways.

As used herein, "double stranded RNA" or "dsRNA" refers to RNA molecules that are comprised of two strands. Double-stranded molecules include those comprised of a single RNA molecule that doubles back on itself to form a two-stranded structure. For example, the stem loop structure of the progenitor molecules from which the single-stranded miRNA is derived, called the pre-miRNA (Bartel et al. 2004. Cell 1 16:281-297), comprises a dsRNA molecule.

Antibodies

In certain embodiments, the one or more agents is an antibody. The term "antibody" is used interchangeably with the term "immunoglobulin" herein, and includes intact antibodies, fragments of antibodies, e.g., Fab, F(ab')2 fragments, and intact antibodies and fragments that have been mutated either in their constant and/or variable region (e.g., mutations to produce chimeric, partially humanized, or fully humanized antibodies, as well as to produce antibodies with a desired trait, e.g., enhanced binding and/or reduced FcR binding). The term "fragment" refers to a part or portion of an antibody or antibody chain comprising fewer amino acid residues than an intact or complete antibody or antibody chain. Fragments can be obtained via chemical or enzymatic treatment of an intact or complete antibody or antibody chain. Fragments can also be obtained by recombinant means. Exemplary fragments include Fab, Fab', F(ab')2, Fabc, Fd, dAb, $V_{HH}$ and scFv and/or Fv fragments.

As used herein, a preparation of antibody protein having less than about 50% of non-antibody protein (also referred to herein as a "contaminating protein"), or of chemical precursors, is considered to be "substantially free." 40%, 30%, 20%, 10% and more preferably 5% (by dry weight), of non-antibody protein, or of chemical precursors is considered to be substantially free. When the antibody protein or biologically active portion thereof is recombinantly produced, it is also preferably substantially free of culture medium, i.e., culture medium represents less than about 30%, preferably less than about 20%, more preferably less than about 10%, and most preferably less than about 5% of the volume or mass of the protein preparation.

The term "antigen-binding fragment" refers to a polypeptide fragment of an immunoglobulin or antibody that binds antigen or competes with intact antibody (i.e., with the intact antibody from which they were derived) for antigen binding (i.e., specific binding). As such these antibodies or fragments thereof are included in the scope of the invention, provided that the antibody or fragment binds specifically to a target molecule.

It is intended that the term "antibody" encompass any Ig class or any Ig subclass (e.g. the IgG1, IgG2, IgG3, and IgG4 subclasses of IgG) obtained from any source (e.g., humans and non-human primates, and in rodents, lagomorphs, caprines, bovines, equines, ovines, etc.).

The term "Ig class" or "immunoglobulin class", as used herein, refers to the five classes of immunoglobulin that have been identified in humans and higher mammals, IgG, IgM, IgA, IgD, and IgE. The term "Ig subclass" refers to the two subclasses of IgM (H and L), three subclasses of IgA (IgA1, IgA2, and secretory IgA), and four subclasses of IgG (IgG1, IgG2, IgG3, and IgG4) that have been identified in humans and higher mammals. The antibodies can exist in monomeric or polymeric form; for example, IgM antibodies exist in pentameric form, and IgA antibodies exist in monomeric, dimeric or multimeric form.

The term "IgG subclass" refers to the four subclasses of immunoglobulin class IgG-IgG1, IgG2, IgG3, and IgG4 that have been identified in humans and higher mammals by the heavy chains of the immunoglobulins, VI-γ4, respectively. The term "single-chain immunoglobulin" or "single-chain antibody" (used interchangeably herein) refers to a protein having a two-polypeptide chain structure consisting of a heavy and a light chain, said chains being stabilized, for example, by interchain peptide linkers, which has the ability to specifically bind antigen. The term "domain" refers to a globular region of a heavy or light chain polypeptide comprising peptide loops (e.g., comprising 3 to 4 peptide loops) stabilized, for example, by p pleated sheet and/or intrachain disulfide bond. Domains are further referred to herein as "constant" or "variable", based on the relative lack of sequence variation within the domains of various class members in the case of a "constant" domain, or the significant variation within the domains of various class members in the case of a "variable" domain. Antibody or polypeptide "domains" are often referred to interchangeably in the art as antibody or polypeptide "regions". The "constant" domains of an antibody light chain are referred to interchangeably as "light chain constant regions", "light chain constant domains", "CL" regions or "CL" domains. The "constant" domains of an antibody heavy chain are referred to interchangeably as "heavy chain constant regions", "heavy chain constant domains", "CH" regions or "CH" domains). The "variable" domains of an antibody light chain are referred to interchangeably as "light chain variable regions", "light chain variable domains", "VL" regions or "VL" domains). The "variable" domains of an antibody heavy chain are referred to interchangeably as "heavy chain constant regions", "heavy chain constant domains", "VH" regions or "VH" domains).

The term "region" can also refer to a part or portion of an antibody chain or antibody chain domain (e.g., a part or portion of a heavy or light chain or a part or portion of a constant or variable domain, as defined herein), as well as more discrete parts or portions of said chains or domains. For example, light and heavy chains or light and heavy chain variable domains include "complementarity determining regions" or "CDRs" interspersed among "framework regions" or "FRs", as defined herein.

The term "conformation" refers to the tertiary structure of a protein or polypeptide (e.g., an antibody, antibody chain, domain or region thereof). For example, the phrase "light (or heavy) chain conformation" refers to the tertiary structure of a light (or heavy) chain variable region, and the phrase "antibody conformation" or "antibody fragment conformation" refers to the tertiary structure of an antibody or fragment thereof.

The term "antibody-like protein scaffolds" or "engineered protein scaffolds" broadly encompasses proteinaceous non-immunoglobulin specific-binding agents, typically obtained by combinatorial engineering (such as site-directed random mutagenesis in combination with phage display or other molecular selection techniques). Usually, such scaffolds are derived from robust and small soluble monomeric proteins (such as Kunitz inhibitors or lipocalins) or from a stably folded extra-membrane domain of a cell surface receptor (such as protein A, fibronectin or the ankyrin repeat).

Such scaffolds have been extensively reviewed in Binz et al. (Engineering novel binding proteins from non-immunoglobulin domains. Nat Biotechnol 2005, 23:1257-1268), Gebauer and Skerra (Engineered protein scaffolds as next-generation antibody therapeutics. Curr Opin Chem Biol. 2009, 13:245-55), Gill and Damle (Biopharmaceutical drug discovery using novel protein scaffolds. Curr Opin Biotechnol 2006, 17:653-658), Skerra (Engineered protein scaffolds for molecular recognition. J Mol Recognit 2000, 13:167-187), and Skerra (Alternative non-antibody scaffolds for molecular recognition. Curr Opin Biotechnol 2007, 18:295-304), and include without limitation affibodies, based on the Z-domain of staphylococcal protein A, a three-helix bundle of 58 residues providing an interface on two of its alpha-helices (Nygren, Alternative binding proteins: Affibody binding proteins developed from a small three-helix bundle scaffold. FEBS J 2008, 275:2668-2676); engineered Kunitz domains based on a small (ca. 58 residues) and robust, disulphide-crosslinked serine protease inhibitor, typically of human origin (e.g. LACI-D1), which can be engineered for different protease specificities (Nixon and Wood, Engineered protein inhibitors of proteases. Curr Opin Drug Discov Dev 2006, 9:261-268); monobodies or adnectins based on the 10th extracellular domain of human fibronectin III (1° F.n3), which adopts an Ig-like beta-sandwich fold (94 residues) with 2-3 exposed loops, but lacks the central disulphide bridge (Koide and Koide, Monobodies: antibody mimics based on the scaffold of the fibronectin type III domain. Methods Mol Biol 2007, 352:95-109); anticalins derived from the lipocalins, a diverse family of eight-stranded beta-barrel proteins (ca. 180 residues) that naturally form binding sites for small ligands by means of four structurally variable loops at the open end, which are abundant in humans, insects, and many other organisms (Skerra, Alternative binding proteins: Anticalins harnessing the structural plasticity of the lipocalin ligand pocket to engineer novel binding activities. FEBS J 2008, 275:2677-2683); DARPins, designed ankyrin repeat domains (166 residues), which provide a rigid interface arising from typically three repeated beta-turns (Stumpp et al., DARPins: a new generation of protein therapeutics. Drug Discov Today 2008, 13:695-701); avimers (multimerized LDLR-A module) (Silverman et al., Multivalent avimer proteins evolved by exon shuffling of a family of human receptor domains. Nat Biotechnol 2005, 23:1556-1561); and cysteine-rich knottin peptides (Kolmar, Alternative binding proteins: biological activity and therapeutic potential of cystine-knot miniproteins. FEBS J 2008, 275:2684-2690).

"Specific binding" of an antibody means that the antibody exhibits appreciable affinity for a particular antigen or epitope and, generally, does not exhibit significant cross reactivity. "Appreciable" binding includes binding with an affinity of at least 25 μM. Antibodies with affinities greater than $1\times10^7$ $M^{-1}$ (or a dissociation coefficient of 1 M or less or a dissociation coefficient of 1 nm or less) typically bind with correspondingly greater specificity. Values intermediate of those set forth herein are also intended to be within the scope of the present invention and antibodies of the invention bind with a range of affinities, for example, 100 nM or less, 75 nM or less, 50 nM or less, 25 nM or less, for example 10 nM or less, 5 nM or less, 1 nM or less, or in embodiments 500 pM or less, 100 pM or less, 50 pM or less or 25 pM or less. An antibody that "does not exhibit significant cross reactivity" is one that will not appreciably bind to an entity other than its target (e.g., a different epitope or a different molecule). For example, an antibody that specifically binds to a target molecule will appreciably bind the target molecule but will not significantly react with non-target molecules or peptides. An antibody specific for a particular epitope will, for example, not significantly cross-react with remote epitopes on the same protein or peptide. Specific binding can be determined according to any art-recognized means for determining such binding. Preferably, specific binding is determined according to Scatchard analysis and/or competitive binding assays.

As used herein, the term "affinity" refers to the strength of the binding of a single antigen-combining site with an antigenic determinant. Affinity depends on the closeness of stereochemical fit between antibody combining sites and antigen determinants, on the size of the area of contact between them, on the distribution of charged and hydrophobic groups, etc. Antibody affinity can be measured by equilibrium dialysis or by the kinetic BIACORE™ method. The dissociation constant, Kd, and the association constant, Ka, are quantitative measures of affinity.

As used herein, the term "monoclonal antibody" refers to an antibody derived from a clonal population of antibody-producing cells (e.g., B lymphocytes or B cells) which is homogeneous in structure and antigen specificity. The term "polyclonal antibody" refers to a plurality of antibodies originating from different clonal populations of antibody-producing cells which are heterogeneous in their structure and epitope specificity but which recognize a common antigen. Monoclonal and polyclonal antibodies may exist within bodily fluids, as crude preparations, or may be purified, as described herein.

The term "binding portion" of an antibody (or "antibody portion") includes one or more complete domains, e.g., a pair of complete domains, as well as fragments of an antibody that retain the ability to specifically bind to a target molecule. It has been shown that the binding function of an antibody can be performed by fragments of a full-length antibody. Binding fragments are produced by recombinant DNA techniques, or by enzymatic or chemical cleavage of intact immunoglobulins. Binding fragments include Fab, Fab', F(ab')2, Fabc, Fd, dAb, Fv, single chains, single-chain antibodies, e.g., scFv, and single domain antibodies.

"Humanized" forms of non-human (e.g., murine) antibodies are chimeric antibodies that contain minimal sequence derived from non-human immunoglobulin. For the most part, humanized antibodies are human immunoglobulins (recipient antibody) in which residues from a hypervariable region of the recipient are replaced by residues from a hypervariable region of a non-human species (donor antibody) such as mouse, rat, rabbit or nonhuman primate having the desired specificity, affinity, and capacity. In some instances, FR residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable regions correspond to those of a non-human immunoglobulin and all or substantially all of the FR regions are those of a human immunoglobulin sequence. The humanized antibody optionally also will comprise at least a portion of an immunoglobulin constant region (Fc), typically that of a human immunoglobulin.

Examples of portions of antibodies or epitope-binding proteins encompassed by the present definition include: (i) the Fab fragment, having $V_L$, $C_L$, $V_H$ and $C_H1$ domains; (ii) the Fab' fragment, which is a Fab fragment having one or more cysteine residues at the C-terminus of the $C_H1$ domain; (iii) the Fd fragment having $V_H$ and $C_H1$ domains; (iv) the Fd' fragment having $V_H$ and $C_H1$ domains and one or more cysteine residues at the C-terminus of the CHI domain; (v) the Fv fragment having the $V_L$ and $V_H$ domains of a single arm of an antibody; (vi) the dAb fragment (Ward et al., 341 Nature 544 (1989)) which consists of a $V_H$ domain or a $V_L$ domain that binds antigen; (vii) isolated CDR regions or isolated CDR regions presented in a functional framework; (viii) F(ab')$_2$ fragments which are bivalent fragments including two Fab' fragments linked by a disulphide bridge at the hinge region; (ix) single chain antibody molecules (e.g., single chain Fv; scFv) (Bird et al., 242 Science 423 (1988); and Huston et al., 85 PNAS 5879 (1988)); (x) "diabodies" with two antigen binding sites, comprising a heavy chain variable domain ($V_H$) connected to a light chain variable domain ($V_L$) in the same polypeptide chain (see, e.g., EP 404,097; WO 93/11161; Hollinger et al., 90 PNAS 6444 (1993)); (xi) "linear antibodies" comprising a pair of tandem Fd segments ($V_H$-$C_h1$-$V_H$-$C_h1$) which, together with complementary light chain polypeptides, form a pair of antigen binding regions (Zapata et al., Protein Eng. 8(10): 1057-62 (1995); and U.S. Pat. No. 5,641,870).

As used herein, a "blocking" antibody or an antibody "antagonist" is one which inhibits or reduces biological activity of the antigen(s) it binds. In certain embodiments, the blocking antibodies or antagonist antibodies or portions thereof described herein completely inhibit the biological activity of the antigen(s).

Antibodies may act as agonists or antagonists of the recognized polypeptides. For example, the present invention includes antibodies which disrupt receptor/ligand interactions either partially or fully. The invention features both receptor-specific antibodies and ligand-specific antibodies. The invention also features receptor-specific antibodies which do not prevent ligand binding but prevent receptor activation. Receptor activation (i.e., signaling) may be determined by techniques described herein or otherwise known in the art. For example, receptor activation can be determined by detecting the phosphorylation (e.g., tyrosine or serine/threonine) of the receptor or of one of its down-stream substrates by immunoprecipitation followed by western blot analysis. In specific embodiments, antibodies are provided that inhibit ligand activity or receptor activity by at least 95%, at least 90%, at least 85%, at least 80%, at least 75%, at least 70%, at least 60%, or at least 50% of the activity in absence of the antibody.

The invention also features receptor-specific antibodies which both prevent ligand binding and receptor activation as well as antibodies that recognize the receptor-ligand complex. Likewise, encompassed by the invention are neutralizing antibodies which bind the ligand and prevent binding of the ligand to the receptor, as well as antibodies which bind the ligand, thereby preventing receptor activation, but do not prevent the ligand from binding the receptor. Further included in the invention are antibodies which activate the receptor. These antibodies may act as receptor agonists, i.e., potentiate or activate either all or a subset of the biological activities of the ligand-mediated receptor activation, for example, by inducing dimerization of the receptor. The antibodies may be specified as agonists, antagonists or inverse agonists for biological activities comprising the specific biological activities of the peptides disclosed herein. The antibody agonists and antagonists can be made using methods known in the art. See, e.g., PCT publication WO 96/40281; U.S. Pat. No. 5,811,097; Deng et al., Blood 92(6):1981-1988 (1998); Chen et al., Cancer Res. 58(16): 3668-3678 (1998); Harrop et al., J. Immunol. 161(4):1786-1794 (1998); Zhu et al., Cancer Res. 58(15):3209-3214 (1998); Yoon et al., J. Immunol. 160(7):3170-3179 (1998); Prat et al., J. Cell. Sci. III (Pt2):237-247 (1998); Pitard et al., J. Immunol. Methods 205(2):177-190 (1997); Liautard et al., Cytokine 9(4):233-241 (1997); Carlson et al., J. Biol. Chem. 272(17):11295-11301 (1997); Taryman et al., Neuron 14(4): 755-762 (1995); Muller et al., Structure 6(9):1153-1167 (1998); Bartunek et al., Cytokine 8(1):14-20 (1996).

The antibodies as defined for the present invention include derivatives that are modified, i.e., by the covalent attachment of any type of molecule to the antibody such that covalent attachment does not prevent the antibody from generating an anti-idiotypic response. For example, but not by way of limitation, the antibody derivatives include antibodies that have been modified, e.g., by glycosylation, acetylation, pegylation, phosphorylation, amidation, derivatization by known protecting/blocking groups, proteolytic cleavage, linkage to a cellular ligand or other protein, etc. Any of numerous chemical modifications may be carried out by known techniques, including, but not limited to specific chemical cleavage, acetylation, formylation, metabolic synthesis of tunicamycin, etc. Additionally, the derivative may contain one or more non-classical amino acids.

Simple binding assays can be used to screen for or detect agents that bind to a target protein, or disrupt the interaction between proteins (e.g., a receptor and a ligand). Because certain targets of the present invention are transmembrane proteins, assays that use the soluble forms of these proteins rather than full-length protein can be used, in some embodiments. Soluble forms include, for example, those lacking the transmembrane domain and/or those comprising the IgV domain or fragments thereof which retain their ability to bind their cognate binding partners. Further, agents that inhibit or enhance protein interactions for use in the compositions and methods described herein, can include recombinant peptidomimetics.

Detection methods useful in screening assays include antibody-based methods, detection of a reporter moiety, detection of cytokines as described herein, and detection of a gene signature as described herein.

Another variation of assays to determine binding of a receptor protein to a ligand protein is through the use of affinity biosensor methods. Such methods may be based on the piezoelectric effect, electrochemistry, or optical methods, such as ellipsometry, optical wave guidance, and surface plasmon resonance (SPR).

Aptamers

In certain embodiments, the one or more agents is an aptamer. Nucleic acid aptamers are nucleic acid species that have been engineered through repeated rounds of in vitro selection or equivalently, SELEX (systematic evolution of ligands by exponential enrichment) to bind to various molecular targets such as small molecules, proteins, nucleic acids, cells, tissues and organisms. Nucleic acid aptamers have specific binding affinity to molecules through interactions other than classic Watson-Crick base pairing. Aptamers are useful in biotechnological and therapeutic applications as they offer molecular recognition properties similar to antibodies. In addition to their discriminate recognition, aptamers offer advantages over antibodies as they can be engineered completely in a test tube, are readily produced by chemical synthesis, possess desirable storage properties, and elicit little or no immunogenicity in therapeutic applications. In certain embodiments, RNA aptamers may be expressed from a DNA construct. In other embodiments, a nucleic acid aptamer may be linked to another polynucleotide sequence. The polynucleotide sequence may be a double stranded DNA polynucleotide sequence. The aptamer may be covalently linked to one strand of the polynucleotide sequence. The aptamer may be ligated to the polynucleotide sequence. The polynucleotide sequence may be configured, such that the polynucleotide sequence may be linked to a solid support or ligated to another polynucleotide sequence.

Aptamers, like peptides generated by phage display or monoclonal antibodies ("mAbs"), are capable of specifically binding to selected targets and modulating the target's activity, e.g., through binding, aptamers may block their target's ability to function. A typical aptamer is 10-15 kDa in size (30-45 nucleotides), binds its target with sub-nanomolar affinity, and discriminates against closely related targets (e.g., aptamers will typically not bind other proteins from the same gene family). Structural studies have shown that aptamers are capable of using the same types of binding interactions (e.g., hydrogen bonding, electrostatic complementarity, hydrophobic contacts, steric exclusion) that drives affinity and specificity in antibody-antigen complexes.

Aptamers have a number of desirable characteristics for use in research and as therapeutics and diagnostics including high specificity and affinity, biological efficacy, and excellent pharmacokinetic properties. In addition, they offer specific competitive advantages over antibodies and other protein biologics. Aptamers are chemically synthesized and are readily scaled as needed to meet production demand for research, diagnostic or therapeutic applications. Aptamers are chemically robust. They are intrinsically adapted to regain activity following exposure to factors such as heat and denaturants and can be stored for extended periods (>1 yr) at room temperature as lyophilized powders. Not being bound by a theory, aptamers bound to a solid support or beads may be stored for extended periods.

Oligonucleotides in their phosphodiester form may be quickly degraded by intracellular and extracellular enzymes such as endonucleases and exonucleases. Aptamers can include modified nucleotides conferring improved characteristics on the ligand, such as improved in vivo stability or improved delivery characteristics. Examples of such modifications include chemical substitutions at the ribose and/or phosphate and/or base positions. SELEX identified nucleic acid ligands containing modified nucleotides are described, e.g., in U.S. Pat. No. 5,660,985, which describes oligonucleotides containing nucleotide derivatives chemically modified at the 2' position of ribose, 5 position of pyrimidines, and 8 position of purines, U.S. Pat. No. 5,756,703 which describes oligonucleotides containing various 2'-modified pyrimidines, and U.S. Pat. No. 5,580,737 which describes highly specific nucleic acid ligands containing one or more nucleotides modified with 2'-amino (2'-$NH_2$), 2'-fluoro (2'-F), and/or 2'-o-methyl (2'-OMe) substituents. Modifications of aptamers may also include, modifications at exocyclic amines, substitution of 4-thiouridine, substitution of 5-bromo or 5-iodouracil; backbone modifications, phosphorothioate or allyl phosphate modifications, methylations, and unusual base-pairing combinations such as the isobases isocytidine and isoguanosine. Modifications can also include 3' and 5' modifications such as capping. As used herein, the term phosphorothioate encompasses one or more non-bridging oxygen atoms in a phosphodiester bond replaced by one or more sulfur atoms. In further embodiments, the oligonucleotides comprise modified sugar groups, for example, one or more of the hydroxyl groups is replaced with halogen, aliphatic groups, or functionalized as ethers or amines. In one embodiment, the 2'-position of the furanose residue is substituted by any of an O-methyl, O-alkyl, O-allyl, S-alkyl, S-allyl, or halo group. Methods of synthesis of 2'-modified sugars are described, e.g., in Sproat, et al., Nucl. Acid Res. 19:733-738 (1991); Cotten, et al, Nucl. Acid Res. 19:2629-2635 (1991); and Hobbs, et al, Biochemistry 12:5138-5145 (1973). Other modifications are known to one of ordinary skill in the art. In certain embodiments, aptamers include aptamers with improved off-rates as described in International Patent Publication No. WO 2009012418, "Method for generating aptamers with improved off-rates," incorporated herein by reference in its entirety. In certain embodiments aptamers are chosen from a library of aptamers. Such libraries include, but are not limited to those described in Rohloff et al., "Nucleic Acid Ligands With Protein-like Side Chains: Modified Aptamers and Their Use as Diagnostic and Therapeutic Agents," Molecular Therapy Nucleic Acids (2014) 3, e201. Aptamers are also commercially available (see, e.g., SomaLogic, Inc., Boulder, Colo.). In certain embodiments, the present invention may utilize any aptamer containing any modification as described herein.

Adoptive Cell Transfer

In certain embodiments, T cells differentiated according to the present invention are used in adoptive cell transfer to treat an aberrant inflammatory response (e.g., autoimmune response, cancer). In certain embodiments, a modulating agent according to the present invention is used in combination with ACT to prevent an aberrant immune response.

As used herein, "ACT", "adoptive cell therapy" and "adoptive cell transfer" may be used interchangeably. In certain embodiments, Adoptive cell therapy (ACT) can refer to the transfer of cells to a patient with the goal of transferring the functionality and characteristics into the new host by engraftment of the cells (see, e.g., Mettananda et al., Editing an α-globin enhancer in primary human hematopoietic stem cells as a treatment for β-thalassemia, Nat Commun. 2017 Sep. 4; 8(1):424). As used herein, the term "engraft" or "engraftment" refers to the process of cell incorporation into a tissue of interest in vivo through contact with existing cells of the tissue. Adoptive cell therapy (ACT) can refer to the transfer of cells, most commonly immune-derived cells, back into the same patient or into a new recipient host with the goal of transferring the immunologic functionality and characteristics into the new host. If possible, use of autologous cells helps the recipient by minimizing GVHD issues. The adoptive transfer of autologous tumor infiltrating lymphocytes (TIL) (Zacharakis et al., (2018) Nat Med. 2018 June; 24(6):724-730; Besser et al., (2010) Clin. Cancer Res 16 (9) 2646-55; Dudley et al., (2002) Science 298 (5594): 850-4; and Dudley et al., (2005) Journal of Clinical Oncology 23 (10): 2346-57.) or genetically re-directed peripheral blood mononuclear cells (Johnson et al., (2009) Blood 114 (3): 535-46; and Morgan et al., (2006) Science 314(5796) 126-9) has been used to successfully treat patients with advanced solid tumors, including melanoma, metastatic breast cancer and colorectal carcinoma, as well as patients with CD19-expressing hematologic malignancies (Kalos et al., (2011) Science Translational Medicine 3 (95): 95ra73). In certain embodiments, allogenic cells immune cells are transferred (see, e.g., Ren et al., (2017) Clin Cancer Res 23 (9) 2255-2266). As described further herein, allogenic cells can be edited to reduce alloreactivity and prevent graft-versus-host disease. Thus, use of allogenic cells allows for cells to be obtained from healthy donors and prepared for use in patients as opposed to preparing autologous cells from a patient after diagnosis.

Aspects of the invention involve the adoptive transfer of immune system cells, such as T cells, specific for selected antigens, such as tumor associated antigens or tumor specific neoantigens (see, e.g., Maus et al., 2014, Adoptive Immunotherapy for Cancer or Viruses, Annual Review of Immunology, Vol. 32: 189-225; Rosenberg and Restifo, 2015, Adoptive cell transfer as personalized immunotherapy for human cancer, Science Vol. 348 no. 6230 pp. 62-68; Restifo et al., 2015, Adoptive immunotherapy for cancer: harnessing the T cell response. Nat. Rev. Immunol. 12(4): 269-281; and Jenson and Riddell, 2014, Design and implementation of adoptive therapy with chimeric antigen receptor-modified T cells. Immunol Rev. 257(1): 127-144; and Rajasagi et al., 2014, Systematic identification of personal tumor-specific neoantigens in chronic lymphocytic leukemia. Blood. 2014 Jul. 17; 124(3):453-62).

In certain embodiments, an antigen (such as a tumor antigen) to be targeted in adoptive cell therapy (such as particularly CAR or TCR T-cell therapy) of a disease (such as particularly of tumor or cancer) may be selected from a group consisting of: B cell maturation antigen (BCMA) (see, e.g., Friedman et al., Effective Targeting of Multiple BCMA-Expressing Hematological Malignancies by Anti-BCMA CAR T Cells, Hum Gene Ther. 2018 Mar. 8; Berdeja J G, et al. Durable clinical responses in heavily pretreated patients with relapsed/refractory multiple myeloma: updated results from a multicenter study of bb2121 anti-Bcma CAR T cell therapy. Blood. 2017; 130:740; and Mouhieddine and Ghobrial, Immunotherapy in Multiple Myeloma: The Era of CAR T Cell Therapy, Hematologist, May-June 2018, Volume 15, issue 3); PSA (prostate-specific antigen); prostate-specific membrane antigen (PSMA); PSCA (Prostate stem cell antigen); Tyrosine-protein kinase transmembrane receptor ROR1; fibroblast activation protein (FAP); Tumor-associated glycoprotein 72 (TAG72); Carcinoembryonic antigen (CEA); Epithelial cell adhesion molecule (EPCAM); Mesothelin; Human Epidermal growth factor Receptor 2 (ERBB2 (Her2/neu)); Prostate; Prostatic acid phosphatase (PAP); elongation factor 2 mutant (ELF2M); Insulin-like growth factor 1 receptor (IGF-1R); gpl00; BCR-ABL (breakpoint cluster region-Abelson); tyrosinase; New York esophageal squamous cell carcinoma 1 (NY-ESO-1); κ-light chain, LAGE (L antigen); MAGE (melanoma antigen); Melanoma-associated antigen 1 (MAGE-A1); MAGE A3; MAGE A6; legumain; Human papillomavirus (HPV) E6; HPV E7; prostein; survivin; PCTA1 (Galectin 8); Melan-A/MART-1; Ras mutant; TRP-1 (tyrosinase related protein 1, or gp75); Tyrosinase-related Protein 2 (TRP2); TRP-2/INT2 (TRP-2/intron 2); RAGE (renal antigen); receptor for advanced glycation end products 1 (RAGE1); Renal ubiquitous 1, 2 (RU1, RU2); intestinal carboxyl esterase (iCE); Heat shock protein 70-2 (HSP70-2) mutant; thyroid stimulating hormone receptor (TSHR); CD123; CD171; CD19; CD20; CD22; CD26; CD30; CD33; CD44v7/8 (cluster of differentiation 44, exons 7/8); CD53; CD92; CD100; CD148; CD150; CD200; CD261; CD262; CD362; CS-1 (CD2 subset 1, CRACC, SLAMF7, CD319, and 19A24); C-type lectin-like molecule-1 (CLL-1); ganglioside GD3 (aNeu5Ac (2-8)aNeu5Ac(2-3)bDGalp(1-4)bDGlcp(1-1)Cer); Tn antigen (Tn Ag); Fms-Like Tyrosine Kinase 3 (FLT3); CD38; CD138; CD44v6; B7H3 (CD276); KIT (CD117); Interleukin-13 receptor subunit alpha-2 (IL-13Ra2); Interleukin 11 receptor alpha (IL-11Ra); prostate stem cell antigen (PSCA); Protease Serine 21 (PRSS21); vascular endothelial growth factor receptor 2 (VEGFR2); Lewis(Y) antigen; CD24; Platelet-derived growth factor receptor beta (PDGFR-beta); stage-specific embryonic antigen-4 (SSEA-4); Mucin 1, cell surface associated (MUC1); mucin 16 (MUC16); epidermal growth factor receptor (EGFR); epidermal growth factor receptor variant III (EGFRvIII); neural cell adhesion molecule (NCAM); carbonic anhydrase IX (CAIX); Proteasome (Prosome, Macropain) Subunit, Beta Type, 9 (LMP2); ephrin type-A receptor 2 (EphA2); Ephrin B2; Fucosyl GMi; sialyl Lewis adhesion molecule (sLe); ganglioside GM3 (aNeu5Ac(2-3)bDGalp(1-4)bDGlcp(1-1) Cer); TGS5; high molecular weight-melanoma-associated antigen (HMWMAA); o-acetyl-GD2 ganglioside (OAcGD2); Folate receptor alpha; Folate receptor beta; tumor endothelial marker 1 (TEM1/CD248); tumor endothelial marker 7-related (TEM7R); claudin 6 (CLDN6); G protein-coupled receptor class C group 5, member D (GPRC5D); chromosome X open reading frame 61 (CX-ORF61); CD97; CD179a; anaplastic lymphoma kinase (ALK); Polysialic acid; placenta-specific 1 (PLAC1); hexasaccharide portion of globoH glycoceramide (GloboH); mammary gland differentiation antigen (NY-BR-1); uroplakin 2 (UPK2); Hepatitis A virus cellular receptor 1 (HAVCR1); adrenoceptor beta 3 (ADRB3); pannexin 3 (PANX3); G protein-coupled receptor 20 (GPR20); lymphocyte antigen 6 complex, locus K 9 (LY6K); Olfactory receptor 51E2 (OR51E2); TCR Gamma Alternate Reading Frame Protein (TARP); Wilms tumor protein (WT1); ETS translocation-variant gene 6, located on chromosome 12p (ETV6-AML); sperm protein 17 (SPA17); X Antigen Family, Member 1A (XAGE1); angiopoietin-binding cell surface receptor 2 (Tie 2); CT (cancer/testis (antigen)); melanoma cancer testis antigen-1 (MAD-CT-1); melanoma cancer testis antigen-2 (MAD-CT-2); Fos-related antigen 1; p53; p53 mutant; human Telomerase reverse transcriptase (hTERT); sarcoma translocation breakpoints; melanoma inhibitor of apoptosis (ML-IAP); ERG (transmembrane protease, serine 2 (TMPRSS2) ETS fusion gene); N-Acetyl glucosaminyltransferase V (NA17); paired box protein Pax-3 (PAX3); Androgen receptor; Cyclin B1; Cyclin D1; v-myc avian myelocytomatosis viral oncogene neuroblastoma derived homolog (MYCN); Ras Homolog Family Member C (RhoC); Cytochrome P450 1B1 (CYP1B1); CCCTC-Binding Factor (Zinc Finger Protein)-Like (BORIS); Squamous Cell Carcinoma Antigen Recognized By T Cells-1 or 3 (SART1, SART3); Paired box protein Pax-5 (PAX5); proacrosin binding protein sp32 (OY-TES1); lymphocyte-specific protein tyrosine kinase (LCK); A kinase anchor protein 4 (AKAP-4); synovial sarcoma, X breakpoint-1, -2, -3 or -4 (SSX1, SSX2, SSX3, SSX4); CD79a; CD79b; CD72; Leukocyte-associated immunoglobulin-like receptor 1 (LAIR1); Fc fragment of IgA receptor (FCAR); Leukocyte immunoglobulin-like receptor subfamily A member 2 (LILRA2); CD300 molecule-like family member f (CD300LF); C-type lectin domain family 12 member A (CLEC12A); bone marrow stromal cell antigen 2 (BST2); EGF-like module-containing mucin-like hormone receptor-like 2 (EMR2); lymphocyte antigen 75 (LY75); Glypican-3 (GPC3); Fc receptor-like 5 (FCRL5); mouse double minute 2 homolog (MDM2); livin; alpha fetoprotein (AFP); transmembrane activator and CAML Interactor (TACI); B-cell activating factor receptor (BAFF-R); V-Ki-ras2 Kirsten rat sarcoma viral oncogene homolog (KRAS); immunoglobulin lambda-like polypeptide 1 (IGLL1); 707-AP (707 alanine proline); ART-4 (adenocarcinoma antigen recognized by T4 cells); BAGE (B antigen; b-catenin/m, b-catenin/mutated); CAMEL (CTL-recognized antigen on melanoma); CAP1 (carcinoembryonic antigen peptide 1); CASP-8 (caspase-8); CDC27m (cell-division cycle 27 mutated); CDK4/m (cycline-dependent kinase 4 mutated); Cyp-B (cyclophilin B); DAM (differentiation antigen melanoma); EGP-2 (epithelial glycoprotein 2); EGP-40 (epithelial glycoprotein 40); Erbb2, 3, 4 (erythroblastic leukemia viral oncogene homolog-2, -3, 4); FBP (folate binding protein); fAchR (Fetal acetylcholine receptor); G250 (glycoprotein 250); GAGE (G antigen); GnT-V (N-acetylglucosaminyltransferase V); HAGE (helicase antigen); ULA-A (human leukocyte antigen-A); HST2 (human signet ring tumor 2); KIAA0205; KDR (kinase insert domain receptor); LDLR/FUT (low density lipid receptor/GDP L-fucose: b-D-galactosidase 2-a-L fucosyl-transferase); L1CAM (L1 cell adhesion molecule); MC1R (melanocortin 1 receptor); Myosin/m (myosin mutated); MUM-1, -2, -3 (melanoma ubiquitous mutated 1, 2, 3); NA88-A (NA cDNA clone of patient M88); KG2D (Natural killer group 2, member D) ligands; oncofetal antigen (h5T4); p190 minor bcr-abl (protein of 190KD bcr-abl); Pml/RARa (promyelocytic leukaemia/retinoic acid receptor a); PRAME (preferentially expressed antigen of melanoma); SAGE (sarcoma antigen); TEL/AML1 (translocation Ets-family leukemia/acute myeloid leukemia 1); TPI/m (triose-phosphate isomerase mutated); CD70; and any combination thereof.

In certain embodiments, an antigen to be targeted in adoptive cell therapy (such as particularly CAR or TCR T-cell therapy) of a disease (such as particularly of tumor or cancer) is a tumor-specific antigen (TSA).

In certain embodiments, an antigen to be targeted in adoptive cell therapy (such as particularly CAR or TCR T-cell therapy) of a disease (such as particularly of tumor or cancer) is a neoantigen.

In certain embodiments, an antigen to be targeted in adoptive cell therapy (such as particularly CAR or TCR T-cell therapy) of a disease (such as particularly of tumor or cancer) is a tumor-associated antigen (TAA).

In certain embodiments, an antigen to be targeted in adoptive cell therapy (such as particularly CAR or TCR T-cell therapy) of a disease (such as particularly of tumor or cancer) is a universal tumor antigen. In certain preferred embodiments, the universal tumor antigen is selected from the group consisting of: a human telomerase reverse transcriptase (hTERT), survivin, mouse double minute 2 homolog (MDM2), cytochrome P450 1B 1 (CYP1B), HER2/neu, Wilms' tumor gene 1 (WT1), livin, alpha fetoprotein (AFP), carcinoembryonic antigen (CEA), mucin 16 (MUC16), MUC1, prostate-specific membrane antigen (PSMA), p53, cyclin (Dl), and any combinations thereof.

In certain embodiments, an antigen (such as a tumor antigen) to be targeted in adoptive cell therapy (such as particularly CAR or TCR T-cell therapy) of a disease (such as particularly of tumor or cancer) may be selected from a group consisting of: CD19, BCMA, CD70, CLL-1, MAGE A3, MAGE A6, HPV E6, HPV E7, WT1, CD22, CD171, ROR1, MUC16, and SSX2. In certain preferred embodiments, the antigen may be CD19. For example, CD19 may be targeted in hematologic malignancies, such as in lymphomas, more particularly in B-cell lymphomas, such as without limitation in diffuse large B-cell lymphoma, primary mediastinal b-cell lymphoma, transformed follicular lymphoma, marginal zone lymphoma, mantle cell lymphoma, acute lymphoblastic leukemia including adult and pediatric ALL, non-Hodgkin lymphoma, indolent non-Hodgkin lymphoma, or chronic lymphocytic leukemia. For example, BCMA may be targeted in multiple myeloma or plasma cell leukemia (see, e.g., 2018 American Association for Cancer Research (AACR) Annual meeting Poster: Allogeneic Chimeric Antigen Receptor T Cells Targeting B Cell Maturation Antigen). For example, CLL1 may be targeted in acute myeloid leukemia. For example, MAGE A3, MAGE A6, SSX2, and/or KRAS may be targeted in solid tumors. For example, HPV E6 and/or HPV E7 may be targeted in cervical cancer or head and neck cancer. For example, WT1 may be targeted in acute myeloid leukemia (AML), myelodysplastic syndromes (MDS), chronic myeloid leukemia (CML), non-small cell lung cancer, breast, pancreatic, ovarian or colorectal cancers, or mesothelioma. For example, CD22 may be targeted in B cell malignancies, including non-Hodgkin lymphoma, diffuse large B-cell lymphoma, or acute lymphoblastic leukemia. For example, CD171 may be targeted in neuroblastoma, glioblastoma, or lung, pancreatic, or ovarian cancers. For example, ROR1 may be targeted in ROR1+ malignancies, including non-small cell lung cancer, triple negative breast cancer, pancreatic cancer, prostate cancer, ALL, chronic lymphocytic leukemia, or mantle cell lymphoma. For example, MUC16 may be targeted in MUC16ecto+ epithelial ovarian, fallopian tube or primary peritoneal cancer. For example, CD70 may be targeted in both hematologic malignancies as well as in solid cancers such as renal cell carcinoma (RCC), gliomas (e.g., GBM), and head and neck cancers (HNSCC). CD70 is expressed in both hematologic malignancies as well as in solid cancers, while its expression in normal tissues is restricted to a subset of lymphoid cell types (see, e.g., 2018 American Association for Cancer Research (AACR) Annual meeting Poster: Allogeneic CRISPR Engineered Anti-CD70 CAR-T Cells Demonstrate Potent Preclinical Activity Against Both Solid and Hematological Cancer Cells).

Various strategies may for example be employed to genetically modify T cells by altering the specificity of the T cell receptor (TCR) for example by introducing new TCR a and R chains with selected peptide specificity (see U.S. Pat. No. 8,697,854; PCT Patent Publications: WO2003020763, WO2004033685, WO2004044004, WO2005114215, WO2006000830, WO2008038002, WO2008039818, WO2004074322, WO2005113595, WO2006125962, WO2013166321, WO2013039889, WO2014018863, WO2014083173; U.S. Pat. No. 8,088,379).

As an alternative to, or addition to, TCR modifications, chimeric antigen receptors (CARs) may be used in order to generate immuno-responsive cells, such as T cells, specific for selected targets, such as malignant cells, with a wide variety of receptor chimera constructs having been described (see U.S. Pat. Nos. 5,843,728; 5,851,828; 5,912,170; 6,004,811; 6,284,240; 6,392,013; 6,410,014; 6,753,162; 8,211,422; and, PCT Publication WO9215322).

In general, CARs are comprised of an extracellular domain, a transmembrane domain, and an intracellular domain, wherein the extracellular domain comprises an antigen-binding domain that is specific for a predetermined target. While the antigen-binding domain of a CAR is often an antibody or antibody fragment (e.g., a single chain variable fragment, scFv), the binding domain is not particularly limited so long as it results in specific recognition of a target. For example, in some embodiments, the antigen-binding domain may comprise a receptor, such that the CAR is capable of binding to the ligand of the receptor. Alternatively, the antigen-binding domain may comprise a ligand, such that the CAR is capable of binding the endogenous receptor of that ligand.

The antigen-binding domain of a CAR is generally separated from the transmembrane domain by a hinge or spacer. The spacer is also not particularly limited, and it is designed to provide the CAR with flexibility. For example, a spacer domain may comprise a portion of a human Fc domain, including a portion of the CH3 domain, or the hinge region of any immunoglobulin, such as IgA, IgD, IgE, IgG, or IgM, or variants thereof. Furthermore, the hinge region may be modified so as to prevent off-target binding by FcRs or other potential interfering objects. For example, the hinge may comprise an IgG4 Fc domain with or without a S228P, L235E, and/or N297Q mutation (according to Kabat numbering) in order to decrease binding to FcRs. Additional spacers/hinges include, but are not limited to, CD4, CD8, and CD28 hinge regions.

The transmembrane domain of a CAR may be derived either from a natural or from a synthetic source. Where the source is natural, the domain may be derived from any membrane bound or transmembrane protein. Transmembrane regions of particular use in this disclosure may be derived from CD8, CD28, CD3, CD45, CD4, CD5, CDS, CD9, CD 16, CD22, CD33, CD37, CD64, CD80, CD86, CD 134, CD137, CD 154, TCR. Alternatively, the transmembrane domain may be synthetic, in which case it will comprise predominantly hydrophobic residues such as leucine and valine. Preferably a triplet of phenylalanine, tryptophan and valine will be found at each end of a synthetic transmembrane domain. Optionally, a short oligo- or polypeptide linker, preferably between 2 and 10 amino acids in length may form the linkage between the transmembrane domain and the cytoplasmic signaling domain of the CAR. A glycine-serine doublet provides a particularly suitable linker.

Alternative CAR constructs may be characterized as belonging to successive generations. First-generation CARs typically consist of a single-chain variable fragment of an antibody specific for an antigen, for example comprising a VL linked to a VH of a specific antibody, linked by a flexible linker, for example by a CD8α hinge domain and a CD8α transmembrane domain, to the transmembrane and intracellular signaling domains of either CD3ζ or FcRγ (scFv-CD3ζ or scFv-FcRγ; see U.S. Pat. Nos. 7,741,465; 5,912,172; U.S. Pat. No. 5,906,936). Second-generation CARs incorporate the intracellular domains of one or more costimulatory molecules, such as CD28, OX40 (CD134), or 4-1BB (CD137) within the endodomain (for example scFv-CD28/OX40/4-1BB-CD3ζ; see U.S. Pat. Nos. 8,911,993; 8,916,381; 8,975,071; 9,101,584; 9,102,760; 9,102,761). Third-generation CARs include a combination of costimulatory endodomains, such a CD3ζ-chain, CD97, GDI la-CD18, CD2, ICOS, CD27, CD154, CDS, OX40, 4-1BB, CD2, CD7, LIGHT, LFA-1, NKG2C, B7-H3, CD30, CD40, PD-1, or CD28 signaling domains (for example scFv-CD28-4-1BB-CD3ζ or scFv-CD28-OX40-CD3ζ; see U.S. Pat. Nos. 8,906,682; 8,399,645; 5,686,281; PCT Publication No. WO2014134165; PCT Publication No. WO2012079000). In certain embodiments, the primary signaling domain comprises a functional signaling domain of a protein selected from the group consisting of CD3 zeta, CD3 gamma, CD3 delta, CD3 epsilon, common FcR gamma (FCERIG), FcR beta (Fc Epsilon Rib), CD79a, CD79b, Fc gamma RIIa, DAP10, and DAP12. In certain preferred embodiments, the primary signaling domain comprises a functional signaling domain of CD3ζ or FcRγ. In certain embodiments, the one or more costimulatory signaling domains comprise a functional signaling domain of a protein selected, each independently, from the group consisting of: CD27, CD28, 4-1BB (CD137), OX40, CD30, CD40, PD-1, ICOS, lymphocyte function-associated antigen-1 (LFA-1), CD2, CD7, LIGHT, NKG2C, B7-H3, a ligand that specifically binds with CD83, CDS, ICAM-1, GITR, BAFFR, HVEM (LIGHTR), SLAMF7, NKp80 (KLRF1), CD160, CD19, CD4, CD8 alpha, CD8 beta, IL2R beta, IL2R gamma, IL7R alpha, ITGA4, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, ITGB7, TNFR2, TRANCE/RANKL, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), CD69, SLAMF6 (NTB-A, Lyl08), SLAM (SLAMF1, CD150, IPO-3), BLAME (SLAMF8), SELPLG (CD162), LTBR, LAT, GADS, SLP-76, PAG/Cbp, NKp44, NKp30, NKp46, and NKG2D. In certain embodiments, the one or more costimulatory signaling domains comprise a functional signaling domain of a protein selected, each independently, from the group consisting of: 4-1BB, CD27, and CD28. In certain embodiments, a chimeric antigen receptor may have the design as described in U.S. Pat. No. 7,446,190, comprising an intracellular domain of CD3ζ chain (such as amino acid residues 52-163 of the human CD3 zeta chain, as shown in SEQ ID NO: 14 of U.S. Pat. No. 7,446,190), a signaling region from CD28 and an antigen-binding element (or portion or domain; such as scFv). The CD28 portion, when between the zeta chain portion and the antigen-binding element, may suitably include the transmembrane and signaling domains of CD28 (such as amino acid residues 114-220 of SEQ ID NO: 10, full sequence shown in SEQ ID NO: 6 of U.S. Pat. No. 7,446,190; these can include the following portion of CD28 as set forth in Genbank identifier NM_006139 (sequence version 1, 2 or 3): IEVMYPPPYLD-NEKSNGTIIHVKGKHLCPSPLFPGPSKPFWVLVVVGGV-LACYSLLVTVA FIIFWVRSKRSRLLHSDYMNMT-PRRPGPTRKHYQPYAPPRDFAAYRS)) (SEQ. I.D. No. 4). Alternatively, when the zeta sequence lies between the CD28 sequence and the antigen-binding element, intracellular domain of CD28 can be used alone (such as amino sequence set forth in SEQ ID NO: 9 of U.S. Pat. No. 7,446,190). Hence, certain embodiments employ a CAR comprising (a) a zeta chain portion comprising the intracellular domain of human CD3ζ chain, (b) a costimulatory signaling region, and (c) an antigen-binding element (or portion or domain), wherein the costimulatory signaling region comprises the amino acid sequence encoded by SEQ ID NO: 6 of U.S. Pat. No. 7,446,190.

Alternatively, co-stimulation may be orchestrated by expressing CARs in antigen-specific T cells, chosen so as to be activated and expanded following engagement of their native αβTCR, for example by antigen on professional antigen-presenting cells, with attendant costimulation. In addition, additional engineered receptors may be provided on the immunoresponsive cells, for example to improve targeting of a T-cell attack and/or minimize side effects.

By means of an example and without limitation, Kochenderfer et al., (2009) J Immunother. 32 (7): 689-702 described anti-CD19 chimeric antigen receptors (CAR). FMC63-28Z CAR contained a single chain variable region moiety (scFv) recognizing CD19 derived from the FMC63 mouse hybridoma (described in Nicholson et al., (1997) Molecular Immunology 34: 1157-1165), a portion of the human CD28 molecule, and the intracellular component of the human TCR-ζ molecule. FMC63-CD828BBZ CAR contained the FMC63 scFv, the hinge and transmembrane regions of the CD8 molecule, the cytoplasmic portions of CD28 and 4-1BB, and the cytoplasmic component of the TCR-ζ molecule. The exact sequence of the CD28 molecule included in the FMC63-28Z CAR corresponded to Genbank identifier NM_006139; the sequence included all amino acids starting with the amino acid sequence IEVMYPPPY (SEQ. I.D. No. 3) and continuing all the way to the carboxy-terminus of the protein. To encode the anti-CD19 scFv component of the vector, the authors designed a DNA sequence which was based on a portion of a previously published CAR (Cooper et al., (2003) Blood 101: 1637-1644). This sequence encoded the following components in frame from the 5' end to the 3' end: an XhoI site, the human granulocyte-macrophage colony-stimulating factor (GM-CSF) receptor α-chain signal sequence, the FMC63 light chain variable region (as in Nicholson et al., supra), a linker peptide (as in Cooper et al., supra), the FMC63 heavy chain variable region (as in Nicholson et al., supra), and a NotI site. A plasmid encoding this sequence was digested with XhoI and NotI. To form the MSGV-FMC63-28Z retroviral vector, the XhoI and NotI-digested fragment encoding the FMC63 scFv was ligated into a second XhoI and NotI-digested fragment that encoded the MSGV retroviral backbone (as in Hughes et al., (2005) Human Gene Therapy 16: 457-472) as well as part of the extracellular portion of human CD28, the entire transmembrane and cytoplasmic portion of human CD28, and the cytoplasmic portion of the human TCR-ζ molecule (as in Maher et al., (2002) Nature Biotechnology 20: 70-75). The FMC63-28Z CAR is included in the KTE-C19 (axicabtagene ciloleucel) anti-CD19 CAR-T therapy product in development by Kite Pharma, Inc. for the treatment of inter alia patients with relapsed/refractory aggressive B-cell non-Hodgkin lymphoma (NHL). Accordingly, in certain embodiments, cells intended for adoptive cell therapies, more particularly immunoresponsive cells such as T cells, may express the FMC63-28Z CAR as described by Kochenderfer et al. (supra). Hence, in certain embodiments, cells intended for adoptive cell therapies, more particularly immunoresponsive cells such as T cells, may comprise a CAR comprising an extracellular antigen-binding element (or portion or domain; such as scFv) that specifically binds to an antigen, an intracellular signaling domain comprising an intracellular domain of a CD3ζ chain, and a costimulatory signaling region comprising a signaling domain of CD28. Preferably, the CD28 amino acid sequence is as set forth in Genbank identifier NM_006139 (sequence version 1, 2 or 3) starting with the amino acid sequence IEVMYPPPY and continuing all the way to the carboxy-terminus of the protein. The sequence is reproduced herein: IEVMYPPPYLD-NEKSNGTIIHVKGKHLCPSPLFPGPSKPFWVLVVVGGV-LACYSLLVTVA FIIFWVRSKRSRLLHSDYMNMT-PRRPGPTRKHYQPYAPPRDFAAYRS. Preferably, the antigen is CD19, more preferably the antigen-binding element is an anti-CD19 scFv, even more preferably the anti-CD19 scFv as described by Kochenderfer et al. (supra).

Additional anti-CD19 CARs are further described in WO2015187528. More particularly Example 1 and Table 1 of WO2015187528, incorporated by reference herein, demonstrate the generation of anti-CD19 CARs based on a fully human anti-CD19 monoclonal antibody (47G4, as described in US20100104509) and murine anti-CD19 monoclonal antibody (as described in Nicholson et al. and explained above). Various combinations of a signal sequence (human CD8-alpha or GM-CSF receptor), extracellular and transmembrane regions (human CD8-alpha) and intracellular T-cell signalling domains (CD28-CD3ζ; 4-1BB-CD3ζ; CD27-CD3ζ; CD28-CD27-CD3ζ; 4-1BB-CD27-CD3ζ; CD27-4-1BB-CD3ζ; CD28-CD27-FcεRI gamma chain; or CD28-FcεRI gamma chain) were disclosed. Hence, in certain embodiments, cells intended for adoptive cell therapies, more particularly immunoresponsive cells such as T cells, may comprise a CAR comprising an extracellular antigen-binding element that specifically binds to an antigen, an extracellular and transmembrane region as set forth in Table 1 of WO2015187528 and an intracellular T-cell signalling domain as set forth in Table 1 of WO2015187528. Preferably, the antigen is CD19, more preferably the antigen-binding element is an anti-CD19 scFv, even more preferably the mouse or human anti-CD19 scFv as described in Example 1 of WO2015187528. In certain embodiments, the CAR comprises, consists essentially of or consists of an amino acid sequence of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, or SEQ ID NO: 13 as set forth in Table 1 of WO2015187528.

By means of an example and without limitation, chimeric antigen receptor that recognizes the CD70 antigen is described in WO2012058460A2 (see also, Park et al., CD70 as a target for chimeric antigen receptor T cells in head and neck squamous cell carcinoma, Oral Oncol. 2018 March; 78:145-150; and Jin et al., CD70, a novel target of CAR T-cell therapy for gliomas, Neuro Oncol. 2018 Jan. 10; 20(1):55-65). CD70 is expressed by diffuse large B-cell and follicular lymphoma and also by the malignant cells of Hodgkin's lymphoma, Waldenstrom's macroglobulinemia and multiple myeloma, and by HTLV-1- and EBV-associated malignancies. (Agathanggelou et al. Am. J. Pathol. 1995; 147: 1152-1160; Hunter et al., Blood 2004; 104:4881. 26; Lens et al., J Immunol. 2005; 174:6212-6219; Baba et al., J Virol. 2008; 82:3843-3852.) In addition, CD70 is expressed by non-hematological malignancies such as renal cell carcinoma and glioblastoma. (Junker et al., J Urol. 2005; 173:2150-2153; Chahlavi et al., Cancer Res 2005; 65:5428-5438) Physiologically, CD70 expression is transient and restricted to a subset of highly activated T, B, and dendritic cells.

By means of an example and without limitation, chimeric antigen receptor that recognizes BCMA has been described (see, e.g., US20160046724A1; WO2016014789A2; WO2017211900A1; WO2015158671A1; US20180085444A1; WO2018028647A1; US20170283504A1; and WO2013154760A1).

In certain embodiments, the immune cell may, in addition to a CAR or exogenous TCR as described herein, further comprise a chimeric inhibitory receptor (inhibitory CAR) that specifically binds to a second target antigen and is capable of inducing an inhibitory or immunosuppressive or repressive signal to the cell upon recognition of the second target antigen. In certain embodiments, the chimeric inhibitory receptor comprises an extracellular antigen-binding element (or portion or domain) configured to specifically bind to a target antigen, a transmembrane domain, and an intracellular immunosuppressive or repressive signaling domain. In certain embodiments, the second target antigen is an antigen that is not expressed on the surface of a cancer cell or infected cell or the expression of which is downregulated on a cancer cell or an infected cell. In certain embodiments, the second target antigen is an MHC-class I molecule. In certain embodiments, the intracellular signaling domain comprises a functional signaling portion of an immune checkpoint molecule, such as for example PD-1 or CTLA4. Advantageously, the inclusion of such inhibitory CAR reduces the chance of the engineered immune cells attacking non-target (e.g., non-cancer) tissues.

Alternatively, T-cells expressing CARs may be further modified to reduce or eliminate expression of endogenous TCRs in order to reduce off-target effects. Reduction or elimination of endogenous TCRs can reduce off-target effects and increase the effectiveness of the T cells (U.S. Pat. No. 9,181,527). T cells stably lacking expression of a functional TCR may be produced using a variety of approaches. T cells internalize, sort, and degrade the entire T cell receptor as a complex, with a half-life of about 10 hours in resting T cells and 3 hours in stimulated T cells (von Essen, M. et al. 2004. J. Immunol. 173:384-393). Proper functioning of the TCR complex requires the proper stoichiometric ratio of the proteins that compose the TCR complex. TCR function also requires two functioning TCR zeta proteins with ITAM motifs. The activation of the TCR upon engagement of its MHC-peptide ligand requires the engagement of several TCRs on the same T cell, which all must signal properly. Thus, if a TCR complex is destabilized with proteins that do not associate properly or cannot signal optimally, the T cell will not become activated sufficiently to begin a cellular response.

Accordingly, in some embodiments, TCR expression may be eliminated using RNA interference (e.g., shRNA, siRNA, miRNA, etc.), CRISPR, or other methods that target the nucleic acids encoding specific TCRs (e.g., TCR-α and TCR-β) and/or CD3 chains in primary T cells. By blocking expression of one or more of these proteins, the T cell will no longer produce one or more of the key components of the TCR complex, thereby destabilizing the TCR complex and preventing cell surface expression of a functional TCR.

In some instances, CAR may also comprise a switch mechanism for controlling expression and/or activation of the CAR. For example, a CAR may comprise an extracellular, transmembrane, and intracellular domain, in which the extracellular domain comprises a target-specific binding element that comprises a label, binding domain, or tag that is specific for a molecule other than the target antigen that is expressed on or by a target cell. In such embodiments, the specificity of the CAR is provided by a second construct that comprises a target antigen binding domain (e.g., an scFv or a bispecific antibody that is specific for both the target antigen and the label or tag on the CAR) and a domain that is recognized by or binds to the label, binding domain, or tag on the CAR. See, e.g., WO 2013/044225, WO 2016/000304, WO 2015/057834, WO 2015/057852, WO 2016/070061, U.S. Pat. No. 9,233,125, US 2016/0129109. In this way, a T-cell that expresses the CAR can be administered to a subject, but the CAR cannot bind its target antigen until the second composition comprising an antigen-specific binding domain is administered.

Alternative switch mechanisms include CARs that require multimerization in order to activate their signaling function (see, e.g., US 2015/0368342, US 2016/0175359, US 2015/0368360) and/or an exogenous signal, such as a small molecule drug (US 2016/0166613, Yung et al., Science, 2015), in order to elicit a T-cell response. Some CARs may also comprise a "suicide switch" to induce cell death of the CAR T-cells following treatment (Buddee et al., PLoS One, 2013) or to downregulate expression of the CAR following binding to the target antigen (WO 2016/011210).

Alternative techniques may be used to transform target immunoresponsive cells, such as protoplast fusion, lipofection, transfection or electroporation. A wide variety of vectors may be used, such as retroviral vectors, lentiviral vectors, adenoviral vectors, adeno-associated viral vectors, plasmids or transposons, such as a Sleeping Beauty transposon (see U.S. Pat. Nos. 6,489,458; 7,148,203; 7,160,682; 7,985,739; 8,227,432), may be used to introduce CARs, for example using 2nd generation antigen-specific CARs signaling through CD3ζ and either CD28 or CD137. Viral vectors may for example include vectors based on HIV, SV40, EBV, HSV or BPV.

Cells that are targeted for transformation may for example include T cells, natural killer (NK) cells, cytotoxic T lymphocytes (CTL), Treg cells, human embryonic stem cells, tumor-infiltrating lymphocytes (TIL) or a pluripotent stem cell from which lymphoid cells may be differentiated. T cells expressing a desired CAR may for example be selected through co-culture with γ-irradiated activating and propagating cells (AaPC), which co-express the cancer antigen and co-stimulatory molecules. The engineered CAR T-cells may be expanded, for example by co-culture on AaPC in presence of soluble factors, such as IL-2 and IL-21. This expansion may for example be carried out so as to provide memory CAR+ T cells (which may for example be assayed by non-enzymatic digital array and/or multi-panel flow cytometry). In this way, CAR T cells may be provided that have specific cytotoxic activity against antigen-bearing tumors (optionally in conjunction with production of desired chemokines such as interferon-γ). CAR T cells of this kind may for example be used in animal models, for example to treat tumor xenografts.

In certain embodiments, ACT includes co-transferring CD4+Th1 cells and CD8+ CTLs to induce a synergistic antitumour response (see, e.g., Li et al., Adoptive cell therapy with CD4+ T helper 1 cells and CD8+ cytotoxic T cells enhances complete rejection of an established tumour, leading to generation of endogenous memory responses to non-targeted tumour epitopes. Clin Transl Immunology. 2017 October; 6(10): e160).

In certain embodiments, Th17 cells are transferred to a subject in need thereof. Th17 cells have been reported to directly eradicate melanoma tumors in mice to a greater extent than Th1 cells (Muranski P, et al., Tumor-specific Th17-polarized cells eradicate large established melanoma. Blood. 2008 Jul. 15; 112(2):362-73; and Martin-Orozco N, et al., T helper 17 cells promote cytotoxic T cell activation in tumor immunity. Immunity. 2009 Nov. 20; 31(5):787-98). Those studies involved an adoptive T cell transfer (ACT) therapy approach, which takes advantage of CD4$^+$ T cells that express a TCR recognizing tyrosinase tumor antigen. Exploitation of the TCR leads to rapid expansion of Th17 populations to large numbers ex vivo for reinfusion into the autologous tumor-bearing hosts.

In certain embodiments, ACT may include autologous iPSC-based vaccines, such as irradiated iPSCs in autologous anti-tumor vaccines (see e.g., Kooreman, Nigel G. et al., Autologous iPSC-Based Vaccines Elicit Anti-tumor Responses In Vivo, Cell Stem Cell 22, 1-13, 2018, doi.org/10.1016/j.stem.2018.01.016).

Unlike T-cell receptors (TCRs) that are MHC restricted, CARs can potentially bind any cell surface-expressed antigen and can thus be more universally used to treat patients (see Irving et al., Engineering Chimeric Antigen Receptor T-Cells for Racing in Solid Tumors: Don't Forget the Fuel, Front. Immunol., 3 Apr. 2017, doi.org/10.3389/fimmu.2017.00267). In certain embodiments, in the absence of endogenous T-cell infiltrate (e.g., due to aberrant antigen processing and presentation), which precludes the use of TIL therapy and immune checkpoint blockade, the transfer of CAR T-cells may be used to treat patients (see, e.g., Hinrichs C S, Rosenberg S A. Exploiting the curative potential of adoptive T-cell therapy for cancer. Immunol Rev (2014) 257(1):56-71. doi:10.1111/imr.12132).

Approaches such as the foregoing may be adapted to provide methods of treating and/or increasing survival of a subject having a disease, such as a neoplasia, for example by administering an effective amount of an immunoresponsive cell comprising an antigen recognizing receptor that binds a selected antigen, wherein the binding activates the immunoresponsive cell, thereby treating or preventing the disease (such as a neoplasia, a pathogen infection, an autoimmune disorder, or an allogeneic transplant reaction).

In certain embodiments, the treatment can be administered after lymphodepleting pretreatment in the form of chemotherapy (typically a combination of cyclophosphamide and fludarabine) or radiation therapy. Initial studies in ACT had short lived responses and the transferred cells did not persist in vivo for very long (Houot et al., T-cell-based immunotherapy: adoptive cell transfer and checkpoint inhibition. Cancer Immunol Res (2015) 3(10):1115-22; and Kamta et al., Advancing Cancer Therapy with Present and Emerging Immuno-Oncology Approaches. Front. Oncol. (2017) 7:64). Immune suppressor cells like Tregs and MDSCs may attenuate the activity of transferred cells by outcompeting them for the necessary cytokines. Not being bound by a theory lymphodepleting pretreatment may eliminate the suppressor cells allowing the TILs to persist.

In one embodiment, the treatment can be administrated into patients undergoing an immunosuppressive treatment (e.g., glucocorticoid treatment). The cells or population of cells, may be made resistant to at least one immunosuppressive agent due to the inactivation of a gene encoding a receptor for such immunosuppressive agent. In certain embodiments, the immunosuppressive treatment provides for the selection and expansion of the immunoresponsive T cells within the patient.

In certain embodiments, the treatment can be administered before primary treatment (e.g., surgery or radiation therapy) to shrink a tumor before the primary treatment. In another embodiment, the treatment can be administered after primary treatment to remove any remaining cancer cells.

In certain embodiments, immunometabolic barriers can be targeted therapeutically prior to and/or during ACT to enhance responses to ACT or CAR T-cell therapy and to support endogenous immunity (see, e.g., Irving et al., Engineering Chimeric Antigen Receptor T-Cells for Racing in Solid Tumors: Don't Forget the Fuel, Front. Immunol., 3 Apr. 2017, doi.org/10.3389/fimmu.2017.00267).

The administration of cells or population of cells, such as immune system cells or cell populations, such as more particularly immunoresponsive cells or cell populations, as disclosed herein may be carried out in any convenient manner, including by aerosol inhalation, injection, ingestion, transfusion, implantation or transplantation. The cells or population of cells may be administered to a patient subcutaneously, intradermally, intratumorally, intranodally, intramedullary, intramuscularly, intrathecally, by intravenous or intralymphatic injection, or intraperitoneally. In some embodiments, the disclosed CARs may be delivered or administered into a cavity formed by the resection of tumor tissue (i.e. intracavity delivery) or directly into a tumor prior to resection (i.e. intratumoral delivery). In one embodiment, the cell compositions of the present invention are preferably administered by intravenous injection.

The administration of the cells or population of cells can consist of the administration of $10^4$-$10^9$ cells per kg body weight, preferably $10^5$ to $10^6$ cells/kg body weight including all integer values of cell numbers within those ranges. Dosing in CAR T cell therapies may for example involve administration of from $10^6$ to $10^9$ cells/kg, with or without a course of lymphodepletion, for example with cyclophosphamide. The cells or population of cells can be administrated in one or more doses. In another embodiment, the effective amount of cells are administrated as a single dose. In another embodiment, the effective amount of cells are administrated as more than one dose over a period time. Timing of administration is within the judgment of managing physician and depends on the clinical condition of the patient. The cells or population of cells may be obtained from any source, such as a blood bank or a donor. While individual needs vary, determination of optimal ranges of effective amounts of a given cell type for a particular disease or conditions are within the skill of one in the art. An effective amount means an amount which provides a therapeutic or prophylactic benefit. The dosage administrated will be dependent upon the age, health and weight of the recipient, kind of concurrent treatment, if any, frequency of treatment and the nature of the effect desired.

In another embodiment, the effective amount of cells or composition comprising those cells are administrated parenterally. The administration can be an intravenous administration. The administration can be directly done by injection within a tumor.

To guard against possible adverse reactions, engineered immunoresponsive cells may be equipped with a transgenic safety switch, in the form of a transgene that renders the cells vulnerable to exposure to a specific signal. For example, the herpes simplex viral thymidine kinase (TK) gene may be used in this way, for example by introduction into allogeneic T lymphocytes used as donor lymphocyte infusions following stem cell transplantation (Greco, et al., Improving the safety of cell therapy with the TK-suicide gene. Front. Pharmacol. 2015; 6: 95). In such cells, administration of a nucleoside prodrug such as ganciclovir or acyclovir causes cell death. Alternative safety switch constructs include inducible caspase 9, for example triggered by administration of a small-molecule dimerizer that brings together two nonfunctional icasp9 molecules to form the active enzyme. A wide variety of alternative approaches to implementing cellular proliferation controls have been described (see U.S. Patent Publication No. 20130071414; PCT Patent Publication WO2011146862; PCT Patent Publication WO2014011987; PCT Patent Publication WO2013040371; Zhou et al. BLOOD, 2014, 123/25:3895-3905; Di Stasi et al., The New England Journal of Medicine 2011; 365:1673-1683; Sadelain M, The New England Journal of Medicine 2011; 365:1735-173; Ramos et al., Stem Cells 28(6):1107-15 (2010)).

In a further refinement of adoptive therapies, genome editing may be used to tailor immunoresponsive cells to alternative implementations, for example providing edited CAR T cells (see Poirot et al., 2015, Multiplex genome edited T-cell manufacturing platform for "off-the-shelf" adoptive T-cell immunotherapies, Cancer Res 75 (18): 3853; Ren et al., 2017, Multiplex genome editing to generate universal CAR T cells resistant to PD1 inhibition, Clin Cancer Res. 2017 May 1; 23(9):2255-2266. doi: 10.1158/1078-0432.CCR-16-1300. Epub 2016 Nov. 4; Qasim et al., 2017, Molecular remission of infant B-ALL after infusion of universal TALEN gene-edited CAR T cells, Sci Transl Med. 2017 Jan. 25; 9(374); Legut, et al., 2018, CRISPR-mediated TCR replacement generates superior anticancer transgenic T cells. Blood, 131(3), 311-322; and Georgiadis et al., Long Terminal Repeat CRISPR-CAR-Coupled "Universal" T Cells Mediate Potent Anti-leukemic Effects, Molecular Therapy, In Press, Corrected Proof, Available online 6 Mar. 2018). Cells may be edited using any CRISPR system and method of use thereof as described herein. CRISPR systems may be delivered to an immune cell by any method described herein. In preferred embodiments, cells are edited ex vivo and transferred to a subject in need thereof. Immunoresponsive cells, CAR T cells or any cells used for adoptive cell transfer may be edited. Editing may be performed for example to insert or knock-in an exogenous gene, such as an exogenous gene encoding a CAR or a TCR, at a preselected locus in a cell (e.g. TRAC locus); to eliminate potential alloreactive T-cell receptors (TCR) or to prevent inappropriate pairing between endogenous and exogenous TCR chains, such as to knock-out or knock-down expression of an endogenous TCR in a cell; to disrupt the target of a chemotherapeutic agent in a cell; to block an immune checkpoint, such as to knock-out or knock-down expression of an immune checkpoint protein or receptor in a cell; to knock-out or knock-down expression of other gene or genes in a cell, the reduced expression or lack of expression of which can enhance the efficacy of adoptive therapies using the cell; to knock-out or knock-down expression of an endogenous gene in a cell, said endogenous gene encoding an antigen targeted by an exogenous CAR or TCR; to knock-out or knock-down expression of one or more IHC constituent proteins in a cell; to activate a T cell; to modulate cells such that the cells are resistant to exhaustion or dysfunction; and/or increase the differentiation and/or proliferation of functionally exhausted or dysfunctional CD8+ T-cells (see PCT Patent Publications: WO2013176915, WO2014059173, WO2014172606, WO2014184744, and WO2014191128).

In certain embodiments, editing may result in inactivation of a gene. By inactivating a gene, it is intended that the gene of interest is not expressed in a functional protein form. In a particular embodiment, the CRISPR system specifically catalyzes cleavage in one targeted gene thereby inactivating said targeted gene. The nucleic acid strand breaks caused are commonly repaired through the distinct mechanisms of homologous recombination or non-homologous end joining (NHEJ). However, NHEJ is an imperfect repair process that often results in changes to the DNA sequence at the site of the cleavage. Repair via non-homologous end joining (NHEJ) often results in small insertions or deletions (Indel) and can be used for the creation of specific gene knockouts. Cells in which a cleavage induced mutagenesis event has occurred can be identified and/or selected by well-known methods in the art. In certain embodiments, homology directed repair (HDR) is used to concurrently inactivate a gene (e.g., TRAC) and insert an endogenous TCR or CAR into the inactivated locus.

Hence, in certain embodiments, editing of cells (such as by CRISPR/Cas), particularly cells intended for adoptive cell therapies, more particularly immunoresponsive cells such as T cells, may be performed to insert or knock-in an exogenous gene, such as an exogenous gene encoding a CAR or a TCR, at a preselected locus in a cell. Conventionally, nucleic acid molecules encoding CARs or TCRs are transfected or transduced to cells using randomly integrating vectors, which, depending on the site of integration, may lead to clonal expansion, oncogenic transformation, variegated transgene expression and/or transcriptional silencing of the transgene. Directing of transgene(s) to a specific locus in a cell can minimize or avoid such risks and advantageously provide for uniform expression of the transgene(s) by the cells. Without limitation, suitable 'safe harbor' loci for directed transgene integration include CCR5 or AAVS1. Homology-directed repair (HDR) strategies are known and described elsewhere in this specification allowing to insert transgenes into desired loci (e.g., TRAC locus).

Further suitable loci for insertion of transgenes, in particular CAR or exogenous TCR transgenes, include without limitation loci comprising genes coding for constituents of endogenous T-cell receptor, such as T-cell receptor alpha locus (TRA) or T-cell receptor beta locus (TRB), for example T-cell receptor alpha constant (TRAC) locus, T-cell receptor beta constant 1 (TRBC1) locus or T-cell receptor beta constant 2 (TRBC1) locus. Advantageously, insertion of a transgene into such locus can simultaneously achieve expression of the transgene, potentially controlled by the endogenous promoter, and knock-out expression of the endogenous TCR. This approach has been exemplified in Eyquem et al., (2017) Nature 543: 113-117, wherein the authors used CRISPR/Cas9 gene editing to knock-in a DNA molecule encoding a CD19-specific CAR into the TRAC locus downstream of the endogenous promoter; the CAR-T cells obtained by CRISPR were significantly superior in terms of reduced tonic CAR signaling and exhaustion.

T cell receptors (TCR) are cell surface receptors that participate in the activation of T cells in response to the presentation of antigen. The TCR is generally made from two chains, α and β, which assemble to form a heterodimer and associates with the CD3-transducing subunits to form the T cell receptor complex present on the cell surface. Each α and β chain of the TCR consists of an immunoglobulin-like N-terminal variable (V) and constant (C) region, a hydrophobic transmembrane domain, and a short cytoplasmic region. As for immunoglobulin molecules, the variable region of the α and β chains are generated by V(D)J recombination, creating a large diversity of antigen specificities within the population of T cells. However, in contrast to immunoglobulins that recognize intact antigen, T cells are activated by processed peptide fragments in association with an MHC molecule, introducing an extra dimension to antigen recognition by T cells, known as MHC restriction. Recognition of MHC disparities between the donor and recipient through the T cell receptor leads to T cell proliferation and the potential development of graft versus host disease (GVHD). The inactivation of TCRα or TCRβ can result in the elimination of the TCR from the surface of T cells preventing recognition of alloantigen and thus GVHD. However, TCR disruption generally results in the elimination of the CD3 signaling component and alters the means of further T cell expansion.

Hence, in certain embodiments, editing of cells (such as by CRISPR/Cas), particularly cells intended for adoptive cell therapies, more particularly immunoresponsive cells such as T cells, may be performed to knock-out or knock-down expression of an endogenous TCR in a cell. For example, NHEJ-based or HDR-based gene editing approaches can be employed to disrupt the endogenous TCR alpha and/or beta chain genes. For example, gene editing system or systems, such as CRISPR/Cas system or systems, can be designed to target a sequence found within the TCR beta chain conserved between the beta 1 and beta 2 constant region genes (TRBC1 and TRBC2) and/or to target the constant region of the TCR alpha chain (TRAC) gene.

Allogeneic cells are rapidly rejected by the host immune system. It has been demonstrated that, allogeneic leukocytes present in non-irradiated blood products will persist for no more than 5 to 6 days (Boni, Muranski et al. 2008 Blood 1; 112(12):4746-54). Thus, to prevent rejection of allogeneic cells, the host's immune system usually has to be suppressed to some extent. However, in the case of adoptive cell transfer the use of immunosuppressive drugs also have a detrimental effect on the introduced therapeutic T cells. Therefore, to effectively use an adoptive immunotherapy approach in these conditions, the introduced cells would need to be resistant to the immunosuppressive treatment. Thus, in a particular embodiment, the present invention further comprises a step of modifying T cells to make them resistant to an immunosuppressive agent, preferably by inactivating at least one gene encoding a target for an immunosuppressive agent. An immunosuppressive agent is an agent that suppresses immune function by one of several mechanisms of action. An immunosuppressive agent can be, but is not limited to a calcineurin inhibitor, a target of rapamycin, an interleukin-2 receptor α-chain blocker, an inhibitor of inosine monophosphate dehydrogenase, an inhibitor of dihydrofolic acid reductase, a corticosteroid or an immunosuppressive antimetabolite. The present invention allows conferring immunosuppressive resistance to T cells for immunotherapy by inactivating the target of the immunosuppressive agent in T cells. As non-limiting examples, targets for an immunosuppressive agent can be a receptor for an immunosuppressive agent such as: CD52, glucocorticoid receptor (GR), a FKBP family gene member and a cyclophilin family gene member.

In certain embodiments, editing of cells (such as by CRISPR/Cas), particularly cells intended for adoptive cell therapies, more particularly immunoresponsive cells such as T cells, may be performed to block an immune checkpoint, such as to knock-out or knock-down expression of an immune checkpoint protein or receptor in a cell. Immune checkpoints are inhibitory pathways that slow down or stop immune reactions and prevent excessive tissue damage from uncontrolled activity of immune cells. In certain embodiments, the immune checkpoint targeted is the programmed death-1 (PD-1 or CD279) gene (PDCD1). In other embodiments, the immune checkpoint targeted is cytotoxic T-lymphocyte-associated antigen (CTLA-4). In additional embodiments, the immune checkpoint targeted is another member of the CD28 and CTLA4 Ig superfamily such as BTLA, LAG3, ICOS, PDL1 or KIR. In further additional embodiments, the immune checkpoint targeted is a member of the TNFR superfamily such as CD40, OX40, CD137, GITR, CD27 or TIM-3.

Additional immune checkpoints include Src homology 2 domain-containing protein tyrosine phosphatase 1 (SHP-1) (Watson H A, et al., SHP-1: the next checkpoint target for cancer immunotherapy? Biochem Soc Trans. 2016 Apr. 15; 44(2):356-62). SHP-1 is a widely expressed inhibitory protein tyrosine phosphatase (PTP). In T-cells, it is a negative regulator of antigen-dependent activation and proliferation. It is a cytosolic protein, and therefore not amenable to antibody-mediated therapies, but its role in activation and proliferation makes it an attractive target for genetic manipulation in adoptive transfer strategies, such as chimeric antigen receptor (CAR) T cells. Immune checkpoints may also include T cell immunoreceptor with Ig and ITIM domains (TIGIT/Vstm3/WUCAM/VSIG9) and VISTA (Le Mercier I, et al., (2015) Beyond CTLA-4 and PD-1, the generation Z of negative checkpoint regulators. Front. Immunol. 6:418).

WO2014172606 relates to the use of MT1 and/or MT2 inhibitors to increase proliferation and/or activity of exhausted CD8+ T-cells and to decrease CD8+ T-cell exhaustion (e.g., decrease functionally exhausted or unresponsive CD8+ immune cells). In certain embodiments, metallothioneins are targeted by gene editing in adoptively transferred T cells.

In certain embodiments, targets of gene editing may be at least one targeted locus involved in the expression of an immune checkpoint protein. Such targets may include, but are not limited to CTLA4, PPP2CA, PPP2CB, PTPN6, PTPN22, PDCD1, ICOS (CD278), PDL1, KIR, LAG3, HAVCR2, BTLA, CD160, TIGIT, CD96, CRTAM, LAIR1, SIGLEC7, SIGLEC9, CD244 (2B4), TNFRSF10B, TNFRSF10A, CASP8, CASP10, CASP3, CASP6, CASP7, FADD, FAS, TGFBRII, TGFRBRI, SMAD2, SMAD3, SMAD4, SMAD10, SKI, SKIL, TGIF1, IL10RA, IL10RB, HMOX2, IL6R, IL6ST, EIF2AK4, CSK, PAG1, SIT1, FOXP3, PRDM1, BATF, VISTA, GUCY1A2, GUCY1A3, GUCY1B2, GUCY1B3, MT1, MT2, CD40, OX40, CD137, GITR, CD27, SHP-1, TIM-3, CEACAM-1, CEACAM-3, or CEACAM-5. In preferred embodiments, the gene locus involved in the expression of PD-1 or CTLA-4 genes is targeted. In other preferred embodiments, combinations of genes are targeted, such as but not limited to PD-1 and TIGIT.

By means of an example and without limitation, WO2016196388 concerns an engineered T cell comprising (a) a genetically engineered antigen receptor that specifically binds to an antigen, which receptor may be a CAR; and (b) a disrupted gene encoding a PD-L1, an agent for disruption of a gene encoding a PD-L1, and/or disruption of a gene encoding PD-LI, wherein the disruption of the gene may be mediated by a gene editing nuclease, a zinc finger nuclease (ZFN), CRISPR/Cas9 and/or TALEN. WO2015142675 relates to immune effector cells comprising a CAR in combination with an agent (such as CRISPR, TALEN or ZFN) that increases the efficacy of the immune effector cells in the treatment of cancer, wherein the agent may inhibit an immune inhibitory molecule, such as PD1, PD-L1, CTLA-4, TIM-3, LAG-3, VISTA, BTLA, TIGIT, LAIR1, CD160, 2B4, TGFR beta, CEACAM-1, CEACAM-3, or CEACAM-5. Ren et al., (2017) Clin Cancer Res 23 (9) 2255-2266 performed lentiviral delivery of CAR and electro-transfer of Cas9 mRNA and gRNAs targeting endogenous TCR, 3-2 microglobulin (B2M) and PD1 simultaneously, to generate gene-disrupted allogeneic CAR T cells deficient of TCR, HLA class I molecule and PD1.

In certain embodiments, cells may be engineered to express a CAR, wherein expression and/or function of methylcytosine dioxygenase genes (TET1, TET2 and/or TET3) in the cells has been reduced or eliminated, such as by CRISPR, ZNF or TALEN (for example, as described in WO201704916).

In certain embodiments, editing of cells (such as by CRISPR/Cas), particularly cells intended for adoptive cell therapies, more particularly immunoresponsive cells such as T cells, may be performed to knock-out or knock-down expression of an endogenous gene in a cell, said endogenous gene encoding an antigen targeted by an exogenous CAR or TCR, thereby reducing the likelihood of targeting of the engineered cells. In certain embodiments, the targeted antigen may be one or more antigen selected from the group consisting of CD38, CD138, CS-1, CD33, CD26, CD30, CD53, CD92, CD100, CD148, CD150, CD200, CD261, CD262, CD362, human telomerase reverse transcriptase (hTERT), survivin, mouse double minute 2 homolog (MDM2), cytochrome P450 1B1 (CYP1B), HER2/neu, Wilms' tumor gene 1 (WT1), livin, alpha fetoprotein (AFP), carcinoembryonic antigen (CEA), mucin 16 (MUC16), MUC1, prostate-specific membrane antigen (PSMA), p53, cyclin (D1), B cell maturation antigen (BCMA), transmembrane activator and CAML Interactor (TACI), and B-cell activating factor receptor (BAFF-R) (for example, as described in WO2016011210 and WO2017011804).

In certain embodiments, editing of cells (such as by CRISPR/Cas), particularly cells intended for adoptive cell therapies, more particularly immunoresponsive cells such as T cells, may be performed to knock-out or knock-down expression of one or more MHC constituent proteins, such as one or more HLA proteins and/or beta-2 microglobulin (B2M), in a cell, whereby rejection of non-autologous (e.g., allogeneic) cells by the recipient's immune system can be reduced or avoided. In preferred embodiments, one or more HLA class I proteins, such as HLA-A, B and/or C, and/or B2M may be knocked-out or knocked-down. Preferably, B2M may be knocked-out or knocked-down. By means of an example, Ren et al., (2017) Clin Cancer Res 23 (9) 2255-2266 performed lentiviral delivery of CAR and electro-transfer of Cas9 mRNA and gRNAs targeting endogenous TCR, 3-2 microglobulin (B2M) and PD1 simultaneously, to generate gene-disrupted allogeneic CAR T cells deficient of TCR, HLA class I molecule and PD1.

In other embodiments, at least two genes are edited. Pairs of genes may include, but are not limited to PD1 and TCRα, PD1 and TCRβ, CTLA-4 and TCRα, CTLA-4 and TCRβ, LAG3 and TCRα, LAG3 and TCRβ, Tim3 and TCRα, Tim3 and TCRβ, BTLA and TCRα, BTLA and TCRβ, BY55 and TCRα, BY55 and TCRβ, TIGIT and TCRα, TIGIT and TCRβ, B7H5 and TCRα, B7H5 and TCRβ, LAIR1 and TCRα, LAIR1 and TCRβ, SIGLEC10 and TCRα, SIGLEC1O and TCRβ, 2B4 and TCRα, 2B4 and TCRβ, B2M and TCRα, B2M and TCRβ.

In certain embodiments, a cell may be multiply edited (multiplex genome editing) as taught herein to (1) knock-out or knock-down expression of an endogenous TCR (for example, TRBC1, TRBC2 and/or TRAC), (2) knock-out or knock-down expression of an immune checkpoint protein or receptor (for example PD1, PD-L1 and/or CTLA4); and (3) knock-out or knock-down expression of one or more MHC constituent proteins (for example, HLA-A, B and/or C, and/or B2M, preferably B2M).

Whether prior to or after genetic modification of the T cells, the T cells can be activated and expanded generally using methods as described, for example, in U.S. Pat. Nos. 6,352,694; 6,534,055; 6,905,680; 5,858,358; 6,887,466; 6,905,681; 7,144,575; 7,232,566; 7,175,843; 5,883,223; 6,905,874; 6,797,514; 6,867,041; and 7,572,631. T cells can be expanded in vitro or in vivo.

Immune cells may be obtained using any method known in the art. In one embodiment, allogenic T cells may be obtained from healthy subjects. In one embodiment T cells that have infiltrated a tumor are isolated. T cells may be removed during surgery. T cells may be isolated after removal of tumor tissue by biopsy. T cells may be isolated by any means known in the art. In one embodiment, T cells are obtained by apheresis. In one embodiment, the method may comprise obtaining a bulk population of T cells from a tumor sample by any suitable method known in the art. For example, a bulk population of T cells can be obtained from a tumor sample by dissociating the tumor sample into a cell suspension from which specific cell populations can be selected. Suitable methods of obtaining a bulk population of T cells may include, but are not limited to, any one or more of mechanically dissociating (e.g., mincing) the tumor, enzymatically dissociating (e.g., digesting) the tumor, and aspiration (e.g., as with a needle).

The bulk population of T cells obtained from a tumor sample may comprise any suitable type of T cell. Preferably, the bulk population of T cells obtained from a tumor sample comprises tumor infiltrating lymphocytes (TILs).

The tumor sample may be obtained from any mammal. Unless stated otherwise, as used herein, the term "mammal" refers to any mammal including, but not limited to, mammals of the order Lagomorpha, such as rabbits; the order Carnivora, including Felines (cats) and Canines (dogs); the order Artiodactyla, including Bovines (cows) and Swines (pigs); or of the order Perissodactyla, including Equines (horses). The mammals may be non-human primates, e.g., of the order Primates, Ceboids, or Sigmoids (monkeys) or of the order Anthropoids (humans and apes). In some embodiments, the mammal may be a mammal of the order Rodentia, such as mice and hamsters. Preferably, the mammal is a non-human primate or a human. An especially preferred mammal is the human.

T cells can be obtained from a number of sources, including peripheral blood mononuclear cells (PBMC), bone marrow, lymph node tissue, spleen tissue, and tumors. In certain embodiments of the present invention, T cells can be obtained from a unit of blood collected from a subject using any number of techniques known to the skilled artisan, such as Ficoll separation. In one preferred embodiment, cells from the circulating blood of an individual are obtained by apheresis or leukapheresis. The apheresis product typically contains lymphocytes, including T cells, monocytes, granulocytes, B cells, other nucleated white blood cells, red blood cells, and platelets. In one embodiment, the cells collected by apheresis may be washed to remove the plasma fraction and to place the cells in an appropriate buffer or media for subsequent processing steps. In one embodiment of the invention, the cells are washed with phosphate buffered saline (PBS). In an alternative embodiment, the wash solution lacks calcium and may lack magnesium or may lack many if not all divalent cations. Initial activation steps in the absence of calcium lead to magnified activation. As those of ordinary skill in the art would readily appreciate a washing step may be accomplished by methods known to those in the art, such as by using a semi-automated "flow-through" centrifuge (for example, the Cobe 2991 cell processor) according to the manufacturer's instructions. After washing, the cells may be resuspended in a variety of biocompatible buffers, such as, for example, Ca-free, Mg-free PBS. Alternatively, the undesirable components of the apheresis sample may be removed and the cells directly resuspended in culture media.

In another embodiment, T cells are isolated from peripheral blood lymphocytes by lysing the red blood cells and depleting the monocytes, for example, by centrifugation through a PERCOLL™ gradient. A specific subpopulation of T cells, such as CD28+, CD4+, CDC, CD45RA+, and CD45RO+ T cells, can be further isolated by positive or negative selection techniques. For example, in one preferred embodiment, T cells are isolated by incubation with anti-CD3/anti-CD28 (i.e., 3×28)-conjugated beads, such as DYNABEADS® M-450 CD3/CD28 T, or XCYTE DYNABEADS™ for a time period sufficient for positive selection of the desired T cells. In one embodiment, the time period is about 30 minutes. In a further embodiment, the time period ranges from 30 minutes to 36 hours or longer and all integer values there between. In a further embodiment, the time period is at least 1, 2, 3, 4, 5, or 6 hours. In yet another preferred embodiment, the time period is 10 to 24 hours. In one preferred embodiment, the incubation time period is 24 hours. For isolation of T cells from patients with leukemia, use of longer incubation times, such as 24 hours, can increase cell yield. Longer incubation times may be used to isolate T cells in any situation where there are few T cells as compared to other cell types, such in isolating tumor infiltrating lymphocytes (TIL) from tumor tissue or from immunocompromised individuals. Further, use of longer incubation times can increase the efficiency of capture of CD8+ T cells.

Enrichment of a T cell population by negative selection can be accomplished with a combination of antibodies directed to surface markers unique to the negatively selected cells. A preferred method is cell sorting and/or selection via negative magnetic immunoadherence or flow cytometry that uses a cocktail of monoclonal antibodies directed to cell surface markers present on the cells negatively selected. For example, to enrich for CD4+ cells by negative selection, a monoclonal antibody cocktail typically includes antibodies to CD14, CD20, CD11b, CD16, HLA-DR, and CD8.

Further, monocyte populations (i.e., CD14+ cells) may be depleted from blood preparations by a variety of methodologies, including anti-CD14 coated beads or columns, or utilization of the phagocytotic activity of these cells to facilitate removal. Accordingly, in one embodiment, the invention uses paramagnetic particles of a size sufficient to be engulfed by phagocytotic monocytes. In certain embodiments, the paramagnetic particles are commercially available beads, for example, those produced by Life Technologies under the trade name Dynabeads™. In one embodiment, other non-specific cells are removed by coating the paramagnetic particles with "irrelevant" proteins (e.g., serum proteins or antibodies). Irrelevant proteins and antibodies include those proteins and antibodies or fragments thereof that do not specifically target the T cells to be isolated. In certain embodiments, the irrelevant beads include beads coated with sheep anti-mouse antibodies, goat anti-mouse antibodies, and human serum albumin.

In brief, such depletion of monocytes is performed by preincubating T cells isolated from whole blood, apheresed peripheral blood, or tumors with one or more varieties of irrelevant or non-antibody coupled paramagnetic particles at any amount that allows for removal of monocytes (approximately a 20:1 bead:cell ratio) for about 30 minutes to 2 hours at 22 to 37 degrees C., followed by magnetic removal of cells which have attached to or engulfed the paramagnetic particles. Such separation can be performed using standard methods available in the art. For example, any magnetic separation methodology may be used including a variety of which are commercially available, (e.g., DYNAL® Magnetic Particle Concentrator (DYNAL MPC®)). Assurance of requisite depletion can be monitored by a variety of methodologies known to those of ordinary skill in the art, including flow cytometric analysis of CD14 positive cells, before and after depletion.

For isolation of a desired population of cells by positive or negative selection, the concentration of cells and surface (e.g., particles such as beads) can be varied. In certain embodiments, it may be desirable to significantly decrease the volume in which beads and cells are mixed together (i.e., increase the concentration of cells), to ensure maximum contact of cells and beads. For example, in one embodiment, a concentration of 2 billion cells/ml is used. In one embodiment, a concentration of 1 billion cells/ml is used. In a further embodiment, greater than 100 million cells/ml is used. In a further embodiment, a concentration of cells of 10, 15, 20, 25, 30, 35, 40, 45, or 50 million cells/ml is used. In yet another embodiment, a concentration of cells from 75, 80, 85, 90, 95, or 100 million cells/ml is used. In further embodiments, concentrations of 125 or 150 million cells/ml can be used. Using high concentrations can result in increased cell yield, cell activation, and cell expansion. Further, use of high cell concentrations allows more efficient capture of cells that may weakly express target antigens of interest, such as CD28-negative T cells, or from samples where there are many tumor cells present (i.e., leukemic blood, tumor tissue, etc). Such populations of cells may have therapeutic value and would be desirable to obtain. For example, using high concentration of cells allows more efficient selection of CD8+ T cells that normally have weaker CD28 expression.

In a related embodiment, it may be desirable to use lower concentrations of cells. By significantly diluting the mixture of T cells and surface (e.g., particles such as beads), interactions between the particles and cells is minimized. This selects for cells that express high amounts of desired antigens to be bound to the particles. For example, CD4+ T cells express higher levels of CD28 and are more efficiently captured than CD8+ T cells in dilute concentrations. In one embodiment, the concentration of cells used is $5 \times 10^6$/ml. In other embodiments, the concentration used can be from about $1 \times 10^5$/ml to $1 \times 10^6$/ml, and any integer value in between.

T cells can also be frozen. Wishing not to be bound by theory, the freeze and subsequent thaw step provides a more uniform product by removing granulocytes and to some extent monocytes in the cell population. After a washing step to remove plasma and platelets, the cells may be suspended in a freezing solution. While many freezing solutions and parameters are known in the art and will be useful in this context, one method involves using PBS containing 20% DMSO and 8% human serum albumin, or other suitable cell freezing media, the cells then are frozen to −80° C. at a rate of 1° per minute and stored in the vapor phase of a liquid nitrogen storage tank. Other methods of controlled freezing may be used as well as uncontrolled freezing immediately at −20° C. or in liquid nitrogen.

T cells for use in the present invention may also be antigen-specific T cells. For example, tumor-specific T cells can be used. In certain embodiments, antigen-specific T cells can be isolated from a patient of interest, such as a patient afflicted with a cancer or an infectious disease. In one embodiment, neoepitopes are determined for a subject and T cells specific to these antigens are isolated. Antigen-specific cells for use in expansion may also be generated in vitro using any number of methods known in the art, for example, as described in U.S. Patent Publication No. US 20040224402 entitled, Generation and Isolation of Antigen-Specific T Cells, or in U.S. Pat. No. 6,040,177. Antigen-specific cells for use in the present invention may also be generated using any number of methods known in the art, for example, as described in Current Protocols in Immunology, or Current Protocols in Cell Biology, both published by John Wiley & Sons, Inc., Boston, Mass.

In a related embodiment, it may be desirable to sort or otherwise positively select (e.g. via magnetic selection) the antigen specific cells prior to or following one or two rounds of expansion. Sorting or positively selecting antigen-specific cells can be carried out using peptide-MHC tetramers (Altman, et al., Science. 1996 Oct. 4; 274(5284):94-6). In another embodiment, the adaptable tetramer technology approach is used (Andersen et al., 2012 Nat Protoc. 7:891-902). Tetramers are limited by the need to utilize predicted binding peptides based on prior hypotheses, and the restriction to specific HLAs. Peptide-MHC tetramers can be generated using techniques known in the art and can be made with any MHC molecule of interest and any antigen of interest as described herein. Specific epitopes to be used in this context can be identified using numerous assays known in the art. For example, the ability of a polypeptide to bind to MHC class I may be evaluated indirectly by monitoring the ability to promote incorporation of $^{125}I$ labeled β2-microglobulin (β2m) into MHC class I/β2m/peptide heterotrimeric complexes (see Parker et al., J. Immunol. 152:163, 1994).

In one embodiment cells are directly labeled with an epitope-specific reagent for isolation by flow cytometry followed by characterization of phenotype and TCRs. In one embodiment, T cells are isolated by contacting with T cell specific antibodies. Sorting of antigen-specific T cells, or generally any cells of the present invention, can be carried out using any of a variety of commercially available cell sorters, including, but not limited to, MoFlo sorter (DakoCytomation, Fort Collins, Colo.), FACSAria™, FACSArray™, FACSVantage™, BD™ LSR II, and FACSCalibur™ (BD Biosciences, San Jose, Calif.).

In a preferred embodiment, the method comprises selecting cells that also express CD3. The method may comprise specifically selecting the cells in any suitable manner. Preferably, the selecting is carried out using flow cytometry. The flow cytometry may be carried out using any suitable method known in the art. The flow cytometry may employ any suitable antibodies and stains. Preferably, the antibody is chosen such that it specifically recognizes and binds to the particular biomarker being selected. For example, the specific selection of CD3, CD8, TIM-3, LAG-3, 4-1BB, or PD-1 may be carried out using anti-CD3, anti-CD8, anti-TIM-3, anti-LAG-3, anti-4-1BB, or anti-PD-1 antibodies, respectively. The antibody or antibodies may be conjugated to a bead (e.g., a magnetic bead) or to a fluorochrome. Preferably, the flow cytometry is fluorescence-activated cell sorting (FACS). TCRs expressed on T cells can be selected based on reactivity to autologous tumors. Additionally, T cells that are reactive to tumors can be selected for based on markers using the methods described in patent publication Nos. WO2014133567 and WO2014133568, herein incorporated by reference in their entirety. Additionally, activated T cells can be selected for based on surface expression of CD107a.

In one embodiment of the invention, the method further comprises expanding the numbers of T cells in the enriched cell population. Such methods are described in U.S. Pat. No. 8,637,307 and is herein incorporated by reference in its entirety. The numbers of T cells may be increased at least about 3-fold (or 4-, 5-, 6-, 7-, 8-, or 9-fold), more preferably at least about 10-fold (or 20-, 30-, 40-, 50-, 60-, 70-, 80-, or 90-fold), more preferably at least about 100-fold, more preferably at least about 1,000 fold, or most preferably at least about 100,000-fold. The numbers of T cells may be expanded using any suitable method known in the art. Exemplary methods of expanding the numbers of cells are described in patent publication No. WO 2003057171, U.S. Pat. No. 8,034,334, and U.S. Patent Application Publication No. 2012/0244133, each of which is incorporated herein by reference.

In one embodiment, ex vivo T cell expansion can be performed by isolation of T cells and subsequent stimulation or activation followed by further expansion. In one embodiment of the invention, the T cells may be stimulated or activated by a single agent. In another embodiment, T cells are stimulated or activated with two agents, one that induces a primary signal and a second that is a co-stimulatory signal. Ligands useful for stimulating a single signal or stimulating a primary signal and an accessory molecule that stimulates a second signal may be used in soluble form. Ligands may be attached to the surface of a cell, to an Engineered Multivalent Signaling Platform (EMSP), or immobilized on a surface. In a preferred embodiment both primary and secondary agents are co-immobilized on a surface, for example a bead or a cell. In one embodiment, the molecule providing the primary activation signal may be a CD3 ligand, and the co-stimulatory molecule may be a CD28 ligand or 4-1BB ligand.

In certain embodiments, T cells comprising a CAR or an exogenous TCR, may be manufactured as described in WO2015120096, by a method comprising: enriching a population of lymphocytes obtained from a donor subject; stimulating the population of lymphocytes with one or more T-cell stimulating agents to produce a population of activated T cells, wherein the stimulation is performed in a closed system using serum-free culture medium; transducing the population of activated T cells with a viral vector comprising a nucleic acid molecule which encodes the CAR or TCR, using a single cycle transduction to produce a population of transduced T cells, wherein the transduction is performed in a closed system using serum-free culture medium; and expanding the population of transduced T cells for a predetermined time to produce a population of engineered T cells, wherein the expansion is performed in a closed system using serum-free culture medium. In certain embodiments, T cells comprising a CAR or an exogenous TCR, may be manufactured as described in WO2015120096, by a method comprising: obtaining a population of lymphocytes; stimulating the population of lymphocytes with one or more stimulating agents to produce a population of activated T cells, wherein the stimulation is performed in a closed system using serum-free culture medium; transducing the population of activated T cells with a viral vector comprising a nucleic acid molecule which encodes the CAR or TCR, using at least one cycle transduction to produce a population of transduced T cells, wherein the transduction is performed in a closed system using serum-free culture medium; and expanding the population of transduced T cells to produce a population of engineered T cells, wherein the expansion is performed in a closed system using serum-free culture medium. The predetermined time for expanding the population of transduced T cells may be 3 days. The time from enriching the population of lymphocytes to producing the engineered T cells may be 6 days. The closed system may be a closed bag system. Further provided is population of T cells comprising a CAR or an exogenous TCR obtainable or obtained by said method, and a pharmaceutical composition comprising such cells.

In certain embodiments, T cell maturation or differentiation in vitro may be delayed or inhibited by the method as described in WO2017070395, comprising contacting one or more T cells from a subject in need of a T cell therapy with an AKT inhibitor (such as, e.g., one or a combination of two or more AKT inhibitors disclosed in claim 8 of WO2017070395) and at least one of exogenous Interleukin-7 (IL-7) and exogenous Interleukin-15 (IL-15), wherein the resulting T cells exhibit delayed maturation or differentiation, and/or wherein the resulting T cells exhibit improved T cell function (such as, e.g., increased T cell proliferation; increased cytokine production; and/or increased cytolytic activity) relative to a T cell function of a T cell cultured in the absence of an AKT inhibitor.

In certain embodiments, a patient in need of a T cell therapy may be conditioned by a method as described in WO2016191756 comprising administering to the patient a dose of cyclophosphamide between 200 mg/m$^2$/day and 2000 mg/m$^2$/day and a dose of fludarabine between 20 mg/m$^2$/day and 900 mg/m$^2$/day.

Administration of Pharmaceutical Compositions

A "pharmaceutical composition" refers to a composition that usually contains an excipient, such as a pharmaceutically acceptable carrier that is conventional in the art and that is suitable for administration to cells or to a subject.

The pharmaceutical composition according to the present invention can, in one alternative, include a prodrug. When a pharmaceutical composition according to the present invention includes a prodrug, prodrugs and active metabolites of a compound may be identified using routine techniques known in the art. (See, e.g., Bertolini et al., J. Med. Chem., 40, 2011-2016 (1997); Shan et al., J. Pharm. Sci., 86 (7), 765-767; Bagshawe, Drug Dev. Res., 34, 220-230 (1995); Bodor, Advances in Drug Res., 13, 224-331 (1984); Bundgaard, Design of Prodrugs (Elsevier Press 1985); Larsen, Design and Application of Prodrugs, Drug Design and Development (Krogsgaard-Larsen et al., eds., Harwood Academic Publishers, 1991); Dear et al., J. Chromatogr. B, 748, 281-293 (2000); Spraul et al., J. Pharmaceutical & Biomedical Analysis, 10, 601-605 (1992); and Prox et al., Xenobiol., 3, 103-112 (1992)).

The term "pharmaceutically acceptable" as used throughout this specification is consistent with the art and means compatible with the other ingredients of a pharmaceutical composition and not deleterious to the recipient thereof.

As used herein, "carrier" or "excipient" includes any and all solvents, diluents, buffers (such as, e.g., neutral buffered saline or phosphate buffered saline), solubilizers, colloids, dispersion media, vehicles, fillers, chelating agents (such as, e.g., EDTA or glutathione), amino acids (such as, e.g., glycine), proteins, disintegrants, binders, lubricants, wetting agents, emulsifiers, sweeteners, colorants, flavorings, aromatizers, thickeners, agents for achieving a depot effect, coatings, antifungal agents, preservatives, stabilizers, antioxidants, tonicity controlling agents, absorption delaying agents, and the like. The use of such media and agents for pharmaceutical active components is well known in the art. Such materials should be non-toxic and should not interfere with the activity of the cells or active components.

The precise nature of the carrier or excipient or other material will depend on the route of administration. For example, the composition may be in the form of a parenterally acceptable aqueous solution, which is pyrogen-free and has suitable pH, isotonicity and stability. For general principles in medicinal formulation, the reader is referred to Cell Therapy: Stem Cell Transplantation, Gene Therapy, and Cellular Immunotherapy, by G. Morstyn & W. Sheridan eds., Cambridge University Press, 1996; and Hematopoietic Stem Cell Therapy, E. D. Ball, J. Lister & P. Law, Churchill Livingstone, 2000.

The pharmaceutical composition can be applied parenterally, rectally, orally or topically. Preferably, the pharmaceutical composition may be used for intravenous, intramuscular, subcutaneous, peritoneal, peridural, rectal, nasal, pulmonary, mucosal, or oral application. In a preferred embodiment, the pharmaceutical composition according to the invention is intended to be used as an infusion. The skilled person will understand that compositions which are to be administered orally or topically will usually not comprise cells, although it may be envisioned for oral compositions to also comprise cells, for example when gastro-intestinal tract indications are treated. Each of the cells or active components (e.g., immunomodulants) as discussed herein may be administered by the same route or may be administered by a different route. By means of example, and without limitation, cells may be administered parenterally and other active components may be administered orally.

Liquid pharmaceutical compositions may generally include a liquid carrier such as water or a pharmaceutically acceptable aqueous solution. For example, physiological saline solution, tissue or cell culture media, dextrose or other saccharide solution or glycols such as ethylene glycol, propylene glycol or polyethylene glycol may be included.

The composition may include one or more cell protective molecules, cell regenerative molecules, growth factors, anti-apoptotic factors or factors that regulate gene expression in the cells. Such substances may render the cells independent of their environment.

Such pharmaceutical compositions may contain further components ensuring the viability of the cells therein. For example, the compositions may comprise a suitable buffer system (e.g., phosphate or carbonate buffer system) to achieve desirable pH, more usually near neutral pH, and may comprise sufficient salt to ensure isoosmotic conditions for the cells to prevent osmotic stress. For example, suitable solution for these purposes may be phosphate-buffered saline (PBS), sodium chloride solution, Ringer's Injection or Lactated Ringer's Injection, as known in the art. Further, the composition may comprise a carrier protein, e.g., albumin (e.g., bovine or human albumin), which may increase the viability of the cells.

Further suitably pharmaceutically acceptable carriers or additives are well known to those skilled in the art and for instance may be selected from proteins such as collagen or gelatine, carbohydrates such as starch, polysaccharides, sugars (dextrose, glucose and sucrose), cellulose derivatives like sodium or calcium carboxymethylcellulose, hydroxypropyl cellulose or hydroxypropylmethyl cellulose, pregelatinized starches, pectin agar, carrageenan, clays, hydrophilic gums (acacia gum, guar gum, arabic gum and xanthan gum), alginic acid, alginates, hyaluronic acid, polyglycolic and polylactic acid, dextran, pectins, synthetic polymers such as water-soluble acrylic polymer or polyvinylpyrrolidone, proteoglycans, calcium phosphate and the like.

In certain embodiments, a pharmaceutical cell preparation as taught herein may be administered in a form of liquid composition. In embodiments, the cells or pharmaceutical composition comprising such can be administered systemically, topically, within an organ or at a site of organ dysfunction or lesion.

Preferably, the pharmaceutical compositions may comprise a therapeutically effective amount of the specified immune cells and/or other active components (e.g., immunomodulants). The term "therapeutically effective amount" refers to an amount which can elicit a biological or medicinal response in a tissue, system, animal or human that is being sought by a researcher, veterinarian, medical doctor or other clinician, and in particular can prevent or alleviate one or more of the local or systemic symptoms or features of a disease or condition being treated.

It will be appreciated that administration of therapeutic entities in accordance with the invention will be administered with suitable carriers, excipients, and other agents that are incorporated into formulations to provide improved transfer, delivery, tolerance, and the like. A multitude of appropriate formulations can be found in the formulary known to all pharmaceutical chemists: Remington's Pharmaceutical Sciences (15th ed, Mack Publishing Company, Easton, Pa. (1975)), particularly Chapter 87 by Blaug, Seymour, therein. These formulations include, for example, powders, pastes, ointments, jellies, waxes, oils, lipids, lipid (cationic or anionic) containing vesicles (such as Lipofectin™), DNA conjugates, anhydrous absorption pastes, oil-in-water and water-in-oil emulsions, emulsions carbowax (polyethylene glycols of various molecular weights), semi-solid gels, and semi-solid mixtures containing carbowax. Any of the foregoing mixtures may be appropriate in treatments and therapies in accordance with the present invention, provided that the active ingredient in the formulation is not inactivated by the formulation and the formulation is physiologically compatible and tolerable with the route of administration. See also Baldrick P. "Pharmaceutical excipient development: the need for preclinical guidance." Regul. Toxicol Pharmacol. 32(2):210-8 (2000), Wang W. "Lyophilization and development of solid protein pharmaceuticals." Int. J. Pharm. 203(1-2):1-60 (2000), Charman W N "Lipids, lipophilic drugs, and oral drug delivery-some emerging concepts." J Pharm Sci. 89(8):967-78 (2000), Powell et al. "Compendium of excipients for parenteral formulations" PDA J Pharm Sci Technol. 52:238-311 (1998) and the citations therein for additional information related to formulations, excipients and carriers well known to pharmaceutical chemists.

The medicaments of the invention are prepared in a manner known to those skilled in the art, for example, by means of conventional dissolving, lyophilizing, mixing, granulating or confectioning processes. Methods well known in the art for making formulations are found, for example, in Remington: The Science and Practice of Pharmacy, 20th ed., ed. A. R. Gennaro, 2000, Lippincott Williams & Wilkins, Philadelphia, and Encyclopedia of Pharmaceutical Technology, eds. J. Swarbrick and J. C. Boylan, 1988-1999, Marcel Dekker, New York.

Administration of medicaments of the invention may be by any suitable means that results in a compound concentration that is effective for treating or inhibiting (e.g., by delaying) the development of a disease. The compound is admixed with a suitable carrier substance, e.g., a pharmaceutically acceptable excipient that preserves the therapeutic properties of the compound with which it is administered. One exemplary pharmaceutically acceptable excipient is physiological saline. The suitable carrier substance is generally present in an amount of 1-95% by weight of the total weight of the medicament. The medicament may be provided in a dosage form that is suitable for administration. Thus, the medicament may be in form of, e.g., tablets, capsules, pills, powders, granulates, suspensions, emulsions, solutions, gels including hydrogels, pastes, ointments, creams, plasters, drenches, delivery devices, injectables, implants, sprays, or aerosols.

Administration can be systemic or local. In addition, it may be advantageous to administer the composition into the central nervous system by any suitable route, including intraventricular and intrathecal injection. Pulmonary administration may also be employed by use of an inhaler or nebulizer, and formulation with an aerosolizing agent. It may also be desirable to administer the agent locally to the area in need of treatment; this may be achieved by, for example, and not by way of limitation, local infusion during surgery, topical application, by injection, by means of a catheter, by means of a suppository, or by means of an implant.

Various delivery systems are known and can be used to administer the pharmacological compositions including, but not limited to, encapsulation in liposomes, microparticles, microcapsules; minicells; polymers; capsules; tablets; and the like. In one embodiment, the agent may be delivered in a vesicle, in particular a liposome. In a liposome, the agent is combined, in addition to other pharmaceutically acceptable carriers, with amphipathic agents such as lipids which exist in aggregated form as micelles, insoluble monolayers, liquid crystals, or lamellar layers in aqueous solution. Suitable lipids for liposomal formulation include, without limitation, monoglycerides, diglycerides, sulfatides, lysolecithin, phospholipids, saponin, bile acids, and the like. Preparation of such liposomal formulations is within the level of skill in the art, as disclosed, for example, in U.S. Pat. Nos. 4,837,028 and 4,737,323. In yet another embodiment, the pharmacological compositions can be delivered in a controlled release system including, but not limited to: a delivery pump (See, for example, Saudek, et al., New Engl. J. Med. 321: 574 (1989) and a semi-permeable polymeric material (See, for example, Howard, et al., J. Neurosurg. 71: 105 (1989)). Additionally, the controlled release system can be placed in proximity of the therapeutic target (e.g., a tumor), thus requiring only a fraction of the systemic dose. See, for example, Goodson, In: Medical Applications of Controlled Release, 1984. (CRC Press, Boca Raton, Fla.).

The amount of the agents which will be effective in the treatment of a particular disorder or condition will depend on the nature of the disorder or condition, and may be determined by standard clinical techniques by those of skill within the art. In addition, in vitro assays may optionally be employed to help identify optimal dosage ranges. The precise dose to be employed in the formulation will also depend on the route of administration, and the overall seriousness of the disease or disorder, and should be decided according to the judgment of the practitioner and each patient's circumstances. Ultimately, the attending physician will decide the amount of the agent with which to treat each individual patient. In certain embodiments, the attending physician will administer low doses of the agent and observe the patient's response. Larger doses of the agent may be administered until the optimal therapeutic effect is obtained for the patient, and at that point the dosage is not increased further. Effective doses may be extrapolated from dose-response curves derived from in vitro or animal model test systems. Ultimately the attending physician will decide on the appropriate duration of therapy using compositions of the present invention. Dosage will also vary according to the age, weight and response of the individual patient.

There are a variety of techniques available for introducing nucleic acids into viable cells. The techniques vary depending upon whether the nucleic acid is transferred into cultured cells in vitro, or in vivo in the cells of the intended host. Techniques suitable for the transfer of nucleic acid into mammalian cells in vitro include the use of liposomes, electroporation, microinjection, cell fusion, DEAE-dextran, the calcium phosphate precipitation method, etc. The currently preferred in vivo gene transfer techniques include transfection with viral (typically retroviral) vectors and viral coat protein-liposome mediated transfection.

Biomarkers

In certain embodiments, biomarker or biomarkers are used for diagnosing and/or monitoring diseases. A biomarker can be a physiological metric, a pathological metric, a pathological indication, or a molecule comprising protein, nucleic acid, metabolite, small molecule, polypeptide, amino acid, antibody, antibody fragment, or any combination thereof.

The terms "diagnosis" and "monitoring" are commonplace and well-understood in medical practice. By means of further explanation and without limitation the term "diagnosis" generally refers to the process or act of recognizing, deciding on or concluding on a disease or condition in a subject on the basis of symptoms and signs and/or from results of various diagnostic procedures (such as, for example, from knowing the presence, absence and/or quantity of one or more biomarkers characteristic of the diagnosed disease or condition).

The term "monitoring" generally refers to the follow-up of a disease or a condition in a subject for any changes which may occur over time.

The terms "prognosing" or "prognosis" generally refer to an anticipation on the progression of a disease or condition and the prospect (e.g., the probability, duration, and/or extent) of recovery. A good prognosis of the diseases or conditions taught herein may generally encompass anticipation of a satisfactory partial or complete recovery from the diseases or conditions, preferably within an acceptable time period. A good prognosis of such may more commonly encompass anticipation of not further worsening or aggravating of such, preferably within a given time period. A poor prognosis of the diseases or conditions as taught herein may generally encompass anticipation of a substandard recovery and/or unsatisfactorily slow recovery, or to substantially no recovery or even further worsening of such.

The terms also encompass prediction of a disease. The terms "predicting" or "prediction" generally refer to an advance declaration, indication or foretelling of a disease or condition in a subject not (yet) having said disease or condition. For example, a prediction of a disease or condition in a subject may indicate a probability, chance or risk that the subject will develop said disease or condition, for example within a certain time period or by a certain age. Said probability, chance or risk may be indicated inter alia as an absolute value, range or statistics, or may be indicated relative to a suitable control subject or subject population (such as, e.g., relative to a general, normal or healthy subject or subject population). Hence, the probability, chance or risk that a subject will develop a disease or condition may be advantageously indicated as increased or decreased, or as fold-increased or fold-decreased relative to a suitable control subject or subject population. As used herein, the term "prediction" of the conditions or diseases as taught herein in a subject may also particularly mean that the subject has a 'positive' prediction of such, i.e., that the subject is at risk of having such (e.g., the risk is significantly increased vis-à-vis a control subject or subject population). The term "prediction of no" diseases or conditions as taught herein as described herein in a subject may particularly mean that the subject has a 'negative' prediction of such, i.e., that the subject's risk of having such is not significantly increased vis-à-vis a control subject or subject population.

The term "biomarker" is widespread in the art and commonly broadly denotes a biological molecule, more particularly an endogenous biological molecule, and/or a detectable portion thereof, whose qualitative and/or quantitative evaluation in a tested object (e.g., in or on a cell, cell population, tissue, organ, or organism, e.g., in a biological sample of a subject) is predictive or informative with respect to one or more aspects of the tested object's phenotype and/or genotype. The terms "marker" and "biomarker" may be used interchangeably throughout this specification. Biomarkers as intended herein may be nucleic acid-based or peptide-, polypeptide- and/or protein-based. For example, a marker may be comprised of peptide(s), polypeptide(s) and/or protein(s) encoded by a given gene, or of detectable portions thereof. Further, whereas the term "nucleic acid" generally encompasses DNA, RNA and DNA/RNA hybrid molecules, in the context of markers the term may typically refer to heterogeneous nuclear RNA (hnRNA), pre-mRNA, messenger RNA (mRNA), or complementary DNA (cDNA), or detectable portions thereof. Such nucleic acid species are particularly useful as markers, since they contain qualitative and/or quantitative information about the expression of the gene. Particularly preferably, a nucleic acid-based marker may encompass mRNA of a given gene, or cDNA made of the mRNA, or detectable portions thereof. Any such nucleic acid(s), peptide(s), polypeptide(s) and/or protein(s) encoded by or produced from a given gene are encompassed by the term "gene product(s)".

The terms "gene product" and "product of gene" as used throughout this invention are interchangeable. They both mean "gene product" that is a functional product or products of a gene. In the same meaning, the terms "gene products" and "products of genes" as used throughout this invention are interchangeable.

Preferably, markers as intended herein may be extracellular or cell surface markers, as methods to measure extracellular or cell surface marker(s) need not disturb the integrity of the cell membrane and may not require fixation/permeabilization of the cells.

Unless otherwise apparent from the context, reference herein to any marker, such as a peptide, polypeptide, protein, or nucleic acid, may generally also encompass modified forms of said marker, such as bearing post-expression modifications including, for example, phosphorylation, glycosylation, lipidation, methylation, cysteinylation, sulphonation, glutathionylation, acetylation, oxidation of methionine to methionine sulphoxide or methionine sulphone, and the like.

The term "peptide" as used throughout this specification preferably refers to a polypeptide as used herein consisting essentially of 50 amino acids or less, e.g., 45 amino acids or less, preferably 40 amino acids or less, e.g., 35 amino acids or less, more preferably 30 amino acids or less, e.g., 25 or less, 20 or less, 15 or less, 10 or less or 5 or less amino acids.

The term "polypeptide" as used throughout this specification generally encompasses polymeric chains of amino acid residues linked by peptide bonds. Hence, insofar a protein is only composed of a single polypeptide chain, the terms "protein" and "polypeptide" may be used interchangeably herein to denote such a protein. The term is not limited to any minimum length of the polypeptide chain. The term may encompass naturally, recombinantly, semi-synthetically or synthetically produced polypeptides. The term also encompasses polypeptides that carry one or more co- or post-expression-type modifications of the polypeptide chain, such as, without limitation, glycosylation, acetylation, phosphorylation, sulfonation, methylation, ubiquitination, signal peptide removal, N-terminal Met removal, conversion of pro-enzymes or pre-hormones into active forms, etc. The term further also includes polypeptide variants or mutants which carry amino acid sequence variations vis-à-vis a corresponding native polypeptide, such as, e.g., amino acid deletions, additions and/or substitutions. The term contemplates both full-length polypeptides and polypeptide parts or fragments, e.g., naturally-occurring polypeptide parts that ensue from processing of such full-length polypeptides.

The term "protein" as used throughout this specification generally encompasses macromolecules comprising one or more polypeptide chains, i.e., polymeric chains of amino acid residues linked by peptide bonds. The term may encompass naturally, recombinantly, semi-synthetically or synthetically produced proteins. The term also encompasses proteins that carry one or more co- or post-expression-type modifications of the polypeptide chain(s), such as, without limitation, glycosylation, acetylation, phosphorylation, sulfonation, methylation, ubiquitination, signal peptide removal, N-terminal Met removal, conversion of pro-enzymes or pre-hormones into active forms, etc. The term further also includes protein variants or mutants which carry amino acid sequence variations vis-à-vis a corresponding native protein, such as, e.g., amino acid deletions, additions and/or substitutions. The term contemplates both full-length proteins and protein parts or fragments, e.g., naturally-occurring protein parts that ensue from processing of such full-length proteins.

The reference to any marker, including any peptide, polypeptide, protein, or nucleic acid, corresponds to the marker commonly known under the respective designations in the art. The terms encompass such markers of any organism where found, and particularly of animals, preferably warm-blooded animals, more preferably vertebrates, yet more preferably mammals, including humans and non-human mammals, still more preferably of humans.

The terms particularly encompass such markers, including any peptides, polypeptides, proteins, or nucleic acids, with a native sequence, i.e., ones of which the primary sequence is the same as that of the markers found in or derived from nature. A skilled person understands that native sequences may differ between different species due to genetic divergence between such species. Moreover, native sequences may differ between or within different individuals of the same species due to normal genetic diversity (variation) within a given species. Also, native sequences may differ between or even within different individuals of the same species due to somatic mutations, or post-transcriptional or post-translational modifications. Any such variants or isoforms of markers are intended herein. Accordingly, all sequences of markers found in or derived from nature are considered "native". The terms encompass the markers when forming a part of a living organism, organ, tissue or cell, when forming a part of a biological sample, as well as when at least partly isolated from such sources. The terms also encompass markers when produced by recombinant or synthetic means.

In certain embodiments, markers, including any peptides, polypeptides, proteins, or nucleic acids, may be human, i.e., their primary sequence may be the same as a corresponding primary sequence of or present in a naturally occurring human markers. Hence, the qualifier "human" in this connection relates to the primary sequence of the respective markers, rather than to their origin or source. For example, such markers may be present in or isolated from samples of human subjects or may be obtained by other means (e.g., by recombinant expression, cell-free transcription or translation, or non-biological nucleic acid or peptide synthesis).

The reference herein to any marker, including any peptide, polypeptide, protein, or nucleic acid, also encompasses fragments thereof. Hence, the reference herein to measuring (or measuring the quantity of) any one marker may encompass measuring the marker and/or measuring one or more fragments thereof.

For example, any marker and/or one or more fragments thereof may be measured collectively, such that the measured quantity corresponds to the sum amounts of the collectively measured species. In another example, any marker and/or one or more fragments thereof may be measured each individually. The terms encompass fragments arising by any mechanism, in vivo and/or in vitro, such as, without limitation, by alternative transcription or translation, exo- and/or endo-proteolysis, exo- and/or endo-nucleolysis, or degradation of the peptide, polypeptide, protein, or nucleic acid, such as, for example, by physical, chemical and/or enzymatic proteolysis or nucleolysis.

The term "fragment" as used throughout this specification with reference to a peptide, polypeptide, or protein generally denotes a portion of the peptide, polypeptide, or protein, such as typically an N- and/or C-terminally truncated form of the peptide, polypeptide, or protein. Preferably, a fragment may comprise at least about 30%, e.g., at least about 50% or at least about 70%, preferably at least about 80%, e.g., at least about 85%, more preferably at least about 90%, and yet more preferably at least about 95% or even about 99% of the amino acid sequence length of said peptide, polypeptide, or protein. For example, insofar not exceeding the length of the full-length peptide, polypeptide, or protein, a fragment may include a sequence of ≥5 consecutive amino acids, or ≥10 consecutive amino acids, or ≥20 consecutive amino acids, or ≥30 consecutive amino acids, e.g., ≥40 consecutive amino acids, such as for example ≥50 consecutive amino acids, e.g., ≥60, ≥70, ≥80, ≥90, ≥100, ≥200, ≥300, ≥400, ≥500 or ≥600 consecutive amino acids of the corresponding full-length peptide, polypeptide, or protein.

The term "fragment" as used throughout this specification with reference to a nucleic acid (polynucleotide) generally denotes a 5'- and/or 3'-truncated form of a nucleic acid. Preferably, a fragment may comprise at least about 30%, e.g., at least about 50% or at least about 70%, preferably at least about 80%, e.g., at least about 85%, more preferably at least about 90%, and yet more preferably at least about 95% or even about 99% of the nucleic acid sequence length of said nucleic acid. For example, insofar not exceeding the length of the full-length nucleic acid, a fragment may include a sequence of ≥5 consecutive nucleotides, or ≥10 consecutive nucleotides, or ≥20 consecutive nucleotides, or ≥30 consecutive nucleotides, e.g., ≥40 consecutive nucleotides, such as for example ≥50 consecutive nucleotides, e.g., ≥60, ≥70, ≥80, ≥90, ≥100, ≥200, ≥300, ≥400, ≥500 or ≥600 consecutive nucleotides of the corresponding full-length nucleic acid.

Cells such as immune cells as disclosed herein may in the context of the present specification be said to "comprise the expression" or conversely to "not express" one or more markers, such as one or more genes or gene products; or be described as "positive" or conversely as "negative" for one or more markers, such as one or more genes or gene products; or be said to "comprise" a defined "gene or gene product signature".

Such terms are commonplace and well-understood by the skilled person when characterizing cell phenotypes. By means of additional guidance, when a cell is said to be positive for or to express or comprise expression of a given marker, such as a given gene or gene product, a skilled person would conclude the presence or evidence of a distinct signal for the marker when carrying out a measurement capable of detecting or quantifying the marker in or on the cell. Suitably, the presence or evidence of the distinct signal for the marker would be concluded based on a comparison of the measurement result obtained for the cell to a result of the same measurement carried out for a negative control (for example, a cell known to not express the marker) and/or a positive control (for example, a cell known to express the marker). Where the measurement method allows for a quantitative assessment of the marker, a positive cell may generate a signal for the marker that is at least 1.5-fold higher than a signal generated for the marker by a negative control cell or than an average signal generated for the marker by a population of negative control cells, e.g., at least 2-fold, at least 4-fold, at least 10-fold, at least 20-fold, at least 30-fold, at least 40-fold, at least 50-fold higher or even higher. Further, a positive cell may generate a signal for the marker that is 3.0 or more standard deviations, e.g., 3.5 or more, 4.0 or more, 4.5 or more, or 5.0 or more standard deviations, higher than an average signal generated for the marker by a population of negative control cells.

A marker, for example a gene or gene product, for example a peptide, polypeptide, protein, or nucleic acid, or a group of two or more markers, is "detected" or "measured" in a tested object (e.g., in or on a cell, cell population, tissue, organ, or organism, e.g., in a biological sample of a subject) when the presence or absence and/or quantity of said marker or said group of markers is detected or determined in the tested object, preferably substantially to the exclusion of other molecules and analytes, e.g., other genes or gene products.

The terms "increased" or "increase" or "upregulated" or "upregulate" as used herein generally mean an increase by a statically significant amount. For avoidance of doubt, "increased" means a statistically significant increase of at least 10% as compared to a reference level, including an increase of at least 20%, at least 30%, at least 40%, at least 50%, at least 60%, at least 70%, at least 80%, at least 90%, at least 100% or more, including, for example at least 2-fold, at least 3-fold, at least 4-fold, at least 5-fold, at least 10-fold increase or greater as compared to a reference level, as that term is defined herein.

The term "reduced" or "reduce" or "decrease" or "decreased" or "downregulate" or "downregulated" or "inhibited" or "inhibit" or "inhibiting" or "diminishing" or "diminish" or "remove" or "removed" or "removing" as used herein generally means a decrease by a statistically significant amount relative to a reference. For avoidance of doubt, "reduced" means statistically significant decrease of at least 10% as compared to a reference level, for example a decrease by at least 20%, at least 30%, at least 40%, at least 50%, or at least 60%, or at least 70%, or at least 80%, at least 90% or more, up to and including a 100% decrease (i.e., absent level as compared to a reference sample), or any decrease between 10-100% as compared to a reference level, as that.

The terms "quantity", "amount" and "level" are synonymous and generally well-understood in the art. The terms as used throughout this specification may particularly refer to an absolute quantification of a marker in a tested object (e.g., in or on a cell, cell population, tissue, organ, or organism, e.g., in a biological sample of a subject), or to a relative quantification of a marker in a tested object, i.e., relative to another value such as relative to a reference value, or to a range of values indicating a base-line of the marker. Such values or ranges may be obtained as conventionally known.

An absolute quantity of a marker may be advantageously expressed as weight or as molar amount, or more commonly as a concentration, e.g., weight per volume or mol per volume. A relative quantity of a marker may be advantageously expressed as an increase or decrease or as a fold-increase or fold-decrease relative to said another value, such as relative to a reference value. Performing a relative comparison between first and second variables (e.g., first and second quantities) may but need not require determining first the absolute values of said first and second variables. For example, a measurement method may produce quantifiable readouts (such as, e.g., signal intensities) for said first and second variables, wherein said readouts are a function of the value of said variables, and wherein said readouts may be directly compared to produce a relative value for the first variable vs. the second variable, without the actual need to first convert the readouts to absolute values of the respective variables.

Reference values may be established according to known procedures previously employed for other cell populations, biomarkers and gene or gene product signatures. For example, a reference value may be established in an individual or a population of individuals characterized by a particular diagnosis, prediction and/or prognosis of said disease or condition (i.e., for whom said diagnosis, prediction and/or prognosis of the disease or condition holds true). Such population may comprise without limitation 2 or more, 10 or more, 100 or more, or even several hundred or more individuals.

A "deviation" of a first value from a second value may generally encompass any direction (e.g., increase: first value>second value; or decrease: first value<second value) and any extent of alteration.

For example, a deviation may encompass a decrease in a first value by, without limitation, at least about 10% (about 0.9-fold or less), or by at least about 20% (about 0.8-fold or less), or by at least about 30% (about 0.7-fold or less), or by at least about 40% (about 0.6-fold or less), or by at least about 50% (about 0.5-fold or less), or by at least about 60% (about 0.4-fold or less), or by at least about 70% (about 0.3-fold or less), or by at least about 80% (about 0.2-fold or less), or by at least about 90% (about 0.1-fold or less), relative to a second value with which a comparison is being made.

For example, a deviation may encompass an increase of a first value by, without limitation, at least about 10% (about 1.1-fold or more), or by at least about 20% (about 1.2-fold or more), or by at least about 30% (about 1.3-fold or more), or by at least about 40% (about 1.4-fold or more), or by at least about 50% (about 1.5-fold or more), or by at least about 60% (about 1.6-fold or more), or by at least about 70% (about 1.7-fold or more), or by at least about 80% (about 1.8-fold or more), or by at least about 90% (about 1.9-fold or more), or by at least about 100% (about 2-fold or more), or by at least about 150% (about 2.5-fold or more), or by at least about 200% (about 3-fold or more), or by at least about 500% (about 6-fold or more), or by at least about 700% (about 8-fold or more), or like, relative to a second value with which a comparison is being made.

Preferably, a deviation may refer to a statistically significant observed alteration. For example, a deviation may refer to an observed alteration which falls outside of error margins of reference values in a given population (as expressed, for example, by standard deviation or standard error, or by a predetermined multiple thereof, e.g., ±1×SD or ±2×SD or ±3×SD, or 1×SE or ±2×SE or ±3×SE). Deviation may also refer to a value falling outside of a reference range defined by values in a given population (for example, outside of a range which comprises ≥40%, ≥50%, ≥60%, ≥70%, ≥75% or ≥80% or ≥85% or ≥90% or ≥95% or even ≥100% of values in said population).

In a further embodiment, a deviation may be concluded if an observed alteration is beyond a given threshold or cut-off. Such threshold or cut-off may be selected as generally known in the art to provide for a chosen sensitivity and/or specificity of the prediction methods, e.g., sensitivity and/or specificity of at least 50%, or at least 60%, or at least 70%, or at least 80%, or at least 85%, or at least 90%, or at least 95%.

For example, receiver-operating characteristic (ROC) curve analysis can be used to select an optimal cut-off value of the quantity of a given immune cell population, biomarker or gene or gene product signatures, for clinical use of the present diagnostic tests, based on acceptable sensitivity and specificity, or related performance measures which are well-known per se, such as positive predictive value (PPV), negative predictive value (NPV), positive likelihood ratio (LR+), negative likelihood ratio (LR−), Youden index, or similar.

Detection of a biomarker may be by any means known in the art. Methods of detection include, but are not limited to enzymatic assays, flow cytometry, mass cytometry, fluorescence activated cell sorting (FACS), fluorescence microscopy, affinity separation, magnetic activated cell separation (MACS), microfluidic separation, RNA-seq (e.g., bulk or single cell), quantitative PCR, MERFISH (multiplex (in situ) RNA FISH), immunological assay methods by specific binding between a separable, detectable and/or quantifiable immunological binding agent (antibody) and the marker, mass spectrometry analysis methods, chromatography methods and combinations thereof. Immunological assay methods include without limitation immunohistochemistry, immunocytochemistry, flow cytometry, mass cytometry, fluorescence microscopy, fluorescence based cell sorting using microfluidic systems, immunoaffinity adsorption based techniques such as affinity chromatography, magnetic particle separation, magnetic activated cell sorting or bead based cell sorting using microfluidic systems, enzyme-linked immunosorbent assay (ELISA) and ELISPOT based techniques, radioimmunoassay (RIA), Western blot, etc. While particulars of chromatography are well known in the art, for further guidance see, e.g., Meyer M., 1998, ISBN: 047198373X, and "Practical HPLC Methodology and Applications", Bidlingmeyer, B. A., John Wiley & Sons Inc., 1993. Exemplary types of chromatography include, without limitation, high-performance liquid chromatography (HPLC), normal phase HPLC (NP-HPLC), reversed phase HPLC (RP-HPLC), ion exchange chromatography (IEC), such as cation or anion exchange chromatography, hydrophilic interaction chromatography (HILIC), hydrophobic interaction chromatography (HIC), size exclusion chromatography (SEC) including gel filtration chromatography or gel permeation chromatography, chromatofocusing, affinity chromatography such as immunoaffinity, immobilised metal affinity chromatography, and the like.

In some embodiments, an antibody or antibody fragment that binds to ST2 can induce antibody-dependent cell-mediated cytotoxicity (ADCC) of cells. In a preferred embodiment, the cells targeted by anti-ST2 antibody or antibody fragment are effector Treg cells. In a further preferred embodiment, the anti-ST2 antibody or antibody fragment targeted effector Treg cells are in a population of heterogeneous cells. The population of heterogeneous cells are in a tumor microenvironment.

"Antibody-dependent cell-mediated cytotoxicity" (ADCC) refers to a cell-mediated reaction in which non-specific cytotoxic cells (e.g., natural killer (NK) cells, neutrophils, and macrophages) recognize bound antibody on a target cell and subsequently cause lysis of the target cell. In preferred embodiments, such cells are effector Treg cells. While not wishing to be limited to any particular mechanism of action, these cytotoxic cells that mediate ADCC generally express Fc receptors (FcRs). The primary cells for mediating ADCC, NK cells, express FcγRIII, whereas monocytes express FcγRI, FcγRII, FcγRIII and/or FcγRIV. FcR expression on hematopoietic cells is summarized in Ravetch and Kinet, Annu. Rev. Immunol., 9:457-92 (1991). To assess ADCC activity of a molecule, an in vitro ADCC assay, such as that described in U.S. Pat. No. 5,500,362 or 5,821,337 may be performed. Useful effector cells for such assays include peripheral blood mononuclear cells (PBMC) and Natural Killer (NK) cells. Alternatively, or additionally, ADCC activity of the molecules of interest may be assessed in vivo, e.g., in an animal model such as that disclosed in Clynes et al., PNAS (USA), 95:652-656 (1998).

Specific high-affinity IgG antibodies directed to the surface of target cells "arm" the cytotoxic cells and are absolutely required for such killing. Lysis of the target cell is extracellular, requires direct cell-to-cell contact, and does not involve complement. It is contemplated that, in addition to antibodies, other proteins comprising Fc regions, specifically Fc fusion proteins, having the capacity to bind specifically to an antigen-bearing target cell will be able to effect cell-mediated cytotoxicity. For simplicity, the cell-mediated cytotoxicity resulting from the activity of an Fc fusion protein is also referred to herein as ADCC activity.

The ability of any particular Fc variant protein to mediate lysis of the target cell by ADCC can be assayed. To assess ADCC activity an Fc variant protein of interest is added to target cells in combination with immune effector cells, which may be activated by the antigen antibody complexes resulting in cytolysis of the target cell. Cytolysis is generally detected by the release of label (e.g. radioactive substrates, fluorescent dyes or natural intracellular proteins) from the lysed cells. Useful effector cells for such assays include peripheral blood mononuclear cells (PBMC) and Natural Killer (NK) cells. Specific examples of in vitro ADCC assays are described in Wisecarver et al., 1985, 79:277-282; Bruggemann et al., 1987, J Exp Med, 166:1351-1361; Wilkinson et al., 2001, J Immunol Methods, 258:183-191; Patel et al., 1995, J Immunol Methods, 184:29-38. Alternatively, or additionally, ADCC activity of the Fc variant protein of interest may be assessed in vivo, e.g., in an animal model such as that disclosed in Clynes et al., 1998, PNAS USA, 95:652-656.

In one embodiment, an Fc variant protein has enhanced ADCC activity relative to a comparable molecule. In a specific embodiment, an Fc variant protein has ADCC activity that is at least 2-fold, or at least 3-fold, or at least 5-fold or at least 10-fold or at least 50-fold or at least 100-fold greater than that of a comparable molecule. In another specific embodiment, an Fc variant protein has enhanced binding to the Fc receptor FcγRIIIA and has enhanced ADCC activity relative to a comparable molecule. In other embodiments, the Fc variant protein has both enhanced ADCC activity and enhanced serum half-life relative to a comparable molecule.

The invention is further described in the following examples, which do not limit the scope of the invention described in the claims.

EXAMPLES

Example 1—CD103 and KLRG1 Mark an Activated, Heterogeneous Population of Lung Tissue $T_{reg}$ Cells The applicants have previously demonstrated that tumor development in the KP model is associated with the expansion of lung-infiltrating $T_{regs}$, a large proportion of which express CD103 (integrin αE) and killer cell lectin-like receptor 1 (KLRG1), which have been associated with $T_{reg}$ effector activity and terminal differentiation, respectively (Beyersdorf et al., 2007; Cheng et al., 2012; Huehn et al., 2004; Lehmann et al., 2002; Sather et al., 2007). The applicants characterized the heterogeneity of the $T_{reg}$ population in KP mice with advanced disease. While $T_{reg}$ cells in the draining lymph node (dLN) were predominantly CD103-KLRG1-(double-negative, DN) or CD103$^+$KLRG1$^-$ (single-positive, SP), nearly 40% of lung $T_{regs}$ from late-stage, tumor-bearing KP mice were CD103$^+$KLRG1$^+$ (double-positive, DP) (FIG. 1A). DP $T_{regs}$ in late-stage, tumor-bearing mice had increased expression of genes associated with enhanced $T_{reg}$ cell activity, including GITR, CD39, and PD-1, compared to SP and DN $T_{regs}$ (Joshi et al., 2015). The applicants therefore hypothesized that these $T_{reg}$ subsets may have distinct tissue and tumor-specific transcriptional programs.

To identify such a program, the applicants bred KP mice to Foxp3 reporter mice to facilitate isolation and manipulation of $T_{regs}$ from tumor-bearing mice. Using a previously-described method (Anderson et al., 2012), mice were injected with antibody prior to sacrifice to label intravascular cells and distinguish tissue-infiltrating populations. The applicants profiled DP, SP, and DN $T_{regs}$ isolated from the lungs of tumor-bearing KP-Foxp3$^{RFP}$ mice at 20 weeks post infection (p.i.) with Lenti-LucOS by bulk RNA-Seq (FIG. 1A). The applicants also profiled SP and DN $T_{regs}$ from matching mediastinal lymph nodes (msLNs) and DN $T_{regs}$ from the spleen of one tumor-bearing mouse for comparison.

The most significant distinction in the data by Independent Component Analysis (ICA) was between lung-infiltrating and peripheral $T_{regs}$ (FIG. 8A). A 284 gene signature strongly distinguished lung-infiltrating $T_{reg}$ cells ("KPLung_TR signature genes", FIG. 1B), which The applicants confirmed by quantitative RT-PCR (qPCR) of Pparg1, Nr4a1, Areg, and Gata1 expression (FIG. 8B). This KPLung_TR signature was enriched for signatures of other tissue $T_{regs}$, including $T_{regs}$ in visceral adipose tissue (VAT), colonic lamina propria, and wounded muscle (FIG. 8C). Genes upregulated in the KPLung_TR signature also included activation, differentiation, and growth factor signaling genes (FIG. 8D), consistent with prior reports that $T_{regs}$ promote tissue repair (Arpaia et al., 2015; Burzyn et al., 2013). Notably, the signature was enriched for orthologs of genes induced in human colorectal cancer (CRC) and NSCLC-associated $T_{regs}$ (De Simone et al., 2016) (FIG. 8E), suggesting that lung $T_{regs}$ in human cancer and the KP model have a common "tissue $T_{reg}$" phenotype.

Several lines of evidence further suggest that the DP population is activated. First, genes upregulated and down-regulated transiently in activated $T_{regs}$ were differentially expressed in DP vs. DN $T_{regs}$ (FIG. 8F), which may reflect antigen exposure of this $T_{reg}$ population in the tumor microenvironment (van der Veeken et al., 2016). Second, genes upregulated in DP $T_{regs}$ vs. all other $T_{reg}$, in tumor-bearing lungs (FIG. 1C) were associated with T cell activation and putative $T_{reg}$ effector functions (e.g., Nr4a1, Cd69, Il1rl1, Areg, Srgn, and Fg/2). Notably, Cxcr3, which has been associated with a T-bet$^+$ $T_{reg}$ phenotype specialized to counter Th1 inflammation (Koch et al., 2009; Levine et al., 2017), was downregulated in DP $T_{regs}$ vs. SP and DN $T_{regs}$ (FIG. 1C). The DP $T_{re}$ phenotype may thus represent an effector cell state different from Cxcr3$^+$ T-bet$^+$ $T_{regs}$.

While the DP subset of lung $T_{regs}$ may be particularly active and an attractive target for immunotherapy, PD-1 and CD69 expression across DN, SP, and DP $T_{regs}$ revealed considerable heterogeneity within each subset (FIG. 1D). In particular, 52% of DP $T_{regs}$ expressed PD-1 and 68% expressed CD69. Applicants thus turned to more fully characterize the variation within $T_{regs}$ in the tumor microenvironment.

Figure 2C:
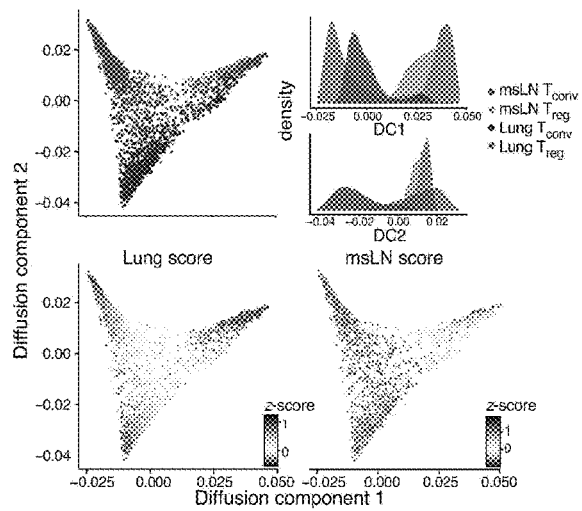

Example 2—scRNA-Seq Reveals Heterogeneity within Tumor-Associated CD4+ $T_{conv}$ Cells The applicants sought to characterize patterns of heterogeneity in tumor-associated CD4+ T cells over time to contextualize the diversity of $T_{reg}$ responses in relation to their Foxp3-CD4+ T cell ($T_{conv}$) counterparts. By scRNA-seq we profiled 1,254 $T_{conv}$ and 1,679 $T_{regs}$ sorted from the lungs and msLN of non-tumor bearing KP-Foxp3$^{GFP}$ mice and tumor-bearing mice at weeks 5, 8, 12, and 20 after tumor induction with Lenti-LucOS (FIG. 2A, ~4 mice per timepoint).

Figure 2B:
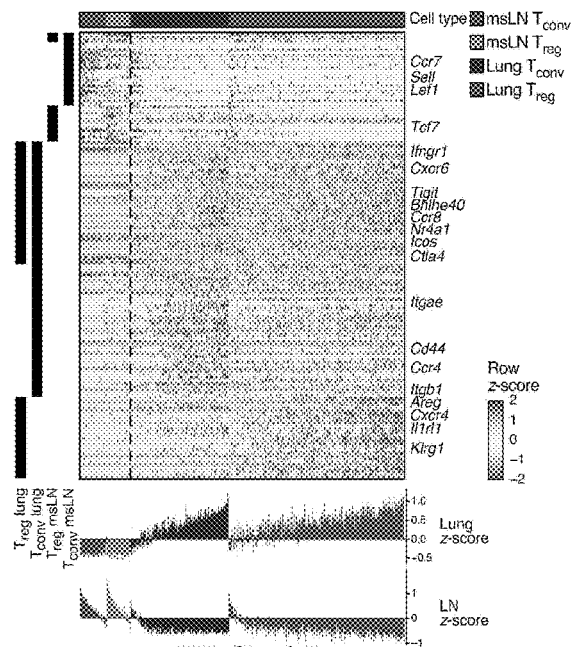
Figure 2D:
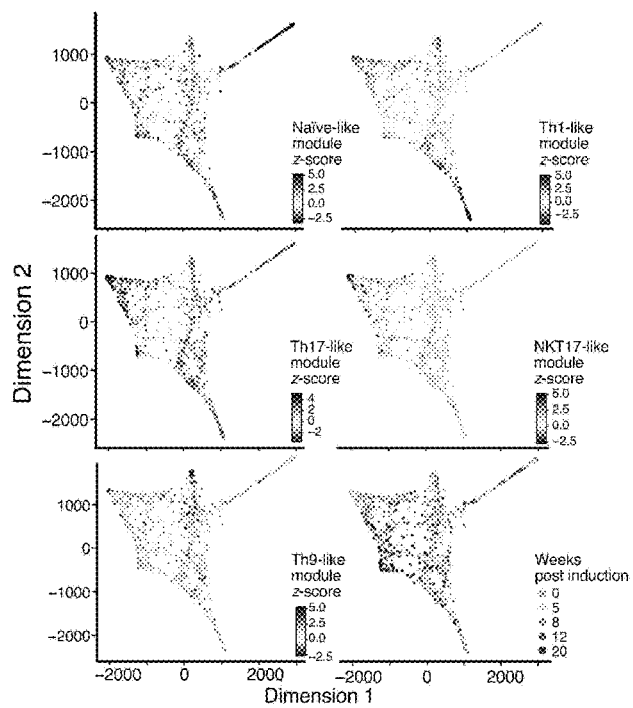

The tissue-specific expression program partitioned into genes shared by lung infiltrating $T_{conv}$ and $T_{regs}$, and genes uniquely upregulated in each (FIG. 2B, Table 1). For example, lung-infiltrating $T_{regs}$ expressed high levels of Il1rl1, Cxcr4, Areg, and Klrg1, while $T_{conv}$ cells expressed Cd44, Ccr4 and Itgb1 (FIG. 2B). Genes from the KPLungTR signature and from a recently described trajectory of tissue-resident $T_{regs}$ (Miragaia et al. 2017) were both differentially expressed in the scRNA-seq profiles (FIG. 9A).

TABLE 1

Differentially expressed genes between LN and Lung $T_{conv}$ and $T_{reg}$ from scRNA-Seq

| | $T_{conv}$.DN | $T_{reg}$.DN | $T_{conv}$.UP |
|---|---|---|---|
| Cdk6 | 0 | 0 | 1 |
| Gadd45b | 0 | 0 | 1 |
| Tnfaip3 | 0 | 0 | 1 |
| Gm14446 | 1 | 0 | 0 |
| Gm4956 | 0 | 1 | 0 |
| Ifngr1 | 0 | 0 | 1 |
| P2ry10 | 0 | 0 | 1 |
| Maf | 0 | 0 | 1 |
| Rgs1 | 0 | 0 | 1 |
| Srgn | 0 | 0 | 1 |
| Id2 | 0 | 0 | 0 |
| Areg | 0 | 0 | 0 |
| Cxcr4 | 0 | 0 | 0 |
| Tmem176b | 0 | 0 | 1 |
| Bcl2a1b | 0 | 0 | 1 |
| Dennd4a | 0 | 0 | 1 |
| Rgcc | 0 | 0 | 0 |
| Rora | 0 | 0 | 1 |
| Samsn1 | 0 | 0 | 0 |
| Limd2 | 1 | 1 | 0 |
| Dapl1 | 1 | 0 | 0 |
| Bcl2 | 0 | 1 | 0 |
| Tspan32 | 1 | 0 | 0 |
| Il1rl1 | 0 | 0 | 0 |
| Acsbg1 | 0 | 0 | 1 |
| Polg2 | 0 | 0 | 1 |
| Ramp3 | 0 | 0 | 1 |
| Odc1 | 0 | 0 | 1 |
| Arl5a | 0 | 0 | 0 |
| Cish | 0 | 0 | 1 |
| Ccr2 | 0 | 0 | 1 |
| Igfbp4 | 1 | 0 | 0 |
| Lamc1 | 0 | 0 | 0 |
| Cxcr6 | 0 | 0 | 1 |
| Gna15 | 0 | 0 | 1 |
| S100a6 | 0 | 0 | 1 |
| Fgl2 | 0 | 0 | 0 |
| Lmna | 0 | 0 | 1 |
| Il16 | 1 | 0 | 0 |
| Il2rb | 0 | 0 | 1 |
| Fasl | 0 | 0 | 1 |
| Dgat1 | 0 | 0 | 1 |
| Pdk1 | 1 | 0 | 0 |
| Gm7367 | 0 | 0 | 0 |
| Dusp1 | 0 | 0 | 1 |
| Als2cl | 1 | 0 | 0 |
| Folr4 | 1 | 1 | 0 |
| Art2b | 1 | 0 | 0 |
| Rgs2 | 0 | 0 | 1 |
| Pim1 | 0 | 0 | 1 |
| Ccr7 | 1 | 0 | 0 |
| Itgae | 0 | 0 | 1 |
| Tmie | 1 | 0 | 0 |
| Pmaip1 | 0 | 0 | 1 |
| Ggt5 | 1 | 0 | 0 |
| Emp1 | 0 | 0 | 1 |
| Lgals3 | 0 | 0 | 1 |
| Evl | 0 | 1 | 0 |
| Vps37b | 0 | 0 | 1 |
| Sik1 | 0 | 0 | 1 |
| Gp49a | 0 | 0 | 1 |
| Runx2 | 0 | 0 | 1 |
| Lilrb4 | 0 | 0 | 0 |
| Ctla2b | 0 | 0 | 0 |
| Stard5 | 1 | 0 | 0 |
| Tigit | 0 | 0 | 1 |
| Nkg7 | 0 | 0 | 1 |
| Psd | 0 | 0 | 1 |
| Fosl2 | 0 | 0 | 1 |
| P2rx7 | 0 | 1 | 0 |
| Coq10b | 0 | 0 | 1 |
| Rpl36a | 0 | 1 | 0 |
| Treml2 | 1 | 0 | 0 |
| Pacsin1 | 1 | 0 | 0 |
| Sell | 1 | 0 | 0 |
| Bcl2a1d | 0 | 0 | 1 |
| N4bp1 | 0 | 0 | 0 |
| Anxa2 | 0 | 0 | 1 |
| Fntb | 1 | 0 | 0 |
| Osbpl3 | 0 | 0 | 1 |
| Il18r1 | 0 | 0 | 1 |
| Klrg1 | 0 | 0 | 0 |
| S100a4 | 0 | 0 | 1 |
| Nr4a3 | 0 | 0 | 1 |
| Lef1 | 1 | 0 | 0 |
| Tbxa2r | 1 | 0 | 0 |
| Arid5a | 0 | 0 | 1 |
| Hip1r | 0 | 0 | 1 |
| Tnfsf11 | 0 | 0 | 1 |
| Tgif1 | 0 | 0 | 0 |
| S100a11 | 0 | 0 | 1 |
| Abi3 | 1 | 0 | 0 |
| Dusp5 | 0 | 0 | 1 |
| Cd44 | 0 | 0 | 1 |
| Cited2 | 0 | 0 | 1 |
| Rnf19b | 0 | 0 | 1 |
| Dusp4 | 0 | 0 | 0 |
| Tnfrsf1b | 0 | 0 | 1 |
| Klrk1 | 0 | 0 | 1 |
| Mxd1 | 0 | 0 | 1 |
| Bhlhe40 | 0 | 0 | 1 |
| Rps17 | 0 | 1 | 0 |
| AI467606 | 1 | 1 | 0 |
| Gem | 0 | 0 | 0 |
| Klf6 | 0 | 0 | 1 |
| Ccr8 | 0 | 0 | 1 |
| Nr4a1 | 0 | 0 | 1 |
| Lgals1 | 0 | 0 | 1 |
| Icos | 0 | 0 | 1 |
| Ccl5 | 0 | 0 | 0 |
| Bcl2a1c | 0 | 0 | 1 |
| Ccr4 | 0 | 0 | 1 |
| Gpr83 | 0 | 1 | 0 |
| Itgav | 0 | 0 | 0 |
| Ppp1r15a | 0 | 0 | 0 |

TABLE 1-continued

Differentially expressed genes between LN and Lung $T_{conv}$ and $T_{reg}$ from scRNA-Seq

| | $T_{conv}$.DN | $T_{reg}$.DN | $T_{conv}$.UP |
|---|---|---|---|
| Fam46a | 0 | 0 | 0 |
| Phlda1 | 0 | 0 | 0 |
| Rnf125 | 0 | 0 | 1 |
| Gm14085 | 0 | 1 | 0 |
| Glrx | 0 | 0 | 0 |
| Per1 | 0 | 0 | 1 |
| Cd27 | 1 | 0 | 0 |
| Il18rap | 0 | 0 | 1 |
| Ifrd1 | 0 | 0 | 1 |
| Neb | 0 | 0 | 0 |
| Btg2 | 0 | 0 | 1 |
| Fos | 0 | 0 | 1 |
| Atp1b1 | 1 | 0 | 0 |
| Crem | 0 | 0 | 1 |
| Myo1f | 0 | 0 | 1 |
| Fam110a | 0 | 0 | 0 |
| Errfi1 | 0 | 0 | 1 |
| Junb | 0 | 0 | 1 |
| Nfil3 | 0 | 0 | 0 |
| Tcf7 | 0 | 1 | 0 |
| Tmem176a | 0 | 0 | 1 |
| Fam129a | 0 | 0 | 1 |
| Ctla4 | 0 | 0 | 1 |
| Lta | 0 | 1 | 0 |
| Itgb1 | 0 | 0 | 1 |
| Ctla2a | 0 | 0 | 0 |
| Tmem64 | 0 | 0 | 1 |
| Nsg2 | 0 | 1 | 0 |
| Id3 | 0 | 1 | 0 |
| Tnfrsf4 | 0 | 0 | 1 |
| Ern1 | 0 | 0 | 1 |
| Ahnak | 0 | 0 | 1 |
| St6galnac3 | 0 | 0 | 1 |

Both the lung and msLN cells spanned a phenotypic continuum, with the lung cells showing particular diversity (FIG. 2C, DC1 $p<10^{-13}$; DC2 $p<10^{-16}$, Levene's test). The spectrum of cell states was apparent when scoring for the expression of lung $T_{conv}$ or $T_{reg}$ signatures, and when cells were arranged along diffusion components that describe their tissue-specific expression program (FIG. 2C). Both $T_{regs}$ and $T_{conv}$ in the msLN expressed genes associated with a naive or central memory phenotype, including Lef1, Sell, and Ccr7 (FIG. 2B). Conversely, cells were more activated in the lung (FIG. 2B). Subsets of lung $T_{conv}$ and $T_{reg}$ cells that scored highly for the msLN signature also expressed genes associated with TCR signaling, including Nr4a1 and Junb, suggesting that they may be recently activated (FIG. 2C). Lung-infiltrating $T_{conv}$ and $T_{reg}$ cells that scored highly for the respective lung signature may represent cells that were more tissue-adapted or localized to a particular region of the lung.

Figure 2E:
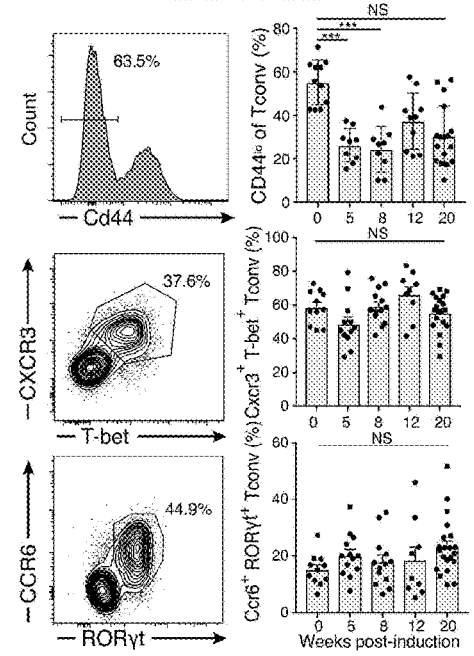
Figure 2F:
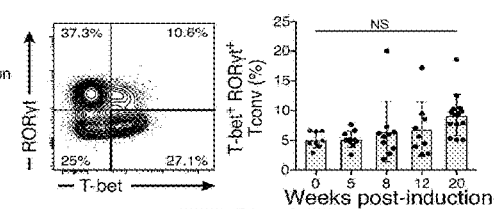

Example 3—Lung $T_{conv}$ Subsets Remain in Stable Proportions Throughout Tumor Development Lung $T_{conv}$ subsets expressed programs associated with different CD4+ T cell subsets, including naïve T, Th17, Th1, Th9 and NKT17 cells (FIG. 2D-2E), whose proportions remained largely stable over time. Within Th1 cells, a subset expressed Eomes and Gzmk, which may reflect cytolytic function, and Cxcr3 and Ccr5, which promote antigen-specific CD4+ T cell recruitment to lungs during respiratory virus infection (Kohlmeier et al., 2009) (FIG. 9D). Some of the Th17-like cells expressed Zbtb16, a marker for NKT cells, and also scored highly for a gene module that includes genes associated with natural killer T17 (NKT17) cells, such as Blk and Gpr114 (FIG. 9E) (Engel et al., 2016). Furthermore, these cells had lower expression of CD4 than other $T_{conv}$ (FIG. 9F) and did not express TCR chains associated with γδ T cells. The applicants found little evidence of Th2-like cells, despite their role in lung inflammation in other settings (Walker and McKenzie, 2018), but did observe a small population of Th9-like cells expressing Il9r, Il4, and Il1rl1, which have been implicated in driving anti-tumor immune responses (Vegran et al., 2015) (FIG. 9G). Finally, the applicants identified a population that scored highly for both the Th1 and the Th17 modules. The applicants validated the presence of cells expressing both RORγt and T-bet (FIG. 2F); such cells have been described as a plastic, Th17-derived population in other pathogenic states (Lee et al., 2012, 2009; Wang et al., 2014). The overall expression of the gene modules associated with these $T_{conv}$ subsets showed subtle variation over time by scRNA-Seq, but the relative cell proportions measured by flow cytometry remained stable during tumor development (FIG. 2E-2F).

Figure 3A:
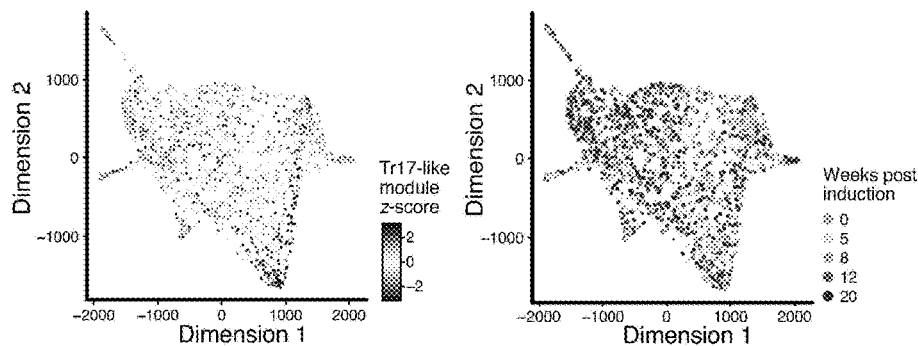
Figure 3B:
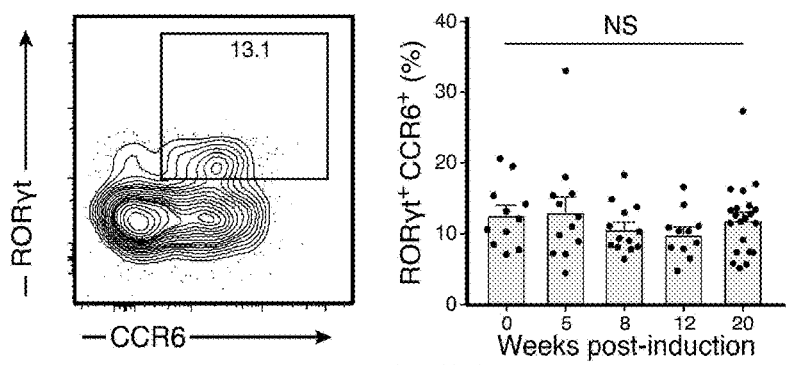
Figure 3C:
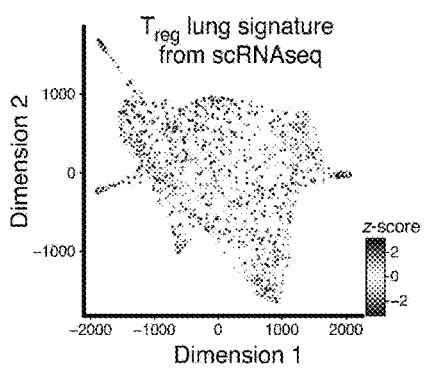
Figure 3D:
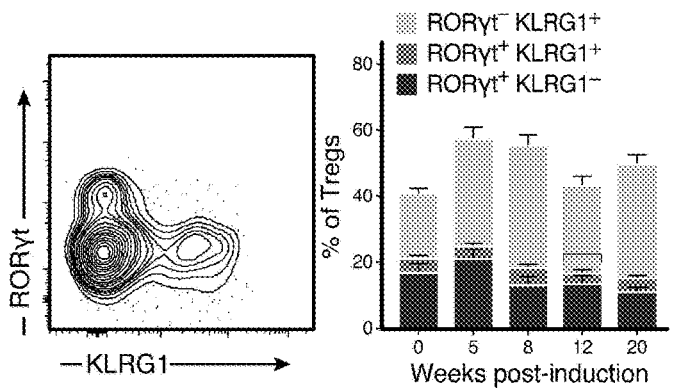
Figure 3E:
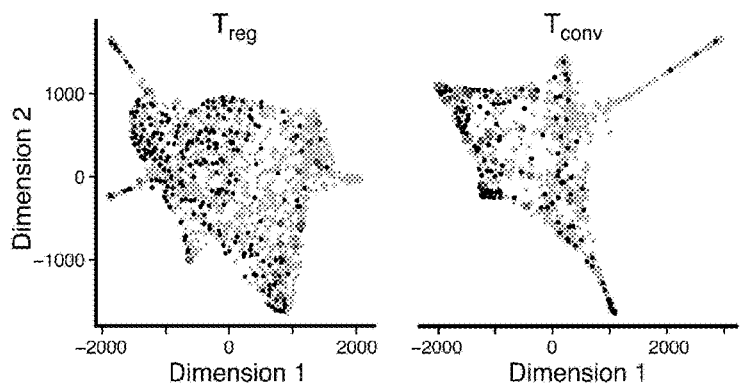

Example 4—a RORγt+ $T_{reg}$ Population is Present Throughout Tumor Development and May have Shared Clonal Origin with Th17 $T_{conv}$ Cells Lung-infiltrating $T_{regs}$ expressed several gene modules with similar features to those in transcriptional signatures of previously-described $T_{reg}$ subsets (FIG. 10A). For example, Module 18 includes genes that characterize a resting, or central, $T_{reg}$ ($rT_{reg}$) phenotype, such as Sell, Ccr7, and Tcf7 (Campbell, 2015; Li and Rudensky, 2016), whereas Module 13 identified a $T_{reg}$ population expressing Rorc and Il17a (FIG. 3A), reminiscent of Th17-like $T_{regs}$ (Tr17), a subset with immunosuppressive activity directed at Th17 responses (Kim et al., 2017). The applicants validated this population by flow cytometry and found that RORγt+ $T_{regs}$ comprise roughly 10% of lung-infiltrating $T_{regs}$ throughout tumor progression (FIG. 3B). The Tr17-like cells represented a distinct state among lung $T_{regs}$ and the expression of Tr17-associated genes was inversely correlated with the expression of genes previously identified in lung-resident $T_{regs}$, including KLRG1 (FIG. 3C-3D). Additionally, whereas Ccr6 expression within the $T_{conv}$ was restricted to Th17 cells (FIG. 2E), Ccr6 was expressed in multiple $T_{reg}$ subsets (FIG. 10B), consistent with previous findings (Yamazaki et al., 2008), which may result in the localization of different $T_{reg}$ subsets to common sites in the lung.

Remarkably, shared clonotypes between $T_{reg}$ and $T_{conv}$ cells were predominantly Tr17-like and Th17-like cells, respectively. Specifically, based on paired-chain T cell receptor (TCR) sequences of profiled cells (FIG. 10B), 12 TCR clonotypes were shared across $T_{reg}$ and $T_{conv}$ cells. Indeed, dedicated TCR profiling of $T_{regs}$ and $T_{conv}$ from KP mice with advanced disease showed that ~5% of $T_{reg}$ clones were shared with $T_{conv}$ on average in advanced disease (FIG. 10C). Of the 19 $T_{regs}$ and 20 $T_{conv}$ cells belonging to the 12 TCR clonotypes shared between $T_{conv}$ and $T_{reg}$, the $T_{reg}$ cells were predominantly of the Tr17-like phenotype (13 of 19 $T_{regs}$ had a z-score >1.5 in the Tr17-like Module, hypergeometric p-value $<10^{-5}$, FIG. 3F). The $T_{conv}$ cells were also predominantly of the Th17 phenotype, although this was not a significant enrichment. 67 out of 178 identified $T_{conv}$ clones were of the Th17 phenotype (hypergeometric p=0.68), of which 8 were clonotypes shared with $T_{regs}$ (FIG. 3F). Thus, Tr17 differentiation may reflect a shared clonal origin with Th17 cells.

Figure 4A:
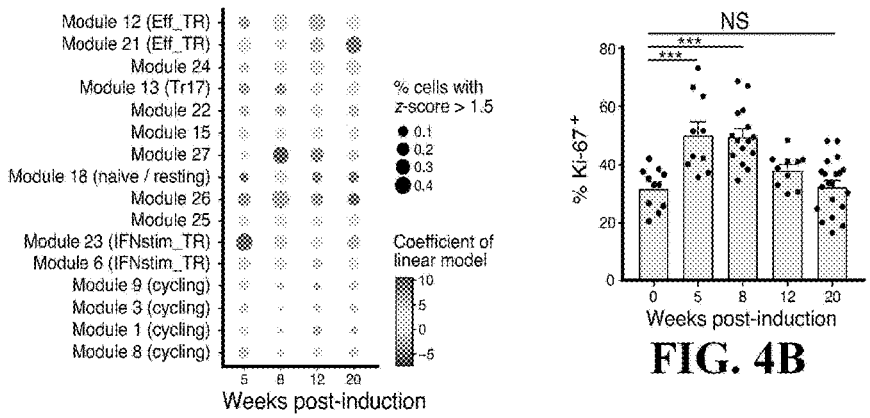
Figure 4B:
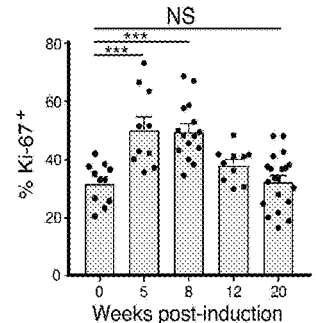
Figure 4C:
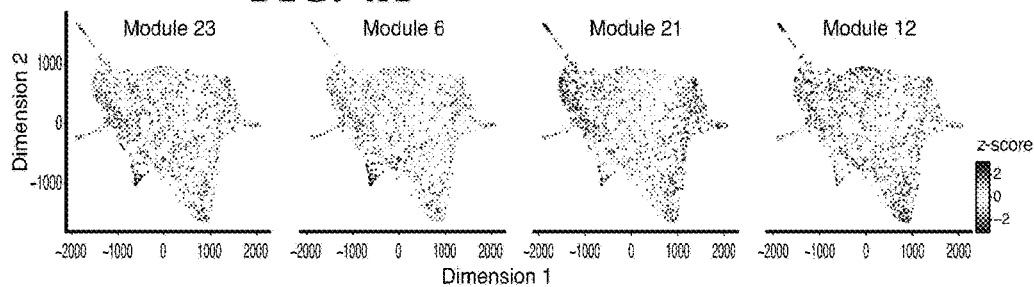

Example 5—an Effector-Like $T_{reg}$ Phenotype Becomes Predominant During Tumor Development In contrast to Tr17-like cells, where a program was expressed by a fixed proportion of cells during tumor development, other Treg programs changed in prominence throughout tumor development (FIG. 4A). For example, there was decreased expression of Modules 1, 3, 8, and 9, which mark cycling cells, after 8 weeks (FIG. 4A), corresponding to a decline in Ki67 expression on $T_{regs}$ (FIG. 4B). Two other programs also changed over time, reflecting an interferon response and a T effector program (FIG. 4A).

Figure 11A:
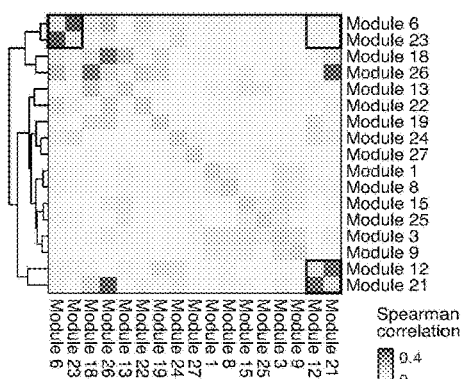
Figure 11B:
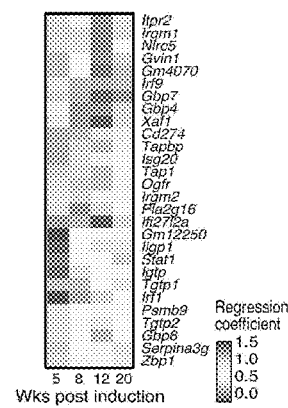
Figure 11C:
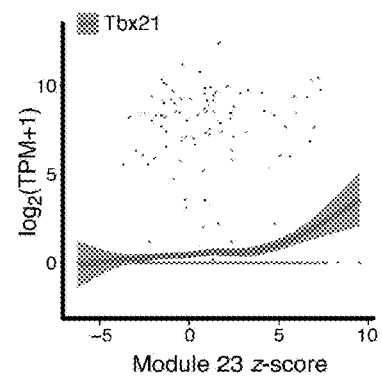
Figure 11D:
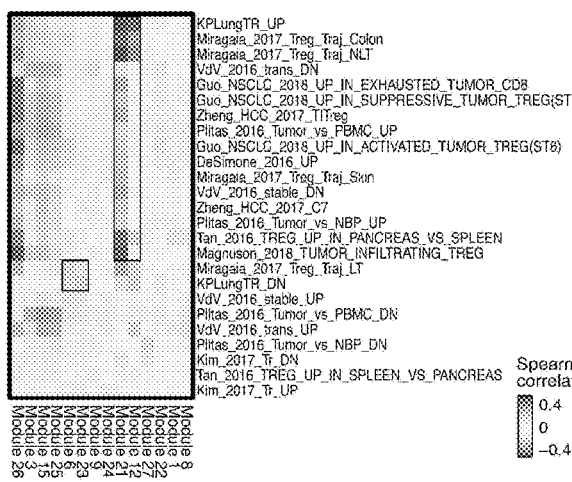
Figure 11E:
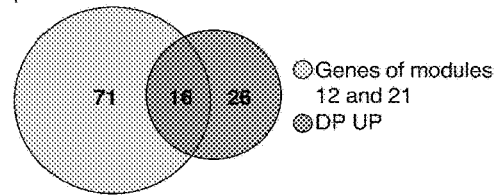
Figure 11F:
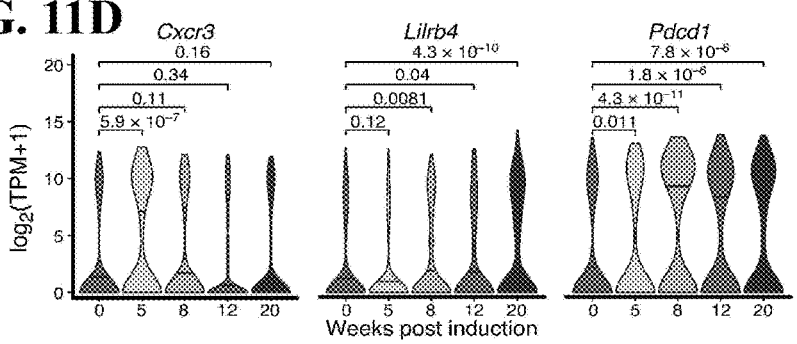

The interferon program ("IFNstim_TR") was characterized by the expression of Modules 6 and 23 (FIG. 4C), which included many interferon-stimulated genes (ISGs) downstream of either type I or II interferon (IFN) signaling, including Stat1, guanylate binding protein genes (GBPs), type I interferon-specific genes (e.g., oligoadenylate synthetase family members), and IFNγ-specific genes (e.g., Irf1, Irf9) (Der et al., 1998). 28 genes from the IFNstim_TR program were significantly downregulated by $T_{regs}$ during tumor progression (FIG. 11B). IFNγ promotes a $Tbet^+$ $CXCR3^+Th1$-like $T_{reg}$ cell population that can suppress Th1 responses (Hall et al., 2012; Koch et al., 2009, 2012). Neither Cxcr3 nor Tbx21 are IFNstim_TR genes, but IFNstim_TR expression was correlated with Tbx21 expression (FIG. 11C). Moreover, the program was enriched for genes expressed by lymphoid tissue $T_{regs}$ and genes downregulated in DP $T_{regs}$ (FIG. 11D), which include Cxcr3. IFNstim_TR expression may thus reflect recent arrival to the lung, consistent with its presence early in tumor development.

The T effector program ("Eff_TR") was characterized by the expression of Modules 12 and 21 (FIG. 4C), which were enriched for genes in the DP signature (p-value≤$10^{-25}$, FIG. 11E) and genes upregulated in $T_{regs}$ from mouse non-lymphoid tissues and human breast cancer, NSCLC, and CRC (De Simone et al., 2016; Guo et al., 2018; Magnuson et al., 2018; Miragaia et al., 2017; Plitas et al., 2016; Zheng et al., 2017) (FIG. 11D), confirming the distinct expression profile we had previously identified in the DP $T_{reg}$ subpopulation.

Figure 4D:
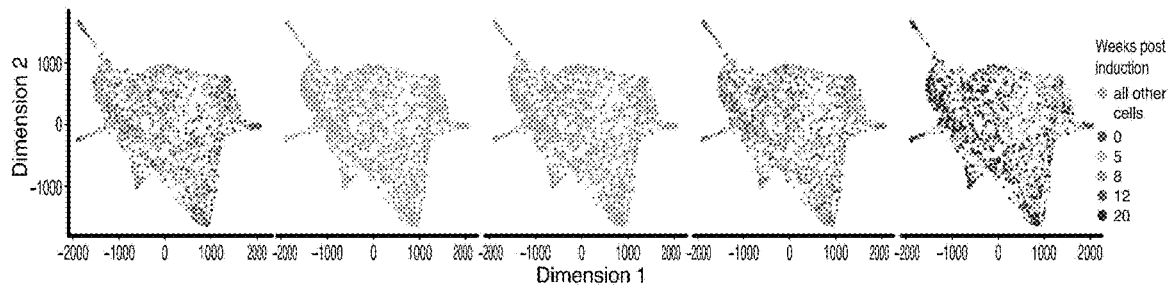
Figure 4E:
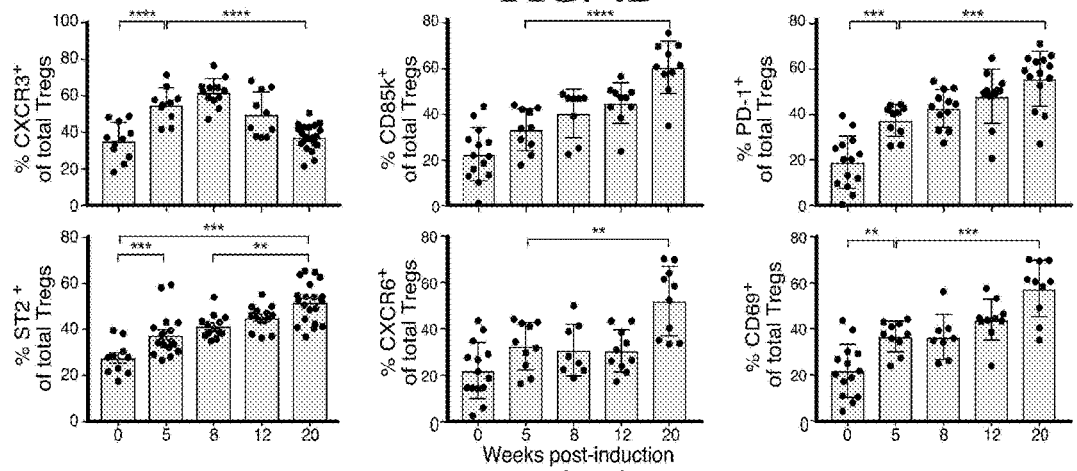
Figure 11G:
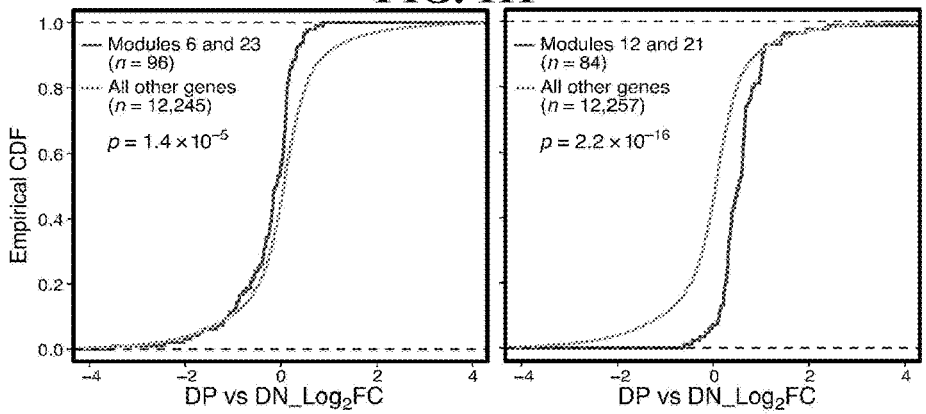

The interferon and effector programs represented independent phenotypes of $T_{regs}$ within each timepoint but followed opposite patterns over time: expression of IFNstim_TR genes was highest in cells from week 5 and declined thereafter, while expression of Eff_TR genes increased and remained elevated (FIG. 4A,4D). This temporal transition was also highlighted when testing for individual temporally varying genes: Cxcr3 expression decreased with time, and Pdcd1 and Lilrb4 (Module 21) increased in expression during tumor development (FIG. 11F), consistent with down-regulation of Cxcr3 in DP $T_{reg}$ cells (FIG. 1D). More generally, Eff_TR genes were upregulated in DP $T_{regs}$ compared to DN $T_{regs}$ in mice with late-stage tumor burden, whereas IFNstim_TR genes were significantly downregulated (FIG. 11G). The applicants confirmed that protein levels of Cxcr3 decreased, and proteins encoded by Eff_TR genes, including CD85k, CD69, CXCR6, PD-1 and ST2, increased during tumor progression (FIG. 4E).

Taken together, the data suggest that tumor progression may be associated with a shift from a $T_{reg}$ cell phenotype specialized for responding to Th1 inflammation to an effector $T_{reg}$ cell population. In particular, the applicants hypothesized that the strong immunosuppression associated with the late-stage tumor environment may be a result of the emergence and stabilization of cells with the Eff_TR phenotype.

Figure 5A:
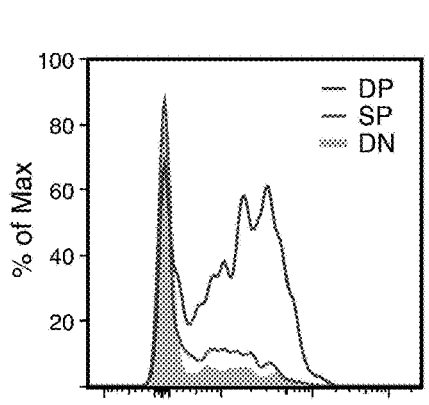
Figure 5B:
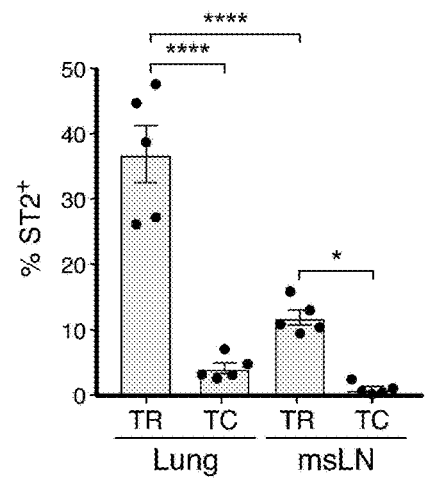
Figure 5C:
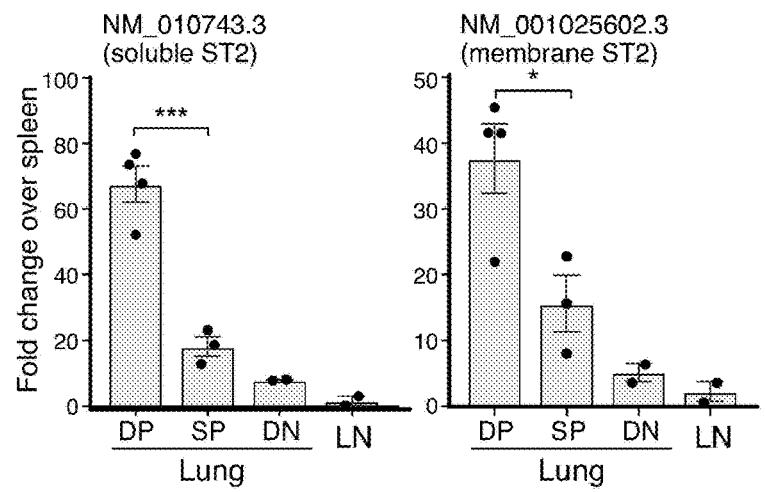
Figure 5D:
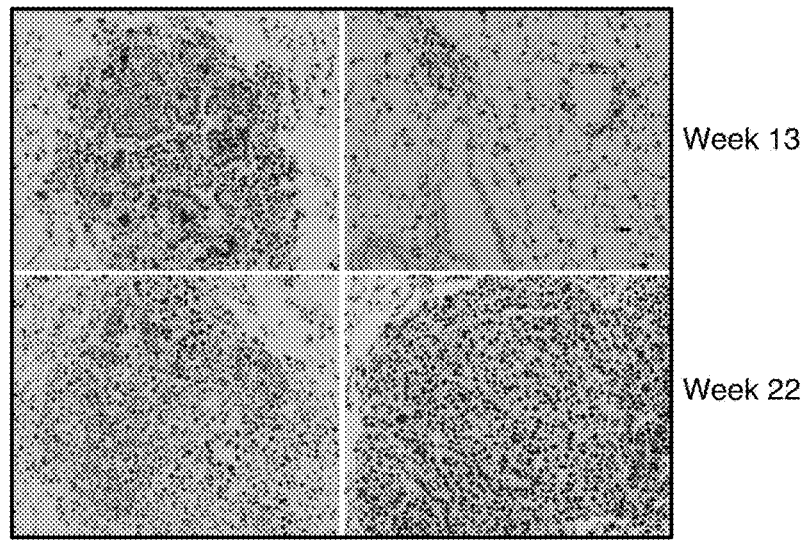

Example 6—ST2 is Upregulated on Effector $T_{regs}$ in Mice Bearing Advanced Lung Tumors The applicants reasoned that Il1rl1, an Eff_TR gene that encodes the interleukin 33 (IL-33) receptor ST2, may highlight a pathway that could be targeted to alter longitudinal changes in $T_{reg}$ cell phenotype and prevent the accumulation of effector $T_{regs}$ in advanced tumors. First, Il1rl1/ST2 levels tracked with the effector $T_{reg}$ phenotype; Il1rl1 is a member of Module 21 in the Eff_TR program and ST2 was most highly expressed in DP lung $T_{regs}$ (FIG. 5A), and its expression in $T_{regs}$ increased during tumor development (FIG. 4D). Moreover, ST2 was expressed by ~40% of lung $T_{regs}$ vs. ~10% of $T_{regs}$ in the msLN, and <5% of T, cells in the lung in late-stage tumor-bearing mice (FIG. 5B). Second, $T_{reg}$ cells from tumor-bearing KP, LucOS-infected mice expressed both the membrane-bound and soluble isoforms of ST2 (FIG. 5C); soluble ST2 (sST2) is thought to diminish ST2 signaling through sequestration of IL-33, the only known ligand of ST2 and an alarmin that recruits immune cells to sites of tissue damage (Cayrol and Girard, 2014). Finally, IL-33 was highly expressed in normal lung, and in early and late lung adenocarcinomas in the KP model (FIG. 5D). In normal lung, IL-33 was predominantly expressed on surfactant protein C (SPC)-expressing type II epithelial cells (FIG. 12). The applicants thus hypothesized that ST2 may be a critical mediator of $T_{reg}$ cell function in the lung tumor environment.

Example 7—Recombinant IL-33 Treatment Increases Effector $T_{regs}$ in Tumor-Bearing Lungs To determine the effect of IL-33 on the immune microenvironment of tumors, the applicants administered recombinant mouse IL-33 (rIL-33) intratracheally to tumor-bearing KP, Lenti-LucOS-infected mice (FIG. 6A). Consistent with prior reports (Kondo et al., 2008; Schmitz et al., 2005), rIL-33 induced significant inflammatory infiltration and epithelial thickening in tumors and throughout the lung (FIG. 6B). rIL-33-treated mice had greater numbers of eosinophils (FIG. 6C) and $CD4^+$ and $CD8^+$ T cells per lung weight (FIG. 6D), although the proportion of tumor-specific, SIINFEKL tetramer-positive cells among $CD8^+$ T cells was unchanged (FIG. 6E). The applicants observed similar inflammation in non-tumor bearing wild-type mice treated with rIL-33 (data not shown). $CD4^+$ T cells in rIL-33-treated mice had an increased proportion of $T_{regs}$(FIG. 6F), of which 64% were DP compared to 34% in PBS-treated controls, with proportionally fewer SP and DN $T_{regs}$ (FIG. 6G). rIL-33 treatment of ST2-deficient mice failed to elicit the same change in the proportion of $T_{regs}$, which was similar to that of untreated, wild-type mice (FIG. 13). Taken together, rIL-33 administration is sufficient to drive both a major increase in the lung $T_{reg}$ population in general, and to promote an increase in effector $T_{regs}$ cells in particular.

Example 8—$T_{reg}$-Specific ST2 is Required for the Increase in Effector $T_{regs}$ During Tumor Progression To test whether ST2 signaling on $T_{regs}$ was necessary for the development of a robust effector $T_{reg}$ cell response in tumors, the applicants studied the effects of $T_{reg}$-specific Il1rl1 deletion. The applicants used a modified version of the KP model wherein FlpO recombinase drives expression of oncogenic K-ras and loss of p53 (KPfrt: FSF-Kras$^{G12D}$, p53$^{frt/frt}$), which allowed us to use the Cre-lox system to study $T_{reg}$-specific Il1rl1 deletion. The applicants crossed KPfrt mice to Foxp3$^{YFP-Cre}$ and Il1rl1$^{fl/fl}$ mice to model lung adenocarcinoma development in the setting of $T_{reg}$-specific ST2 deficiency (FIG. 7A). The applicants infected the mice with a lentivirus expressing FlpO recombinase and GFP fused to Ova and SIYRGYYL (FlpO-GFP-OS) in order to induce tumors that would express the same strong T cell antigens as those in the Lenti-LucOS model.

Early-stage KPfrt, Foxp3$^{YFP-Cre}$, Il1rl1$^{fl/fl}$ mice did not differ from KPfrt, Foxp3$^{YFP-Cre}$ mice in the fraction of CD4$^+$ T cells that were $T_{conv}$ $T_{reg}$ cells, but late in tumor progression there was a slight reduction in the proportion of $T_{reg}$ cells (FIG. 7B), a significantly lower proportion of DP $T_{regs}$, and a higher proportion of SP cells (FIG. 7C). Expression profiles of DP, SP, and DN $T_{regs}$ from KPfrt, Foxp3$^{YFP-Cre}$, Il1rl1$^{fl/fl}$ and KPfrt, Foxp3$^{YFP-Cre}$ control mice identified an expression signature lower in ST2-deficient vs. wild-type $T_{regs}$, where it was highest among wild-type DP $T_{regs}$ (FIG. 7D). The signature was enriched for KPLungTR and DP signature genes, including Dgat2, Furin and Nfkbia, as well as for genes upregulated by $T_{regs}$ in human NSCLC (FIG. 7E). ST2-deficient $T_{regs}$ also showed higher expression of some genes, including Itgb1, Il10, Klf6, and Fos (FIG. 7E), suggesting that they may adopt alternative phenotypes. Taken together, the present data supports the hypothesis that ST2 regulates the accumulation of effector $T_{regs}$ in the tumor microenvironment over time by promoting the expression of DP signature genes.

Example 9—$T_{reg}$-Specific ST2 Ablation Leads to Increased CD8$^+$ T Cell Infiltration and a Reduction in Tumor Burden Finally, the applicants found that tumors from KPfrt, Foxp3$^{YFP-Cre}$, Il2rl1$^{fl/fl}$ mice had over 50% higher CD8$^+$ T cell infiltration than tumors from control mice by immunohistochemistry (FIG. 7E). KPfrt, Foxp3$^{YFP-Cre}$, Il1rl1$^{fl/fl}$ mice also had a significantly lower total tumor burden and lower average tumor size compared to control mice (FIG. 7F,7G), suggesting that greater CD8+ T cell infiltration of tumors may result in better inhibition of tumor growth. Overall, the applicants' studies suggest that Treg-specific inhibition of ST2 signaling may result in a less immunosuppressive tumor microenvironment characterized by increased anti-tumor CD8 T cell activity and lower tumor burden.

Example 10. scRNA-Seq Reveals Lung-Specific Transcriptional Programs for Tumor-Associated CD4$^+$ $T_{conv}$ and $T_{reg}$ Cells Consistent with prior reports that tumor development in the KP model is associated with the expansion of lung-infiltrating $T_{reg}$s (Joshi et al., 2015), the fraction of Ki-67-positive $T_{regs}$ by flow cytometry was elevated in lungs with early tumors compared to healthy lung (FIG. 15A), while the fraction of Ki-67-positive Foxp3$^-$CD4$^+$ T cells was modestly increased at 5 and 8 weeks, but returned to baseline by 12 weeks (FIG. 19A).

The applicants hypothesized that early proliferation of $T_{regs}$ may be associated with changes in $T_{reg}$ diversity. To assess this, the applicants used scRNA-Seq to characterize patterns of heterogeneity in tumor-associated CD4$^+$ T cells over time, and how the diversity of $T_{reg}$ responses relates to that of their $T_{conv}$ counterparts. The applicants profiled 1,254 $T_{conv}$ and 1,679 $T_{regs}$ sorted from the lungs and msLN of non-tumor bearing KP-Foxp3$^{GFP}$ mice and tumor-bearing mice at weeks 5, 8, 12, and 20 after tumor induction with Lenti-LucOS (FIG. 15B, ~4 mice per timepoint).

Tissue-specific expression programs defined genes shared by lung infiltrating $T_{conv}$ and $T_{regs}$, and genes uniquely upregulated in each (FIG. 15C, Table 1). For example, lung-infiltrating $T_{regs}$ expressed high levels of Il1rl1, Cxcr4, Areg, and Klrg1 compared to $T_{regs}$ from the msLN, while $T_{conv}$ cells expressed Cd44, Ccr4 and Itgb1 (FIG. 15C). A recently described transcriptional trajectory of tissue-resident $T_{regs}$ (Miragaia et al., 2019) was consistent with the scRNA-seq profiles of lung-infiltrating cells (FIG. 19B).

Figure 14B:
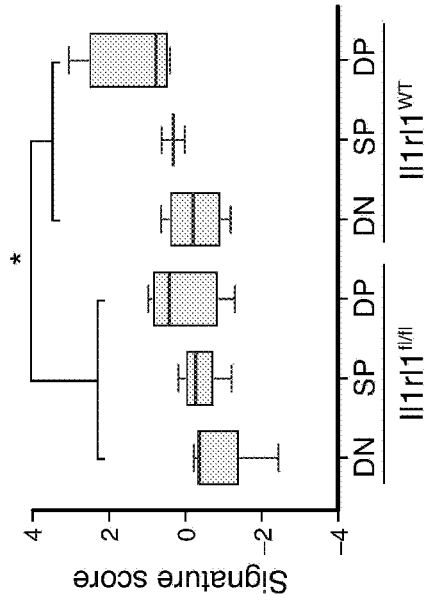
Figure 14D:
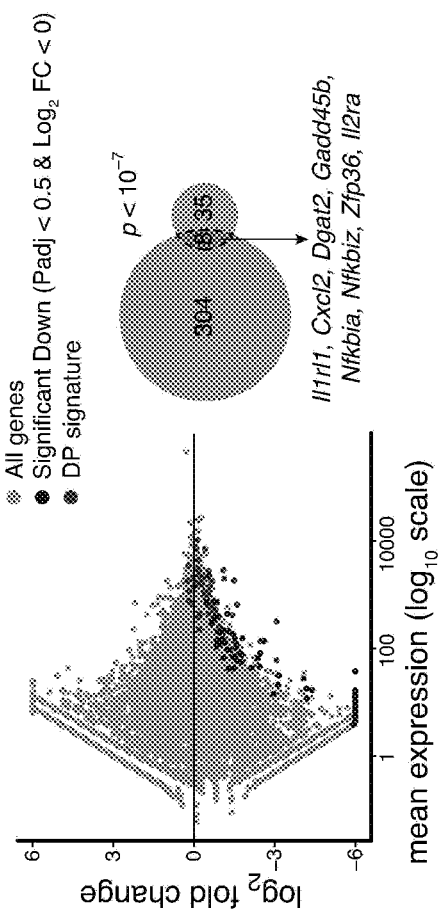
Figure 14A:
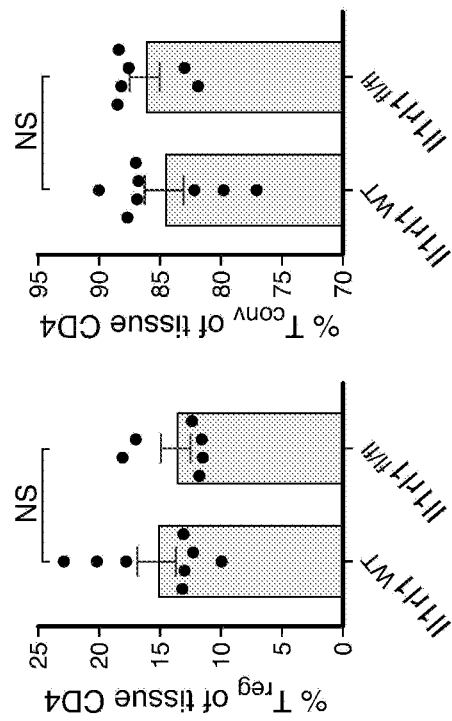
Figure 14C:
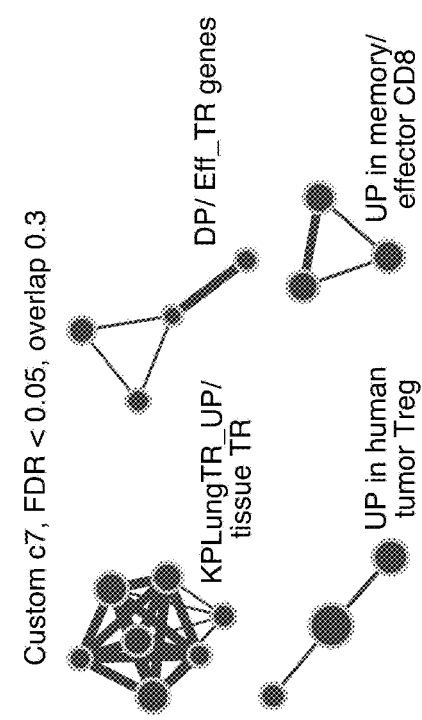

Both the lung and msLN cells spanned a phenotypic continuum, with the lung cells showing particularly higher diversity (FIGS. 14D, 19C, DC1 p<10$^{-13}$; DC2 p<10$^{-16}$, Levene's test). The spectrum of cell states was apparent in the range of scores for the expression of lung $T_{conv}$ or $T_{reg}$ gene signatures (FIG. 15D, bottom). A similar continuum emerged when we used the genes in these signatures to create a diffusion map (FIG. 15D), a low-dimensional non-linear embedding that captures continuous, global neighborhood structure better than other dimensionality reduction techniques (Haghverdi et al., 2015). Both $T_{reg}$ and $T_{conv}$ cells in the msLN expressed genes associated with a naive or central memory phenotype, including Lef1, Sell, and Ccr7 (FIGS. 15C, 19D). Conversely, cells were more activated in the lung (FIG. 15C). Subsets of lung $T_{conv}$ and $T_{reg}$ cells that scored highly for the msLN signature also expressed genes associated with TCR signaling, including Nr4a1 and Junb, suggesting that they may be recently activated (FUG. 19D). Lung-infiltrating $T_{conv}$ and $T_{reg}$ cells that scored highly for the respective lung signature may represent cells that were more tissue-adapted or localized to a particular region of the lung, which is consistent with prior data that T cells in the KP model are located in tumors or tertiary lymphoid structures (TLS) (DuPage et al., 2011; Joshi et al., 2015).

Example 11. Lung $T_{conv}$ and $T_{reg}$ Subsets Share a Limited Number of Gene Expression Programs, Including a Th17-Like Phenotype In order to assess the different transcriptional programs of $T_{conv}$ and $T_{reg}$ subsets in the lung, the applicants performed PAthway and Gene set OverDispersion Analysis (PAGODA) (Fan et al., 2016) to identify groups of genes with co-varying expression (FIG. 19E-19F, Table 2). The relative cell proportions of these $T_{conv}$ programs remained stable during tumor development (FIG. 19G). $T_{conv}$ and $T_{reg}$ subsets expressed several overlapping programs (FIG. 15E). Programs associated with naive/resting T cells and interferon (IFN) signaling were highly correlated between $T_{conv}$ and $T_{regs}$.

TABLE 2

PAGODA modules for $T_{conv}$ and $T_{reg}$ cells

| Module 1 | Module 2 | Module 4 | Module 5 | Module 6 | Module 7 | Module 8 | Module 9 | Module 10 |
|---|---|---|---|---|---|---|---|---|
| Abtb2 | Gbp2 | Acsbg1 | 9430020K01Rik | AA467197 | BC094916 | Atf3 | 4930511M06Rik | 2210039B01Rik |
| Actn1 | Gbp3 | Actn2 | Abi3bp | Ahnak | Dtx3l | Csrnp1 | 5730577I03Rik | Gm5860 |
| Als2cl | Gbp4 | Aqp3 | Blk | Anxa1 | Gm14446 | Dusp5 | A130077B15Rik | H2-Q4 |
| Atp1b1 | Gbp6 | Atf6 | Cd16311 | Anxa2 | I830012O16Rik | Egr1 | A630089N07Rik | H2-Q6 |
| Bach2 | Gbp7 | Bcl2a1a | Gpr114 | Capg | Ifit1 | Fos | A730017L22Rik | H2-Q8 |
| Ccr7 | Gbp8 | Ccr4 | Kcnk1 | Cd44 | Ifit3 | Fosb | Fut8 | Nlrp1a |
| Cd27 | Gbp9 | Ccr6 | Ly6g5b | Cd82 | Irf7 | Gadd45b | Gm11128 | |
| Cers6 | Gm2250 | Ckb | Plxnd1 | Cd97 | Irf9 | Hspa5 | Gm17644 | |
| Elovl6 | Gm17757 | Cpm | Rln3 | Crip1 | Isg15 | Ier2 | Gm17821 | |
| Fam101b | Gm4070 | Dhrs3 | Sox13 | Crip2 | Isg20 | Ifrd1 | Gm9159 | |
| Gm14085 | Gm4759 | Ikzf3 | St3gal3 | Cxcr6 | Mnda | Kdm6b | Grk1 | |
| Hmgn1 | Gm5595 | Il17a | | Emp1 | Mx1 | Nfkbia | Grk4 | |
| Ifngr2 | Gm8979 | Il17f | | Iqgap1 | Mx2 | Nfkbid | Kcnq1ot1 | |
| Igfbp4 | Gvin1 | Il17re | | Lgals1 | Oas1a | Nfkbiz | Maoa | |
| Il21r | Ifi47 | Il1rl1 | | Lgals3 | Oasl2 | Nr4a1 | Mcmdc2 | |
| Il4ra | Igtp | Il23r | | Lmna | Palm | Nr4a5 | Olfr613 | |
| Il6st | Iigp1 | Irs2 | | Myadm | Parp10 | Per1 | Olfr856-ps1 | |
| Jun | Irgm1 | Itgae | | Rbpj | Parp9 | Pim1 | Prlr | |
| Lef1 | Irgm2 | Lmo4 | | S100a10 | Phf11a | Zfp36 | Slc18b1 | |
| Ly6c1 | Serpina3f | Mbd2 | | S100a11 | Phf11b | | Tyms | |
| Myb | Stat1 | Mmp25 | | S100a4 | Phf11c | | Vmn1r58 | |
| Nme7 | Tgtp1 | Pxdc1 | | S100a6 | Pml | | Zfp277 | |
| Pde2a | Tgtp2 | Ramp1 | | Tagln2 | Pydc3 | | Zfp488 | |
| Pik3ip1 | | Rorc | | Vim | Pydc4 | | Zfp71-rs1 | |
| Ppp1r15a | | Serpinb1a | | | Pyhin1 | | Zfp937 | |
| Prf1 | | Sla | | | Rnf31 | | | |
| Rab3ip | | Smox | | | Rsad2 | | | |
| Rn4.5s | | Tex2 | | | Rtp4 | | | |
| Satb1 | | Tmem176a | | | Samhd1 | | | |
| Sell | | Tmem176b | | | Slfn1 | | | |
| Smc4 | | Tmem64 | | | Slfn8 | | | |
| Ttyh3 | | | | | Trim30a | | | |
| Tubb2a | | | | | Trim30d | | | |
| Txk | | | | | Xafl | | | |
| Zfp281 | | | | | Zbp1 | | | |

| Module 13 | Module 14 | Module 15 | Module 16 | Module 17 | Module 18 | Module 21 | Module 22 |
|---|---|---|---|---|---|---|---|
| Dlg5 | Ccl5 | Abcb10 | Eef1a1 | Adam19 | Ap4e1 | 3110082I17Rik | 4632428N05Rik |
| Ifitm1 | Ccr5 | AI836003 | Eef1b2 | Adam8 | Apobec3 | Asf1b | Abcf1 |
| Ifitm2 | Chd7 | Apbb2 | Eef2 | Anxa5 | Areg | C330027C09Rik | Ablim1 |
| Ifitm3 | Ctsw | Cd81 | Gas5 | Arnt2 | Arfgef1 | Cdc45 | Acot2 |
| Klrc1 | Cxcr3 | Chdh | Gm12191 | Asb2 | Arhgap26 | Cdk1 | Acss1 |
| Klrc2 | Cyb561d1 | Fam213a | Gm15772 | Bcl2 | Atp2b1 | Cenpk | Adk |
| Klrc3 | Dusp2 | Ikbip | Gnb2l1 | Bcl2l1 | Bcl2a1b | Dhfr | Arhgap15 |
| Klrd1 | Entpd1 | Il17rb | Npm1 | Ccr2 | Bcl2a1c | Dtl | Arid4a |
| Kirk1 | Eomes | Il1rl1 | Rpl10 | Ccrl2 | Bcl2a1d | Hist2h3b | Arid5a |
| Ly6c2 | Esm1 | Il4 | Rpl10a | Cdk6 | Bhlhe40 | Hus1 | Atp1b3 |
| Prss16 | Fasl | Kit | Rpl12 | Cyth4 | Btg2 | Kdm4a | Brd2 |
| | Gm8909 | Klrg1 | Rpl14 | Dkkl1 | Cd4 | Kif15 | Btg1 |
| | Gzmk | Lif | Rpl15 | Ech1 | Cd69 | Lig1 | Cblb |
| | H2-D1 | Lpcat2 | Rpl17 | Eif4e3 | Cdkn1a | Lrrc47 | Cd53 |
| | H2-K1 | Myo1d | Rpl18 | Eroll | Celf2 | Mcm3 | Cenpa |
| | H2-Q5 | Ptgir | Rpl24 | F2r | Cish | Micu1 | Crlf3 |
| | H2-Q7 | Rcn1 | Rpl27 | Fam110a | Crem | Mki67 | Cybasc3 |
| | H2-Q9 | Rnf128 | Rpl27a | Fam129a | Ctla4 | Ncapg2 | Dgka |
| | Nkg7 | Slc7a8 | Rpl29 | Fgl2 | D16Ertd472e | Nup85 | Dnajc5 |
| | Rab5c | Spry2 | Rpl3 | Gp49a | Dennd4a | Pitrm1 | Dusp10 |
| | Ret | Stab2 | Rpl32 | Hk2 | Dgat1 | Prim1 | Eif3e |
| | Rnf138 | Vipr2 | Rpl34-ps1 | Il2ra | Dusp1 | Prim2 | Elf1 |
| | Serpinb6b | | Rpl35 | Lilrb4 | Emb | Rangap1 | Epb4.1 |
| | Serpinb9 | | Rpl35a | Lta | Ern1 | Rcan3 | Fam65b |
| | Sidt1 | | Rpl41 | Ltb4r1 | Faah | Rnaseh2b | Fam78a |
| | Tbx21 | | Rpl7a | Nqo2 | Fam210a | Rpa2 | Foxp1 |
| | | | Rplp1 | Osbpl3 | Fes | Rrm2 | G3bp2 |
| | | | Rplp2 | Plp2 | Fosl2 | Rtel1 | Gimap1 |
| | | | Rps12 | Podnl1 | Furin | Stmn1 | Gimap3 |
| | | | Rps13 | Prickle3 | Gabpb1 | Top2a | Gimap4 |
| | | | Rps15a | Rarg | Gna13 | Tube1 | Gimap6 |
| | | | Rps15a-ps4 | Sdc4 | Hif1a | | Gltscr2 |
| | | | Rps15a-ps6 | Sept11 | Icos | | Got1 |
| | | | Rps17 | Sept8 | Ifngr1 | | Gramd3 |
| | | | Rps18 | Serpina3g | Il18r1 | | Gtf2i |
| | | | Rps19 | Serpina3h | Il2rb | | Hmha1 |

TABLE 2-continued

PAGODA modules for $T_{conv}$ and $T_{reg}$ cells

| | | | |
|---|---|---|---|
| Rps20 | Serpina3i | Il7r | Il6ra |
| Rps25 | Slc35c2 | Irf2bp2 | Inadl |
| Rps27a | Socs2 | Irf4 | Irgq |
| Rpsa | Syne3 | Junb | Itga4 |
| | Tbcb | Jund | Kat7 |
| | | Klf4 | Kif21b |
| | | Kpna1 | Lbr |
| | | Ldlrad4 | Mbp |
| | | Lmnb1 | Ms4a4b |
| | | Lpxn | Ms4a6b |
| | | Maf | Opa1 |
| | | Mapkapk3 | Pitpnc1 |
| | | Mif4gd | Plcxd2 |
| | | Mrfap1 | Pnpla7 |
| | | Nabp1 | Polr2e |
| | | Neurl3 | Ppm1h |
| | | Nfkb2 | Rapgef4 |
| | | Nlrc5 | Rasa3 |
| | | Notch2 | Rbck1 |
| | | Nr3c1 | Rnf145 |
| | | Odc1 | S1pr1 |
| | | P2ry10 | Scfd1 |
| | | Papd7 | Scml4 |
| | | Pde4b | Sec24c |
| | | Prelid2 | Senp2 |
| | | Psd | Sepp1 |
| | | Ptpn22 | Slamf6 |
| | | Rab8b | Smg9 |
| | | Rabac1 | Snrpg |
| | | Ramp3 | Socs3 |
| | | Relb | Sp100 |
| | | Rgs1 | Ssh2 |
| | | Rgs2 | Stat5b |
| | | Rora | Tcf7 |
| | | Samsn1 | Tecpr1 |
| | | Sh2d2a | Tgfbr2 |
| | | Skil | Thada |
| | | Slamf1 | Tmem66 |
| | | Synj2 | Tnfrsf26 |
| | | Syt11 | Trib2 |
| | | Tank | Usp19 |
| | | Tgif1 | Zc3hav1 |
| | | Tigit | |
| | | Tmem154 | |
| | | Tnc | |
| | | Tnfaip3 | |
| | | Tnfrsf1b | |
| | | Tnfrsf4 | |
| | | Tnfsf11 | |
| | | Tnfsf8 | |
| | | Traf1 | |
| | | Ttc21a | |
| | | Ttc39b | |
| | | U2af1 | |
| | | Ubxn4 | |
| | | Vmp1 | |
| | | Vps37b | |
| | | Zc3h12a | |

Of the $T_{conv}$ programs associated with different CD4+ T cell subsets, including naïve T, Th17, and Th1 cells, only the Th17 program was highly-correlated with a $T_{reg}$ program ("Program 13", FIG. 15E). Program 13 marks a $T_{reg}$ population expressing Rorc and Il17a (FIG. 19H), reminiscent of Th17-like effector $T_{regs}$ (Tr17), a subset with immunosuppressive activity directed at Th17 responses (Kim et al., 2017). The applicants validated this population by flow cytometry and found that RORγt+ $T_{regs}$ comprise roughly 10% of lung-infiltrating $T_{regs}$ throughout tumor progression (FIG. 19I). The Tr17-like cells represented a distinct state among lung $T_{regs}$ and the expression of Tr17-associated genes was inversely correlated with the expression of genes identified in lung-resident $T_{regs}$ (FIG. 19J-19K).

Surprisingly, T cell receptor (TCR) clonotypes shared between $T_{reg}$ and $T_{conv}$ cells were predominantly from Tr17-like and Th17-like cells, respectively. Specifically, based on paired-chain TCR sequences of profiled cells, 12 TCR clonotypes were shared across $T_{reg}$ and $T_{conv}$ cells (Table 3, 275 $T_{regs}$ and 178 $T_{conv}$ made up 111 and 62 different clonotypes respectively). Of the 19 $T_{regs}$ and 20 $T_{conv}$ cells belonging to these 12 TCR clonotypes shared between $T_{conv}$ and $T_{regs}$, the $T_{regs}$ were predominantly of the Tr17-like phenotype (13 of 19 $T_{regs}$ had a z-score >1.5 in the Tr17-like module, p-value <$10^{-5}$, hypergeometric test, FIG. 19L-19M). Notably, because the applicants were only able to identify several clonotypic families, no temporal trend could be detected reliably. Overall this suggests that Tr17 differentiation may reflect a shared clonal origin with Th17 cells.

TABLE 3

Shared clonotypes between T_reg and T_conv cells

| Cellname | A_productive | A_unproductive | B_productive | B_unproductive | clonal_group | group_size | mouse | cell.id | tissue |
|---|---|---|---|---|---|---|---|---|---|
| 336_CD4_Lung_93_S93_P1 | TRAV7-2_AAGCAACCAG_TRAJ15 | | | TRBV2_CAAGATGAGGGAAAACA_TRBJ1-1 | 4 | 2 | 336 | Tconv | Lung |
| 3839_Treg_Lung_16_S304_P1 | TRAV7-2_AAGCAACCAG_TRAJ15 | | TRBV13-2_GTGATTACTCCTATG_TRBJ2-1 | | 4 | 2 | 3839 | Treg | Lung |
| 3642_CD4_Lung_18_S18_P1 | TRAV7-4_AGGGATAGCA_TRAJ33 | | TRBV5_CAAGACGGGGTTAACCA_TRBJ2-5 | | 10 | 4 | 3642 | Tconv | Lung |
| 3642_CD4_Lung_4_S4_P1 | TRAV7-4_AGGGATAGCA_TRAJ33 | TRAV13D-2_TATAGGGGGGAGGAA_TRAJ40 | TRBV5_CAAGACGGGGTTAACCA_TRBJ2-5 | | 10 | 4 | 3642 | Tconv | Lung |
| 3642_CD4_Lung_94_S94_P1 | TRAV7-4_AGGGATAGCA_TRAJ33 | | TRBV5_CAAGACGGGGTTAACCA_TRBJ2-5 | | 10 | 4 | 3642 | Tconv | Lung |
| 4578_Treg_Lung_66_S354_P1 | TRAV7-4_AGGGATAGCA_TRAJ33 | TRAV6-5_TCTGACCCCCAACAG_TRAJ37 | TRBV5_CAAGACGGGGTTAACCA_TRBJ2-5 | | 10 | 4 | 4578 | Treg | Lung |
| 3839_CD4_Lung_81_S177_P1 | TRAV12N-3_AGTGATGCCTCGG_TRAJ11 | | TRBV4_AGCTATGGAGGGGACAGCACAG_TRBJ1-1 | | 31 | 2 | 3839 | Tconv | Lung |
| 3839_Treg_Lung_22_S310_P1 | TRAV12N-3_AGTGATGCCTCGG_TRAJ11 | | TRBV4_AGCTATGGAGGGGACAGCACAG_TRBJ1-1 | | 31 | 2 | 3839 | Treg | Lung |
| 3889_CD4_Lung_19_S307_P2 | TRAV7D-4_AGGGATAGCA_TRAJ33 | | TRBV5_CAAGATGGGGTTAACCA_TRBJ2-5 | | 42 | 3 | 3889 | Tconv | Lung |
| 3889_Treg_Lung_19_S19_P2 | TRAV7D-4_AGGGATAGCA_TRAJ33 | | TRBV5_CAAGATGGGGTTAACCA_TRBJ2-5 | | 42 | 3 | 3889 | Treg | Lung |
| 3889_Treg_Lung_34_S34_P1 | TRAV7D-4_AGGGATAGCA_TRAJ33 | | TRBV5_CAAGATGGGGTTAACCA_TRBJ2-5 | | 42 | 3 | 3889 | Treg | Lung |
| 3889_CD4_Lung_32_S128_P1 | TRAV13D-1_GTGCTTTGGAACGTG_GCACCA_TRAJ27 | | TRBV3_GCTTATCGGGTCTTGGAA_TRBJ1-3 | | 46 | 2 | 3889 | Tconv | Lung |
| 3889_Treg_Lung_66_S66_P1 | TRAV13D-1_GTGCTTTGGAACGTG_GCACCA_TRAJ27 | TRAV12D-2_AGTGATTGACT_TRAJ11 | TRBV3_GCTTATCGGGTCTTGGAA_TRBJ1-3 | | 46 | 2 | 3889 | Treg | Lung |
| 3889_CD4_Lung_46_S334_P2 | TRAV12N-3_AGTGAGAACCAG_TRAJ15 | | TRBV4_CAGCTTTGGGACTGGACAAGA_TRBJ2-5 | | 49 | 2 | 3889 | Tconv | Lung |
| 3889_Treg_Lung_62_S62_P1 | TRAV12N-3_AGTGAGAACCAG_TRAJ15 | | TRBV4_CAGCTTTGGGACTGGACAAGA_TRBJ2-5 | | 49 | 2 | 3889 | Treg | Lung |
| 3889_CD4_Lung_55_S151_P1 | TRAV12D-1_TCTGAAGGGGGACTAT_TRAJ47 | | TRBV13-2_GGTGACCCTCAGGGAAGAACAGA_TRBJ1-1 | TRBV31_GGAGCAAGGACAGTTTCC_TRBJ1-4 | 51 | 4 | 3889 | Tconv | Lung |

TABLE 3-continued

Shared clonotypes between T_reg and T_conv cells

| Cellname | A_productive | A_unproductive | B_productive | B_unproductive | clonal_group | group_size | mouse | cell.id | tissue |
|---|---|---|---|---|---|---|---|---|---|
| 3889_CD4_Lung_89_S377_P2 | TRAV12D-1_TCTGAAGGGGGACTAT_TRAJ47 | TRAV6D-7_GCTCTCATACA_TRAJ45 | TRBV13-2_GGTGACCCTCAGGGAAGAACAGA_TRBJ1-1 | TRBV31_TGGAGCAAGGACAGTTTCC_TRBJ1-4 | 51 | 4 | 3889 | Tconv | Lung |
| 3889_Treg_Lung_34_S34_P2 | TRAV12D-1_TCTGAAGGGGGACTAT_TRAJ47 | TRAV6-5_GCTCTCATACA_TRAJ45 | TRBV13-2_GGTGACCCTCAGGGAAGAACAGA_TRBJ1-1 | TRBV31_GGAGCAAGGACAGTTTCC_TRBJ1-4 | 51 | 4 | 3889 | Treg | Lung |
| 3889_Treg_Lung_91_S91_P2 | TRAV12D-1_TCTGAAGGGGGACTAT_TRAJ47 | TRAV6-7_DV9_GCTCTCATACA_TRAJ45 | TRBV13-2_GGTGACCCTCAGGGAAGAACAGA_TRBJ1-1 | | 51 | 4 | 3889 | Treg | Lung |
| 3889_CD4_Lung_93_S381_P2 | TRAV6-5_TGAGTCCTTCC_TRAJ34 | | TRBV5_CAAGATGGGGTTAACCA_TRBJ2-5 | | 56 | 2 | 3889 | Tconv | Lung |
| 3889_Treg_Lung_71_S71_P1 | TRAV6-5_TGAGTCCTTCC_TRAJ34 | | TRBV5_CAAGATGGGGTTAACCA_TRBJ2-5 | TRBV19_AACAGGGCGCTGAAC_TRBJ2-7 | 56 | 2 | 3889 | Treg | Lung |
| 3964_CD4_Lung_21_S21_P2 | TRAV12D-2_CTTTGCTCCGGAAT_TRAJ31 | | | TRBV13-2_TGATGCTGGGGGAAAGCTCCT_TRBJ2-7 | 74 | 9 | 3964 | Tconv | Lung |
| 3964_CD4_Lung_47_S47_P2 | TRAV12D-2_CTTTGCTCCGGAAT_TRAJ31 | TRAV13D-2_CACCAGGGAG_TRAJ15 | TRBV13-2_GGTGAACAGGGAGGGTACACC_TRBJ2-5 | | 74 | 9 | 3964 | Tconv | Lung |
| 3964_CD4_Lung_94_S94_P2 | | TRAV13D-2_CACCAGGGAG_TRAJ15 | TRBV13-2_GGTGAACAGGGAGGGTACACC_TRBJ2-5 | | 74 | 9 | 3964 | Tconv | Lung |
| 3964_CD4_Lung_96_S96_P2 | TRAV12D-2_CTTTGCTCCGGAAT_TRAJ31 | | TRBV13-2_GGTGAACAGGGAGGGTACACC_TRBJ2-5 | | 74 | 9 | 3964 | Tconv | Lung |
| 3964_Treg_Lung_12_S204_P2 | TRAV12D-2_CTTTGCTCCGGAAT_TRAJ31 | TRAV13D-2_CACCAGGGAG_TRAJ15 | TRBV13-2_GGTGAACAGGGAGGGTACACC_TRBJ2-5 | | 74 | 9 | 3964 | Treg | Lung |
| 3964_Treg_Lung_36_S228_P2 | TRAV12D-2_CTTTGCTCCGGAAT_TRAJ31 | | TRBV13-2_GGTGAACAGGGAGGGTACACC_TRBJ2-5 | | 74 | 9 | 3964 | Treg | Lung |
| 3964_Treg_Lung_70_S70_P1 | TRAV12D-2_CTTTGCTCCGGAAT_TRAJ31 | | TRBV13-2_GGTGAACAGGGAGGGTACACC_TRBJ2-5 | | 74 | 9 | 3964 | Treg | Lung |
| 3964_Treg_Lung_81_S81_P1 | TRAV12D-2_CTTTGCTCCGGAAT_TRAJ31 | | TRBV13-2_GGTGAACAGGGAGGGTACACC_TRBJ2-5 | | 74 | 9 | 3964 | Treg | Lung |
| 3964_Treg_Lung_95_S95_P1 | TRAV12D-2_CTTTGCTCCGGAAT_TRAJ31 | | TRBV13-2_GGTGAACAGGGAGGGTACACC_TRBJ2-5 | | 74 | 9 | 3964 | Treg | Lung |

TABLE 3-continued

Shared clonotypes between T_reg and T_conv cells

| Cellname | A_productive | A_unproductive | B_productive | B_unproductive | clonal_group | group_size | mouse | cell.id | tissue |
|---|---|---|---|---|---|---|---|---|---|
| 6226_CD4_Lung_17_S113_P1 | TRAV6D-7_GGGTGGTAGAGGA_TRAJ42 | | | | 148 | 4 | 6226 | Tconv | Lung |
| 6226_CD4_Lung_27_S123_P1 | TRAV6D-7_GGGTGGTAGAGGA_TRAJ42 | | TRBV4_GCAGCCTTGGGCCCTATG_TRBJ2-1 | | 148 | 4 | 6226 | Tconv | Lung |
| 6226_CD4_Lung_96_S192_P1 | TRAV6D-7_GGGTGGTAGAGGA_TRAJ42 | | TRBV4_GCAGCCTTGGGCCCTATG_TRBJ2-1 | | 148 | 4 | 6226 | Tconv | Lung |
| 6226_Treg_Lung_42_S138_P1 | TRAV6D-7_GGGTGGTAGAGGA_TRAJ42 | | TRBV4_GCAGCCTTGGGCCCTATG_TRBJ2-1 | | 148 | 4 | 6226 | Treg | Lung |
| 6226_CD4_Lung_40_S136_P1 | TRAV21_DV12_AGTAGTGGCGAATC_TRAJ57 | TRAV15N-1_GCGGGATAACA_TRAJ37 | TRBV26_GTCTGCCCACAGTTTCTG_TRBJ1-3 | | 149 | 3 | 6226 | Tconv | Lung |
| 6226_Treg_Lung_61_S157_P1 | TRAV21_DV12_AGTAGTGGCGAATC_TRAJ57 | | TRBV26_GTCTGCCCACAGTTTCTG_TRBJ1-3 | | 149 | 3 | 6226 | Treg | Lung |
| 6226_Treg_Lung_66_S162_P1 | TRAV21_DV12_AGTAGTGGCGAATC_TRAJ57 | | TRBV26_GTCTGCCCACAGTTTCTG_TRBJ1-3 | | 149 | 3 | 6226 | Treg | Lung |
| 6226_CD4_Lung_71_S167_P1 | TRAV14-2_AAGTGATAGC_TRAJ33 | TRAV7N-5_GTGCATCTTAATTC_TRAJ42 | TRBV5_CAAGATGGGGGGTCAAAC_TRBJ1-1 | | 152 | 2 | 6226 | Tconv | Lung |
| 6226_Treg_Lung_70_S166_P1 | TRAV14-2_AAGTGATAGC_TRAJ33 | | TRBV5_CAAGATGGGGGGTCAAAC_TRBJ1-1 | | 152 | 2 | 6226 | Treg | Lung |

Figure 16A:
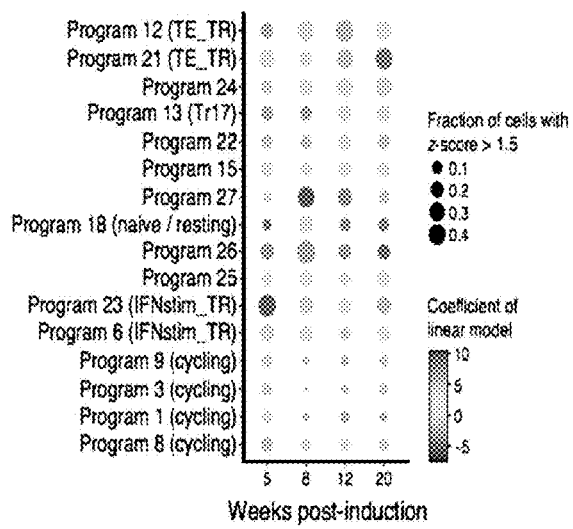

Example 12. A Klrg1+Areg+ Effector-Like T_Reg Cell Program Becomes Predominant During Tumor Development In contrast to Tr17-like cells, where a program was expressed by a mostly fixed proportion of cells during tumor development, other T_reg programs changed in prominence throughout tumor development (FIG. 16A). For example, after 8 weeks there was decreased expression of programs 1, 3, 8, and 9, which marked cycling cells (FIG. 16A), corresponding to the decline in Ki67-positive T_regs observed by flow cytometry (FIG. 15A). Two other programs also changed over time, reflecting an interferon response (Programs 6 and 23, FIG. 16A-16C, 20A) and a Klrg1+Areg+ activated effector-like program (Programs 12 and 21, FIGS. 16A-16C, 20A-20B).

Figure 20A:
Figure 20B:
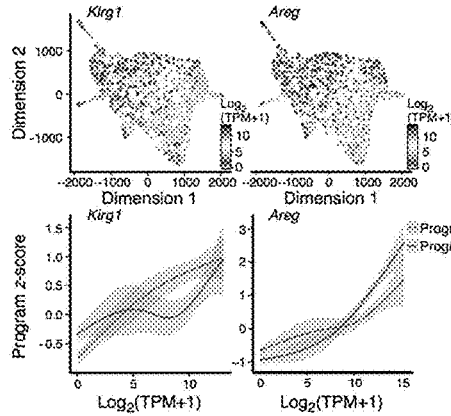
Figure 20C:
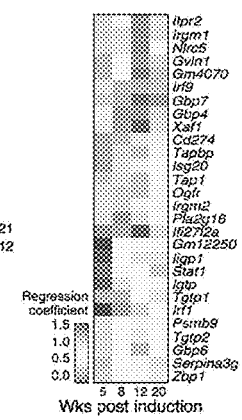
Figure 20D:
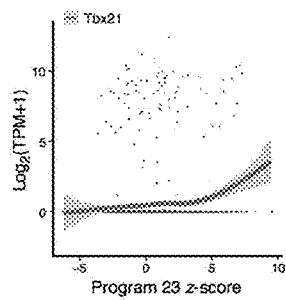

The interferon-responsive effector-like T_reg program ("IFNstim_TR") was characterized by the expression of Programs 6 and 23 (FIG. 16A-16B, 20A), which included many interferon-stimulated genes (ISGs) downstream of either type I or II interferon (IFN) signaling These included Stat1, guanylate binding protein genes (GBPs), type I interferon-specific genes (e.g., oligoadenylate synthetase family members), and IFNγ-specific genes (e.g., Irf1, Irf9) (Der et al., 1998). 28 genes from the IFNstim_TR program were significantly downregulated in T_regs during tumor progression (FIG. 20C). IFNγ promotes a Tbet+CXCR3+ T_reg cell population that can suppress Th1 responses (Hall et al., 2012; Koch et al., 2009, 2012). Neither Cxcr3 nor Tbx21 are IFNstim_TR genes, but IFNstim_TR expression was correlated with Tbx21 expression (FIG. 20D). Moreover, cells scoring highly for the IFNstim_TR program also scored highly for a lymphoid tissue T_reg program (FIG. 20E), and msLN T_regs had higher expression of IFNstim_TR genes compared to lung T_regs at 12 and 20 weeks p.i. (FDR<$10^{-3}$, t-test, FIG. 20F). Taken together, T_regs expressing the interferon-responsive program ("IR T_regs") may have recently arrived to the lung, consistent with the expression of IFNstim_TR genes early in tumor development and in msLN Tregs.

Figure 16B:
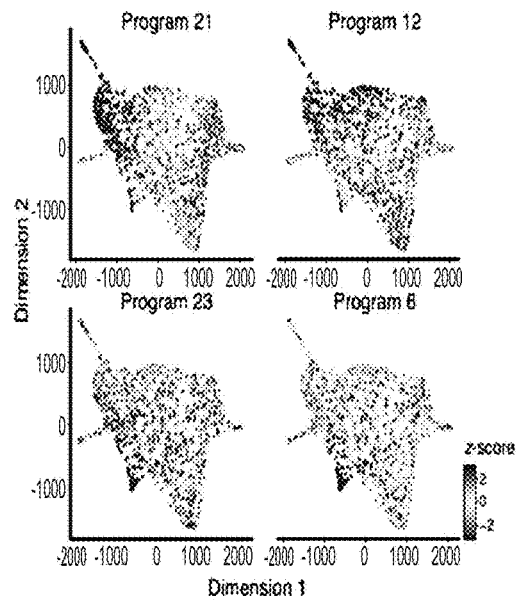
Figure 20E:
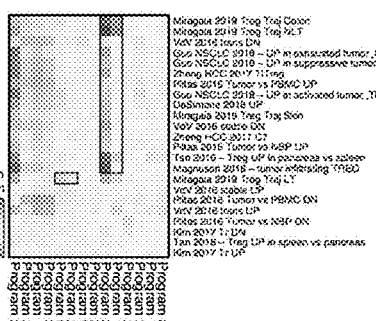
Figure 20F:
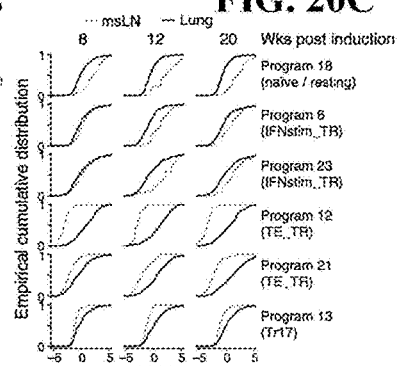
Figure 20G:
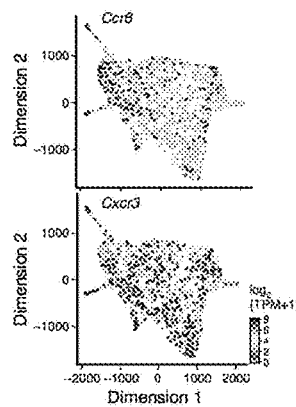

The applicants also identified a Klrg1+Areg+ effector-like T_reg program ("KA_TR") that was characterized by the expression of Programs 12 and 21 (FIGS. 16B and 20A-20B). KA_TR genes were enriched for genes upregulated in $T_{regs}$ from mouse non-lymphoid tissues and human breast cancer, NSCLC, and colorectal cancer (FIG. 20E). These cells expressed Ccr6 but not Cxcr3, thus representing a population distinct from IR $T_{regs}$ (FIG. 20G). Klrg1 and Areg expression have been associated with $T_{reg}$ differentiation and tissue repair function, respectively (Arpaia et al., 2015; Burzyn et al., 2013; Cheng et al., 2012). We have previously shown that nearly 40% of lung $T_{regs}$ from KP mice with advanced disease are CD103+KLRG1+(double-positive, DP) (Joshi et al., 2015). The KA_TR program was enriched for genes upregulated in DP $T_{regs}$ vs. all other $T_{regs}$ in late-stage tumor-bearing lungs (p-value≤$10^{-25}$, FIG. 20H-20I), which include genes associated with T cell activation and putative $T_{reg}$ effector functions (e.g., Nr4a1, Cd69, Il1rl1, Areg, Srgn, and Fg12). $T_{regs}$ expressing the KA_TR program ("KA $T_{regs}$") and DP $T_{regs}$ have highly overlapping features, including the expression of KLRG1, and both programs are likely representative of a KLRG1+ effector $T_{reg}$ subpopulation.

Figure 16C:
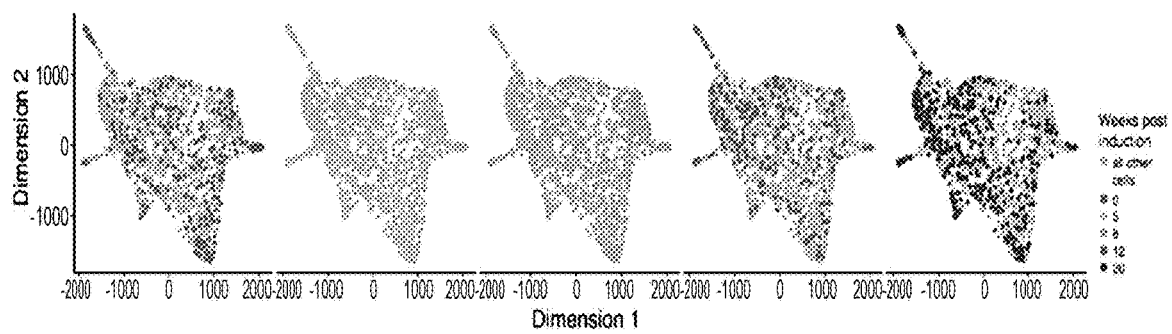
Figure 16D:
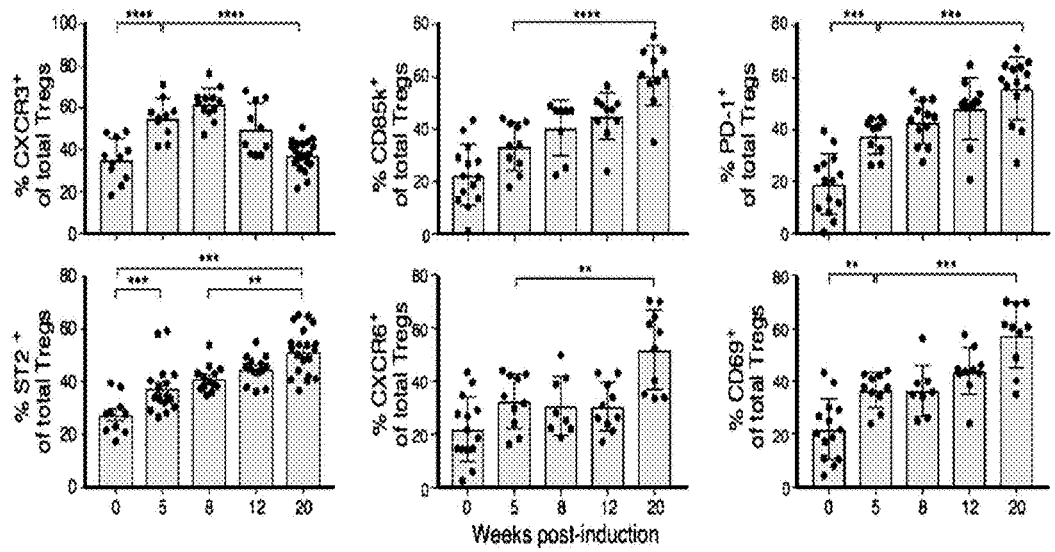
Figure 20H:
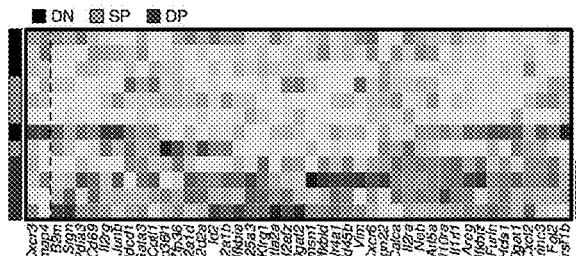
Figure 20I:
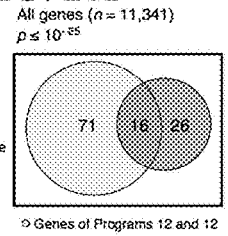
Figure 20J:
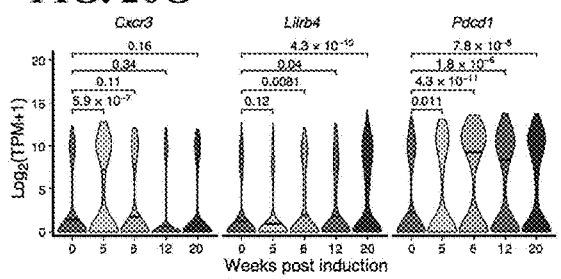
Figure 20K:
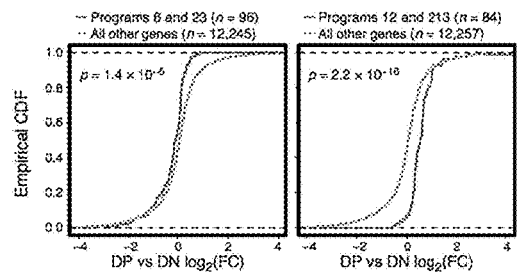

The IR and KA $T_{reg}$ programs represented distinct phenotypes of $T_{regs}$ within each timepoint, and followed opposite patterns over time: expression of IFNstim_TR genes was highest in cells from week 5 and declined thereafter, while expression of KA_TR genes increased and remained elevated (FIG. 16A-16C). This temporal transition was reflected at the level of individual genes: Cxcr3 expression decreased with time, and Pdcd1 and Lilrb4 (Program 21) increased in expression during tumor development (FIG. 20J), consistent with down-regulation of Cxcr3 in DP $T_{reg}$ cells (FIG. 20H). More generally, KA_TR genes were upregulated in DP $T_{regs}$ compared to DN $T_{regs}$ in mice with late-stage tumor burden, whereas IFNstim_TR genes were significantly downregulated (FIG. 20K). We confirmed that CXCR3 protein levels decreased, and proteins encoded by KA_TR genes, including CD85k, CD69, CXCR6, PD-1 and ST2, increased during tumor progression (FIG. 20D). Taken together, our data suggest that tumor progression may be associated with a shift from cells with the IR $T_{reg}$ phenotype, which may be specialized for responding to Th1 inflammation, to cells with the KA $T_{reg}$ program. In particular, we hypothesized that the strong immunosuppression associated with the late-stage tumor environment may be a result of the emergence and stabilization of cells with the KA $T_{reg}$ phenotype.

Figures 21A, 21B:
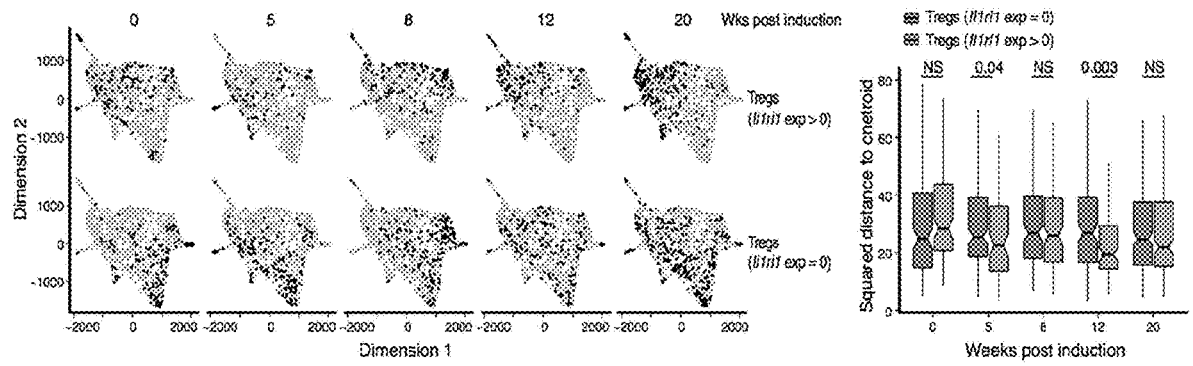
Figure 21C:
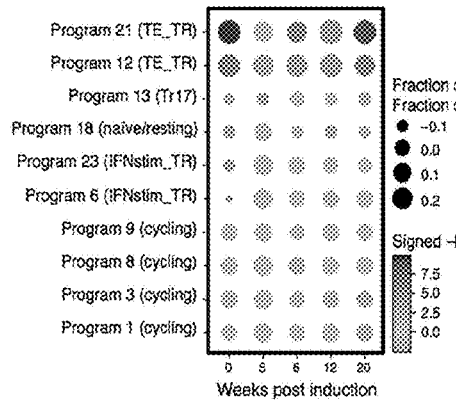
Figure 21D:
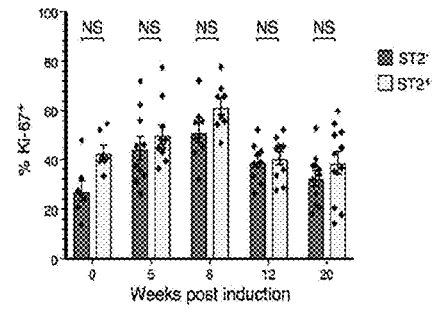
Figure 21E:
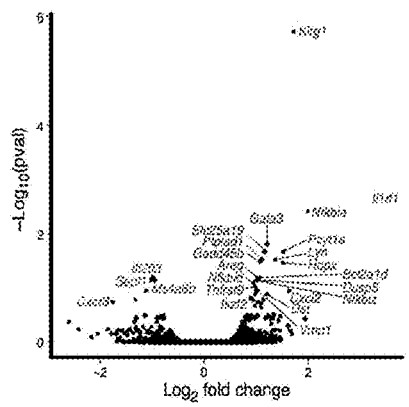
Figure 21F:
Figure 21G:
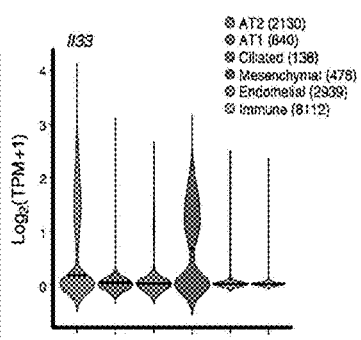

Example 13. ST2 May Promote the KA $T_{reg}$ Phenotype in Mice Bearing Advanced Lung Tumors Il1rl1, a KA_TR gene that encodes the interleukin 33 (IL-33) receptor ST2, marked a heterogeneous $T_{reg}$ population that had higher expression of KA_TR genes. ST2 has been shown to mark an epigenetically-distinct tissue $T_{reg}$ program characterized by KLRG1 and GATA3 expression (Delacher et al., 2017). Il1rl1 transcript and ST2 protein levels tracked with the KA/DP $T_{reg}$ phenotype; Il1rl is a member of Module 21 in the KA_TR program and ST2 was most highly expressed in DP lung $T_{regs}$ (FIG. 17A). However, Il1rl-positive $T_{reg}$ s had overall comparable heterogeneity to Il1rl-negative $T_{regs}$; both populations scored highly for the expression of multiple gene programs (FIG. 21A), and had similar transcriptional diversity (FIG. 21B). Nevertheless, Il1rl1-positive $T_{regs}$ had higher expression of KA_TR genes and lower expression of Th17-like and resting $T_{reg}$ genes at all timepoints (FIGS. 17B and 21C). Il1rl1-positive $T_{regs}$ also had lower expression of IFNstim_TR genes compared to Il1rl1-negative $T_{regs}$ in non-tumor bearing lungs (FIG. 21C). Il1rl1-positive and Il1rl1-negative $T_{regs}$ had similar expression of cell cycle genes (FIG. 21C-21D), suggesting that proliferation does not account for the observed differences in phenotype. Indeed, top significantly differentially-expressed genes in Il1rl1-positive $T_{regs}$ vs. Il1rl1-negative $T_{regs}$ were enriched for KA_TR and DP genes (FIG. 21E). Genes differentially-expressed between Il1rl1-positive and Il1rl1-negative $T_{regs}$ from human colon cancer (Zhang et al., 2018) were enriched for KA_TR genes (Program 21 p=$5.3*10^{-6}$, Program 12 p=$1.5*10^{-5}$, hypergeometric test) (FIG. 17C). ST2 signaling may thus be a conserved pathway in human and mouse $T_{regs}$ that promotes the KA/DP $T_{reg}$ phenotype and/or the proliferation of KA/DP $T_{regs}$. Consistent with the presence of ST2 signaling throughout tumor development, IL-33, the only known ligand of ST2 and an alarmin that recruits immune cells to sites of tissue damage (Cayrol and Girard, 2014), was highly expressed in normal lung, and in early and late lung adenocarcinomas in the KP model (FIG. 17D). Specifically, IL-33 was predominantly expressed on surfactant protein C (SPC)-expressing type II epithelial (AT2) cells in normal lung (FIG. 21F), and AT2 and mesenchymal cells in tumor-bearing lungs (FIG. 21G), which is consistent with prior reports (Treutlein et al., 2014).

Figure 21H:
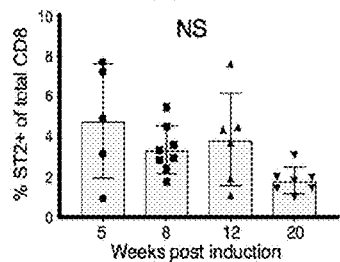

ST2 protein was preferentially expressed by lung-infiltrating $T_{regs}$ late in tumor development. ST2 levels on lung-infiltrating $T_{regs}$ increased with time (FIG. 16D), and ST2 was expressed by ~40% of lung $T_{regs}$ vs. ~10% of $T_{regs}$ in the msLN, and <5% of $T_{conv}$ and CD8+ T cells in the lung in late-stage tumor-bearing mice (FIGS. 17E and 21H). We thus hypothesized that the expansion of ST2+ $T_{regs}$ may drive the increased predominance of KA/DP $T_{regs}$ during lung tumor development.

Figure 18A:
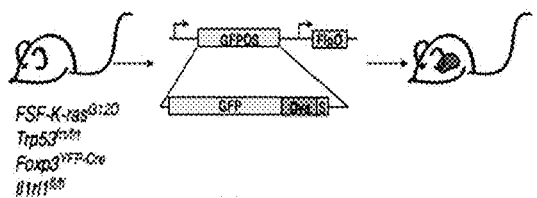
Figure 18B:
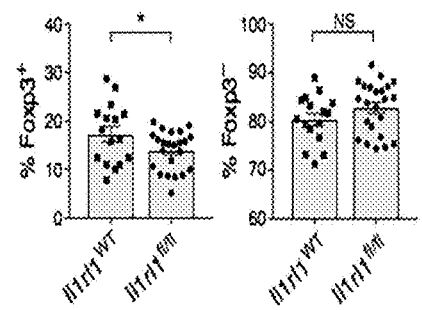

Example 14. $T_{reg}$-Specific ST2 is Required for the Increase in DP $T_{regs}$ During Tumor Progression To test whether ST2 signaling on $T_{regs}$ was necessary for the development of a robust KA/DP effector $T_{reg}$ cell response in tumors, the applicants studied the effects of $T_{reg}$-specific Il1rl1 deletion. The applicants used a modified version of the KP model, where FlpO recombinase drives expression of oncogenic K-ras and loss of p53 (KPfrt: FSF-Kras$^{G12D}$, p53$^{frt/frt}$) (Lee et al., 2012), which allowed us to use the Cre-lox system to study $T_{reg}$-specific Il1rl1 deletion. We crossed KPfrt mice to Foxp3$^{YFP-Cre}$ and Il1rl1$^{fl/fl}$ to model lung adenocarcinoma development in the setting of $T_{reg}$-specific ST2 deficiency (FIG. 18A). The applicants infected the mice with a lentivirus expressing FlpO recombinase and GFP fused to Ova and SIYRGYYL (FlpO-GFP-OS) in order to induce tumors that would express the same strong T cell antigens as those in the Lenti-LucOS model.

Figure 18C:
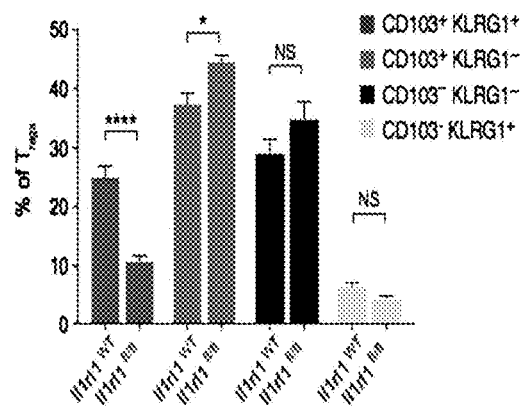

Consistent with $T_{reg}$-specific recombination of the Il1rl1 locus, ST2 expression levels were unchanged in CD8+ T cells and $T_{conv}$ (FIG. 22A). Early-stage KPfrt, Foxp3$^{YFP-Cre}$, Il1rl1$^{fl/fl}$ mice did not differ from KPfrt, Foxp3$^{YFP-Cre}$ mice in the fraction of CD4+ T cells that were $T_{conv}$ or $T_{reg}$ cells (FIG. 22B), but late in tumor progression there was a slight reduction in the proportion of $T_{reg}$ cells (FIG. 18B), a significantly lower proportion of DP $T_{regs}$ out of all $T_{regs}$, and correspondingly a higher proportion of SP cells (FIG. 18C). Notably, Ki-67 expression of DP $T_{regs}$ from KPfrt, Foxp3$^{YFP-Cre}$ and KPfrt, Foxp3$^{YFP-Cre}$, Il1rl1$^{fl/fl}$ mice was not statistically different, suggesting that the decreased fraction of DP $T_{regs}$ in mice with $T_{reg}$-specific ST2 deletion was not due to impaired proliferation (FIG. 22C). msLN and splenic $T_{regs}$ did not demonstrate similar changes in their expression of CD103 and KLRG1 (FIG. 22D). Proportions of Th1, Th17, CD8+ T cells, tumor antigen-specific CD8+ T cells, and alveolar macrophages were also comparable among KP tumor-bearing mice with and without $T_{reg}$-specific ST2 deficiency (FIG. 22E-22H).

Figure 18D:
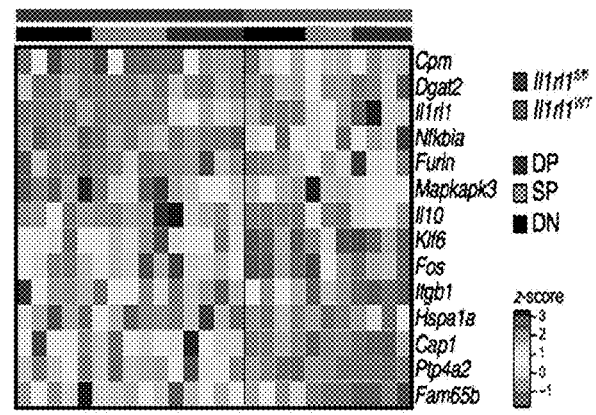

Expression profiles of DP, SP, and DN $T_{regs}$ from KPfrt, Foxp3$^{YFP-Cre}$, Il1rl1$^{fl/fl}$ and KPfrt, Foxp3$^{YFP-Cre}$ control mice identified an expression signature lower in ST2-deficient vs. wild-type $T_{regs}$ and highest among wild-type DP $T_{regs}$ (FIGS. 18D and 22I). The signature was enriched for DP signature genes, including Dgat2, Furin and Nfkbia, genes preferentially expressed in Il1rl1-expressing $T_{regs}$ ($p=1.2*10^{-13}$, hypergeometric test), and genes upregulated by $T_{regs}$ in human NSCLC (FIG. 22J-22K). ST2-deficient $T_{regs}$ also showed higher expression of some genes, including Itgb1, Il10, Klf6, and Fos (FIG. 18D), suggesting that they may adopt alternative phenotypes.

Figure 18E:
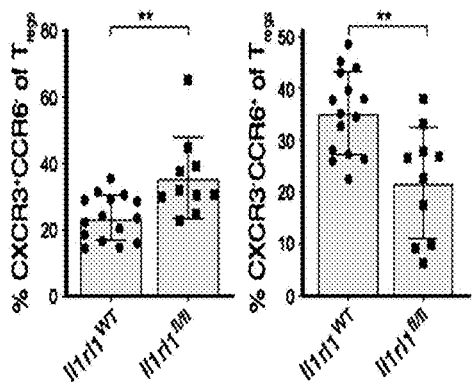
Figure 18F:
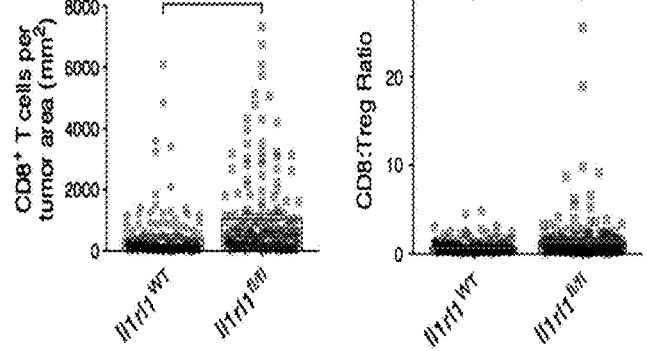
Figure 18G:
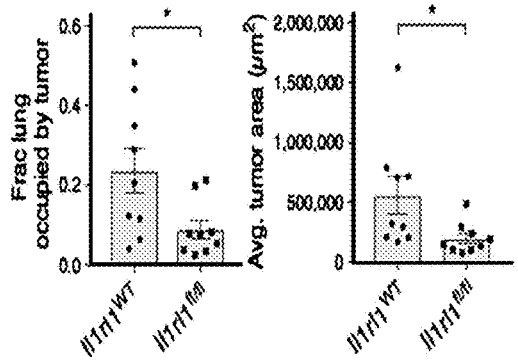

The applicants hypothesized that KPfrt, Foxp3$^{YFP-Cre}$, Il1rl1$^{fl/fl}$ mice may have altered proportions of Tr17-like and CXCR3+ phenotypes identified in our analysis. Indeed, CXCR3+CCR6− $T_{regs}$ were increased, while CXCR3−CCR6+ $T_{regs}$ were decreased, in KPfrt, Foxp3$^{YFP-Cre}$, Il1rl1$^{fl/fl}$ mice compared to KPfrt, Foxp3$^{YFP-Cre}$ control mice with advanced disease (FIGS. 18E and 22L). However, RORγT expression was unchanged between KPfrt, Foxp3$^{YFP-Cre}$, Il1rl1$^{fl/fl}$ and control mice (FIG. 22M), suggesting that a CCR6+ population of $T_{regs}$ exclusive of Tr17-like cells decreases in the setting of $T_{reg}$-specific ST2 deficiency. Nevertheless, earlier in tumor development, mice with $T_{reg}$-specific ST2 deletion had increased fluorescence intensity of CXCR3 on CXCR3+ $T_{regs}$ (FIG. 22N). Taken together, our data supports the hypothesis that ST2 regulates $T_{reg}$ diversity over time by promoting the KA/DP $T_{reg}$ over alternate phenotypes.

Example 15. $T_{reg}$-Specific ST2 Ablation Leads to Increased CD8+ T Cell Infiltration and a Reduction in Tumor Burden The applicants found that tumors from KPfrt, Foxp3$^{YFP-Cre}$, Il1rl1$^{fl/fl}$ mice had over 50% higher CD8+ T cell infiltration than tumors from control mice by immunohistochemistry, resulting in higher CD8:$T_{reg}$ ratios (FIG. 4F). KPfrt, Foxp3$^{YFP-Cre}$, Il1rl1$^{fl/fl}$ mice also had a significantly lower total tumor burden and lower average tumor size compared to control mice (FIGS. 4G and 22O), suggesting that greater CD8+ T cell infiltration of tumors may result in better inhibition of tumor growth. Moreover, tumor infiltration by Foxp3+ T cells was also greater in KPfrt, Foxp3$^{YFP-Cre}$, Il1rl1$^{fl/fl}$ mice (FIG. 22P), supporting the hypothesis that loss of ST2 signaling encourages a pro-inflammatory $T_{reg}$ phenotype rather than reducing $T_{reg}$ numbers. Overall, our studies suggest that $T_{reg}$-specific inhibition of ST2 signaling may result in a less immunosuppressive tumor microenvironment characterized by increased anti-tumor CD8+ T cell activity and lower tumor burden.

Experimental Methods

Mice

KP, KPfrt, Foxp3$^{GFP}$, Foxp3$^{RFP}$, Foxp3$^{GFP/DTR}$, Il1rl1$^{−/−}$ and Il1rl1$^{fl/fl}$ mice have been previously described (Bettelli et al., 2006; Chen et al., 2015; DuPage et al., 2011; Kim et al., 2007; Townsend et al., 2000; Wan and Flavell, 2005; Young et al., 2011). Both male and female mice were used for all experiments, and mice were gender and age-matched within experiments. Experimental and control mice were co-housed whenever appropriate. All studies were performed under an animal protocol approved by the Massachusetts Institute of Technology (MIT) Committee on Animal Care. Mice were assessed for morbidity according to MIT Division of Comparative Medicine guidelines and humanely sacrificed prior to natural expiration.

For in vivo labelling of circulating immune cells, anti-CD4-PE (eBioscience, RM4-4, 1:400) and anti-CD80-PE (eBioscience, 1:400) were diluted in PBS and administered by IV injection 5 minutes before harvest (Anderson et al., 2012). Alternatively, anti-CD45-PE-CF594 (30-F11, BD Biosciences, 1:200) was also used for intravascular labeling and was administered 2 minutes before sacrifice.

For rIL-33 treatment studies, 200 ng of recombinant mouse IL-33 (BioLegend) was diluted in 50 mL of PBS and administered intratracheally to mice as described previously (Li et al., 2014). Control mice received PBS only.

Lentiviral Production and Tumor Induction

The lentiviral backbone Lenti-LucOS has been described previously (DuPage et al., 2011). Lentiviral plasmids and packaging vectors were prepared using endo-free maxiprep kits (Qiagen). The pGK::GFP-LucOS::EFS::FlpO lentiviral plasmid was cloned using Gibson assembly (Akama-Garren et al., 2016; Gibson et al., 2009). Briefly, GFP-OS was created as a protein fusion of GFP and ovalbumin$_{257-383}$, which includes the SIINFEKL and AAHAEINEA epitopes, and SIYRYYGL antigen. Lentiviral plasmids and packaging vectors were prepared using endo-free maxiprep kits (Qiagen). Lentiviruses were produced by co-transfection of 293FS* cells with Lenti-LucOS or FlpO-GFP-OS, psPAX2 (gag/pol), and VSV-G vectors at a 4:2:1 ratio with Mirus TransIT LT1 (Mirus Bio, LLC). Virus-containing supernatant was collected 48 and 72 h after transfection and filtered through 0.45 mm filters before concentration by ultracentrifugation (25,000 RPM for 2 hours with low decel.). Virus was then resuspended in 1:1 Opti-MEM (Gibco)-HBSS. Aliquots of virus were stored at −80° C. and titered using the GreenGo 3TZ cell line (Sinchez-Rivera et al., 2014).

For tumor induction, mice between 8-15 weeks of age received $2.5 \times 10^4$ PFU of Lenti-LucOS or $4.5 \times 10^4$ PFU of FlpO-GFP-OS intratracheally as described previously (DuPage et al., 2009).

Tissue Isolation and Preparation of Single Cell Suspensions

After sacrifice, lungs were placed in 2.5 mL collagenase/DNAse buffer (Joshi et al., 2015) in gentleMACS C tubes (Miltenyi) and processed using program m_impTumor_01.01. Lungs were then incubated at 37° C. for 30 minutes with gentle agitation. The tissue suspension was filtered through a 100 μm cell strainer and centrifuged at 1700 RPM for 10 minutes. Red blood cell lysis was performed by incubation with ACK Lysis Buffer (Life Technologies) for 3 minutes. Samples were filtered and centrifuged again, followed by resuspension in RPMI 1640 (VWR) supplemented with 1% heat-inactivated FBS and 1× penicillin-streptomycin (Gibco), and 1×L-glutamine (Gibco).

Spleens and lymph nodes were dissociated using the frosted ends of microscope slides into RPMI 1640 supplemented with 1% heat-inactivated FBS and 1× penicillin-streptomycin (Gibco), and 1×L-glutamine (Gibco). Spleen cell suspensions were spun down at 1500 RPM for 5 minutes, and red blood cell lysis with ACK Lysis Buffer was performed for 5 minutes. Cells were filtered through 40 μm nylon mesh and, after centrifugation, resuspended in supplemented RPMI 1640. Lymph node suspensions were filtered through a 40 μm nylon mesh, spun down at 1500 RPM for 5 minutes, and resuspended in supplemented RPMI 1640.

For ex vivo T cell stimulation experiments to detect intracellular cytokines, $0.5 \times 10^5$ cells were plated in a 96-well U-bottom plate (BD Biosciences) in RPMI 1640 (VWR) supplemented with 10% heat-inactivated FBS, 1× penicillin-streptomycin (Gibco), 1×L-glutamine (Gibco), 1×HEPES (Gibco), 1× GlutaMAX (Gibco), 1 mM sodium pyruvate (Thermo Fisher), 1×MEM non-essential amino acids (Sigma), 50 µM beta-mercaptoethanol (Gibco), 1× Cell Stimulation Cocktail (eBioscience), 1× monensin (BioLegend), and 1× brefeldin A (BioLegend). Cells were incubated in a tissue culture incubator at 37° C. with 5% $CO_2$ for 4 hours.

Staining for Flow Cytometric Analysis

Approximately $0.5-1\times10^6$ cells were stained for 15-30 minutes at 4° C. in 96-well U-bottom plates (BD Biosciences) with directly conjugated antibodies (Table 4). SIINFEKL-Kb tetramer was prepared using streptavidin-APC (Prozyme) and SIINFEKL-Kb monomer from the NIH Tetramer Core.

After staining, cells were fixed with Cytofix/Cytoperm Buffer (BD). Samples that were destined for Foxp3 or other transcription factor staining were fixed with the Foxp3 Transcription Factor Staining Buffer Kit (eBioscience). Intracellular cytokine and transcription factor staining were performed right before analysis using either the BD Perm/Wash Buffer (BD) or the Foxp3 Transcription Factor Staining Buffer Kit (eBioscience); staining was performed for 45 minutes at 4° C. Analysis was performed on an LSR II (BD) with 405, 488, 561, and 635 lasers. Data analysis was performed using FlowJo software.

Isolation of $T_{reg}$ Populations for Bulk RNA-Seq

For sequencing of LucOS-infected, KP, Foxp3-RFP mice: 100-200 DP, SP, and DN Treg cells were sorted into Buffer TCL (Qiagen) plus 1% b-mercaptoethanol using a MoFlo Astrios cell sorter. cDNA was prepared by the SMART-Seq2 protocol (Picelli et al., 2013) with the following modifications: RNA was purified using 2.2X RNAclean SPRI beads (Beckman Coulter) without final elution, after which beads were air-dried and immediately resuspended with water and oligoDT for annealing, and 18 cycles of preamplification were used for cDNA. cDNA was then mechanically sheared and prepared into sequencing libraries using the Thru-Plex FD Kit (Rubicon Genomics). Sequencing was performed on an Illumina HiSeq 2000 instrument to obtain 50 nt paired-end reads.

For comparison of wild-type and ST2-deficient Tregs and CD8+ T cells: 100-200 DP, SP, and DN Tregs or SIINFEKL-tetramer-positive and negative CD8+ T cells were sorted and cDNA was prepared with 14 cycles of preamplification. Nextera library preparation was performed as previously described (Picelli et al., 2013) and sequencing was performed with 50×25 paired end reads using two kits on the NextSeq 500 5 instrument.

Single-Cell Sorting of $T_{conv}$ and $T_{reg}$ Populations for RNA Sequencing $T_{conv}$ (DAPIneg, i.v. neg, Thy1.2+CD4+ Foxp3-GFPneg) and Treg (DAPIneg, i.v. neg, Thy1.2+CD4+Foxp3-GFP-positive) cells were single-cell sorted into Buffer TCL (Qiagen) plus 1% B-mercaptoethanol in 96-well plates using a MoFlo Astrios cell sorter. Each plate had 30-100 cell population well and an empty well as controls. Following sorting, plates were spun down for 1" at 2000 RPM and frozen immediately at −80° C.

Droplet-Based scRNA-Seq of CD45+ and CD45− Populations from Tumor-Bearing Lungs

Tumors were microdissected under dissection microscope and dissociated into single cell suspensions as previously described. Samples were pelleted at 1700 RPM for 5 minutes and resuspended in 500 ul of MACS buffer containing PBS, 0.5% bovine serum albumin (BSA), and 2 mM EDTA. CD45+ and CD45− cells were then magnetically separated using MACS CD45 MicroBeads (Miltenyi Biotec) as per manufacturer's instructions. Briefly, cells were stained with CD45 MicroBeads for 15 minutes at 4° C. Samples were washed with MACS buffer and pelleted at 1700 rpm for 5 minutes. Samples were resuspended in 1 ml of MACS buffer and added to LS MACS column on LS Separator magnet (Miltenyi Biotec). Flow through was collected as CD45-population. Columns were washed 3× with MACS buffer and flow-through was added to CD45-population. 5 ml of MACS buffer was then then added to column, the column was removed from the magnet, and cells were expelled from column into conical using plunger; this was the CD45+ sample. CD45+ and CD45− samples were pelleted at 1700 RPM for 5 minutes and resuspended in PBS with 0.01% BSA before proceeding to droplet based scRNA-seq.

Single cells were processed through the 10× Genomics Single Cell 3' platform using the Chromium Single Cell 3' Library & Gel Bead Kit V2 kit (10× Genomics), per manufacturer's protocol. Briefly, 6,000 cells were loaded onto each channel and partitioned into Gel Beads in Emulsion in the Chromium instrument. Cell lysis and barcoding occur, followed by amplification, fragmentation, adaptor ligation and index library PCR. Libraries were sequenced on an Illumina HiSeqX at a read length of 98 base pairs.

Preparation of scRNAseq Libraries

Plates were thawed and RNA was purified using 2.2X RNAclean SPRI beads (Beckman Coulter) without final elution (Shalek et al., 2013). SMART-seq2 and Nextera library preparation was performed as previously described (Picelli et al., 2013), with some modifications as described in a previous study (Singer et al., 2017). Plates were pooled into 384 single-cell libraries, and sequenced 50×25 paired end reads using a single kit on the NextSeq 500 5 instrument.

Quantitative PCR for Validation of RNA-Seq Experiments

Quantitative PCR was performed using various primer sets. 1 ng of cDNA generated using SMART-Seq2 was included in a reaction with 1 µL of each primer (2 µM stock) and 5 µL of KAPA SYBR Fast LightCycler 480 (KAPA Biosystems). Cp values were measured using a LightCycler 480 Real-Time PCR System (Roche). Relative fold-change in expression values were calculated using the following formula: $2^{(\Delta Cp(Sample)-\Delta Cp(Spleen))}$, where $\Delta Cp(Sample)$=Sample $Cp_{Gene\ of\ Interest}$−Sample $Cp_{GAPDH}$, and $\Delta Cp(Spleen)$=Spleen $Cp_{Gene\ of\ Interest}$−Spleen $Cp_{GAPDH}$.

Population-Level TCR Beta Chain Sequencing and Analysis

For bulk TCR beta chain sequencing, T cells were sorted directly into 250 µl RNAprotect buffer (Qiagen), spun down for 1 minute at 2000 RPM, and immediately frozen at −80° C. Samples were sent to iRepertoire (Huntsville, Ala.) for library preparation and sequencing. TCR sequences were analyzed and compared with VDJtools software (Shugay et al., 2015).

Immunohistochemistry (IHC) and Immunofluorescence Staining

Lung lobes and spleens allocated for IHC and IF were perfused with 4% paraformaldehyde in PBS and fixed overnight at 4° C. Lung lobes and/or spleen were transferred to histology cassettes and stored in 70% ethanol until paraffin embedding and sectioning (KI Histology Facility). H&E stains were performed by the core facility using standard methods.

For IHC, 5 µm unstained slides were dewaxed, boiled in citrate buffer (1 g NaOH, 2.1 g citric acid in 1L H2O, pH 6), for 5 minutes at 125° C. in a decloaking chamber (Biocare Medical), washed with 3× with 0.1% Tween-20 (Sigma) in TBS, and blocked and stained in Sequenza slide racks (Thermo Fisher). Slides were blocked with Dual Endogenous Peroxidase and Alkaline Phosphatase Block (Dako) and then with 2.5% Horse Serum (Vector Labs). Slides were incubated in primary antibody overnight, following by washing and incubation in HRP-polymer-conjugated secondary antibodies (ImmPRESS HRP mouse-adsorbed anti-rat and anti-goat, Vector Laboratories). Slides were developed with ImmPACT DAB (Vector Laboratories). Primary antibodies used were goat anti-IL-33 (R&D, AF3626) and rat anti-CD8a (Thermo Fisher, 4SM16). Stains were counterstained with hematoxylin using standard methods before dehydrating and mounting.

After fixation, lung lobes and spleen allocated for IF were perfused with 30% sucrose in PBS for cryoprotection for 6-8 h at 4° C. Tissues were then perfused with 30% optimum cutting temperature (O.C.T.) compound (Tissue-Tek) in PBS and frozen in 100% O.C.T in cryomolds on dry ice. 6 µm sections were cut using a CryoStar NX70 cryostat (Thermo), and air-dried for 60-90 minutes at room temperature. Sections were incubated in ice-cold acetone (Sigma) for 10 minutes at −20° C. and then washed 3×5 minutes with PBS. Samples were permeabilized with 0.1% Triton-X-100 (Sigma) in PBS followed by blocking with 0.5% PNB in PBS (Perkin Elmer). Primary antibodies were incubated overnight. Primary antibodies used were rabbit anti-prosurfactant protein C (SPC) (Millipore, AB3786, 1:500) and goat anti-IL-33 (R&D, AF3626, 1:200). After washing 3×5 minutes, samples were incubated in species-specific secondary antibodies conjugated to Alexa Fluor 568 and Alexa Fluor 488, respectively, at 1:500. Sections were then fixed in 1% PFA and mounted using Vectashield mounting media with DAPI (Vector Laboratories).

Immunohistochemistry and immunofluorescence tissue section images were acquired using a Nikon 80 Eclipse 80i fluorescence microscope using 10× and 20× objectives and an attached Andor camera. Stained IHC slides were scanned using the Aperio ScanScope AT2 at 20× magnification.

Bulk RNA-Seq Data Processing

Bulk RNA-Seq reads that passed quality metrics were mapped to the annotated UCSC mm9 mouse genome build (genome.ucsc.edu/) using RSEM (v1.2.12) (deweylab.github.io/RSEM/) (Li and Dewey, 2011) using RSEM's default Bowtie (v1.0.1) alignment program (Langmead et al., 2009). Expected read counts estimated from RSEM were upper-quartile normalized to a count of 1000 per sample (Bullard et al., 2010). Genes with normalized counts less than an upper-quartile threshold of 20 across all samples were considered lowly expressed and excluded from further analyses to increase the robustness of signature scoring, as previously described (Rau et al., 2013; Sha et al., 2015). As outlined below, signature analyses were conducted either on a log 2 transformed version of the filtered gene expression matrix to overcome data skewness, or on the non-transformed version for increased sensitivity by avoiding compression of weaker signals (Ashour et al., 2015; Singh and Shree, 2016).

Signature Analysis in Bulk RNA-Seq

Signature analyses between bulk $T_{reg}$ cell populations were performed using a blind source separation methodology based on Independent Component Analysis (ICA) (Hyvarinen and Oja, 2000), using the R implementation of the core JADE algorithm (Joint Approximate Diagonalization of Eigenmatrices) (Biton et al., 2014; Nordhausen et al., 2014; Rutledge and Jouan-Rimbaud Bouveresse, 2013) along with custom R utilities. Multi-sample signatures were visualized using relative signature profile boxplots (Li et al., 2018). Heatmaps were generated with the Heatplus package in R using agglomerative hierarchical clustering with default euclidean distance measure, Ward's minimum variance method for row-clustering, and complete linkage for column clustering (FIGS. 18D, 20H).

DP $T_{reg}$ Signature

The applicants identified a signature distinguishing $CD103^+KLRG1^+$ lung $T_{regs}$ from other populations. The non-transformed expression matrix was decomposed using ICA with the JADE algorithm (described above) as: E=AS where E is the expression matrix (input), A is the mixing matrix (mixing weights, basis vectors), and S is the signature matrix (independent components or latent variables yielding standardized gene-scores per signature). Biologically relevant signatures were identified through two approaches: (1) Quantitative assessment of significance using a 2-sample Mann-Whitney-Wilcoxon non-parametric test between mixing weights (from A) grouped by biological condition per signature; and (b) visual inspection of a Hinton plot derived from the mixing matrix A. Corresponding signatures from S were selected for downstream analyses. Up and down genes per signature were selected using a |gene-score|>=3 threshold (standardized score, #s.d. above/below mean). Genes with |z-score|>3 were selected for downstream analysis (75 up-regulated and 31 down-regulated genes). An additional expression level filter was implemented to narrow the list of genes of interest. For upregulated genes, expression in all $CD103^+KLRG1^+$ lung $T_{reg}$ samples had to be greater than all but a maximum of 3 other samples (3 out of a total 8 other samples). A similar filtering scheme was employed in the other direction for down-regulated genes. This yielded a total of 43 up-regulated and 2 down-regulated genes in $CD103^+KLRG1^+$ lung $T_{regs}$. This set of genes was used to illustrate gene expression level changes across samples (FIG. 20H).

ST2-Deficient $T_{regs}$ Signature

A signature distinguishing ST2-deficient $T_{regs}$ from wild-type $T_{regs}$ was identified using ICA on the non-transformed expression matrix. To identify particular genes of interest, signature genes (|z-score|>3) were filtered to include only genes that had an absolute fold change exceeding 1.5× within any of the $CD103^+$ $KLRG1^+$ (DP), $CD103^+KLRG1^-$ (SP), $CD103^-KLRG1^-$ (DN) sample types between wild-type and ST2-deficient $T_{regs}$. These gene lists were further filtered to retain only those genes that appeared in at least two of the three sample types (i.e. up/down-regulated in wild-type or ST2-deficient in at least two of DP/DN/SP comparisons). Genes with opposite directionality across the three sample types (n=5 genes) were dropped. Expression levels of the resulting curated set of 14 genes were visualized using a row-normalized heatmap (FIG. 18D).

Gene Set Enrichment Analysis (GSEA)

Selected signatures (from S) were run through the Gene Set Enrichment Analysis (GSEA) using the rank-based input format. All genes per signature were used, ranked by gene-scores from S. We used gene-sets from MsigDB v5.1 (Subramanian et al., 2005). Custom gene set additions were made to version 4.0 of the MSigDB immunologic signatures library (c7). Normalized Enrichment Score (NES), p-values and FDR for the custom gene-sets were calculated in the context of the combined c7 v4.0 MSigDB collection.

Network representations of GSEA results were generated using EnrichmentMap (www.baderlab.org/Software/EnrichmentMap) for Cytoscape v3.3.0 (www.cytoscape.org).

TABLE 4

FACS antibodies and qPCR primers

| Antigen | Clone | Fluorophore | Source | Concentration | RRID |
|---|---|---|---|---|---|
| KLRG1 | 2F1 | PE-Cy7 | Thermo Fisher | 1:800 | AB_1518768 |
| CD103 | 2E7 | APC | BioLegend | 1:400 | AB_1227502 |
| CD4 | RM4-5 | APC-eFluor780 | Thermo Fisher | 1:1000 | AB_1272183 |
| Foxp3 | FJK-16s | FITC | Thermo Fisher | 1:100 | AB_465243 |
| IL-17 | eBiol7B7 | PerCP-Cy5.5 | Thermo Fisher | 1:200 | AB_925753 |
| CD44 | IM7 | Alexa Fluor 700 | Thermo Fisher | 1:200 | AB_494011 |
| CD62L | MEL-14 | eFluor450 | Thermo Fisher | 1:200 | AB_1963590 |
| CCR6 | 29-2L17 | PE/Dazzle 594 | BioLegend | 1:200 | AB_2687019 |
| RORgt | Q31-378 | Alexa Fluor 647 | BD Biosciences | 1:100 | AB_2738916 |
| T-bet | O4-46 | PE | BD Biosciences | 1:25 | AB_10564071 |
| PD-1 | J43 | PE-Cy7 | BioLegend | 1:200 | AB_572017 |
| CD69 | H1.2F3 | BV785 | BioLegend | 1:200 | AB_2629640 |
| CXCR3 | CXCR3-173 | BV421 | BD Biosciences | 1:200 | AB_10900974 |
| ST2 | U29-93 | Brilliant Blue 700 | BD Biosciences | 1:200 | AB_2743483 |
| CD85k | H1.1 | PE | Biolegend | 1:200 | AB_2561653 |
| Ki-67 | B56 | BV786 | BD Biosciences | 1:100 | AB_2732007 |
| CD45.2 | 104 | V500 | BD Biosciences | 1:200 | AB_10897142 |
| Thy1.2 | 30-H12 | APC-eFluor780 | Thermo Fisher | 1:400 | AB_1272187 |
| CD103 | 2E7 | BV510 | BioLegend | 1:200 | AB_2562713 |
| CD4 | RM4-5 | BUV737 | BD Biosciences | 1:200 | AB_2738734 |
| CD8a | 53-6.7 | BUV395 | BD Biosciences | 1:200 | AB_2739421 |
| CD45 | 30-F11 | PE-CF594 | BD Biosciences | i.v. 1:200 | AB_11154401 |
| CD45 | 30-F11 | APC-Ef780 | Thermo Fisher | 1:40 | AB_1548781 |
| CXCR6 | SA051D1 | PE/Dazzle 594 | Biolegend | 1:200 | AB_2721700 |
| KLRG1 | 2F1 | BV711 | BioLegend | 1:200 | AB_2629721 |
| CD11c | HL3 | PE-Cy7 | BD Biosciences | 1:800 | AB_469590 |
| Siglec F | E50-2440 | PE | BD Biosciences | 1:200 | AB_394341 |
| CD4 | RM4-4 | PE | Biolegend | i.v. 1:400 | AB_313691 |
| CD8b | eBioH35-17.2 | PE | Thermo Fisher | i.v. 1:400 | AB_657768 |

Pre-Processing of SMART-Seq2 scRNA-Seq Data

BAM files were converted to de-multiplexed FASTQs using the Illumina-provided Bcl2Fastq software package v2.17.1.14. Paired-end reads were mapped to the UCSC mm10 mouse transcriptome using Bowtie with parameters '-n 0 -m 10', which allows alignment of sequences with zero mismatches and allows for multi-mapping of a maximum of ten times.

Expression levels of genes were quantified using TPM values calculated by RSEM v1.2.8 in paired-end mode. For each cell, the number of detected genes (TPM>0) was calculated and cells with less than 600 or more than 4,000 genes detected were excluded as well as cells that had a mapping rate to the transcriptome below 1500. To further remove potential doublets (mostly of B cells and epithelial cells), we calculated the sum $\log_2(TPM+1)$ over Cd79a, Cd19, Lyz1, Lyz2 and Sftpc, and excluded any cell that scored higher than 3. Applicants retained only genes expressed above $\log_2 TPM$ of 3 in at least five cells in the whole dataset.

Since applicants could not sort for $T_{reg}$ for two of the mice (#336 and #338), we had to infer which cells are $T_{regs}$ from these data. To this end, the applicants trained a random forest classifier for mice for which we have sorted both $T_{conv}$ and $T_{regs}$, using the train function from the caret package in R, based on the expression of the following genes: Foxp3, Ikzf2, Areg, Il1rl1, Folr4, Wls, Tnfrsf9, Klrg1, Il2ra, Dusp4, Ctla4, Neb, Itgb1, and Cd40lg. The labeled data was partitioned into training and test sets. The model has a sensitivity and specificity above 90% in cross validation. The applicants then applied the classifier on the unlabeled data and cells with a probability above 0.6 to be either $T_{conv}$ or $T_{reg}$ were given the corresponding label. The remaining 4% of cells were discarded as unambiguous.

Identifying Tissue-Specific Gene Programs for $T_{reg}$ and $T_{conv}$ Cells

To identify genes that are differentially expressed between lung and msLN in $T_{reg}$ and/or $T_{conv}$ cells, the applicants performed a regression analysis. The applicants focused on the proportion of cells expressing a gene, and hence on logistic regression. The applicants performed logistic regression using the bayesglm function from the arm package in R, including only those mice (#338, #3642, #3839, #3889) for which we had matched cells from both lung and msLN, as well as for $T_{reg}$ and $T_{conv}$, and excluding all genes expressed in >95% or <5% of cells in lung and msLN. The applicants ran the logistic regression with expression data binarized at a $\log_2(TPM+1)$ of 2 and using the following full model: gene expression~genes detected+batch effect+tissue versus a reduced model: gene expression~genes detected+batch effect. The applicants corrected for multiple hypothesis by computing an FDR of the likelihood ratio test p-value, and retained genes as differentially expressed between lung and msLN with $P<10^{-5}$ and an |coefficient|>2.

Comparing the Extent of Cell Heterogeneity Between Lung and msLN

Diffusion components were calculated on a gene expression matrix limited to genes that were differentially expressed between lung and msLN using the Diffusion Map function from the destiny package in R (Angerer et al., 2016) with a k of 30 and a local sigma. In order to be able to compare the variance in distributions in diffusion component 1 and 2 between lung and msLN $T^{reg}/T_{conv}$, the applicants downsampled the cells from the lung to the (lower) numbers of cells from the msLN. To test for significant differences in variance in the distributions of lung and msLN $T_{reg}/T_{conv}$, the applicants used Levene's test for the equality of variances on the distributions of the coefficients of the downsampled cells in each of diffusion components 1 and 2.

Identifying Gene Modules and their Time Dependence

Gene modules were identified using PAGODA using the scde R package version 2.6.0. (Fan et al., 2016) on the counts table from RSEM after cleaning the data using the clean.counts function (min.lib.size=600,min.detected=5). The knn.error.model function was run using a k of 30, which is much lower than default, but yields statistically indistinguishable results from the default k (#cells/4). The applicants then ran the pagoda.varnorm to normalize gene expression variance, and the pagoda.subtract.aspect function to control for sequencing depth which then allowed us to run pagoda.gene.clusters which identifies de-novo correlated genes in the dataset. The applicants forced PAGODA to return 100 modules. The applicants identified modules with a significance z.score above 1.96. The applicants removed several highly significant newly identified gene modules consisting of paralog groups with high expression correlation, likely because of multimapping of reads.

Mean module expression was calculated by averaging over the genes in each module of the centered and scaled gene expression table and transforming to a z-score over 1,000 randomly selected gene sets with matched mean-variance patterns. As an initial step, all genes were binned into 10 bins based on their mean expression across cells, and into 10 (separate) bins based on their variance of expression across cells. Given a gene signature (e.g. list of genes in a module), a cell-specific signature score was computed for each cell as follows: First, 1,000 random gene lists were generated, where each instance of a random gene-list was generated by sampling (with replacement) for each gene in the gene-list a gene that is equivalent to it with respect to the mean and variance bins it was placed in. Then, the sum of gene expression in the given cell was computed for all gene-lists (given the 1,000 random lists generated) and the z-score of the original gene-list for the generated 1,000 sample distribution is returned, as in (Singer et al., 2017).

Another module of highly correlated genes identified by PAGODA showed no biological relevance based on gene annotation, but was associated with cells processed on specific dates, suggested they reflect a contamination or batch effect. The applicants scored each cell for this module with the above described method for scoring cells for gene signatures. When testing for differential gene expression over tumor development (described below), we included this batch effect score as a covariate in the regression analysis to control for genes that are correlated with it.

To test if a module's expression changes over the course of tumor development, the applicants estimated a linear model for each module and compared with a likelihood ratio test a full model: module.activity~detected genes+time point to a reduced model: module.activity~detectedgenes. For the time point covariate, healthy lung was taken as reference. The applicants corrected the likelihood ratio test p-values for multiple hypotheses for the number of modules using the p.adjust function computing the false discovery rate in the stats package.

Dimensionality Reduction Using Diffusion Component Analysis

Diffusion components were calculated on a gene expression matrix limited to genes from modules of interest: modules 1,4,5,14,15 and 21 for $T_{conv}$, and modules 1,3,6,8, 9,12,13,18,21,23 and 26 for $T_{reg}$. Gene expression was scaled for $T_{regs}$ only across all cells. Diffusion components were calculated using the Diffusion Map function from the destiny package in R (Angerer et al., 2016) with a k of 30 and a local sigma. Significant diffusion components identified by the elbow in the eigenvalues were further used for dimensionality reduction to two dimensions. The eigenvectors of the significant diffusion components were imported into gephi 0.9.2 and a force directed layout using forceatlas 2 was run until it converged to get a two-dimensional embedding.

Testing for Differential Gene Expression During Tumor Development

To test whether individual genes change in gene expression over the course of tumor growth, we performed a two-step regression analysis. The applicants focused on the proportion of cells expressing a gene, and hence on logistic regression. The applicants performed logistic regression using the bayesglm function from the arm package in R. Because gender is often confounded with a particular time point in our experiment, the applicants did not include it as a covariate in the model, but did remove all Y chromosome genes from analysis. The applicants also excluded all genes expressed in >95% or <5% of cells in each mouse. The applicants ran the logistic regression with expression data binarized at a log 2(TPM+1) of 2 and using the following full model: gene expression~genes detected+batch effect+weekp.i. (healthy lung as reference) versus a reduced model: gene expression~genes detected+batch effect. The applicants identified a threshold for significance by the elbow method, identifying the peak of the second derivative of the ordered FDR distribution of the likelihood ratio test for each time point. To remove significant genes whose signal was driven by only one mouse, the applicants performed another logistic regression using a mixed effect model, accounting for mouse variability: To this end, the applicants added to the significant genes 1,000 randomly selected genes that were non-significant by the initial test to serve as background genes, and performed a mixed effect logistic regression using the glmer function of the lme4 package in R, with the model gene expression~tmp+(1|mouse), allowing the intercept to vary by mouse. The applicants combined the elbow method above and the background genes to select an FDR cutoff for significance of 0.01. A gene was classified as significantly varying during tumor development if it passed this FDR cutoff in at least one time point.

T Cell Receptor (TCR) Reconstruction and Clonotype Calling

TCR were reconstructed using Tracer (Stubbington et al., 2016), run in short read mode with the following settings '--inchworm_only=T--trinity_kmer_length=17'. To call shared clonotypes between $T_{reg}$ and $T_{conv}$ cells, the applicants required all cells of a clone to have identical productive TCRA and TCRB.

Comparison of Bulk and scRNA-Seq Signatures to Published Signatures

Lists of differentially expressed genes in human cancer $T_{regs}$, mouse tissue $T_{regs}$, Tr17 cells from mice, and mouse activated $T_{regs}$ were collected either from the supplementary tables of the relevant publications, or generously provided by the authors upon request (De Simone et al., 2016; Kim et al., 2017; Miragaia et al., 2017; Plitas et al., 2016; van der Veeken et al., 2016).

ST2 Transcriptional Programs in Human Colorectal Cancer $T_{regs}$

To examine the generalizability of our findings and their relevance to human cancer, we identified gene programs that co-vary with ST2 expression in human colorectal cancer $T_{regs}$ (Zhang et al., 2018). The applicants compared cells in which ST2 was detected (ST2+) and cells in which ST2 was not detected (ST2$^-$) to identify an ST2$^+$ program. Differential expression analysis was performed using t-test on the log-transformed TPM values. The applicants confirmed that the program was not confounded by cell quality and ensured that it captured differences between ST2+ and ST2− cells within each tumor (data not shown). To this end, the applicants first computed the overall expression (OE) of the program across the relevant T cells, in a way that eliminates technical noise, as previously described (Jerby-Amon et al., 2018). The applicants then tested whether the OE of the program was higher in ST2+ cells compared to ST2− by using a mix-effected multilevel (random intercepts) regression model, where the program OE is the dependent variable and ST2 detection is provided as a binary covariate. The model included patient-specific intercepts to control for the dependency between the scRNA-seq profiles of cells from the same tumor, and controlled for cell complexity with a covariate that denotes the number of genes detected in each cell. The model was implemented using the lme4 and lmerTest R packages (CRAN.R-project.org/package=lme4).

Processing and Analysis of Droplet-Based scRNA-Seq

De-multiplexing, alignment to the mm10 transcriptome and unique molecular identifier (UMI)-collapsing were performed using the Cellranger toolkit from 10× Genomics version 1.1.0. For each cell, we quantified the number of genes for which at least one read was mapped, and then excluded all cells with fewer than 500 detected genes. Genes that were detected in less than 3 cells were excluded. Expression values $E_{i,j}$ for gene i in cell j were calculated by dividing UMI counts for gene i by the sum of the UMI counts in cell j, to normalize for differences in coverage, and then multiplying by 10,000 to create TPM-like values (TP10K), and finally computing $\log_2(TP10K+1)$.

Selection of variable genes was performed by fitting a logistic regression to the cellular detection fraction (often referred to as a), using the total number of UMIs per gene as a predictor (Montoro et al., 2018). Outliers from this curve are genes that are expressed in a lower fraction of cells than would be expected given the total number of UMIs mapping to that gene, that is, likely cell-type or state-specific genes. We used a threshold of deviance of <−0.15 and a minimum of 100 total UMIs. The applicants restricted the expression matrix to this subset of variable genes and values were centered and scaled and capped at a z-score of 10.

The applicants restricted the expression matrix to the subsets of variable genes and high-quality cells noted above, and then centered and scaled values before inputting them into principal component analysis (PCA), implemented using 'RunPCA' in Seurat which runs the irlba function. After PCA, significant principal components were identified using the elbow-method when looking at the distribution of singular values. Scores from only those significant principal components were used as the input to further analysis. For visualization purposes, the dimensionality of the datasets was further reduced to 2D embeddings using the RunUMAP( ) function on the first 14 PCs and clusters were identified using the FindNeighborso and FindClusterso functions of the Seurat package in R. Clusters were post-hoc merged to six major cell populations using canonical markers for all cell types detected.

Population-Level TCR Beta Chain Sequencing and Analysis
Analysis of IHC Images

QuPath software was used to annotate tumor and lobe areas (Bankhead et al., 2017). CD8-stained images were standardized to a common set of stain vector parameters. CD8+cell detection was performed using the PositiveCell-Detection plugin with the following parameters:

runPlugin('qupath.imagej.detect.nuclei.PositiveCellDetection', '{"detectionImage Brightfield": "Optical density sum", "requestedPixelSizeMicrons":0.5, "backgroundRadiusMicrons":8.0, "medianRadiusMicrons":0.0, "sigmaMicrons":1.5, "minAreaMicrons":7.0, "maxAreaMicrons": 125.0, "threshold":0.3, "maxBackground":2.0, "watershedPostProcess": true, "excludeDAB": false, "cellExpansionMicrons": 2.0, "includeNuclei": false, "smoothBoundaries": false, "makeMeasurements": true, "thresholdCompartment": "Cytoplasm: DAB OD max", "thresholdPositive1": 0.7, "thresholdPositive2": 0.4, "thresholdPositive3": 0.6, "singleThreshold": true}'). Scored cells were normalized to tumor area.

Additional statistical analyses: Unpaired, two-tailed Student's t tests, Mann-Whitney tests, Tukey's multiple comparisons tests, and Sidak's multiple comparisons tests were used for all statistical comparisons using GraphPad Prism software.

REFERENCES

Akama-Garren, E. H., Joshi, N. S., Tammela, T., Chang, G. P., Wagner, B. L., Lee, D.-Y., Rideout, W. M., 3rd, Papagiannakopoulos, T., Xue, W., and Jacks, T. (2016). A Modular Assembly Platform for Rapid Generation of DNA Constructs. Sci. Rep. 6, 16836.

Anderson, K. G., Sung, H., Skon, C. N., Lefrancois, L., Deisinger, A., Vezys, V., and Masopust, D. (2012). Cutting edge: intravascular staining redefines lung CD8 T cell responses. J. Immunol. 189, 2702-2706.

Angerer, P., Haghverdi, L., Buttner, M., Theis, F. J., Marr, C., and Buettner, F. (2016). destiny: diffusion maps for large-scale single-cell data in R. Bioinformatics 32, 1241-1243.

Arpaia, N., Green, J. A., Moltedo, B., Arvey, A., Hemmers, S., Yuan, S., Treuting, P. M., and Rudensky, A. Y. (2015). A Distinct Function of Regulatory T Cells in Tissue Protection. Cell 162, 1078-1089.

Bankhead, P., Loughrey, M. B., Fernandez, J. A., Dombrowski, Y., McArt, D. G., Dunne, P. D., McQuaid, S., Gray, R. T., Murray, L. J., Coleman, H. G., et al. (2017). QuPath: Open source software for digital pathology image analysis. Sci. Rep. 7, 16878.

Bettelli, E., Carrier, Y., Gao, W., Korn, T., Strom, T. B., Oukka, M., Weiner, H. L., and Kuchroo, V. K. (2006). Reciprocal developmental pathways for the generation of pathogenic effector TH17 and regulatory T cells. Nature 441, 235-238.

Beyersdorf, N., Ding, X., Tietze, J. K., and Hanke, T. (2007). Characterization of mouse CD4 T cell subsets defined by expression of KLRG1. Eur. J. Immunol. 37, 3445-3454.

Biton, A., Bernard-Pierrot, I., Lou, Y., Krucker, C., Chapeaublanc, E., Rubio-Perez, C., López-Bigas, N., Kamoun, A., Neuzillet, Y., Gestraud, P., et al. (2014). Independent component analysis uncovers the landscape of the bladder tumor transcriptome and reveals insights into luminal and basal subtypes. Cell Rep. 9, 1235-1245.

Bos, P. D., Plitas, G., Rudra, D., Lee, S. Y., and Rudensky, A. Y. (2013). Transient regulatory T cell ablation deters oncogene-driven breast cancer and enhances radiotherapy. J. Exp. Med. 210, 2435-2466.

Bullard, J. H., Purdom, E., Hansen, K. D., and Dudoit, S. (2010). Evaluation of statistical methods for normalization and differential expression in mRNA-Seq experiments. BMC Bioinformatics 11, 94.

Burzyn, D., Kuswanto, W., Kolodin, D., Shadrach, J. L., Cerletti, M., Jang, Y., Sefik, E., Tan, T. G., Wagers, A. J., Benoist, C., et al. (2013). A special population of regulatory T cells potentiates muscle repair. Cell 155, 1282-1295.

Campbell, D. J. (2015). Control of Regulatory T Cell Migration, Function, and Homeostasis. J. Immunol. 195, 2507-2513.

Caridade, M., Graca, L., and Ribeiro, R. M. (2013). Mechanisms Underlying CD4+ Treg Immune Regulation in the Adult: From Experiments to Models. Front. Immunol. 4, 378.

Cayrol, C., and Girard, J.-P. (2014). IL-33: an alarmin cytokine with crucial roles in innate immunity, inflammation and allergy. Curr. Opin. Immunol. 31, 31-37.

Chen, W.-Y., Hong, J., Gannon, J., Kakkar, R., and Lee, R. T. (2015). Myocardial pressure overload induces systemic inflammation through endothelial cell IL-33. Proc. Natl. Acad. Sci. U.S.A. 112, 7249-7254.

Cheng, G., Yuan, X., Tsai, M. S., Podack, E. R., Yu, A., and Malek, T. R. (2012). IL-2 receptor signaling is essential for the development of Klrg1+ terminally differentiated T regulatory cells. J. Immunol. 189, 1780-1791.

Cipolletta, D., Feuerer, M., Li, A., Kamei, N., Lee, J., Shoelson, S. E., Benoist, C., and Mathis, D. (2012). PPAR-γ is a major driver of the accumulation and phenotype of adipose tissue Treg cells. Nature 486, 549-553.

Der, S. D., Zhou, A., Williams, B. R., and Silverman, R. H. (1998). Identification of genes differentially regulated by interferon alpha, beta, or gamma using oligonucleotide arrays. Proc. Natl. Acad. Sci. U.S.A 95, 15623-15628.

De Simone, M., Arrigoni, A., Rossetti, G., Gruarin, P., Ranzani, V., Politano, C., Bonnal, R. J. P., Provasi, E., Sarnicola, M. L., Panzeri, I., et al. (2016). Transcriptional Landscape of Human Tissue Lymphocytes Unveils Uniqueness of Tumor-Infiltrating T Regulatory Cells. Immunity 45, 1135-1147.

Dranoff, G. (2011). Experimental mouse tumour models: what can be learnt about human cancer immunology? Nat. Rev. Immunol. 12, 61-66.

DuPage, M., Dooley, A. L., and Jacks, T. (2009). Conditional mouse lung cancer models using adenoviral or lentiviral delivery of Cre recombinase. Nat. Protoc. 4, 1064-1072.

DuPage, M., Cheung, A. F., Mazumdar, C., Winslow, M. M., Bronson, R., Schmidt, L. M., Crowley, D., Chen, J., and Jacks, T. (2011). Endogenous T cell responses to antigens expressed in lung adenocarcinomas delay malignant tumor progression. Cancer Cell 19, 72-85.

Engel, I., Seumois, G., Chavez, L., Samaniego-Castruita, D., White, B., Chawla, A., Mock, D., Vijayanand, P., and Kronenberg, M. (2016). Innate-like functions of natural killer T cell subsets result from highly divergent gene programs. Nat. Immunol. 17, 728-739.

Fan, J., Salathia, N., Liu, R., Kaeser, G. E., Yung, Y. C., Herman, J. L., Kaper, F., Fan, J.-B., Zhang, K., Chun, J., et al. (2016). Characterizing transcriptional heterogeneity through pathway and gene set overdispersion analysis. Nat. Methods 13, 241-244.

Feuerer, M., Herrero, L., Cipolletta, D., Naaz, A., Wong, J., Nayer, A., Lee, J., Goldfine, A. B., Benoist, C., Shoelson, S., et al. (2009). Lean, but not obese, fat is enriched for a unique population of regulatory T cells that affect metabolic parameters. Nat. Med. 15, 930-939.

Fridman, W. H., Pages, F., Sautes-Fridman, C., and Galon, J. (2012). The immune contexture in human tumours: impact on clinical outcome. Nat. Rev. Cancer 12, 298-306.

Gibson, D. G., Young, L., Chuang, R.-Y., Venter, J. C., Hutchison, C. A., 3rd, and Smith, H. O. (2009). Enzymatic assembly of DNA molecules up to several hundred kilobases. Nat. Methods 6, 343-345.

Green, J. A., Arpaia, N., Schizas, M., Dobrin, A., and Rudensky, A. Y. (2017). A nonimmune function of T cells in promoting lung tumor progression. J. Exp. Med. 214, 3565-3575.

Guo, X., Zhang, Y., Zheng, L., Zheng, C., Song, J., Zhang, Q., Kang, B., Liu, Z., Jin, L., Xing, R., et al. (2018). Global characterization of T cells in non-small-cell lung cancer by single-cell sequencing. Nat. Med. 24, 978-985.

Halim, L., Romano, M., McGregor, R., Correa, I., Pavlidis, P., Grageda, N., Hoong, S.-J., Yuksel, M., Jassem, W., Hannen, R. F., et al. (2017). An Atlas of Human Regulatory T Helper-like Cells Reveals Features of Th2-like Tregs that Support a Tumorigenic Environment. Cell Rep. 20, 757-770.

Hall, A. O., Beiting, D. P., Tato, C., John, B., Oldenhove, G., Lombana, C. G., Pritchard, G. H., Silver, J. S., Bouladoux, N., Stumhofer, J. S., et al. (2012). The cytokines interleukin 27 and interferon-γ promote distinct Treg cell populations required to limit infection-induced pathology. Immunity 37, 511-523.

Huehn, J., Siegmund, K., Lehmann, J. C. U., Siewert, C., Haubold, U., Feuerer, M., Debes, G. F., Lauber, J., Frey, O., Przybylski, G. K., et al. (2004). Developmental stage, phenotype, and migration distinguish naive- and effector/memory-like CD4+regulatory T cells. J. Exp. Med. 199, 303-313.

Hyvärinen, A., and Oja, E. (2000). Independent component analysis: algorithms and applications. Neural Netw. 13, 411-430.

Jackson, E. L., Olive, K. P., Tuveson, D. A., Bronson, R., Crowley, D., Brown, M., and Jacks, T. (2005). The differential effects of mutant p53 alleles on advanced murine lung cancer. Cancer Res. 65, 10280-10288.

Johdi, N. A., Ait-Tahar, K., Sagap, I., and Jamal, R. (2017). Molecular Signatures of Human Regulatory T Cells in Colorectal Cancer and Polyps. Front. Immunol. 8, 620.

Josefowicz, S. Z., Lu, L.-F., and Rudensky, A. Y. (2012). Regulatory T cells: mechanisms of differentiation and function. Annu. Rev. Immunol. 30, 531-564.

Joshi, N. S., Akama-Garren, E. H., Lu, Y., Lee, D.-Y., Chang, G. P., Li, A., DuPage, M., Tammela, T., Kerper, N. R., Farago, A. F., et al. (2015). Regulatory T Cells in Tumor-Associated Tertiary Lymphoid Structures Suppress Anti-tumor T Cell Responses. Immunity 43, 579-590.

Jovanovic, I. P., Pejnovic, N. N., Radosavljevic, G. D., Pantic, J. M., Milovanovic, M. Z., Arsenijevic, N. N., and Lukic, M. L. (2014). Interleukin-33/ST2 axis promotes breast cancer growth and metastases by facilitating intratumoral accumulation of immunosuppressive and innate lymphoid cells. Int. J. Cancer 134, 1669-1682.

Kim, B.-S., Lu, H., Ichiyama, K., Chen, X., Zhang, Y.-B., Mistry, N. A., Tanaka, K., Lee, Y.-H., Nurieva, R., Zhang, L., et al. (2017). Generation of RORγt+ Antigen-Specific T Regulatory 17 Cells from Foxp3+Precursors in Autoimmunity. Cell Rep. 21, 195-207.

Kim, J. M., Rasmussen, J. P., and Rudensky, A. Y. (2007). Regulatory T cells prevent catastrophic autoimmunity throughout the lifespan of mice. Nat. Immunol. 8, 191-197.

Koch, M. A., Tucker-Heard, G.'s, Perdue, N. R., Killebrew, J. R., Urdahl, K. B., and Campbell, D. J. (2009). The transcription factor T-bet controls regulatory T cell homeostasis and function during type 1 inflammation. Nat. Immunol. 10, 595-602.

Koch, M. A., Thomas, K. R., Perdue, N. R., Smigiel, K. S., Srivastava, S., and Campbell, D. J. (2012). T-bet(+) Treg cells undergo abortive Th1 cell differentiation due to impaired expression of IL-12 receptor β2. Immunity 37, 501-510.

Kohlmeier, J. E., Cookenham, T., Miller, S. C., Roberts, A. D., Christensen, J. P., Thomsen, A. R., and Woodland, D. L. (2009). CXCR3 directs antigen-specific effector CD4+ T cell migration to the lung during parainfluenza virus infection. J. Immunol. 183, 4378-4384.

Kolodin, D., van Panhuys, N., Li, C., Magnuson, A. M., Cipolletta, D., Miller, C. M., Wagers, A., Germain, R. N., Benoist, C., and Mathis, D. (2015). Antigen- and cytokine-driven accumulation of regulatory T cells in visceral adipose tissue of lean mice. Cell Metab. 21, 543-557.

Kondo, Y., Yoshimoto, T., Yasuda, K., Futatsugi-Yumikura, S., Morimoto, M., Hayashi, N., Hoshino, T., Fujimoto, J., and Nakanishi, K. (2008). Administration of IL-33 induces airway hyperresponsiveness and goblet cell hyperplasia in the lungs in the absence of adaptive immune system. Int. Immunol. 20, 791-800.

Kuswanto, W., Burzyn, D., Panduro, M., Wang, K. K., Jang, Y. C., Wagers, A. J., Benoist, C., and Mathis, D., (2016). Poor Repair of Skeletal Muscle in Aging Mice Reflects a Defect in Local, Interleukin-33-Dependent Accumulation of Regulatory T Cells. Immunity 44, 355-367.

Langmead, B., Trapnell, C., Pop, M., and Salzberg, S. L. (2009). Ultrafast and memory-efficient alignment of short DNA sequences to the human genome. Genome Biol. 10, R25.

Lee, Y., Awasthi, A., Yosef, N., Quintana, F. J., Xiao, S., Peters, A., Wu, C., Kleinewietfeld, M., Kunder, S., Hafler, D. A., et al. (2012). Induction and molecular signature of pathogenic TH17 cells. Nat. Immunol. 13, 991-999.

Lee, Y. K., Turner, H., Maynard, C. L., Oliver, J. R., Chen, D., Elson, C. O., and Weaver, C. T. (2009). Late developmental plasticity in the T helper 17 lineage. Immunity 30, 92-107.

Lehmann, J., Huehn, J., de la Rosa, M., Maszyna, F., Kretschmer, U., Krenn, V., Brunner, M., Scheffold, A., and Hamann, A. (2002). Expression of the integrin alpha Ebeta 7 identifies unique subsets of CD25+ as well as CD25− regulatory T cells. Proc. Natl. Acad. Sci. U.S.A 99, 13031-13036.

Levine, A. G., Mendoza, A., Hemmers, S., Moltedo, B., Niec, R. E., Schizas, M., Hoyos, B. E., Putintseva, E. V., Chaudhry, A., Dikiy, S., et al. (2017). Stability and function of regulatory T cells expressing the transcription factor T-bet. Nature 546, 421-425.

Li, B., and Dewey, C. N. (2011). RSEM: accurate transcript quantification from RNA-Seq data with or without a reference genome. BMC Bioinformatics 12, 323.

Li, M. O., and Rudensky, A. Y. (2016). T cell receptor signalling in the control of regulatory T cell differentiation and function. Nat. Rev. Immunol. 16, 220-233.

Li, D., Guabiraba, R., Besnard, A.-G., Komai-Koma, M., Jabir, M. S., Zhang, L., Graham, G. J., Kurowska-Stolarska, M., Liew, F. Y., McSharry, C., et al. (2014). IL-33 promotes ST2-dependent lung fibrosis by the induction of alternatively activated macrophages and innate lymphoid cells in mice. J. Allergy Clin. Immunol. 134, 1422-1432.e11.

Li, L., Zeng, Q., Bhutkar, A., Galvin, J. A., Karamitopoulou, E., Noordermeer, D., Peng, M.-W., Piersigilli, A., Perren, A., Zlobec, I., et al. (2018). GKAP Acts as a Genetic Modulator of NMDAR Signaling to Govern Invasive Tumor Growth. Cancer Cell 33, 736-751.e5.

Magnuson, A. M., Kiner, E., Ergun, A., Park, J. S., Asinovski, N., Ortiz-Lopez, A., Kilcoyne, A., Paoluzzi-Tomada, E., Weissleder, R., Mathis, D., et al. (2018). Identification and validation of a tumor-infiltrating Treg transcriptional signature conserved across species and tumor types. Proc. Natl. Acad. Sci. U.S.A Makkouk, A., and Weiner, G. J. (2015). Cancer immunotherapy and breaking immune tolerance: new approaches to an old challenge. Cancer Res. 75, 5-10.

Marabelle, A., Kohrt, H., Sagiv-Barfi, I., Ajami, B., Axtell, R. C., Zhou, G., Rajapaksa, R., Green, M. R., Torchia, J., Brody, J., et al. (2013). Depleting tumor-specific Tregs at a single site eradicates disseminated tumors. J. Clin. Invest. 123, 2447-2463.

Miragaia, R. J., Gomes, T., Chomka, A., Jardine, L., Riedel, A., Hegazy, A. N., Lindeman, I., Emerton, G., Krausgruber, T., Shields, J., et al. (2017). Single cell transcriptomics of regulatory T cells reveals trajectories of tissue adaptation. bioRxiv 217489.

Nordhausen, K., Cardoso, J. F., Miettinen, J., Oja, H., Ollila, E., and Taskinen, S. (2014). JADE: JADE and other BSS methods as well as some BSS performance criteria. R Package Version 1-9.

Overacre-Delgoffe, A. E., Chikina, M., Dadey, R. E., Yano, H., Brunazzi, E. A., Shayan, G., Horne, W., Moskovitz, J. M., Kolls, J. K., Sander, C., et al. (2017). Interferon-γ Drives Treg Fragility to Promote Anti-tumor Immunity. Cell 169, 1130-1141.e11.

Petersen, R. P., Campa, M. J., Sperlazza, J., Conlon, D., Joshi, M.-B., Harpole, D. H., Jr, and Patz, E. F., Jr (2006). Tumor infiltrating Foxp3+regulatory T-cells are associated with recurrence in pathologic stage I NSCLC patients. Cancer 107, 2866-2872.

Picelli, S., Bjorklund, A. K., Faridani, O. R., Sagasser, S., Winberg, G., and Sandberg, R. (2013). Smart-seq2 for sensitive full-length transcriptome profiling in single cells. Nat. Methods 10, 1096-1098.

Plitas, G., Konopacki, C., Wu, K., Bos, P. D., Morrow, M., Putintseva, E. V., Chudakov, D. M., and Rudensky, A. Y. (2016). Regulatory T Cells Exhibit Distinct Features in Human Breast Cancer. Immunity 45, 1122-1134.

Redjimi, N., Raffin, C., Raimbaud, I., Pignon, P., Matsuzaki, J., Odunsi, K., Valmori, D., and Ayyoub, M. (2012). CXCR3+ T regulatory cells selectively accumulate in human ovarian carcinomas to limit type I immunity. Cancer Res. 72, 4351-4360.

Rutledge, D. N., and Jouan-Rimbaud Bouveresse, D. (2013). Independent Components Analysis with the JADE algorithm. Trends Analyt. Chem. 50, 22-32.

Saito, T., Nishikawa, H., Wada, H., Nagano, Y., Sugiyama, D., Atarashi, K., Maeda, Y., Hamaguchi, M., Ohkura, N., Sato, E., et al. (2016). Two FOXP3(+)CD4(+) T cell subpopulations distinctly control the prognosis of colorectal cancers. Nat. Med. 22, 679-684.

Sakaguchi, S. (2011). Regulatory T cells: history and perspective. Methods Mol. Biol. 707, 3-17.

Sánchez-Rivera, F. J., Papagiannakopoulos, T., Romero, R., Tammela, T., Bauer, M. R., Bhutkar, A., Joshi, N. S., Subbaraj, L., Bronson, R. T., Xue, W., et al. (2014). Rapid modelling of cooperating genetic events in cancer through somatic genome editing. Nature 516, 428-431.

Sather, B. D., Treuting, P., Perdue, N., Miazgowicz, M., Fontenot, J. D., Rudensky, A. Y., and Campbell, D. J. (2007). Altering the distribution of Foxp3(+) regulatory T cells results in tissue-specific inflammatory disease. J. Exp. Med. 204, 1335-1347.

Savage, P. A., Malchow, S., and Leventhal, D. S. (2013). Basic principles of tumor-associated regulatory T cell biology. Trends Immunol. 34, 33-40.

Schiering, C., Krausgruber, T., Chomka, A., Frohlich, A., Adelmann, K., Wohlfert, E. A., Pott, J., Griseri, T., Bollrath, J., Hegazy, A. N., et al. (2014). The alarmin IL-33 promotes regulatory T-cell function in the intestine. Nature 513, 564-568.

Schmitz, J., Owyang, A., Oldham, E., Song, Y., Murphy, E., McClanahan, T. K., Zurawski, G., Moshrefi, M., Qin, J., Li, X., et al. (2005). IL-33, an interleukin-1-like cytokine that signals via the IL-1 receptor-related protein ST2 and induces T helper type 2-associated cytokines. Immunity 23, 479-490.

Shalek, A. K., Satija, R., Adiconis, X., Gertner, R. S., Gaublomme, J. T., Raychowdhury, R., Schwartz, S., Yosef, N., Malboeuf, C., Lu, D., et al. (2013). Single-cell transcriptomics reveals bimodality in expression and splicing in immune cells. Nature 498, 236-240.

Shang, B., Liu, Y., Jiang, S.-J., and Liu, Y. (2015). Prognostic value of tumor-infiltrating FoxP3$^+$ regulatory T cells in cancers: a systematic review and meta-analysis. Sci. Rep. 5, 15179.

Shimizu, K., Nakata, M., Hirami, Y., Yukawa, T., Maeda, A., and Tanemoto, K. (2010). Tumor-infiltrating Foxp3+ regulatory T cells are correlated with cyclooxygenase-2 expression and are associated with recurrence in resected non-small cell lung cancer. J. Thorac. Oncol. 5, 585-590.

Shugay, M., Bagaev, D. V., Turchaninova, M. A., Bolotin, D. A., Britanova, O. V., Putintseva, E. V., Pogorelyy, M. V., Nazarov, V. I., Zvyagin, I. V., Kirgizova, V. I., et al. (2015). VDJtools: Unifying Post-analysis of T Cell Receptor Repertoires. PLoS Comput. Biol. 11, e1004503.

Simpson, T. R., Li, F., Montalvo-Ortiz, W., Sepulveda, M. A., Bergerhoff, K., Arce, F., Roddie, C., Henry, J. Y., Yagita, H., Wolchok, J. D., et al. (2013). Fc-dependent depletion of tumor-infiltrating regulatory T cells co-defines the efficacy of anti-CTLA-4 therapy against melanoma. J. Exp. Med. 210, 1695-1710.

Singer, M., Wang, C., Cong, L., Marjanovic, N. D., Kowalczyk, M. S., Zhang, H., Nyman, J., Sakuishi, K., Kurtulus, S., Gennert, D., et al. (2017). A Distinct Gene Module for Dysfunction Uncoupled from Activation in Tumor-Infiltrating T Cells. Cell 171, 1221-1223.

Soria, J.-C., Marabelle, A., Brahmer, J. R., and Gettinger, S. (2015). Immune Checkpoint Modulation for Non-Small Cell Lung Cancer. Clin. Cancer Res. 21, 2256-2262.

Stubbington, M. J. T., Lonnberg, T., Proserpio, V., Clare, S., Speak, A. O., Dougan, G., and Teichmann, S. A. (2016). T cell fate and clonality inference from single-cell transcriptomes. Nat. Methods 13, 329-332.

Subramanian, A., Tamayo, P., Mootha, V. K., Mukherjee, S., Ebert, B. L., Gillette, M. A., Paulovich, A., Pomeroy, S. L., Golub, T. R., Lander, E. S., et al. (2005). Gene set enrichment analysis: a knowledge-based approach for interpreting genome-wide expression profiles. Proc. Natl. Acad. Sci. U.S.A 102, 15545-15550.

Suzuki, K., Kadota, K., Sima, C. S., Nitadori, J.-I., Rusch, V. W., Travis, W. D., Sadelain, M., and Adusumilli, P. S. (2013). Clinical impact of immune microenvironment in stage I lung adenocarcinoma: tumor interleukin-12 receptor β2 (IL-12Rβ2), IL-7R, and stromal FoxP3/CD3 ratio are independent predictors of recurrence. J. Clin. Oncol. 31, 490-498.

Tanaka, A., and Sakaguchi, S. (2017). Regulatory T cells in cancer immunotherapy. Cell Res. 27, 109-118.

Townsend, M. J., Fallon, P. G., Matthews, D. J., John, H. E., and McKenzie, A. N. (2000). T1/ST2-deficient mice demonstrate the importance of T1/ST2 in developing primary T helper cell type 2 responses. J. Exp. Med. 191, 1069-1076.

Vasanthakumar, A., Moro, K., Xin, A., Liao, Y., Gloury, R., Kawamoto, S., Fagarasan, S., Mielke, L. A., Afshar-Sterle, S., Masters, S. L., et al. (2015). The transcriptional regulators IRF4, BATF and IL-33 orchestrate development and maintenance of adipose tissue-resident regulatory T cells. Nat. Immunol. 16, 276-285.

van der Veeken, J., Gonzalez, A. J., Cho, H., Arvey, A., Hemmers, S., Leslie, C. S., and Rudensky, A. Y. (2016). Memory of Inflammation in Regulatory T Cells. Cell 166, 977-990.

Végran, F., Apetoh, L., and Ghiringhelli, F. (2015). Th9 cells: a novel CD4 T-cell subset in the immune war against cancer. Cancer Res. 75, 475-479.

Vignali, D. A. A., Collison, L. W., and Workman, C. J. (2008). How regulatory T cells work. Nat. Rev. Immunol. 8, 523-532.

Walker, J. A., and McKenzie, A. N. J. (2018). TH2 cell development and function. Nat. Rev. Immunol. 18, 121-133.

Wan, Y. Y., and Flavell, R. A. (2005). Identifying Foxp3-expressing suppressor T cells with a bicistronic reporter. Proc. Natl. Acad. Sci. U.S.A 102, 5126-5131.

Wang, C., Chen, Z., Bu, X., Han, Y., Shan, S., Ren, T., and Song, W. (2016). IL-33 signaling fuels outgrowth and metastasis of human lung cancer. Biochem. Biophys. Res. Commun. 479, 461-468.

Wang, K., Shan, S., Yang, Z., Gu, X., Wang, Y., Wang, C., and Ren, T. (2017). IL-33 blockade suppresses tumor growth of human lung cancer through direct and indirect pathways in a preclinical model. Oncotarget 8, 68571-68582.

Wang, Y., Godec, J., Ben-Aissa, K., Cui, K., Zhao, K., Pucsek, A. B., Lee, Y. K., Weaver, C. T., Yagi, R., and Lazarevic, V. (2014). The transcription factors T-bet and Runx are required for the ontogeny of pathogenic interferon-γ-producing T helper 17 cells. Immunity 40, 355-366.

Yamazaki, T., Yang, X. O., Chung, Y., Fukunaga, A., Nurieva, R., Pappu, B., Martin-Orozco, N., Kang, H. S., Ma, L., Panopoulos, A. D., et al. (2008). CCR6 regulates the migration of inflammatory and regulatory T cells. J. Immunol. 181, 8391-8401.

Young, N. P., Crowley, D., and Jacks, T. (2011). Uncoupling cancer mutations reveals critical timing of p53 loss in sarcomagenesis. Cancer Res. 71, 4040-4047.

Zheng, C., Zheng, L., Yoo, J.-K., Guo, H., Zhang, Y., Guo, X., Kang, B., Hu, R., Huang, J. Y., Zhang, Q., et al. (2017). Landscape of Infiltrating T Cells in Liver Cancer Revealed by Single-Cell Sequencing. Cell 169, 1342-1356.e16.

Various modifications and variations of the described methods, pharmaceutical compositions, and kits of the invention will be apparent to those skilled in the art without departing from the scope and spirit of the invention. Although the invention has been described in connection with specific embodiments, it will be understood that it is capable of further modifications and that the invention as claimed should not be unduly limited to such specific embodiments. Indeed, various modifications of the described modes for carrying out the invention that are obvious to those skilled in the art are intended to be within the scope of the invention. This application is intended to cover any variations, uses, or adaptations of the invention following, in general, the principles of the invention and

What is claimed is:

1. A population of T cells obtained by a method comprising shifting T cell balance in a population of $T_{reg}$ cells comprising contacting ex vivo a population of CD103$^+$ KLRG1$^+$ (double-positive, DP) $T_{reg}$ cells with one or more agents capable of reducing or inhibiting or ablating ST2 and/or IL-33 signaling.

2. The population of T cells of claim 1, wherein the one or more agents for reducing or inhibiting or ablating ST2 and/or IL-33 signaling in $T_{reg}$ cells comprise pharmacological inhibitors and/or genetic ablation of ST2, optionally, wherein the one or more agents comprise a small molecule, genetic modifying agent, antibody, antibody fragment, antibody-like protein scaffold, aptamer, protein, and any combination thereof.

3. The population of T cells of claim 2, wherein the one or more agents are antibody or antibody fragments that bind to ST2 or IL-33 and block ST2/IL-33 signaling; or
   wherein the one or more agents are antibody or antibody fragments thereof that bind to ST2 and induce antibody-dependent cell-mediated cytotoxicity (ADCC) of $T_{reg}$ cells; or
   wherein the genetic modifying agent comprises CRISPR system, RNAi system, zing finger nuclease, TALEN system, meganuclease, or any combination thereof.

4. The population of T cells of claim 3, wherein the CRISPR system comprises Cas9, Cas12, Cas13, or other Cas enzymes; and/or
   wherein the CRISPR system comprises a Cas nickase (nCas) or catalytically inactive Cas (dCas) fused or otherwise linked to a nucleotide deaminase, optionally, wherein the nucleotide deaminase is a cytidine deaminase or an adenosine deaminase; and/or
   wherein the genetic modifying agent reduces ST2 expression and/or edits post-translation modification sites that result in reduced expression, reduced trafficking to cell surface, or increased degradation of ST2.

5. The population of T cells of claim 1, wherein the population of cells is isolated from a subject at risk for or suffering from a disease or condition characterized by an aberrant immune response, or from a healthy donor subject, optionally, wherein the disease or condition is a tumor or cancer.

6. The population of T cells of claim 1, wherein the one or more agents comprise a soluble ST2 molecule; and/or
   wherein the one of more agents comprise an antibody or antibody fragment thereof capable of binding to IL33.

7. An isolated $T_{reg}$ cell genetically modified to ablate IL1RL1, wherein the $T_{reg}$ cell is a CD103$^+$ KLRG1$^+$ (double-positive, DP) Treg cell.

8. The isolated $T_{reg}$ cell of claim 7, wherein the isolated $T_{reg}$ cell is an ex vivo cell isolated from a healthy donor subject or from a subject at risk for or suffering from a disease or condition characterized by an aberrant immune response, optionally, wherein the disease or condition is a tumor or cancer.

* * * * *

UNITED STATES PATENT AND TRADEMARK OFFICE
CERTIFICATE OF CORRECTION

Page 1 of 4

PATENT NO. : 11,739,156 B2
APPLICATION NO. : 16/735187
DATED : August 29, 2023
INVENTOR(S) : Amy Li et al.

It is certified that error appears in the above-identified patent and that said Letters Patent is hereby corrected as shown below:

On the Title Page

On the page 3, in Column 2, item (56) under "Other Publications", Line 53, delete "Man Der" and insert -- Van Der --.

In the Specification

In Column 3, Line 39, delete "SAMSN," and insert -- SAMSN1, --.

In Column 6, Line 52, delete "rTL-33" and insert -- rIL-33 --.

In Column 7, Line 4, delete "rTL-33" and insert -- rIL-33 --.

In Column 7, Line 12, delete "rTL-33" and insert -- rIL-33 --.

In Column 10, Line 45, delete "Tconv." and insert -- $T_{conv.}$ --.

In Column 10, Line 47, delete "Tconv." and insert -- $T_{conv.}$ --.

In Column 11, Line 21, delete "$T_{reg}$ s." and insert -- $T_{regs.}$ --.

In Column 11, Line 23, delete "CD103+KLRG1+" and insert -- $CD103^{+}KLRG1^{+}$ --.

In Column 11, Line 46, delete "("Il1rl1Il1rl1$^{fl/fl}$")" and insert -- ("Il1rl1$^{fl/fl}$") --.

In Column 12, Line 15, delete "Foxp3$^{YFP\text{-}Cre}$" and insert -- Foxp3$^{YFP\text{-}Cre}$, --.

In Column 14, Line 3, delete "CD103+KLRG1+" and insert -- $CD103^{+}KLRG1^{+}$ --.

Signed and Sealed this
Fifth Day of March, 2024

Katherine Kelly Vidal
*Director of the United States Patent and Trademark Office*

CERTIFICATE OF CORRECTION (continued)
U.S. Pat. No. 11,739,156 B2

In Column 14, Line 5, delete "201." and insert -- 20I. --.

In Column 14, Line 42, delete "log 2(fold" and insert -- log$_2$(fold --.

In Column 15, Line 12, delete "Il1r1$^{fl/fl}$" and insert -- Il1rl1$^{fl/fl}$ --.

In Column 15, Line 46, delete "log 2(fold" and insert -- log$_2$(fold --.

In Column 19, Line 46, delete "oncology." and insert -- oncology: --.

In Column 20, Line 4, delete "254rai28;" and insert -- 254ra128; --.

In Column 20, Line 7, delete "oncology." and insert -- oncology: --.

In Column 25, Lines 19-20, delete "nar.oxfordjoumals.org/" and insert -- nar.oxfordjournals.org/ --.

In Column 34, Line 12, delete "(40HT)" and insert -- (4OHT) --.

In Column 40, Line 27, delete "WYLL." and insert -- WYL1. --.

In Column 59, Line 23, delete "VI-γ4," and insert -- V1-γ4, --.

In Column 59, Line 32, delete "p pleated" and insert -- β pleated --.

In Column 60, Line 38, delete "(1° F.n3)," and insert -- (10Fn3), --.

In Column 60, Line 67, delete "1 M" and insert -- 1 μM --.

In Column 62, Line 14, delete "C$_H$i" and insert -- C$_H$1 --.

In Column 67, Line 18, delete "GMi;" and insert -- GM1; --.

In Column 69, Line 44, delete "a and R" and insert -- α and β --.

In Column 70, Line 67, delete "Rib)," and insert -- R1b), --.

In Column 78, Line 31, delete "IHC" and insert -- MHC --.

In Column 79, Line 32, delete "a" and insert -- α --.

In Column 81, Line 33, delete "PD-LI," and insert -- PD-L1, --.

In Column 81, Line 45, delete "3-2" and insert -- β-2 --.

In Column 82, Line 24, delete "3-2" and insert -- β-2 --.

CERTIFICATE OF CORRECTION (continued)
U.S. Pat. No. 11,739,156 B2

In Column 82, Line 35, delete "SIGLEC1O" and insert -- SIGLEC10 --.

In Column 97, Line 57, delete "1×SE" and insert -- ±1×SE --.

In Column 100, Line 56, delete "$T_{reg}$," and insert -- $T_{reg}$ --.

In Column 100, Line 59, delete "Fg/2)." and insert -- Fgl2). --.

In Column 100, Line 63, delete "DP $T_{re}$" and insert -- DP $T_{reg}$ --.

In Column 106, Line 18, delete "T," and insert -- $T_{conv}$ --.

In Column 107, Line 42, delete "Il2rl1$^{fl/fl}$" and insert -- Il1rl1$^{fl/fl}$ --.

In Column 107, Line 62, delete "$T_{reg}$ s" and insert -- $T_{regs}$ --.

In Columns 109-110, Line 6, (TABLE 2), delete "Cd163l1" and insert -- Cd163l1 --.

In Columns 109-110, Line 10, (TABLE 2), delete "Gm2250" and insert -- Gm12250 --.

In Columns 109-110, Line 18, (TABLE 2), delete "Nr4a5" and insert -- Nr4a3 --.

In Columns 109-110, Line 45, (TABLE 2), delete "Bcl2l1" and insert -- Bcl2l1 --.

In Columns 111-112, Line 53, (TABLE 2-continued), delete "Ttc2la" and insert -- Ttc21a --.

In Column 118, Line 63, delete "Tregs." and insert -- $T_{regs}$. --.

In Column 119, Line 15, delete "Fgl2)." and insert -- Fgl2). --.

In Column 119, Line 56, delete "Il1r1" and insert -- Il1rl1 --.

In Column 119, Line 59, delete "Il1r1" and insert -- Il1rl1 --.

In Column 119, Line 59, delete "$T_{reg}$ s" and insert -- $T_{regs}$ --.

In Column 119, Line 60, delete "Il1r1" and insert -- Il1rl1 --.

In Column 120, Line 47, delete "to" and insert -- mice to --.

In Column 121, Line 46, delete "220)," and insert -- 22O), --.

In Column 122, Line 6, delete "CD80" and insert -- CD8β --.

In Column 123, Line 46, delete "CD8+" and insert -- CD8$^+$ --.

CERTIFICATE OF CORRECTION (continued)
U.S. Pat. No. 11,739,156 B2

In Columns 127-128, Line 7 (TABLE 4), delete "eBiol7B7" and insert -- eBio17B7 --.

In Column 127, Line 46, delete "1500." and insert -- 15%. --.

In Column 128, Line 61, delete "$T^{reg}/T_{conv}$," and insert -- $T_{reg}/T_{conv}$, --.

In Column 129, Line 51, delete "detectedgenes." and insert -- detected genes. --.

In Column 130, Line 22, delete "weekp.i." and insert -- week p.i. --.

In Column 131, Line 6, delete "Amon" and insert -- Arnon --.

In Column 131, Line 54, delete "FindNeighborso" and insert -- FindNeighbors() --.

In Column 131, Line 54, delete "FindClusterso" and insert -- FindClusters() --.

In Column 131, Line 63, delete "CD8+cell" and insert -- $CD8^+$ cell --.

In Column 133, Line 21, delete "PPAR-7" and insert -- PPAR-γ --.

In Column 135, Line 61, delete "Galvin," and insert -- Galván, --.

In Column 136, Line 24, delete "Interferon-7" and insert -- Interferon-γ --.

In the Claims

In Column 144, Line 21, in Claim 7, delete "Treg" and insert -- $T_{reg}$ --.